US012760013B2

(12) United States Patent
Lee et al.

(10) Patent No.: US 12,760,013 B2
(45) Date of Patent: Oct. 13, 2026

(54) HETEROARYL DERIVATIVE, METHOD FOR PREPARATION THEREOF, AND PHARMACEUTICAL COMPOSITION COMPRISING SAME AS ACTIVE INGREDIENT

(71) Applicant: VORONOI INC., Incheon (KR)

(72) Inventors: Younho Lee, Incheon (KR); Juhee Kang, Gyeonggi-do (KR); Yikyung Ko, Incheon (KR); Jung Beom Son, Incheon (KR); Eunhwa Ko, Incheon (KR); Sung Hwan Kim, Incheon (KR); Nam Doo Kim, Incheon (KR); Hwan Geun Choi, Seoul (KR)

(73) Assignee: VORONOI INC. (KR)

( * ) Notice: Subject to any disclaimer, the term of this patent is extended or adjusted under 35 U.S.C. 154(b) by 647 days.

(21) Appl. No.: 18/026,793

(22) PCT Filed: Sep. 18, 2021

(86) PCT No.: PCT/KR2021/012915

§ 371 (c)(1),
(2) Date: Mar. 16, 2023

(87) PCT Pub. No.: WO2022/060196

PCT Pub. Date: Mar. 24, 2022

(65) Prior Publication Data

US 2023/0322753 A1 Oct. 12, 2023

(30) Foreign Application Priority Data

Sep. 18, 2020 (KR) ........................ 10-2020-0120731
Sep. 8, 2021 (KR) ........................ 10-2021-0119719

(51) Int. Cl.
*C07D 413/14* (2006.01)
*A61P 35/00* (2006.01)
*C07D 413/04* (2006.01)
*C07D 498/08* (2006.01)

(52) U.S. Cl.
CPC ............ *C07D 413/14* (2013.01); *A61P 35/00* (2018.01); *C07D 413/04* (2013.01); *C07D 498/08* (2013.01)

(58) Field of Classification Search
CPC .. C07D 413/14; C07D 413/04; C07D 498/08; A61P 35/00
See application file for complete search history.

(56) References Cited

U.S. PATENT DOCUMENTS

| | | | |
|---|---|---|---|
| 7,569,561 | B2 | 8/2009 | Stadtmueller et al. |
| 10,377,747 | B2 | 8/2019 | Wu et al. |
| 11,352,352 | B2 | 6/2022 | Zhang et al. |
| 11,466,000 | B2 | 10/2022 | Lee et al. |
| 2012/0252818 | A1 | 10/2012 | Chiosis et al. |
| 2015/0166591 | A1 | 6/2015 | Zhu et al. |
| 2016/0102076 | A1 | 4/2016 | Suh et al. |
| 2016/0229837 | A1 | 8/2016 | Xi et al. |
| 2017/0313714 | A1 | 11/2017 | Wei et al. |
| 2018/0208581 | A1 | 7/2018 | Zhu et al. |
| 2019/0100528 | A1 | 4/2019 | Wei et al. |
| 2019/0127335 | A1 | 5/2019 | Betts et al. |
| 2022/0073505 | A1 | 3/2022 | Lee et al. |
| 2022/0162203 | A1 | 5/2022 | Lee et al. |
| 2022/0289733 | A1 | 9/2022 | Lee et al. |
| 2024/0150337 | A1 | 5/2024 | Lee et al. |

FOREIGN PATENT DOCUMENTS

| | | | |
|---|---|---|---|
| CN | 106132957 | A | 11/2016 |
| CN | 106478607 | A | 3/2017 |
| CN | 108191774 | A | 6/2018 |
| CN | 109280048 | A | 1/2019 |
| CN | 109608394 | A | 4/2019 |
| EA | 041448 | B1 | 10/2022 |
| EP | 3205650 | A1 | 8/2017 |
| EP | 3640248 | A1 | 4/2020 |
| EP | 3943491 | A1 | 1/2022 |
| JP | 2011102241 | A | 5/2011 |
| JP | 2013-502424 | A | 1/2013 |
| JP | 2015-518490 | A | 7/2015 |
| JP | 2017530999 | A | 10/2017 |
| JP | 2017-532326 | A | 11/2017 |
| JP | 2018520190 | A | 7/2018 |
| JP | 2018525431 | A | 9/2018 |
| KR | 20090121399 | A | 11/2009 |
| KR | 20130053240 | A | 5/2013 |
| KR | 20150047855 | A | 5/2015 |

(Continued)

OTHER PUBLICATIONS

CAS Registry No. 1851548-27-0, entry into Registry STN Jan. 24, 2016, American Chemical Society, 2024.
European Search Report and Search Opinion received for European Application No. 21869818.1, mailed on Jul. 22, 2024, 9 pages.
International Preliminary Report on Patentability received for PCT Patent Application No. PCT/KR2020/095044, mailed on Sep. 30, 2021, 14 pages (English Translation).
International Preliminary Report on Patentability received for PCT Patent Application No. PCT/KR2021/012915, mailed on Mar. 30, 2023, 15 pages (English Translation).
International Search Report and Written Opinion received for PCT Patent Application No. PCT/KR2021/012915, mailed on Dec. 24, 2021, 23 pages (English Translation).

(Continued)

*Primary Examiner* — Kamal A Saeed
*Assistant Examiner* — Quincy Mckoy
(74) *Attorney, Agent, or Firm* — MORRISON & FOERSTER LLP

(57) ABSTRACT

The present invention relates to a pharmaceutical composition comprising a compound of the present invention, an isomer thereof, a hydrate thereof, a solvate thereof, or a pharmaceutically acceptable salt thereof as an active ingredient for prevention or treatment of cancer. The compound exhibits high inhibitory activity against epidermal growth factor receptor (EGFR) mutants or at least one of the wild-type or mutant ErbB2 and ErbB4 and as such, can be advantageously used for treatment of the cancer expressing same.

9 Claims, No Drawings

(56) References Cited

FOREIGN PATENT DOCUMENTS

| | | | |
|---|---|---|---|
| KR | 20150067759 | A | 6/2015 |
| KR | 20150131224 | A | 11/2015 |
| KR | 20170066650 | A | 6/2017 |
| KR | 20170118681 | A | 10/2017 |
| KR | 20180030190 | A | 3/2018 |
| KR | 20190108079 | A | 9/2019 |
| KR | 20190108080 | A | 9/2019 |
| KR | 102073854 | B1 | 2/2020 |
| RU | 2017116598 | A | 11/2018 |
| WO | 2002032872 | A1 | 4/2002 |
| WO | 2005026129 | A1 | 3/2005 |
| WO | 2006125616 | A2 | 11/2006 |
| WO | 2008115742 | A1 | 9/2008 |
| WO | 2008150118 | A2 | 12/2008 |
| WO | 2011022440 | A2 | 2/2011 |
| WO | 2013109882 | A1 | 7/2013 |
| WO | 2013169401 | A1 | 11/2013 |
| WO | 2014055928 | A3 | 6/2014 |
| WO | 2014128213 | A1 | 8/2014 |
| WO | 2014141104 | A1 | 9/2014 |
| WO | 2015025936 | A1 | 2/2015 |
| WO | 2015061247 | A2 | 4/2015 |
| WO | 2015175632 | A1 | 11/2015 |
| WO | 2015195228 | A1 | 12/2015 |
| WO | 2016060443 | A2 | 4/2016 |
| WO | 2016105525 | A2 | 6/2016 |
| WO | 2017096301 | A1 | 6/2017 |
| WO | 2017120429 | A1 | 7/2017 |
| WO | 2018109097 | A1 | 6/2018 |
| WO | 2018228446 | A1 | 12/2018 |
| WO | 2019010295 | A1 | 1/2019 |
| WO | 2019081486 | A1 | 5/2019 |
| WO | 2019149164 | A1 | 8/2019 |
| WO | 2019177374 | A1 | 9/2019 |
| WO | 2019177375 | A1 | 9/2019 |
| WO | 2019222093 | A1 | 11/2019 |
| WO | 2020190119 | A1 | 9/2020 |

OTHER PUBLICATIONS

Supplementary European Search Report and Search Opinion received for European Application No. 20774059.8, mailed on Oct. 21, 2022, 6 pages.
Balak, M.N. et al. (Nov. 1, 2006). "Novel D761Y And Common Secondary T790M Mutations In Epidermal Growth Factor Receptor-Mutant Lung Adenocarcinomas With Acquired Resistance To Kinase Inhibitors," Clinical Cancer Research 12(21):6494-6501.
Burger, A. (1991). "Isosterism And Bioisosterism In Drug Design," Progress in Drug Research/Fortschritte der Arzneimittelforschung/ Progrès des Recherches Pharmaceutiques, pp. 287-371.
Carna Biosciences (Feb. 26, 2021). "Drug-Resistant EGFR Mutations In Lung Cancer," Carna Newsletter 9: 2 pages.
Chen, L. et al. (2017). "Recent Progress Of Small-Molecule Epidermal Growth Factor Receptor (EGFR) Inhibitors Against C797S Resistance In Non-Small-Cell Lung Cancer: Miniperspective," Journal Of Medicinal Chemistry 61 (10):4290-4300.
Chen, L. et al. (2018, e-pub. Nov. 10, 2018). "The Synthesis Of 4-Arylamido-2-Arylaminoprimidines As Potent EGFR T790M/ L858R Inhibitors For NSCLC," Bioorganic & Medicinal Chemistry 26(23-24):6087-6095.
Engelman, J. A. et al. (May 18, 2007). "MET Amplification Leads To Gefitinib Resistance In Lung Cancer By Activating ERBB3 Signaling," Science 316(5827): 1039-1043.
Finlay, M. R. V. et al. (2014). "Discovery Of A Potent And Selective EGFR Inhibitor (AZD9291) Of Both Sensitizing And T790M Resistance Mutations That Spares The Wild Type Form Of The Receptor," Journal of Medicinal Chemistry 57:8249-8267.
Fukuoka, M. et al. (Jun. 15, 2003). "Multi-Institutional Randomized Phase II Trial Of Gefitinib For Previously Treated Patients With Advanced Non-Small-Cell Lung Cancer," Journal Of Clinical Oncology 21(12):2237-2246.
Hasako, S. et al. (2018, e-pub. May 10, 2018). "TAS6417, A Novel EGFR Inhibitor Targeting Exon 20 Insertion Mutations," Molecular Cancer Therapeutics 17(8): 1648-1658.
International Search Report and Written Opinion of the International Searching Authority mailed Jun. 24, 2020, for Patent Application No. PCT/KR2020/095044, filed Mar. 19, 2020, 12 pages.
Jang, J. et al. (Sep. 3, 2018). "Discovery Of A Highly Potent And Broadly Effective Epidermal Growth Factor Receptor And HER2 Exon 20 Insertion Mutant Inhibitor," Angewandte Chemie 130(36):11803-11807, 13 pages.
Kang, J. et al. (Apr. 9-10, 2019). "Discovery Of Selective And Potent EGFR Kinase Inhibitors For Exon 20 Ins Mutation," Poster, presented at Drug Discovery Chemistry, San Diego, CA, one page.
Kim, S. et al. (Oct. 16, 2019). "Abstract B002: Discovery of Selective and Potent EGFR Kinase Inhibitors for Exon20 Insertion Mutations," Molecular Cancer Therapeutics 18(12):3 pages, Abstract Only.
Kim, S. et al. (Oct. 28, 2019). "B002: Discovery of Selective and Potent EGFR Kinase Inhibitors for Exon 20 Insertion Mutations," Poster, presented at AACR-NCI-EORTC International Conference on Molecular Targets and Cancer Therapeutic, Boston, MA, one page.
Kobayashi, S. et al. (Feb. 24, 2005). "EGFR Mutation And Resistance Of Non-Small-Cell Lung Cancer To Gefitinib," New England Journal of Medicine 352(8):786-792.
Kosaka, T. et al. (May 15, 2017, e-pub. Mar. 31, 2017). "Response Heterogeneity Of EGFR And HER2 Exon 20 Insertions To Covalent EGFR And HER2 Inhibitors," Cancer Research 77(10):2712-2721.
Kosaka, T. et al. (Oct. 1, 2006). "Analysis Of Epidermal Growth Factor Receptor Gene Mutation In Patients With Non-Small Cell Lung Cancer And Acquired Resistance To Gefitinib," Clinical Cancer Research 12(19):5764-5769.
Kris, M. G. et al. (Oct. 22-29, 2003). "Efficacy Of Gefitinib, An Inhibitor Of The Epidermal Growth Factor Receptor Tyrosine Kinase, In Symptomatic Patients With Non-Small Cell Lung Cancer: A Randomized Trial," JAMA 290 (16):2149-2158.
Lawrence, H. R. et al. (Sep. 13, 2012). "Development Of O-Chlorophenyl Substituted Pyrimidines As Exceptionally Potent Aurora Kinase Inhibitors," Journal Of Medicinal Chemistry 55(17):7392-7416, 56 pages.
Lin, S. Y. et al. (Sep. 28, 2019). "Discovery Of A Furanopyrimidine-Based Epidermal Growth Factor Receptor Inhibitor (DBPR112) As A Clinical Candidate For The Treatment Of Non-Small Cell Lung Cancer," Journal Of Medicinal Chemistry 62(22):10108-10123.
Lu, X. et al. (Aug. 7, 2017). "Targeting EGFRL858R/T790M And EGFRL858R/T790M/C797S Resistance Mutations In NSCLC: Current Developments In Medicinal Chemistry," Medicinal Research Reviews 38(5):1550-1581.
Lynch, T. J. et al. (May 20, 2004). "Activating Mutations In The Epidermal Growth Factor Receptor Underlying Responsiveness Of Non-Small-Cell Lung Cancer To Gefitinib," New England Journal of Medicine 350(21):2129-2139.
Paez, J. G. et al. (Jun. 4, 2004). "EGFR Mutations In Lung Cancer: Correlation With Clinical Response To Gefitinib Therapy," Science 304(5676):1497-1500.
Pao, W. et al. (Mar. 2005). "Acquired Resistance Of Lung Adenocarcinomas To Gefitinib Or Erlotinib Is Associated With A Second Mutation In The EGFR Kinase Domain," Plos Medicine 2(3):e73, pp. 0225-0235.
Rho, J.K. et al. (Mar. 1, 2017, e-pub. Jan. 12, 2017). "Superior Efficacy And Selectivity Of Novel Small-Molecule Kinase Inhibitors Of T790M-Mutant EGFR In Preclinical Models Of Lung Cancer," Cancer Research 77(5):1200-1211.
Robichaux, J. P. et al. (May 2018). "Mechanisms And Clinical Activity Of An EGFR And HER2 Exon 20-Selective Kinase Inhibitor In Non-Small Cell Lung Cancer," Nature Medicine 24(5):638-646, 22 pages.
Sharma, S. V. et al. (Mar. 2007). "Epidermal Growth Factor Receptor Mutations In Lung Cancer," Nature Reviews Cancer 7(3):169-181.
Shepherd, F. A. et al. (Jul. 14, 2005). "Erlotinib In Previously Treated Non-Small-Cell Lung Cancer," New England Journal of Medicine 353(2):123-132.

(56) References Cited

OTHER PUBLICATIONS

Shi, Y. et al. (Mar. 31, 2017). "Synthesis and Biological Activities of Novel Cyanoacrylate Derivatives Carrying 5-Arylisoxazole Group," Journal of Chemistry in Colleges and Universities 38(3):421-428. (English Abstract Only).
Udagawa, H. et al. (2019, e-pub. Aug. 29, 2019). "TAS6417/CLN-081 Is a Pan-Mutation-Selective EGFR Tyrosine Kinase Inhibitor with a Broad Spectrum of Preclinical Activity against Clinically Relevant EGFR Mutations," Molecular Cancer Research 17(11):2233-2243.
Verweij, M. (2000). "Medical-Ethical Dimensions of Preventive Medicine," Chapter 3 in Preventive Medicine Between Obligation and Aspiration, Springer Science and Business Media, vol. 4, pp. 25-48, 31 pages.
Wang, Y. et al. (Mar. 4, 2020). "Discovery And Sars Of 5-Chloro-N 4-Phenyl-N 2-(Pyridin-2-YI) Pyrimidine-2, 4-Diamine Derivatives As Oral Available And Dual CDK 6 And 9 Inhibitors With Potent Antitumor Activity," Journal Of Medicinal Chemistry 63(6):3327-3347.
Xie, Z. et al. (Feb. 2020, e-pub. Dec. 5, 2019). "Discovery Of 4, 6-Pyrimidinediamine Derivatives As Novel Dual EGFR/FGFR Inhibitors Aimed EGFR/FGFR1-Positive NSCLC," European Journal Of Medicinal Chemistry 187:111943, 18 pages.
Yang, H. et al. (2019, e-pub. Dec. 14, 2019). "Design, Synthesis And Biological Evaluation Of 2-Amino-4-(1, 2, 4-Triazol) Pyridine Derivatives As Potent EGFR Inhibitors To Overcome TKI-Resistance," European Journal Of Medicinal Chemistry 187:111966, 36 pages.
Yu, L. et al. (Jan. 27, 2017, e-pub. Dec. 3, 2016). "A Structure-Guided Optimization Of Pyrido [2, 3-D] Pyrimidin-7-Ones As Selective Inhibitors Of EGFRL858R/T790M Mutant With Improved Pharmacokinetic Properties," European Journal Of Medicinal Chemistry 126:1107-1117.
Zhou, P. et al. (2018). "Design, Synthesis And Evaluation Of The Osimertini.B Analogue (C-005) As Potent EGFR Inhibitor Against NSCLC," Bioorganic & Medicinal Chemistry 26:6135-6145.

HETEROARYL DERIVATIVE, METHOD FOR PREPARATION THEREOF, AND PHARMACEUTICAL COMPOSITION COMPRISING SAME AS ACTIVE INGREDIENT

CROSS REFERENCE TO RELATED APPLICATIONS

This application is a U.S. national stage application under 35 U.S.C. § 371 of International Application No. PCT/KR2021/012915, filed on Sep. 18, 2021, which claims the priority benefit of Korean Application No. 10-2020-0120731, filed on Sep. 18, 2020, and Korean Application No. 10-2021-0119719, filed on Sep. 8, 2021, all of which are incorporated herein by reference in their entirety for all purposes.

FIELD OF THE INVENTION

The present invention relates to a heteroaryl derivative, a stereoisomer thereof, a hydrate thereof, a solvate thereof, or a pharmaceutically acceptable salt thereof, a method for preparating the same, and a pharmaceutical composition for the prevention or treatment of cancer, comprising the same as an active ingredient.

BACKGROUND OF THE INVENTION

The occurrence of cancer is related to various environmental factors including chemical substances, radiations and viruses, and to changes of oncogenes, tumor suppressor genes, genes associated with apoptosis and DNA repair and the like. Recently, the molecular mechanism of these cancers could be figured out, and thus it could make a new treatment method, i.e. a targeted cancer therapy possible. In general, targeted therapeutic agents may be so prepared that they may show their effects by targeting the molecules that cancer cells possess as their own characteristics. The genes regarded as a molecular target are those associated with signal transduction pathway of cancer cell, angiogenesis, extracellular matrix, cell cycle regulator, apoptosis and the like. An important targeted therapeutic agent used in the current therapy includes tyrosine kinase inhibitors as well as 'signal transduction pathway inhibitors' and 'angiogenesis inhibitors'. In this connection, it has been found that a protein tyrosine kinase plays an important role in a number of malignant tumors. In particular, it has been known that epidermal growth factor receptor (EGFR), which is a receptor tyrosine kinase of ErbB family, is abnormally activated in a number of epithelial cell tumors including non-small cell lung carcinoma (NSCLC), breast cancer, glioma, squamous cell carcinoma of head and neck, colorectal cancer, rectal adenocarcinoma, head and neck cancer, gastric cancer, and prostate cancer, wherein the activation of the above EGFR-tyrosine kinase causes a persistent cell proliferation, invasion of the surrounding tissue, remote metastasis, and angiogenesis, and increases a cell survival.

Specifically, the EGFR is one of the members of ErbB tyrosine kinase receptors family and also a transmembrane tyrosine kinase having an extracellular ligand-binding domain and an intracellular domain including a tyrosine kinase domain, wherein it can include EGFR (referred to as ErbB1 or HER1), HER-2 (referred to as ErbB2 or neu), ErbB-3, and ErbB-4 (referred to as HER4). If a ligand binds to a receptor forming homodimer or heterodimer, a tyrosine kinase in a cell is activated, so that a signal stimulated by EGFR in this way also activates a signal transduction pathway of phosphatidylinositol 3-kinase (PI3K/AKT/mTOR, RAS/RAF/MAPK and JAK/STAT) (non-patent literature 0001). In particular, EGFR is overexpressed in more than a half of non-small cell lung cancers (NSCLC), and thus a number of studies have been carried out, in which EGFR is a target of a therapy. So EGFR TKI (tyrosine kinase inhibitor), inhibiting an activity of EGFR tyrosine kinase, has been developed, wherein representative drugs thereof include Gefitinib (IRESSA™), erlotinib (TARCEVA™), lapatinib (TYKERB™, TYVERB™) and so on.

On the other hand, in year 2004, it was reported that an activating mutant of EGFR is correlated with a response to gefitinib therapy in non-small cell lung cancer (non-patent Literatures 0002 and 0003). Specifically, it has been known that the above EGFR mutation is largely classified into a sensitizing mutation and a resistant mutation, wherein an exon 19 deletion and an exon 21 L858R point mutations are most important sensitizing mutations and make up about 85 to 90 percent of the sensitizing mutation. Especially, it has been also known that the exon 19 deletion mutation is more sensitizing to the TIK. On the other hand, it has been known that the exon 20 T790M point mutation is a most important resistant mutation and is found in more than 50 percent of acquired resistant patients (non-patent literature 0004).

Somatic mutation identified hitherto includes an in-frame deletion in exon 19 or an insertion in exon 20, as well as a point mutation in which a single nucleic acid residue is modified within an expressed protein (e.g. L858R, G719S, G719C, G719A, L861Q) (non-patent literatures 0005 to 0007).

Despite an initial clinical effect of gefitinib/erlotinib in NSCLC patients with an EGFR mutation, a progressive cancer develops in most patients in the end while these patients are undergoing a therapy using these medicines. In an early study of recurred samples, a secondary EGFR mutation, T790M, was identified, which made the gefitinib and erlotinib to be an ineffective inhibitor of EGFR kinase activity (non-patent literatures 0008 and 0009). It has been proved in the follow-up studies that the EGFR T790M mutation was found in approximately 50 percent (24/48) of tumors derived from the patients who acquired a resistance to the gefitinib or erlotinib (non-patent literatures 0010 to 0012). This secondary genetic modification in the patients treated by a kinase inhibitor is caused in a position similar to a 'gatekeeper' residue and a secondary resistance allele associated therewith (e.g. T3151 within ABL in imatinib resistant CML).

Also, it has been known that EGFR_del19 or EGFR_L858R as EGFR mutation is a major cause of non-small cell lung cancer, and head and neck cancer. Thus, IRESSA and TARCEVA as therapeutic drugs of said cancers were developed and are currently used in clinical trials. However, when such drugs were administrated for cancer patients, an acquired resistance, in which an EGFR secondary mutation based on the structure of the drugs, was observed. In addition, it was also found that such a thing was a major cause of the actual resistance to drugs. For example, if a first generation inhibitor of EGFR is used for 10 months in average, the acquired resistance, referred to as T790M mutation positioned in a gatekeeper of EGFR kinase, occurs, resulting in preventing the first generation inhibitor of EGFR from showing a medicinal effect. That is, EGFR_del19_T790M or EGFR_L858R_T790M double mutation occurs, resulting in preventing existing therapeutic agents from exhibiting a medicinal effect.

PRIOR ART LITERATURES

Non-Patent Literatures (Non-patent literature 0001) Nat Rev Cancer 2007; 7:169-81.

(Non-patent literature 0002) Science 2004; 304:1497-500.

(Non-patent literature 0003) New England Journal of Medicine 2004; 350:2129-39.

(Non-patent literature 0004) Clin Cancer Res 2006; 12:6494-6501.

(Non-patent literature 0005) Fukuoka et al. JCO 2003.

(Non-patent literature 0006) Kris et al. JAMA 2003.

(Non-patent Literature 0007) Shepherd et al. NEJM 2004.

(Non-patent Literature 0008) Kobayashi et al. NEJM 2005.

(Non-patent Literature 0009) Pao et al. PLOS Medicine 2005.

(Non-patent Literature 0010) Kosaka et al. CCR 2006.

(Non-patent Literature 0011) Balak et al. CCR 2006.

(Non-patent Literature 0012) Engelman et al. Science 2007.

SUMMARY OF THE INVENTION

Technical Problem

The objective of one aspect of the present invention is to provide a compound which can be used for the treatment of cancer, a stereoisomer thereof, a hydrate thereof, a solvate thereof or a pharmaceutically acceptable salt thereof.

The objective of other aspect of the present invention is to provide a method for preparing the above compound.

The objective of another aspect of the present invention is to provide a pharmaceutical composition for the prevention or treatment of cancer, the composition comprising the above compound, a stereoisomer thereof, a hydrate thereof, a solvate thereof, or a pharmaceutically acceptable salt thereof, as an active ingredient.

Technical Solution

To achieve the above objectives, the present invention provides a compound represented by a following chemical formula 1 or 2, a stereoisomer thereof, a hydrate thereof, a solvate thereof or a pharmaceutically acceptable salt thereof:

[Chemical Formula 1]

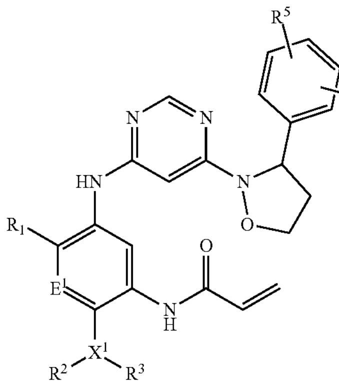

where, in the chemical formula 1, $E^1$ is N or CH;

$R^1$ is hydrogen, $C_{1-5}$ alkoxy, or alkoxy substituted by halogen;

$X^1$ is C, N, O or S, when $X^1$ is C, $R^2$ and $R^3$ form, together with a bonded C, a 3 to 12 atom heteroaryl comprising at least one N, wherein the 3 to 12 atom heteroaryl is substituted or unsubstituted by a $C_{1-5}$ straight chain or branched chain alkyl, when $X^1$ is N, $R^2$ and $R^3$ are each independently hydrogen, or $C_1$-s straight chain or branched chain alkyl, or $R^2$ and $R^3$ form, together with a bonded N, a 3 to 12 atom heterocycloalkyl comprising one or more heteroatoms among N, O and S, wherein the $C_{1-5}$ straight chain or branched chain alkyl is substituted or unsubstituted by a $C_{1-5}$ alkylamino, and wherein the 3 to 12 atom heterocycloalkyl comprising one or more heteroatoms among N, O and S is substituted or unsubstituted by one or more substituents A, selected from a group consisting of $C_{1-5}$ straight chain or branched chain alkyl, $C_{3-6}$ cycloalkyl, $C_{1-5}$ alkylamino, allyl, oxo (=O), $C_{1-3}$ alkylcarbonyl, and 3 to 12 atom heterocycloalkyl comprising one or more heteroatoms among N and O, among the substituents A, the $C_{1-5}$ straight chain or branched chain alkyl is additionally substituted or unsubstituted by a $C_{3-6}$ cycloalkyl, a $C_{1-5}$ alkylamino, or a 3 to 12 atom heterocycloakyl comprising at least one N, and also among the substituents A, the 3 to 12 atom heterocycloalkyl is substituted or unsubstituted by a substituent B, selected from a group consisting of $C_{1-5}$ straight chain or branched chain alkyl, $C_{3-4}$ cycloalkyl, $C_{1-5}$ alkylcarbonyl, and 3 to 12 atom heterocycloalkyl comprising one or more among N and O, and the 3 to 12 atom heterocycloalkyl, comprising one or more among N and O, among the substituents B is additionally substituted or unsubstituted by a $C_{1-5}$ straight chain or branched chain alkyl or a $C_{3-6}$ cycloalkyl;

when $X^1$ is S or O, $R^2$ does not exist and $R^3$ is $C_{1-5}$ alkyl substituted by $C_{1-5}$ alkylamino; and $R^4$ and $R^5$ are each independently hydrogen, halogen or haloalkyl, or $R^4$ and $R^5$ form, together with a benzene, a 7 to 12 atom heteroaryl comprising N, O and S, wherein the 7 to 12 atom heteroaryl is substituted or unsubstituted by a $C_{1-5}$ straight chain or branched chain alkyl; or

[Chemical formula 1]

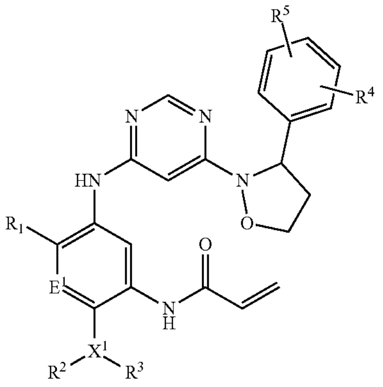

where, in the chemical formula 1, $E^1$ is N or CH;

$R^1$ is hydrogen, $C_{1-5}$ alkoxy, or alkoxy substituted by halogen;

$X^1$ is C, N, O or S, when $X^1$ is C, $R^2$ and $R^3$ form, together with a bonded C, a 3 to 12 atom heteroaryl comprising at least one N, wherein the 3 to 12 atom heteroaryl is substituted or unsubstituted by a $C_{1-5}$ straight chain or branched chain alkyl or a 3 to 12 atom heterocycloalkyl, when $X^1$ is N, $R^2$ and $R^3$ are each independently hydrogen or $C_{1-5}$ straight chain or branched chain alkyl, or $R^2$ and $R^3$ form, together with a bonded N, a 3 to 12 atom heterocycloalkyl, wherein the heterocycloalkyl comprises one or more heteroatoms among N, O and S, wherein the $C_{1-5}$ straight chain or branched chain alkyl is substituted or unsubstituted by a $C_{1-5}$ alkylamino, and wherein the 3 to 12 atom heterocycloalkyl comprising one or more heteroatoms among N, O and S is substituted or unsubstituted by one or more substituents A, selected from a group consisting of $C_{1-5}$ straight chain or branched chain alkyl, $C_{3-6}$ cycloalkyl, $C_{1-5}$ alkylamino, allyl, oxo (=O), $C_{1-3}$ alkylcarbonyl, and 3 to 12 atom heterocycloalkyl comprising one or more heteroatoms among N and 0, among the substituents A, the $C_{1-5}$ straight chain or branched chain alkyl is additionally substituted or unsubstituted by a $C_{3-6}$ cycloalkyl, a $C_{1-5}$ alkylamino, or a 3 to 12 atom heterocycloakyl comprising at least one N, and also among the substituents A, the 3 to 12 atom heterocycloalkyl is substituted or unsubstituted by a substituent B, selected from a group consisting of $C_{1-5}$ straight chain or branched chain alkyl, $C_{3-6}$ cycloalkyl, $C_{1-5}$ alkylcarbonyl, 3 to 12 atom heterocycloalkyl comprising one or more among N and O, and oxo, and among the substituents B, the 3 to 12 atom heterocycloalkyl comprising one or more among N and O is additionally substituted or unsubstituted by a $C_{1-5}$ straight chain or branched chain alkyl or a $C_{3-6}$ cycloalkyl;

when $X^1$ is S or O, $R^2$ does not exist and $R^3$ is $C_{1-5}$ alkyl substituted by $C_{1-5}$ alkylamino;

$R^4$ and $R^5$ are each independently hydrogen, halogen or haloalkyl, or $R^4$ and $R^5$ form, together with a benzene, a 7 to 12 atom heteroaryl comprising one or more heteroatoms selected from N, O and S, wherein the 7 to 12 atom heteroaryl is substituted or unsubstituted by a $C_{1-5}$ straight chain or branched chain alkyl, and

[Chemical formula 2]

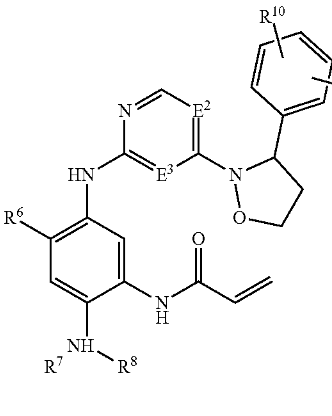

where, in the chemical formula 2, $E^2$ and $E^3$ are each independently N or CH, but the case that $E^2$ is N and $E^3$ is CH, is excluded;

$R^6$ is hydrogen or $C_{1-5}$ alkoxy;

if $R^7$ is $C_{1-5}$ straight chain or branched chain alkyl, then $R^8$ is $C_{1-5}$ straight chain or branched chain alkyl substituted by $C_{1-5}$ alkylamonio, or $R^7$ and $R^8$ form, together with the N to which they are bonded, a 3 to 12 atom heterocycloalkyl, wherein the 3 to 12 atom heterocycloalkyl is substituted or unsubstituted by a $C_{1-5}$ straight chain or branched chain alkyl, or a 3 to 12 atom heterocycloalkyl comprising at least one N, and the 3 to 12 atom heterocycloalkyl comprising at least one N is additionally substituted or unsubstituted by a $C_{3-6}$ cycloalkyl; and $R^9$ and $R^{10}$ are each independently hydrogen, halogen or haloalkyl.

Furthermore, the present invention provides a method for preparing a compound represented by the chemical formula 1 or 2.

In addition, the present invention provides a pharmaceutical composition for the prevention or treatment of cancer, the composition comprising a compound represented by the chemical formula 1 or 2, a stereoisomer thereof, a hydrate thereof, a solvate thereof, or a pharmaceutically acceptable salt thereof, as an active ingredient.

Effects of the Invention

A compound provided according to one aspect of the present invention, a stereoisomer thereof, a hydrate thereof, a solvate thereof or a pharmaceutically acceptable salt thereof exhibit a high suppression ability against EGFR (epidermal growth factor receptor) wild types or mutations as well as against ErbB2, ErbB4 and mutations thereof, and thus can be usefully used for treating the cancers, in which said kinase was expressed.

DETAILED DESCRIPTION OF THE PREFERRED EMBODIMENTS OF THE INVENTION

Hereinafter, the present invention is explained in more details with reference to the aspects.

The embodiments of the present invention may be modified into various different forms, but the scope of the present invention shall not be limited to the aspects explained in the following. In addition, the embodiments of the present invention are provided to more completely explain the present invention to those skilled in the art.

Throughout the present specification, to "comprise" a certain component means that other components may be further included, rather than being excluded, unless specifically stated to the contrary.

In the structural formulas of the present specification, the symbol, "—", bonding atoms and/or groups to each other, may mean a single bond, and the symbol, "=", may mean a double bond. Such symbols may be omitted, but may be also indicated in case that it is necessary to specify the bonded atoms or the bonding positions, etc.

In the present specification, the "linking" between the atoms may not include only the cases that the direct linking between the atoms is made, but also the cases that the indirect linking between the atoms is made through other atoms and/or groups. In this connection, the other atom and/or group may be, but are not limited to, oxygen, sulfur, $C_{1-8}$ alkylamino, $C_{1-8}$ alkylene group and so forth, wherein the above atoms and/or groups may be substituted or unsubstituted.

In the present specification, the expression, "substituted or unsubstituted" may mean that one or a plurality of hydrogen atoms are substituted or unsubstituted by another atom or substituent, unless otherwise stated. The substituent may be one or more selected from a group consisting of halogen (chloro (Cl), iodo (I), bromo (Br), fluoro (F), $C_{1-10}$ alkyl, $C_{2-10}$ alkenyl, $C_{2-10}$ alkynyl, hydroxyl, $C_{1-10}$ alkoxy, amino, nitro, thiol, thioether, imine, cyano, phosphonato, phospine, carboxy, carbamoyl, carbamic acid, acetal, urea, thiocarbonyl, sulfonyl, sulfonamide, ketone, aldehyde, ester, acetyl, acetoxy, amide, oxygen (═O), haloalkyl (e.g. trifluoromethyl), substituted aminoacyl and aminoalkyl, carbon ring cycloalkyls which are single ring or fused or non-fused multiple ring (e.g. cyclopropyl, cyclobutyl, cyclopentyl or cyclohexyl), hetero cycloalkyls which are single ring or fused or non-fused multiple ring (e.g. pyrrolidinyl, piperidinyl, piperazinyl, morpholinyl or thiazinyl), carbon ring or hetero ring, single ring or fused or non-fused multiple ring aryls (e.g. phenyl, naphthalenyl, pyrrolyl, indolyl, furanyl, thienyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothienyl or benzofuranyl), aminos (primary, secondary or tertiary), aryl, aryloxy, and aryl-alkyl, but is not limited thereto. Further, the substituents mentioned above as example may be substituted or unsubstituted again respectively by a substituent selected from the group of those substituents.

In the present specification, the "halogen" may be F, Cl, Br or I.

In the present specification, the "alkyl" may mean, unless otherwise stated, a saturated hydrocarbon of a straight-chain or branched chain noncyclic alkly; a cyclic alkyl; or one formed by the combination of the both above-mentioned alkyls. Further, the "$C_{1-8}$ alkyl" may mean an alkly comprising 1 to 8 carbon atoms. As one example, the noncyclic alkyl may include, but is not limited to, methyl, ethyl, N-propyl, N-butyl, N-pentyl, N-hexyl, N-heptyl, N-octyl, isopropyl, sec-butyl, tert-butyl, isopentyl, 2-methylpentyl, 3-methylpentyl, 4-methylpentyl, 2,3-dimethylbutyl and the like. As one example, the cyclic alkyl may also include, but is not limited to, cyclopropyl, cyclobutyl, cyclopentyl, cyclohexyl, cycloheptyl, or cyclooctyl, etc. The alkyl formed by the combination of the noncyclic and the cyclic alkly may include, but is not limited to, e.g. methylcyclopropyl, cyclopropylmethyl, ethylcyclopropyl, cyclopropylmethyl, methylcyclobutyl, cyclobutylmethyl, ethylcyclopentyl, cyclopentylmethyl and the like.

In case that a "cycloalkyl" is described in the present specification, it may refer to alkyls, in particular mean a cyclic alkyl among the alkyls, wherein the alkyl is as defined in the foregoing.

In the present specification, the "alkoxy" is an alkyl ether group and so may mean a —(O-alkyl), wherein the alkyl is as defined in the foregoing. Further, the "$C_{1-8}$ alkoxy" may mean an alkoxy containing a $C_{1-8}$ akyl, that is, —(O—$C_{1-8}$ alkyl), and wherein as one example, the $C_{1-8}$ alkoxy may include, but is not limited to, methoxy, ethoxy, n-propoxy, isopropoxy, n-butoxy, iso-butoxy, sec-butoxy, tert-butoxy, n-pentoxy and the like.

In the present specification, the "heterocycloalkyl" may mean a ring containing 1 to 5 heteroatoms selected from the ring-forming atoms, i.e. N, O and S, and so may be saturated or partially unsaturated. Unless otherwise stated, the heterocycloalkyl may be a single ring, or a multiple ring, such as spiro ring, bridge ring or fused ring. Further, the "3 to 12 atom heterocycloalkyl" may mean a heterocycloalkyl which comprises 3 to 12 atoms forming a ring, wherein as one example, the heterocycloakyl may include, but is not limited to, pyrrolidine, piperidine, N-methylpiperidine, imidazolidine, pyrazolidine, butyrolactam, valerolactam, imidazolidinone, hydantoin, dioxolane, phthalimide, piperidine, piperidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and the like.

In the present specification, the "alkylamino" may mean a —(NR'R"), wherein R' and R" may be each independently selected from a group consisting of hydrogen and $C_{1-8}$ alkyls, and then the selected R' and R" may be each independently substituted or unsubstituted. Further, the "$C_{1-8}$ alkylamino" may mean an amino containing a $C_{1-8}$ alkyl, that is, —N—H($C_{1-8}$ alkyl) or —N—($C_{1-8}$ alkyl)$_2$ and include, but is not limited to, dimethlyamino, diethylamino, methylethylamino, methylpropylamino, or ethylpropylamino.

In the present specification, the "alkenyl" may mean, unless otherwise stated, a straight chain or branched chain noncyclic or cyclic hydrocarbon having one or more double bonds. Further, the "$C_{2-8}$ alkenyl" may mean an alkenyl comprising 2 to 8 carbon atoms and, as one example, include, but is not limited to, ethenyl, 1-propenyl, prop-2-en-1-yl[-($CH_2$—CH═$CH_2$)](allyl), 2-butenyl, isopropenyl, 3-butenyl, 4-pentenyl, 5-hexenyl, 1-cyclohexenyl, cyclopentadienyl, 1,3-cyclohexadienyl, 1,4-cyclohexadienyl, 1,3-cycloheptadienyl, 1,3,5-cycloheptatrienyl and the like.

In the present specification, the "bicycloalkyl" may mean, unless otherwise stated, a fused, spiro or bridged bicyclic hydrocarbon.

In the present specification, the "oxazabicycloalkyl" may mean a-(oxaza-bicycloalkyl), that is, represent a bicycloalkyl which comprises one oxygen atom and one nitrogen atom in the cycloalkyl. As one example, the oxazabicycloalkyl may include, but is not limited to, oxazabicyclo[2,2,1]heptane, etc.

In the present specification, the "hydrate" may mean a compound of the present invention or a salt thereof, comprising a stoichiometric or non-stoichiometric amount of water bonded by means of a non-covalent intermolecular force. The hydrate of the compound of the present invention represented by the chemical formula 1 may comprise a stoichiometric or non-stoichiometric amount of water bonded by means of the non-covalent intermolecular force. The hydrate may contain more than one equivalent of water, preferably one to five equivalents of water. This hydrate may be prepared by crystallizing the compound of the present invention represented by the chemical formula 1, an isomer thereof or a pharmaceutically acceptable salt thereof, from the water or a solvent containing the water.

In the present specification, the "solvate" may mean the compound of the present invention or the salt thereof, comprising a stoichiometric or non-stoichiometric amount of solvent bonded by means of the non-covalent intermolecular force. In this context, preferred solvents include volatile solvents, nontoxic solvents, and/or solvents suitable to be administered to human.

In the present specification, the term "isomer" means the compound of the present invention or the salt thereof, which has an identical chemical or molecular formula, but is structurally or tridimensionally different. Such isomers include all of structural isomers like tautomer, etc. R or S isomers having asymmetric carbon centers, stereoisomers like geometric isomers (trans, cis), etc. and enantiomer. All such isomers and compounds thereof are also included in the scope of the present invention. Unless otherwise explained, a solid line bond (—), in which a linking to asymmetric carbon atoms takes place, may include a wedged solid line bond ( ) or a wedged dotted line bond ( ) indicating an absolute three-dimensional arrangement.

One aspect of the present invention provides a compound represented by a following chemical formula 1, a stereoisomer thereof, a hydrate thereof, a solvate thereof, or a pharmaceutically acceptable salt thereof:

[Chemical formula 1]

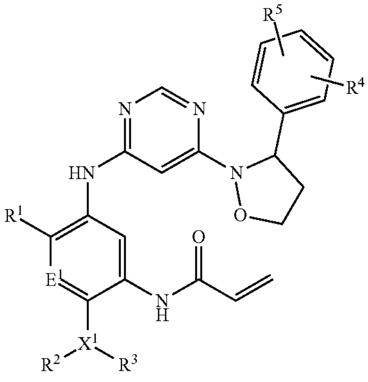

where, in the chemical formula 1, $E^1$ is N or CH;

$R^1$ is hydrogen, $C_{1-5}$ alkoxy, or alkoxy substituted by halogen;

$X^1$ is C, N, O or S, when $X^1$ is C, $R^2$ and $R^3$ form, together with a bonded C, a 3 to 12 atom heteroaryl comprising at least one N, wherein the 3 to 12 atom heteroaryl is substituted or unsubstituted by a $C_{1-5}$ straight chain or branched chain alkyl, when $X^1$ is N, $R^2$ and $R^3$ are each independently hydrogen or $C_{1-5}$ straight chain or branched chain alkyl, or $R^2$ and $R^3$ form, together with a bonded N, a 3 to 12 atom heterocycloalkyl comprising one or more heteroatoms among N, O and S, wherein the $C_{1-5}$ straight chain or branched chain alkyl is substituted or unsubstituted by a $C_{1-5}$ alkylamino, and wherein the 3 to 12 atom heterocycloalkyl comprising one or more heteroatoms among N, O and S is substituted or unsubstituted by one or more substituents A, selected from a group consisting of $C_{1-5}$ straight chain or branched chain alkyl, $C_{3-6}$ cycloalkyl, $C_{1-5}$ alkylamino, allyl, oxo (=O), $C_{1-3}$ alkylcarbonyl, and 3 to 12 atom heterocycloalkyl comprising one or more heteroatoms among N and O, among the substituents A, the $C_{1-5}$ straight chain or branched chain alkyl is additionally substituted or unsubstituted by a $C_{3-6}$ cycloalkyl, a $C_{1-5}$ alkylamino, or a 3 to 12 atom heterocycloakyl comprising at least one N, and also among the substituents A, the 3 to 12 atom heterocycloalkyl is substituted or unsubstituted by a substituent B, selected from a group consisting of $C_{1-5}$ straight chain or branched chain alkyl, $C_{3-6}$ cycloalkyl, $C_{1-5}$ alkylcarbonyl, and 3 to 12 atom heterocycloalkyl comprising one or more among N and O, and among the substituents B, the 3 to 12 atom heterocycloalkyl comprising one or more among N and O is additionally substituted or unsubstituted by a $C_{1-5}$ straight chain or branched chain alkyl or a $C_{3-6}$ cycloalkyl;

when $X^1$ is S or O, $R^2$ does not exist and $R^3$ is $C_{1-5}$ alkyl substituted by $C_{1-5}$ alkylamino; and $R^4$ and $R^5$ are each independently hydrogen, halogen or haloalkyl, or $R^4$ and $R^5$ form, together with a benzene, a 7 to 12 atom heteroaryl comprising N, O and S, wherein the 7 to 12 atom heteroaryl may be substituted or unsubstituted by a $C_{1-5}$ straight chain or branched chain alkyl, or

[Chemical formula 1]

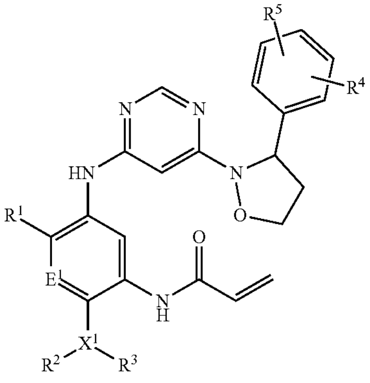

where, in the chemical formula 1, $E^1$ is N or CH;

$R^1$ is hydrogen, $C_{1-5}$ alkoxy, or alkoxy substituted by halogen;

$X^1$ is C, N, O or S,

When $X^1$ is C, $R^2$ and $R^3$ form, together with a bonded C, a 3 to 12 atom heteroaryl comprising at least one N, wherein the 3 to 12 atom heteroaryl is substituted or unsubstituted by a $C_{1-5}$ straight chain or branched chain alkyl or a 3 to 12 atom heterocycloalkyl, when $X^1$ is N, $R^2$ and $R^3$ are each independently hydrogen or $C_{1-5}$ straight chain or branched chain alkyl, or $R^2$ and $R^3$ form, together with a bonded N, a 3 to 12 atom heterocycloalkyl, wherein the heterocycloalkyl comprises one or more heteroatoms among N, O and S, wherein the $C_{1-5}$ straight chain or branched chain alkyl is substituted or unsubstituted by a $C_{1-5}$ alkylamino, and wherein the 3 to 12 atom heterocycloalkyl comprising one or more heteroatoms among N, O and S is substituted or unsubstituted by one or more substituents A, selected from a group consisting of $C_{1-5}$ straight chain or branched chain alkyl, $C_{3-6}$ cycloalkyl, $C_{1-5}$ alkylamino, allyl, oxo (=O), $C_{1-3}$ alkylcarbonyl, and 3 to 12 atom heterocycloalkyl comprising one or more heteroatoms among N and O, among the substituents A, the $C_{1-5}$ straight chain or branched chain alkyl is additionally substituted or unsubstituted by a $C_{3-6}$ cycloalkyl, a $C_{1-5}$ alkylamino, or a 3 to 12 atom heterocycloalkyl comprising at least one N, and also among the substituents A, the 3 to 12 atom heterocycloalkyl is substituted or unsubstituted by a substituent B, selected from a group consisting of $C_{1-5}$ straight chain or branched chain alkyl, $C_{3-6}$ cycloalkyl, $C_{1-5}$ alkylcarbonyl, 3 to 12 atom heterocycloalkyl comprising one or more among N and O, and oxo, and among the substituents B, the 3 to 12 atom heterocycloalkyl comprising one or more among N and O is additionally substituted or unsubstituted by a $C_{1-5}$ straight chain or branched chain alkyl or a $C_{3-6}$ cycloalkyl;

when $X^1$ is S or O, $R^2$ does not exist and $R^3$ is $C_{1-5}$ alkyl substituted by $C_{1-5}$ alkylamino;

$R^4$ and $R^5$ are each independently hydrogen, halogen or haloalkyl, or $R^4$ and $R^5$ form, together with a benzene, a 7 to 12 atom heteroaryl comprising one or more heteroatoms selected from N, O and S, wherein the 7 to 12 atom heteroaryl is substituted or unsubstituted by a $C_{1-5}$ straight chain or branched chain alkyl.

In a specific aspect, a compound is provided, which is represented by a chemical formula 1 in which:

$E^1$ is CH or N;

$R^1$ is hydrogen, $C_{1-3}$ alkoxy, or alkoxy substituted by halogen;

$X^1$ is C, N, O or S,

When $X^1$ is C, $R^2$ and $R^3$ form, together with a bonded C, a 3 to 6 atom heteroaryl comprising at least one N, wherein the 3 to 6 atom heteroaryl is substituted or unsubstituted by a $C_{1-3}$ straight chain or branched chain alkyl, when $X^1$ is N, $R^2$ and $R^3$ are each independently hydrogen, or $C_{1-3}$ straight chain or branched chain alkyl, or $R^2$ and $R^3$ form, together with a bonded N, a 4 to 10 atom heterocycloalkyl comprising one or more heteroatoms among N, O and S, wherein the $C_{1-3}$ straight chain or branched chain alkyl is substituted or unsubstituted by a $C_{1-3}$ alkylamino, and wherein the 4 to 10 atom heterocycloalkyl comprising one or more heteroatoms among N, O and S is substituted or unsubstituted by one or more substituents A, selected from a group consisting of $C_{1-3}$ straight chain or branched chain alkyl, $C_{3-6}$ cycloalkyl, $C_{1-3}$ alkylamino, allyl, oxo (=O), $C_{1-3}$ alkylcarbonyl, and 4 to 10 atom heterocycloalkyl comprising one or more heteroatoms among N and O, among the substituents A, the $C_{1-3}$ straight chain or branched chain alkyl is additionally substituted or unsubstituted by a $C_{3-6}$ cycloalkyl, a $C_{1-3}$ alkylamino, or a 4 to 10 atom heterocycloalkyl comprising at least one N, and also among the substituents A, the 4 to 10 atom heterocycloalkyl is substituted or unsubstituted by a substituent B, selected from a group consisting of $C_{1-3}$ straight chain or branched chain alkyl, $C_{3-6}$ cycloalkyl, $C_{1-3}$ alkylcarbonyl, and 4 to 6 atom heterocycloalkyl comprising one or more among N and O, and among the substituents B, the 4 to 6 atom heterocycloalkyl comprising one or more among N and O is additionally substituted or unsubstituted by a $C_{1-3}$ straight chain or branched chain alkyl or a $C_{3-6}$ cycloalkyl;

when $X^1$ is S or O, $R^2$ does not exist and $R^3$ is alkyl substituted by $C_{1-3}$ alkylamino; and $R^4$ and $R^5$ are each independently hydrogen, halogen or haloalkyl, or $R^4$ and $R^5$ form, together with a benzene, a 8 to 10 atom heteroaryl comprising N, O and S, wherein the 7 to 12 atom heteroaryl may be substituted or unsubstituted by a $C_{1-3}$ straight chain or branched chain alkyl.

In a more specific aspect, a compound is provided, which is represented by a chemical formula 1 in which:

$E^1$ is CH;

$R^1$ is hydrogen or methoxy;

$X^1$ is C, N, S or O;

when $X^1$ is C, $R^2$ and $R^3$ form, together with a bonded C, a pyrazole, wherein the pyrazole is substituted or unsubstituted by a methyl, when $X^1$ is N, $R^2$ is methyl, and $R^3$ is dimethyl-aminoethyl or methyl-aminoethyl, or $R^2$ and $R^3$ form, together with an N bonded thereto, a morpholino, piperazine, piperidine, pyrrolidine, diazepane, thiomorpholino, or oxazabicycloheptane, wherein the morpholino, piperazine, piperidine, pyrrolidine, diazepane, thiomorpholino or oxazabicycloheptane is substituted or unsubstituted by one or more substituents C selected from a group consisting of methyl, ethyl, propyl, isopropyl, cyclopropyl, cyclopropylmethyl, allyl, oxetanyl, dimethylamino, diethylamino, dimethylaminomethyl, azetidinylmethyl, oxo, methylcarbonyl, piperidinyl, piperazinyl, morpholino, azetidinyl, diazepanyl and pyrrolidinyl, among the substituents C, the piperazinyl, piperidinyl, morpholino, and diazepanyl are each independently additionally substituted or unsubstituted by one or more substituents D selected from a group consisting of methyl, isopropyl, piperazinyl, cyclopropyl and oxo, and among the substituents D, the piperazine is additionally substituted or unsubstituted by a methyl or a cyclopropyl;

when $X^1$ is S or O, $R^2$ does not exist, and $R^3$ is dimethylaminoethyl; and $R^4$ and $R^5$ are each independently hydrogen, fluoro, chloro or trifluoromethyl, or form an indazole together with benzene, wherein the indazole may be substituted or unsubstituted by a methyl, or $E^1$ is CH;

$R^1$ is hydrogen or methoxy;

$X^1$ is C, N, S or O;

when $X^1$ is C, $R^2$ and $R^3$ form, together with a bonded C, a pyrazole, wherein the pyrazole is substituted or unsubstituted by a methyl or a N-methylpiperidine, when $X^1$ is N, $R^2$ is methyl, and $R^3$ is dimethylaminoethyl or methylaminoethyl, or $R^2$ and $R^3$ form, together with a N bonded thereto, a morpholino, piperazine, piperidine, pyrrolidine, diazepane, thiomorpholino, or oxazabicycloheptane, wherein the morpholino, piperazine, piperidine, pyrrolidine, diazepane, thiomorpholino or oxazabicycloheptane is substituted or unsubstituted by one or more substituents C selected from a group consisting of methyl, ethyl, propyl, isopropyl, cyclopropyl, cyclopropylmethyl, allyl, oxetanyl, dimethylamino, diethylamino, dimethylaminomethyl, azetidinylmethyl, oxo, methylcarbonyl, piperidinyl, piperazinyl, morpholino, azetidinyl, diazepanyl and pyrrolidinyl, among the substituents C, the piperazinyl, piperidinyl, morpholino and diazepanyl are each independently additionally substituted or unsubstituted by one or more substituents D selected from a group consisting of methyl, isopropyl, piperazinyl, cyclopropyl and oxo, and among the substituents D, the piperazine is additionally substituted or unsubstituted by a methyl or a cyclopropyl;

when $X^1$ is S or O, $R^2$ does not exist, and $R^3$ is dimethylaminoethyl; and $R^4$ and $R^5$ are each independently hydrogen, fluoro, chloro or trifluoromethyl, or form an indazole together with benzene, wherein the indazole is substituted or a methyl.
In a more specific aspect, a compound is provided, which is represented by a chemical formula 1 in which:
the $E^1$ is CH;
the $R^1$ is hydrogen or methoxy;
the
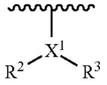
may be
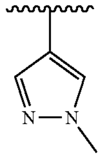, 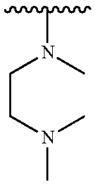, 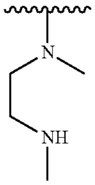, 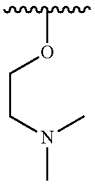,
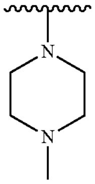, 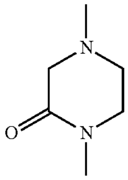, 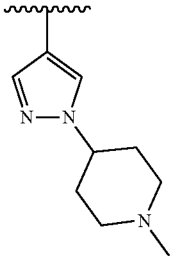,
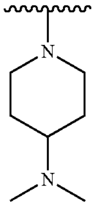, 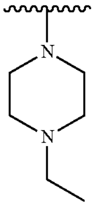, 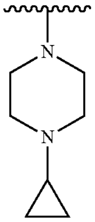, 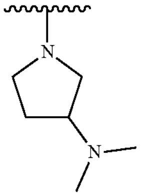,
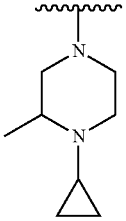, 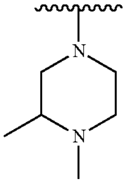, 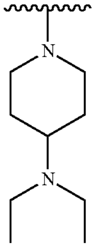, 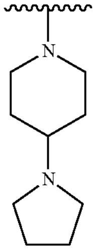,
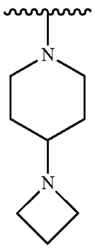, 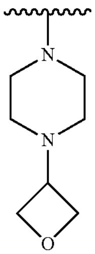, 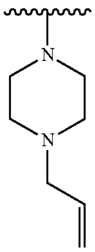, 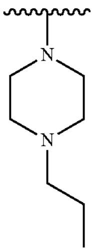,
-continued
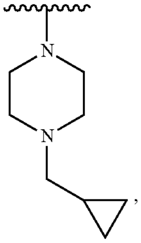, 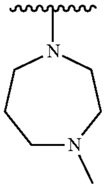, 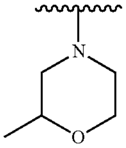, 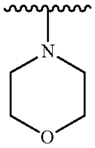,
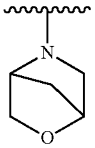, 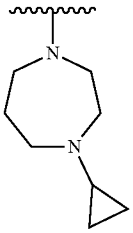, 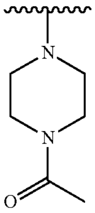,
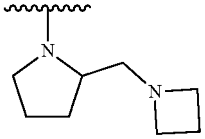, 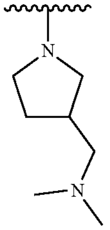, 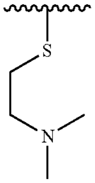,
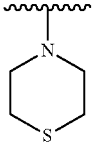, 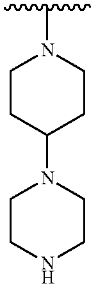, 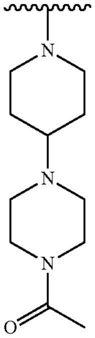, 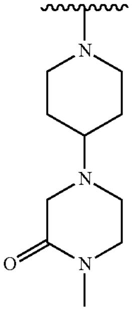,
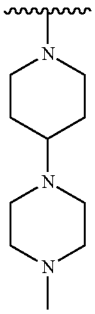, 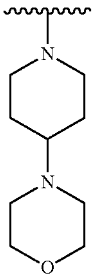, 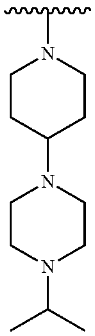, 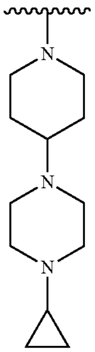, -continued

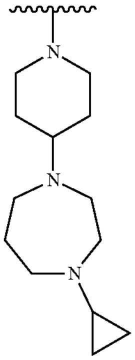
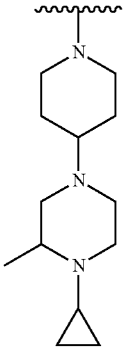
,
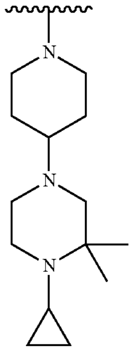
,
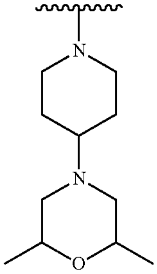
,
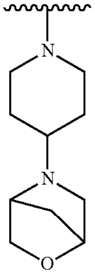
,
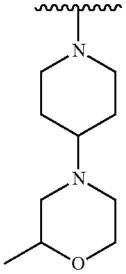
,
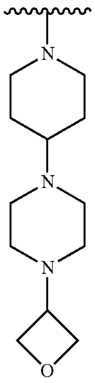
,
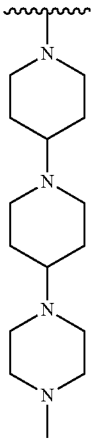
, or
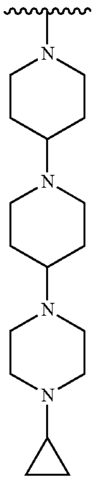
, the

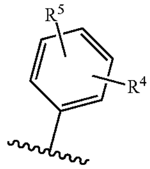

may be

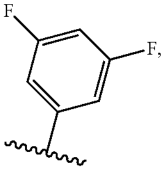
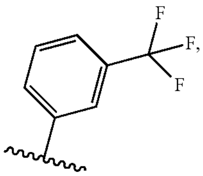

-continued

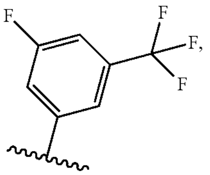
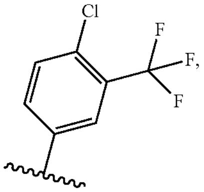
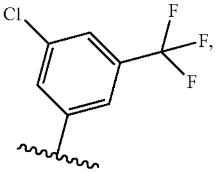
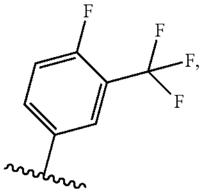
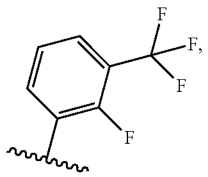
or
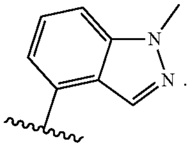
.

In a specific aspect, a compound is provided, which is represented by a chemical formula 1 in which:

$E^1$ is N;

$R^1$ is hydrogen, methoxy, difluoromethoxy or trifluoroethoxy;

$X^1$ is N;

$R^2$ is methyl, and $R^3$ is dimethylaminoethyl or methylaminoethyl, or $R^2$ and $R^3$ form, together with a N bonded thereto, a morpholino, piperazine or piperidine, wherein the morpholino, piperazine or piperidine is substituted or unsubstituted by one or more substituents E selected from a group consisting of methyl, piperazinyl, morpholino and oxazabicycloheptane, and among the substituents E, the piperazinyl is additionally substituted or unsubstituted by a methyl or a cyclopropyl; and $R^4$ and $R^5$ may be each independently hydrogen, fluoro or trifluoromethyl.

In a more specific aspect, a compound is provided, which is represented by a chemical formula 1 in which:

the $E^1$ is N;

the $R^1$ is hydrogen, methoxy, difluoromethoxy or trifluoroethoxy;

the

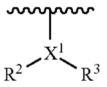

may be

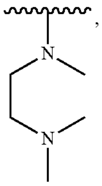, 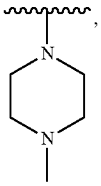, 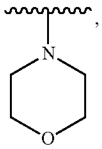, 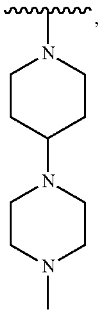, 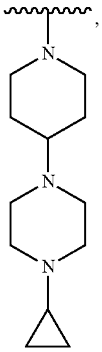,

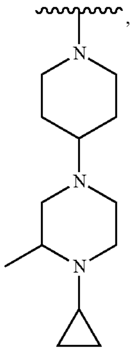, or 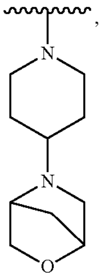, and the

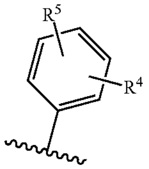

may be

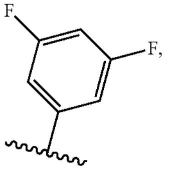, 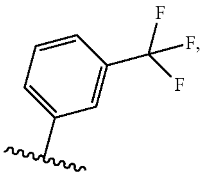,

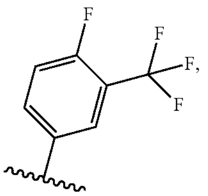, or 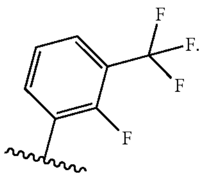.

One other aspect of the present invention provides a compound represented by a following chemical formula 2, a stereoisomer thereof, a hydrate thereof, a solvate thereof, or a pharmaceutically acceptable salt thereof:

[Chemical formula 2]

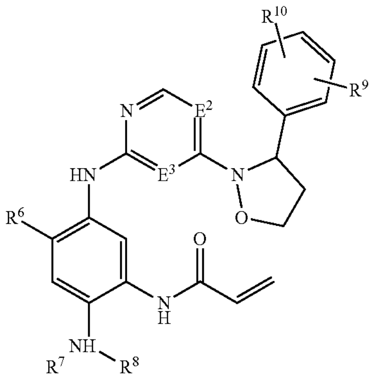

where, in the chemical formula 2, $E^2$ and $E^3$ are each independently N or CH, but the case that $E^2$ is N and $E^3$ is CH, is excluded;

$R^e$ is hydrogen or $C_{1-5}$ alkoxy;

if $R^7$ is $C_{1-5}$ straight chain or branched chain alkyl, then $R^8$ is $C_{1-5}$ straight chain or branched chain alkyl substituted by $C_{1-5}$ alkylamonio, or $R^7$ and $R^8$ form, together with the N to which they are bonded, a 3 to 12 atom heterocycloalkyl, wherein the 3 to 12 atom heterocycloalkyl is substituted or unsubstituted by a $C_{1-5}$ straight chain or branched chain alkyl, or a 3 to 12 atom heterocycloalkyl comprising at least one N, and the 3 to 12 atom heterocycloalkyl comprising at least one N is additionally substituted or unsubstituted by a $C_{3-6}$ cycloalkyl; and $R^9$ and $R^{10}$ may be each independently hydrogen, halogen or haloalkyl.

In a specific aspect, a compound is provided, which is represented by a chemical formula 2 in which:

$E^2$ and $E^3$ are each independently N or CH, but the case that $E^2$ is N and $E^3$ is CH, is excluded;

$R^8$ is hydrogen or $C_{1-3}$ alkoxy;

if $R^7$ is $C_{1-3}$ straight chain or branched chain alkyl, then $R^8$ is $C_{1-3}$ straight chain or branched chain alkyl substituted by $C_{1-3}$ alkylamonio, or $R^7$ and $R^8$ form, together with the N to which they are bonded, a 4 to 6 atom heterocycloalkyl, wherein the 4 to 6 atom heterocycloalkyl is substituted or unsubstituted by a $C_{1-3}$ straight chain or branched chain alkyl, or a 4 to 6 atom heterocycloalkyl comprising at least one N, and the 4 to 6 atom heterocycloalkyl comprising at least one N is additionally substituted or unsubstituted by a $C_{3-6}$ cycloalkyl; and $R^9$ and $R^{10}$ may be each independently hydrogen, halogen or haloalkyl.

In a more specific aspect, a compound is provided, which is represented by a chemical formula 2 in which:

$E^2$ and $E^3$ are each independently N or CH, but the case that $E^2$ is N and $E^3$ is CH, is excluded;

$R^8$ is hydrogen or methoxy;

if $R^7$ is methyl, then $R^8$ is dimethylaminoethyl or methylaminoethyl, or $R^7$ and $R^8$ form, together with a N bonded thereto, a morpholino, piperazine or piperidine, wherein the morpholino, piperazine and piperidine are each independently substituted or unsubstituted by a piperazinyl substituted by methyl or cyclopropyl, and $R^9$ and $R^{10}$ may be hydrogen or fluoro.

In a more specific aspect, a compound is provided, which is represented by a chemical formula 2 in which:

$E^2$ and $E^3$ are each independently N or CH, but the case that $E^2$ is N and $E^3$ is CH, is excluded;

$R^6$ is hydrogen or methoxy;

the

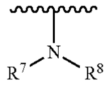

may be

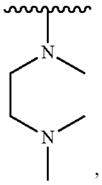
,
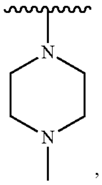
,
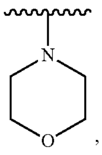
, or
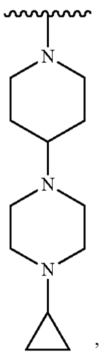
, and the

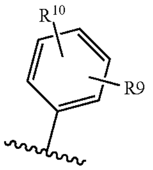

may be

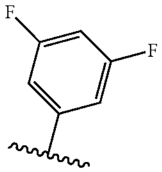
or
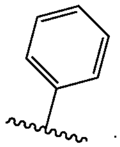
.

The compound represented by Chemical Formula 1 may be any one of the example Compounds 1 through 129 listed in [Table 1] described later.

The compound represented by Chemical formula 1 or 2 of the present invention may be used in the form of a pharmaceutically acceptable salt thereof. In particular, the pharmaceutically acceptable salt may be an acid addition salt formed by a free acid. Here, the acid addition salt may be obtained from inorganic acids, such as hydrochloric acid, nitric acid, phosphoric acid, sulfuric acid, hydrobromic acid, hydroiodic acid, nitrous acid, phosphorous acid and the like; nontoxic organic acids, such as aliphatic mono- and dicarboxylate, phenyl-substituted alkanoate, hydroxy alkanoate and alkanthioate, aromatic acids, aliphatic and aromatic sulfonic acids and the like; and organic acids, such as trifluoro-acetic acid, acetate, benzoic acid, citric acid, lactic acid, maleic acid, gluconic acid, methanesulfonic acid, 4-toluenesulfonic acid, tartaric acid, fumaric acid and the like. These types of pharmaceutically acceptable salts may include sulfate, pyrosulfate, bisulfate, sulfite, bisulfite, nitrate, phosphate, monohydrogenphosphate, dihydrogenphosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate and the like. The acid addition salt may be prepared by using a conventional method, for example, by successively performing following steps of: dissolving the derivative of chemical formula 1 in an organic solvent, such as methanol, ethanol, acetone, methylene chloride, acetonitrile and the like; adding an organic acid or an inorganic acid to a resulting product; and filtering and drying a precipitate generated as a result, or it may be prepared also by successively performing following steps of: distilling a solvent and an excessive acid under reduced pressure; drying a resulting product; and crystallizing a dried product under an organic solvent. Further, the pharmaceutically acceptable salt may be a salt or a metal salt obtained using a base. As an example of a metal salt, an alkali metal or alkaline earth metal salt may be obtained, for example, by dissolving the compound in an excessive alkali metal hydroxide or alkaline earth metal hydroxide solution; filtering the insoluble compound salt; and evaporating and drying the filtrate. Pharmaceutically suitable alkali metal salts may be sodium, potassium or calcium. In addition, the corresponding salt may be obtained by reacting an alkali metal or alkaline earth metal salt with an appropriate silver salt (e.g. silver nitrate).

Furthermore, the present invention may provide the compounds represented by the chemical formula 1 or 2 and the pharmaceutically acceptable salt thereof, as well as the stereoisomer thereof, in particular enantiomer, and the hydrate and/or solvate which may be prepared therefrom.

Other aspect of the present invention may be to provide a method for preparing a compound of a chemical formula 1 according to a following reaction formula 1:

The method for preparing the compound of the chemical formula 1 is one performed according to a following reaction formula 1, wherein the method comprises the steps of:

- reacting compounds of chemical formulas 3 and 4 with each other to prepare a compound of a chemical formula 5 (first step);
- reacting compounds of chemical formulas 5 and 6 with each other to prepare a compound of a chemical formula 7 (second step);
- reacting compounds of chemical formulas 7 and 8 with each other to prepare a compound of a chemical formula 9 (third step);
- reducing the compound of the chemical formula 9 to prepare a compound of a chemical formula 10 (fourth step); and reacting the compound of the chemical formula 10 with an acryloyl chloride or acrylic acid to prepare the compound of the Chemical Formula 1 (fifth step);

[Reaction formula 1]

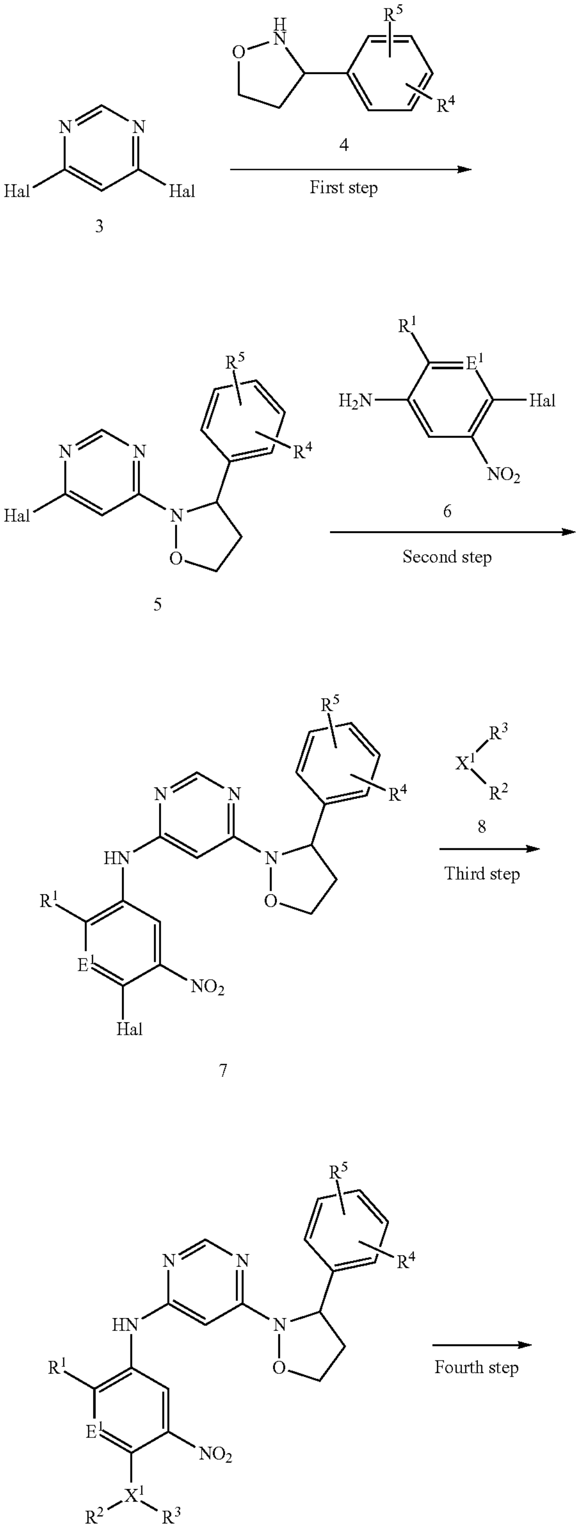

3, 4, 5, 6, 7, 8, 9

-continued

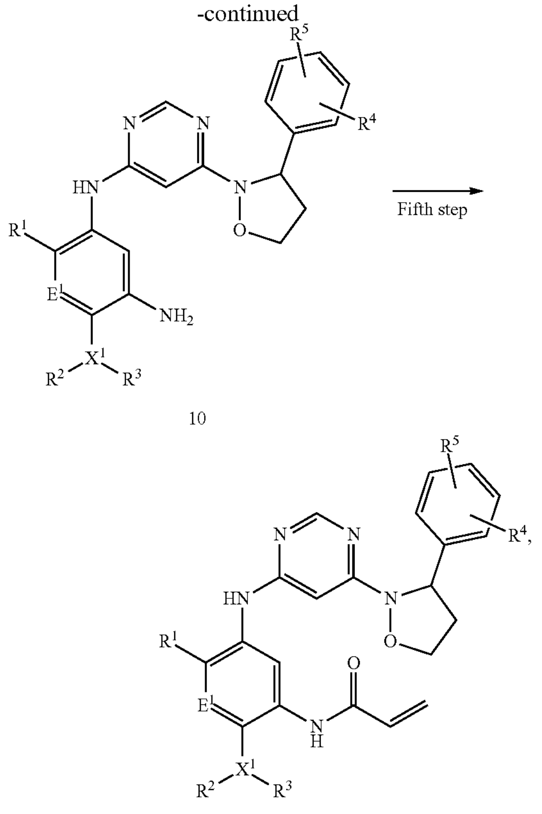

10, 1 wherein, $E^1$, $X^1$ and $R^1$ through $R^5$ may be respectively same as aforementioned in the present specification, and wherein Hal may be a halogen.

Specifically, the first step may be a process in which the compounds of the chemical formulas 3 and 4 are reacted with a diisopropylethylamine (DIPEA) in the presence of a solvent such as dimethyl sulfoxide (DMSO) etc., to prepare the compound of the chemical formula 5.

In the second step, the compound of the chemical formula 5 prepared in the first step and the compound of the chemical formula 6 are reacted with each other and with an added p-toluenesulfonic acid monohydrate (pTSA) in the presence of a solvent such as sec-BuOH, etc., so that the compound of the chemical formula 7 may be prepared.

In the third step, the compound of the chemical formula 7 prepared in the second step and the compound of the chemical formula 8 are reacted with each other and with an added $K_2CO_3$ in the presence of a solvent such as dimethylsulfoxide (DMSO), etc., so that the compound of the chemical formula 9 may be prepared.

In the fourth step, a nitro group in the compound of the chemical formula 9 prepared in the third step is reduced into an amino group, so that the compound of the chemical formula 10 may be prepared. In this case, any reducing agent may be used without restriction, if it can reduce the nitro group, and as one example therefor, $SnCl_2$ may be used.

In the fifth step, the reduced compound of the chemical formula 10 and an acryloyl chloride or acrylic acid are reacted with each other in the presence of a THF solvent, so that the compound of the chemical formula 1 may be prepared.

Another aspect of the present invention may be to provide a method for preparing a compound of a chemical formula 2 according to following reaction formula 2:

[Reaction formula 2]

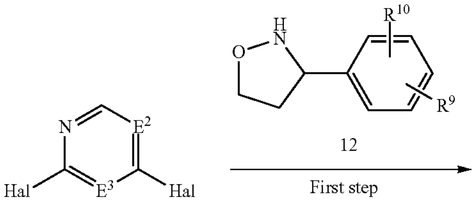

12

11

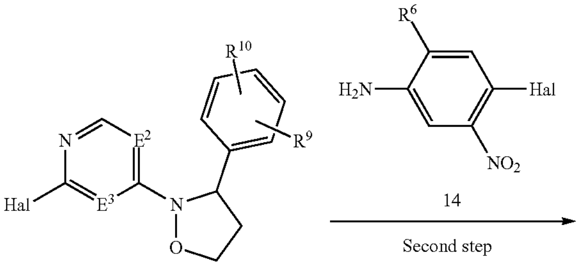

14

13

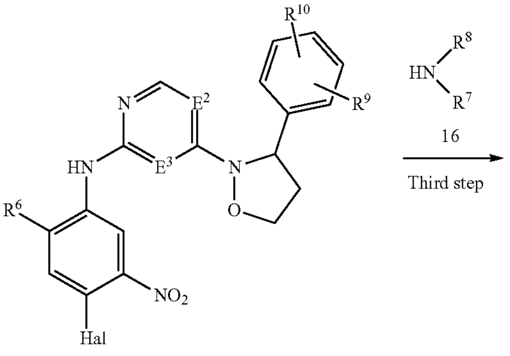

16

15

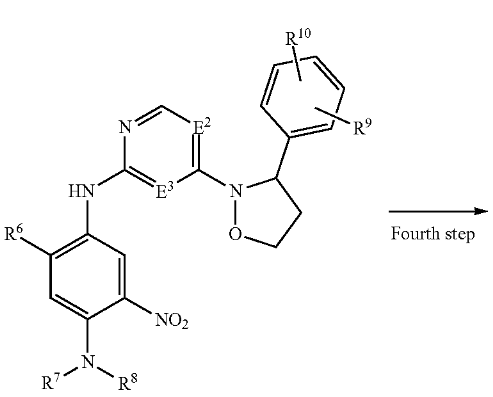

17

-continued

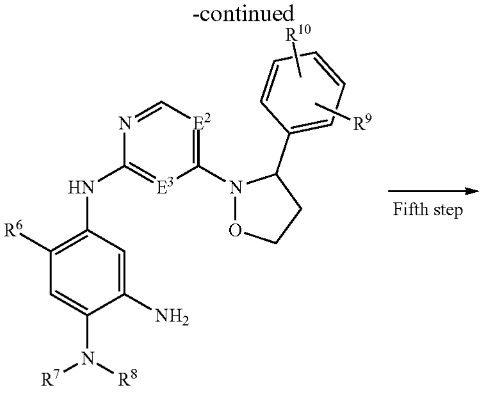

18

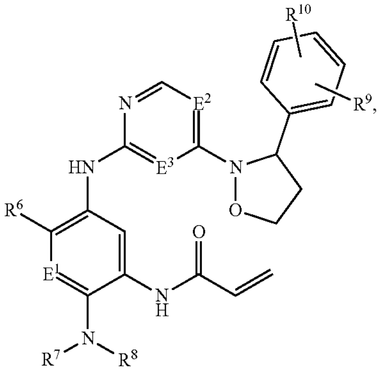

2 where, in the reaction formula 2, $E^2$, $E^3$ and $R^6$ through $R^{10}$ may be respectively same as aforementioned in the present specification, wherein Hal may be halogen.

The specific step-by-step reactions may progress in a similar way to the reaction formula 1.

Another aspect of the present invention may provide a pharmaceutical composition for the prevention or treatment of cancer, the composition comprising the compound of the chemical formula 1, a stereoisomer thereof, a hydrate thereof, a solvate thereof, or a pharmaceutically acceptable salt thereof as an active ingredient.

The compound of the chemical formula 1 may exhibit an inhibitory ability against one or more enzymes among EGFR, ErbB2 and ErbB4. In particular, the compound of the chemical formula 1 or 2 may exhibit a suppression effect against EGFR, ErbB2 and ErbB4, belonging to the ErbB tyrosine kinase receptors family as well as against the mutations thereof.

The EGFR mutation may be one or more selected from a group consisting of EGFR (E746-A750del), EGFR (G719C), EGFR (G719S), EGFR (L747-E749del, A750P), EGFR (L747-S752del, P753S), EGFR (L747-T751del, Sins), EGFR (L858R), EGFR (L858R, T790M), EGFR (L861Q), EGFR (S752-I759del), EGFR (T790M), EGFR Del19, EGFR Del19/T790M, EGFR L858R/T790M/C797S, EGFR Del19/T790M/C797S, EGFR Exon20 ins NPH and EGFR Exon20 ins SVD.

The ErbB2 may be used interchangeably with HER2, and the ErbB2 mutation may be HER2 Exon20 ins YVMA.

In this context, a cancer type is not limited, but it may be one or more types selected from a group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian germ cell cancer, male breast cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, ampulla of Vater cancer, bladder cancer, peritoneal cancer, parathyroid cancer, adrenal gland cancer, nasal cavity and paranasal sinus cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal interstitial cancer, Wilms' cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, and thymic cancer. Specifically, the caner may be lung cancer, more specifically non-small cell lung cancer.

The pharmaceutical composition for the prevention or treatment of cancer according to the present invention may be so prepared that it may be used for the clinical administration and also administered in a variety of oral and non-oral dosage forms.

The pharmaceutical composition of the present invention may contain a pharmaceutically acceptable carrier. This pharmaceutically acceptable carrier may include a filling agent, a bulking agent, a binding agent, a wetting agent, a disintegrating agent, a diluent such as surfactant, etc., or an excipient, wherein the composition of the present invention may be formulated together with such agents.

For example, a solid formulation for the oral administration may be prepared as a tablet, pill, powder, granule and capsule, etc. wherein such solid formulation may be also prepared by mixing one or more compounds with at least one excipient, e.g. starch, calcium carbonate, sucrose or lactose, gelatin, etc. Further, it may be also prepared by using a lubricant such as magnesium stearate, talc, etc. in addition to simple excipients.

Furthermore, a liquid formulation for the oral administration may be prepared as suspension, oral liquids, emulsion, syrup, etc., wherein such liquid formulation may contain various excipients, e.g. wetting agent, sweetening agent, flavor, preservative, etc. in addition to water and liquid paraffin as a simple diluent.

In addition, a formulation for the non-oral administration may be prepared as a sterilized aqueous solution, a non-aqueous solvent, a suspension, an emulsion, etc., wherein a propylene glycol, a polyethylene glycol, a vegetable oil such as olive oil, an injectable ester such as ethyl oleate, etc. may be used as a non-aqueous solvent or dispending agent.

Further, the non-oral administration may be performed by using the injection methods such as subcutaneous injection, intravenous injection, intramuscular injection or intrathoracic injection. Here, for the purpose of formulation into a dosage form for the non-oral administration, the pharmaceutical composition may be prepared as a solution or suspension by mixing the compound represented by the chemical formula 1 or the pharmaceutically acceptable salt together with a stabilizer or buffer in the water and then by preparing the solution of suspension into unit dose-type ampoules or vials. The composition may be sterilized and/or contain a preservative, a stabilizing agent, a wettable powder or emulsificant, a salt for osmotic regulation, and/or an adjuvant such as buffer, etc., and other therapeutically useful substances, and then may be formulated according to conventional mixing, granulation and coating methods.

Hereinafter, the present invention will be explained in further detail with reference to embodiments and experiment examples.

<Conditions for Analysis and Purification>

The compounds synthesized according to the embodiments of the present invention were purified or structurally analyzed under following HPLC conditions:

1. HPLC Conditions for Analysis

HPLC (ACOUITY UPLC H-Class Core System) conditions for Analysis

As an analysis equipment, a UPLC system (ACQUITY UPLC PDA Detector) manufactured by Waters, equipped with a mass QDA Detector also manufactured by Waters was used. A used column was an ACQUITY UPLC® BEH C18 (1.7 μm, 2.1×50 mm) of Waters, wherein the analysis was performed at a column temperature of 30° C.

A water containing 0.1% formic acid was used as a mobile phase A, and an acetonitrile containing 0.1% formic acid was used as a mobile phase B.

Gradient condition (3 minutes with 10-100% B; movement velocity=0.6 ml/min)

Prep-LCMS (Preparative-Liquid Chromatography Mass Spectrometry) for Purification As a purification equipment, an auto purification HPLC system (2767 sample manager, 2545 binary gradient module, 2998 photodiode array detector) manufactured by Waters, equipped with a Waster-manufactured mass QDA detector also manufactured by Waters was used. A used column was a SunFire® Prep C18 OBD™ (5 μm, 19×50 mm) of Waters, wherein the purification was performed at a column temperature of room temperature.

A water containing 0.035% trifluoroacetic acid was used as a mobile phase A, and a methanol containing 0.035% trifluoroacetic acid was used as a mobile phase B.

Gradient condition (10 minutes with 15-100% B; movement velocity=25 ml/min)

Prep-150 LC System (Preparative-Liquid Chromatography UV Spectrometry) for Purification As a purification equipment, a Prep 150 LC system (2545 quaternary gradient module, 2998 photodiode array detector, Fraction collector Ill) manufactured by Waters was used. A used column was a XTERRA® Prep RP18 OBD™ (10 μm, 30×300 mm) of Waters, wherein the purification was performed at a column temperature of room temperature.

Gradient condition (120 minutes with 3-100% B; movement velocity=40 ml/min)

Preparative HPLC System (Preparative-Liquid chromatography UV spectrometry) for Purification As a purification equipment, an ACCQ Prep HP 150 manufactured by Waters was used. A used column was a XTERRA® Prep RP18 OBD™ (10 μm, 30×300 mm) of Waters, wherein the purification was performed at a column temperature of room temperature.

Gradient condition (120 minutes with 10-100% B; movement velocity=42 ml/min)

2. NMR Interpretation

A NMR analysis was carried out using an AVANCE III 400 or AVANCE III 400 HD manufactured by Bruker, and the data thereof was presented in ppm (parts per million (δ)).

A commercially available reagent was directly used here without any additional purification. In the present invention, the term 'room temperature' refers to a temperature of about 5° C. to 40° C., in one example, of about 10° C. to 30° C., and in another example, of about 20° C. to 27° C., but is not limited to within these ranges. A concentration under reduced pressure and a solvent distillation removal were performed by means of a rotary evaporator.

PREPARATION EXAMPLES

1. Preparation of Isoxazolidine derivative

<Preparation Example 1> Preparation of (R)-3-(3-(trifluoromethyl)phenyl)isoxazolidine

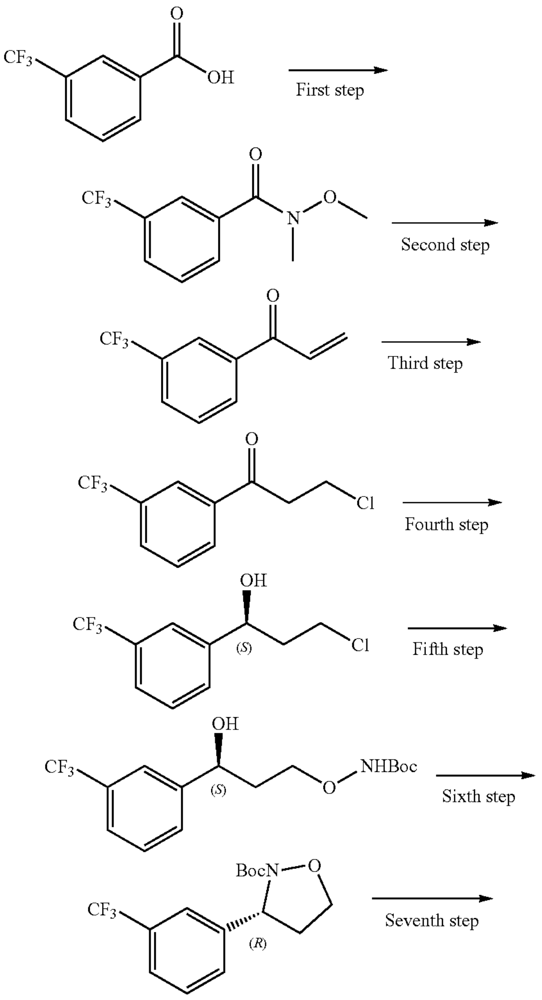

-continued

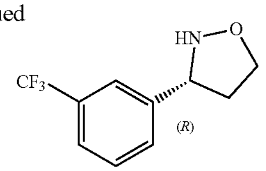

First Step: Preparation of N-methoxy-N-methyl-3-(trifluoromethyl)benzamide

After 3-(trifluoromethyl)benzoic acid (200 g, 1 eq) and N-methoxymethylamine (1.2 eq) were dissolved in dichloromethane (150 mL), 1-ethyl-3-(3-dimethylaminopropyl) carbodiimide (EDCI; 1.2 eq) was added thereinto at 15° C. A resulting reaction mixture was agitated for three hours at a room temperature. As a result of TLC analysis (petroleum ether:ethyl acetate=PE:EA=3:1), all of the starting materials disappeared, and new spots having low polarity were detected. And an organic layer was extracted using a dichloromethane (DCM; 500 mL), a sulfuric acid (2N; 500 mL) and a salt water (200 mL). After the organic layer was dried using a sodium sulfate and then concentrated under reduced pressure, a target compound (210 g; 85.9% yield) in the form of a yellow oil was obtained.

Second Step: Preparation of 1-(3-trifluoromethyl)phenyl) prop-2-en-1-on

After the N-methoxy-N-methyl-3-(trifluoromethyl)benzamide (100 g, 1 eq) obtained in the first step according to the preparation example 1 was dissolved in tetrahydrofuran (THF; 1 L), a bromo(vinyl)magnesium (1 M, 1.05 eq) was dropwise added into a resulting product at 0° C. Thereafter, a resulting reaction mixture was agitated for two hours at 10° C. As a result of TLC analysis (petroleum ether:ethyl acetate=PE:EA=4:1), all of the starting materials disappeared, and new spots having low polarity were detected. Then the reaction was ended by adding a sulfuric acid (4N; 500 mL). After that, the organic layer was extracted using a methyl tert-butyl ether (MTBE; 2000 mL) and a salt water (500 mL). And the organic layer was dried using a sodium sulfate and then concentrated unter reduced pressure. A concentrated compound was purified using chromatography (petroleum ether/ethyl acetate=30/1) to obtain a target compound (90 g, 95% yield) in the form of a yellow oil.

Third Step: Preparation of 3-chloro-1-(3-(trifluoromethyl) phenyl)propan-1-on

After the 1-(3-(trifluoromethyl)phenyl)prop-2-en-1-on (90 g, 1.0 eq) obtained in the Step 2 according to the preparation example 1 was dissolved in a dichloromethane (DCM; 71 mL), a HCl/dioxane (4M, 2.5 eq) was added into a resulting product at 0° C. Thereafter, a resulting reaction mixture was agitated for 1.5 hours at 15° C. As a result of TLC analysis (petroleum ether:ethyl acetate=PE:EA=10:1), all of the starting materials disappeared, and a target compound was detected. A resulting reaction mixture was concentrated under reduced pressure, then a dichloromethane (DCM; 450 mL) and a water (200 mL*5) were added to extract an organic layer. After that, the organic layer was dried using a sodium sulfate and concentrated under reduced pressure, so that a target compound (90 g, 85% yield) in the form of a yellow solid was obtained.

Fourth Step: Preparation of (S)-3-chloro-1-(3-trifluoromethylphenyl)propan-1-ol

After a (3aR)-1-methyl-3,3-diphenyl-3a,4,5,6-tetrahydropyrrolo[1,2-c][1,3,2]oxazaborol (1M, 0.1 eq) was dissolved in a tetrahydrofuran (THF; 1.2 L), a borane tetrahydrofuran ($BH_3$THF; 1M, 186.48 mL, 0.6 eq) was dropwise added into a resulting product in a nitrogen gas stream at −30° C. Then a resulting reaction was agitated at −30° C. for 30 minutes. After that, the 3-chloro-1-(3-(trifluoromethyl)phenyl)propan-1-on obtained in the third step according to the preparation example 1, was previously diluted in a tetrahydrofuran and was dropwise dropped into an agitated reaction mixture at −30° C. Then the reaction mixture was agitated at 20° C. for 12 hours. As a result of TLC analysis (petroleum ether:ethyl acetate=PE:EA=5:1), all of the starting materials disappeared, and a target compound spot was detected. After the reaction was ended by adding methanol (100 mL) at 20° C., the solvent was allowed to be evaporated under reduced pressure. Then an organic layer was extracted from a resulting concentrated compound using dichloromethane (DCM; 100 mL*3) and ammonium chloride ($NH_4Cl$) solution (300 mL). The organic layer was dried using a sodium sulfate, and then concentrated under reduced pressure. A resulting concentrated compound was purified using a silica gel chromatography (petroleum ether:ethyl acetate=PE:EA=50:1 to 5:1), so that a targe compound (70 g, 73% yield, 89.8% purity, 67.2% e.e) in the form of a colorless oil was obtained.

Fifth Step: Preparation of tert-butyl (S)-(3-hydroxy)-3-(3-(trifluoromethyl)phenyl) peroxycarbonate After a Tet-butyl hydroxycarbamate (1.05 eq) was dissolved in a dimethylformamide (DMF; 500 mL), sodium hydride (NaH; 60% purity, 1.1 eq) was added into a resulting product in a nitrogen gas stream at 0° C. A resulting reaction mixture was agitated at 10° C. for 1 hour, and then the (S)-3-chloro-1-(3-(trifluoromethyl)phenyl)propan-1-ol (50 g, 1 eq) obtained in the fourth step according to the preparation example 1, was previously diluted in the dimethylformamide (DMF; 500 mL) and was dropwise added into an agitated reaction mixture at 0° C. and agitated again at 10° C. for 16 hours. As a result of TLC analysis (petroleum ether:ethyl acetate=PE:EA=2:1), all of the starting materials disappeared, and a target compound was detected. After the reaction was ended by adding an ammonium chloride aqueous solution (3 L), an organic layer was extracted using an ethyl acetate (2000 mL) and a salt water (2000 mL). After that, the organic layer was dried using a sodium sulfate and then concentrated under reduced pressure, so that a target compound (47 g, 67% yield) in the form of a bright yellow solid was obtained. This reaction was performed twice using the same method.

Sixth Step: Preparation of tert-butyl(R)-3-(3-(trifluoromethyl)phenyl)oxazolidine-2-carboxylate After the (S)-(3-hydroxy)-3-(3-(trifluoromethyl)phenyl) propoxy)carbamate (94 g, 1 eq) obtained in the fifth step according to the preparation example 1 and a triethylamine ($Et_3N$; 3 eq) were dissolved in a dichloromethane (DCM; 1 L), an anhydrous methanesulfonic acid (1.5 eq) was slowly added into a resulting product at 0° C. A resulting reaction mixture was agitated at 20° C. for 12 hours. As a result of TLC analysis (petroleum ether:ethyl acetate=PE:EA=3:1), all of the starting materials disappeared, and new spots were detected. After the reaction was ended by adding a water (2000 mL), an organic layer was extracted using a dichloromethane (DCM; 200 mL*3). After that, the organic layer was dried using a sodium sulfate and then concentrated under reduced pressure. A resulting concentrated compound was purified by a chromatography (petroleum ether:ethyl acetate=PE:EA=50:1 to 5:1), so that 60 g of a target compound having a value of 74.3% e.e was extracted.

The purity of the enantiomer of the target compound obtained in the sixth step was analyzed under following SFC conditions:

Instrument: CAS-WH-ANA-SFC-C (SHIMADZU LC-30ADsf);

Column: Amycoat 50×4.6 mm I.D., 3 um;

Mobile phase: Phase A for CO2, and Phase B for MeOH (0.05% DEA);

Gradient elution: MeOH (0.05% DEA) in $CO_2$ from 5% to 40%;

Flow rate: 3 mL/min; Detector: PDA; and

Column Temp: 35° C.; Back Pressure: 100 Bar.

Seventh step: Preparation of (R)-3-(3-(trifluoromethylphenyl)isoxazolidine

After a tert-butyl(R)-3-(3-(trifluoromethyl)phenyl)oxazolidine-2-carboxylate (35 g, 1 eq) was dissolved in an ethyl acetate (EA; 200 mL), a HCl/EtOAc (4 M, 6.45 eq) was added into a resulting product at 0° C. Thereafter, a resulting reaction mixture was agitated for 1 hour at 10° C. As a result of LCMS analysis, all of the starting materials disappeared. Then, the concentration under reduced pressure was performed to obtain a solid, so that a target compound (24 g, 100% yield, 90% purity, 75% e.e. HCl) in the form of a white solid was obtained.

For the purpose of the purification or analysis of the enantiomer of the compound obtained in the seventh step, following conditions were used:

Instrument: CAS-WH-ANA-SFC-C (SHIMADZU LC-30ADsf);

Column: Chiralpak AY-3 50×4.6 mm I.D., 3 um;

Mobile phase: Phase A for $CO_2$, and Phase B for IPA (0.05% DEA);

Gradient elution: B in A from 5% to 40%;

Flow rate: 3 mL/min; Detector: PDA; and

Column Temp: 35° C.; Back Pressure: 100 Bar.

The (R)-3-(3-(trifluoromethyl)phenyl)isoxazolidine (24 g) obtained in the seventh step was purified under following SFC conditions, so that a desired enantiomer (15 g, 100% purity, 100% e.e.) was obtained:

(column: DAICEL CHIRALPAK AD-H (250 mm*30 mm, 5 um); and mobile phase: [0.1% NH3H2O MEOH]; B %: 15%-15%, 3.8 min; 600 min).

The compounds of the preparation examples 2 through 9 were prepared using the methods similar to the preparation example 1, and the example compounds of the present invention were prepared using the compounds of the preparation examples 1 through 9.

<Preparation Example 2> Preparation of (R)-3-(3-fluoro-5-(trifluoromethyl)phenyl)isoxazolidine

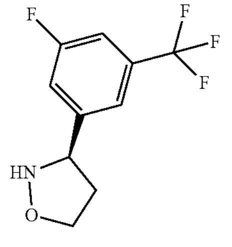 [SMILES: Fc1cc([C@H]2CCON2)cc(C(F)(F)F)c1]

<Preparation Example 3> Preparation of (R)-3-(4-chloro-3-(trifluoromethyl)phenyl)isoxazolidine

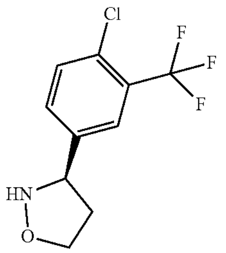 [SMILES: FC(F)(F)c1cc([C@H]2CCON2)ccc1Cl]

<Preparation Example 4> Preparation of 3-(3-chloro-5-(trifluoromethyl)phenyl)isoxazolidine

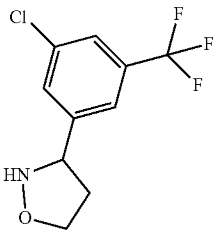 [SMILES: FC(F)(F)c1cc(Cl)cc(C2CCON2)c1]

<Preparation Example 5> Preparation of (R)-3-(4-fluoro-3-(trifluoromethyl)phenyl)Isoxazolidine

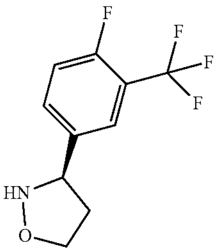 [SMILES: Fc1ccc([C@H]2CCON2)cc1C(F)(F)F]

<Preparation Example 6> Preparation of (R)-3-(2-fluoro-3-(trifluoromethyl)phenyl)isoxazolidine

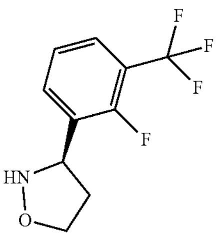 [SMILES: Fc1c([C@H]2CCON2)cccc1C(F)(F)F]

<Preparation Example 7> Preparation of (R)-3-(3,5-difluorophenyl)isoxazolidine

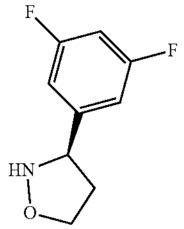 [SMILES: Fc1cc(F)cc([C@H]2CCON2)c1]

<Preparation Example 8> Preparation of (R)-3-phenylisoxazolidine

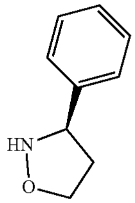 [SMILES: c1ccc([C@H]2CCON2)cc1]

<Preparation Example 9> Preparation of (R)-3-(1-methyl-1H-indazol-4-yl)isoxazolidine

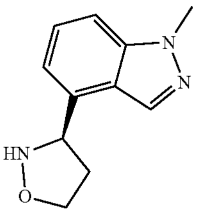

2. Preparation of an Aniline Derivative

<Preparation Example 1> Preparation of N-(5-amino-4-methoxy-2-morpholinophenyl)acrylamide

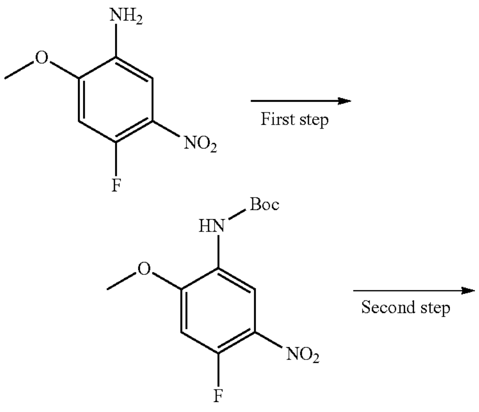

-continued

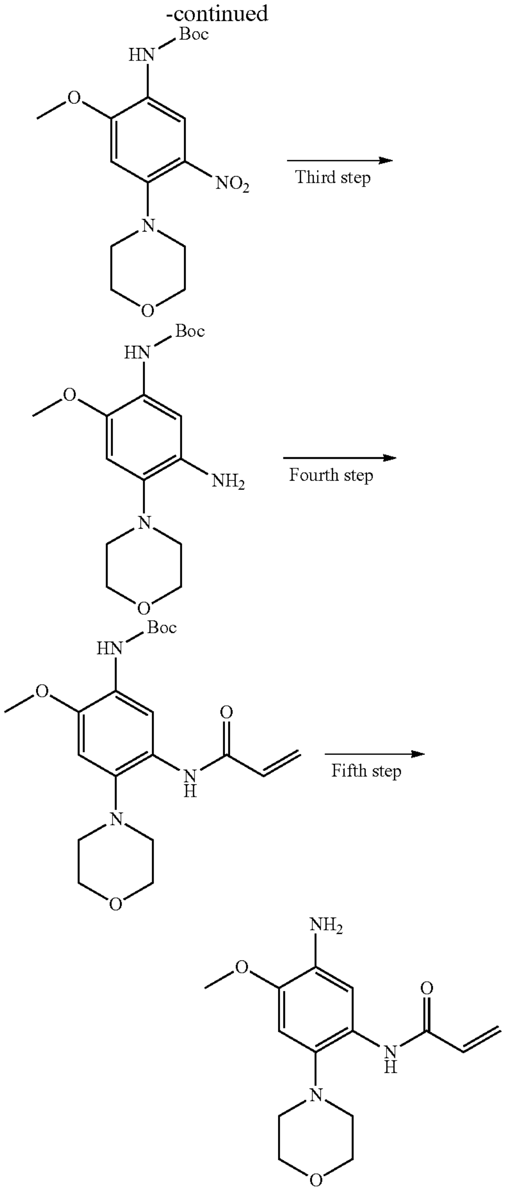

First Step: Preparation of tert-butyl(4-fluoro-2-methoxy-5-nitrophenyl)carbamate After a 4-fluoro-2-methoxy-5-nitroaniline (10 g, 1 eq) was dissolved in DCM (130 mL), a $Boc_2O$ (14.97 mL, 1.2 eq), a 4-dimethylaminopyrdine (DMAP; 0.656 g, 0.1 eq) and a triethylamine (TEA; 14.98 mL, 2 eq) were added thereinto. A resulting reaction mixture was agitated for 12 hours at room temperature. After the reaction was ended and then the concentration under reduced pressure was carried out, a concentrated compound was purified using a chromatography (ethyl acetate/hexane=8/1), so that a target compound (10.5 g, 68.3% yield) was obtained.

Second Step: Preparation of tert-butyl(2-methoxy-4-morpholino-5-nitrophenyl)carbamate After a Tert-butyl(4-fluoro-2-methoxy-5-nitrophenyl)carbamate (500 mg, 1 eq) and a morpholine (0.183 mL, 1.2 eq) were dissolved in DMSO (5 mL), a potassium carbonate ($K_2CO_3$; 362 mg, 1.5 eq) was added into a resulting product, and then agitated for 2 hours at 70° C. After the reaction, an organic layer was extracted using an ethyl acetate (EA; 50 mL) and a water (20 mL). And the organic layer was dried using a sodium sulfate and then concentrated under reduced pressure. A concentrated compound was purified using a chromatography (ethyl acetate/hexane=7/1), so that a target compound (252 mg, 40.8% yield) was obtained.

Third Step: Preparation of tert-butyl(5-amino-2-methoxy-4-morpholinomethyl) carbamate After a Tert-butyl(2-methoxy-4-morpholino-5-nitrophenyl)carbamate (252 mg, 1 eq) was dissolved in a methanol (5 mL), a 10% Pd/C (25 mg, 0.1 w/w) was added into a resulting product and then agitated for 2 hours at room temperature in a hydrogen atmosphere. After the reaction, a filteration using a celite filter was performed, followed by a concentration under reduced pressure, so that a target compound (235 mg, 100% yield) was obtained without purification.

Fourth Step: Preparation of tert-butyl(5-acrylamido-2-methoxy-4-morpholinophenyl)carbamate After a tert-butyl(5-amino-2-methoxy-4-morpholinophenyl)carbamate (340 mg, 1 eq) was dissolved in DCM (4 mL), an acrylic acid (0.094 mL, 1.3 eq), a 1-ethyl-3-(3-dimethylaminopropyl)carbodiimide (EDC; 262 mg, 1.3 eq) and a N,N-diisopropylethylamine (DIPEA; 0.551 mL, 3.0 eq) were added into a resulting product. Then, a resulting reaction mixture was agitated for 2 hours at room temperature. After the reaction, an organic layer was extracted using a dichloromethane (DCM; 50 mL) and a sodium carbonate aqueous solution (20 mL). The organic layer was dried using a sodium sulfate, and then concentrated under reduced pressure. A concentrated compound was purified using a chromatography (dichoromethane/methanol=20/1), so that a target compound (290 mg, 73% yield) was obtained.

Fifth Step: Preparation of N-(5-amino-4-methoxy-2-morpholinophenyl)acrylamide

After a Tert-butyl(5-acrylamido-2-methoxy-4-morpholinophenyl)carbamate (290 mg, 1 eq) was dissolved in a dichloromethane (DCM; 4 mL), a TFA (1 mL, 0.5 v/v) was added into a resulting product. Then, a resulting reaction mixture was agitated for 1 hour at room temperature. After the reaction, the mixture was concentrated under reduced pressure, after which an organic layer was extracted using a dichloromethane (DCM; 50 mL) and a sodium carbonate aqueous solution (20 mL). The organic layer was dried using a sodium sulfate, so that a target compound (210 mg, 98% yield) was obtained without purification.

<Preparation Example 2> Preparation of N-(5-amino-6-methoxy-2-(4-methylpiperazin-1-yl)pyridin-3-yl)acrylamide

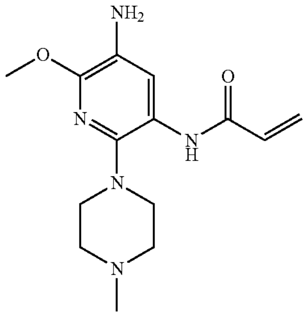 [SMILES: C=CC(=O)Nc1cc(N)c(OC)nc1N1CCN(C)CC1]

So as to prepare the N-(5-amino-6-methoxy-2-(4-methylpiperazin-1-yl)pyridin-3-yl)acrylamide, an intermediate of a following preparation example 2-1 was used to perform the synthesization by means of the methods similar to those of the preparation example 1:

<Preparation Example 2-1> Preparation of 2-methoxy-6-(4-methylpiperazin-1-yl)-5-nitropyridine-3-amine

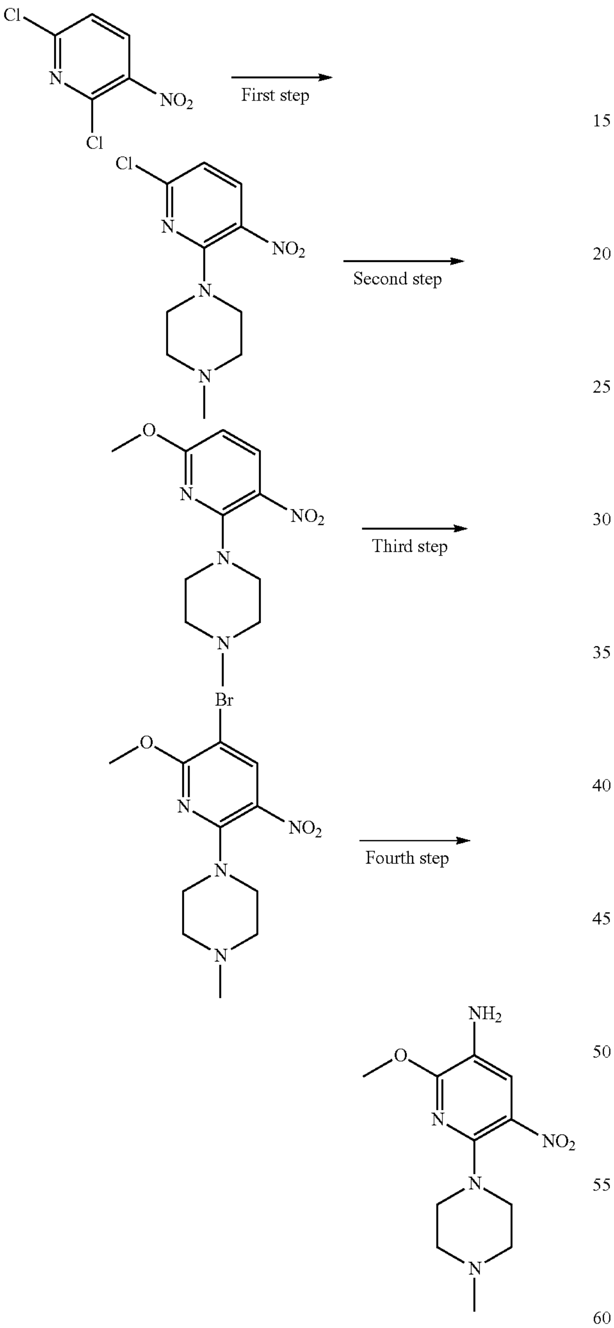

First Step: Preparation of 1-(6-chloro-3-nitropyridin-2-yl)-4-methylpiperazine

After a 2,6-dichloro-3-nitropyridine (5 g, 1.0 eq) was dissolved in an acetonitrile (50 mL), a 1-methylpiperazine (2.88 ml 1.0 eq) and a triethylamine (5.42 ml, 1.5 eq) were sequentially added into a resulting product at 0° C. A resulting reaction mixture was agitated for 10 minutes at room temperature. As a result of UPLC/MS analysis, all of the starting materials disappeared, and a target compound was detected. A Dichloromethane (DCM; 200 mL) was added to the reaction mixture, which then was washed with a water (100 mL) and a salt water (100 mL). Then, an organic layer was dried using a sodium sulfate and then concentrated under reduced pressure. A concentrated compound was purified using a silica gel chromatography (EA in hexane 0% to 100%), so that a target compound (6 g, 90% yield) in the form of a yellow solid was obtained.

Second Step: Preparation of 1-(6-methoxy-3-nitropyridin-2-yl)-4-methylpiperazine After a methanol (0.57 mL, 1.2 eq) was added to a tetrahydrofuran (THF; 40 mL), a sodium hydride (NaH; 0.4 g, 1.4 eq) was slowly added into a resulting product at 0° C. and then a resulting reaction mixture was agitated for 10 minutes at 0° C. Then, the 1-(6-chloro-3-nitropyridin-2-yl)-4-methylpiperazine (3 g, 1.0 eq) obtained in the first step according to the preparation example 2-1 was dissolved in the tetrahydrofuran (THF; 40 mL), and a resulting product was slowly added into the reaction mixture. This reaction mixture was agitated for 1 hour at room temperature in a nitrogen atmosphere. As a result of UPLC/MS analysis, all of the starting materials disappeared, and a target compound was detected. Then, an organic layer was extracted using an ethyl acetate (EA; 100 ml) and a water (50 ml). After that, the organic layer was dried using a sodium sulfate and then concentrated under reduced pressure, so that a target compound (2.9 g, 99% yield) in the form of a yellow solid was obtained.

Third Step: Preparation of 1-(5-bromo-6-methoxy-3-nitropyridin-2-yl)-4-methylpiperazine After the 1-(6-methoxy-3-nitropyridin-2-yl)-4-methylpiperazine (2 g, 1.0 eq) obtained in the second step according to the preparation example 2-1 was dissolved in an acetonitrile (40 ml), a N-bromosuccinimide (NBS; 2.1 g, 1.5 eq) was slowly added into a resulting product at 0° C. Then, a resulting reaction mixture was agitated for 1 hour at room temperature. As a result of UPLC/MS analysis, all of the starting materials disappeared, and a target compound was detected. Then, a precipitate generated by the reaction was filtered under reduced pressure, so that a target compound (1.5 g, 57% yield) in the form of a yellow solid was obtained.

Fourth Step: Preparation of 2-methoxy-6-(4-methylpiperazin-1-yl)-5-nitropyridine-3-amine The 1-(5-bromo-6-methoxy-3-nitropyridin-2-yl)-4-methylpiperazine (0.5 g, 1.0 eq) obtained in the third Step according to the preparation example 2-1 and a dimethyl sulfoxide (DMSO; 5 ml) were inserted into a microwave tube, and then a copper(I) iodide (57 mg, 0.2 eq), a potassium carbonate (313 mg, 1.5 eq), a L-prolyl (69 mg, 0.4 eq) and an ammonium hydroxide (28%, 0.315 ml, 1.5 eq) were added thereto. A resulting reaction compound was agitated for 1 hour at 100° C. using a microwave reactor. As a result of UPLC/MS, all of the starting materials disappeared, and a target compound was detected. From the reaction mixture, an organic layer was extracted using an ethyl acetate (EA; 100 ml) and a water (50 ml). After that, the organic layer was dried using a sodium sulfate and then concentrated under reduced pressure. A concentrated compound was purified using a silica gel chromatography (MeOH in DCM 0% to 20%), so that a target compound (0.08 g, 20% yield) in the form of an orange oil was obtained.

The aniline compounds of following preparation examples 3 through 17 were prepared by means of the methods similar to those of the preparation example 1 or 2. In addition, the example compounds of the present invention were prepared using the aniline prepared by means of the methods according to the preparation examples 1 through 17.

<Preparation Example 3> Preparation of N-(5-amino-2-((2-(dimethylamino)ethylmethyl)amino)-4-methoxyphenyl)acrylamide

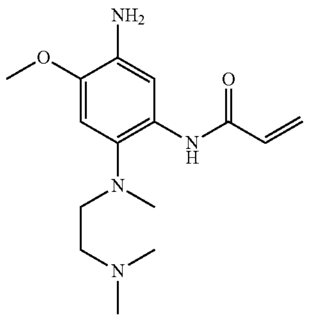 [SMILES: C=CC(=O)Nc1cc(N)c(OC)cc1N(C)CCN(C)C]

<Preparation example 4> Preparation of N-(5-amino-4-methoxy-2-(4-methylpiperazin-1-yl)phenyl) acrylamide

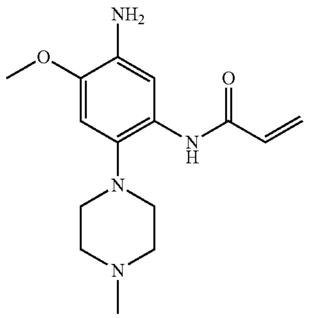 [SMILES: C=CC(=O)Nc1cc(N)c(OC)cc1N1CCN(C)CC1]

<Preparation Example 5> Preparation of N-(5-amino-2-(4-(4-cyclopropylpiperazin-1-yl)piperidin-1-yl)-4-methoxyphenyl)acrylamide

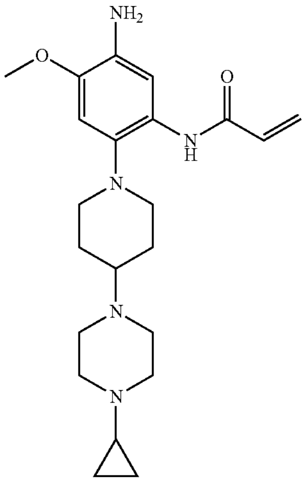 [SMILES: C=CC(=O)Nc1cc(N)c(OC)cc1N1CCC(N2CCN(C3CC3)CC2)CC1]

<Preparation example 6> Preparation of N-(5-amino-4-methoxy-2-thiomorpholinophenyl)acrylamide

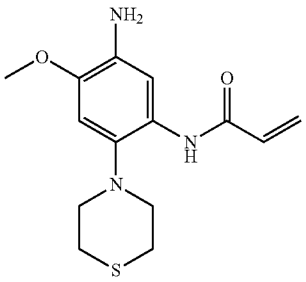 [SMILES: C=CC(=O)Nc1cc(N)c(OC)cc1N1CCSCC1]

<Preparation Example 7> Preparation of N-(5-amino-2((2-(dimethylamino)ethyl)thio)-4-methoxyphenyl)acrylamide

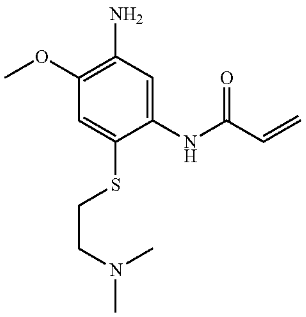 [SMILES: C=CC(=O)Nc1cc(N)c(OC)cc1SCCN(C)C]

<Preparation Example 8> Preparation of N-(5-amino-2-(4-methylpiperazin-1-yl)-6-(2,22-trifluoro-ethoxy)pyridin-3-yl)acrylamide

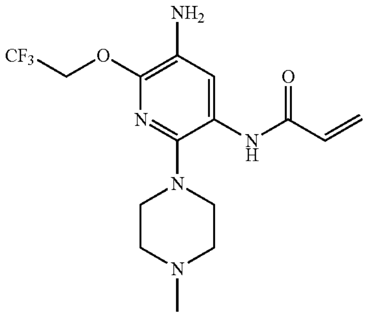 [SMILES: C=CC(=O)Nc1cc(N)c(OCC(F)(F)F)nc1N1CCN(C)CC1]

<Preparation Example 9> Preparation of N-(5-amino-2-((2-(dimethylamino)ethyl)(methyl)amino)-6-methoxypyridin-3-yl)acrylamide

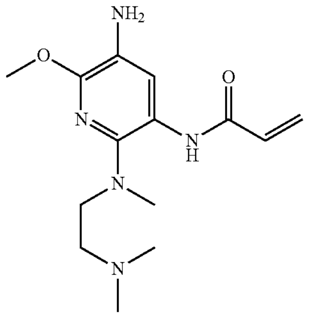

<Preparation Example 10> Preparation of N-(5-amino-6-(difluoromethoxy)-2-(4-methylpiperazin-1-yl)pyridin-3-yl)acrylamide

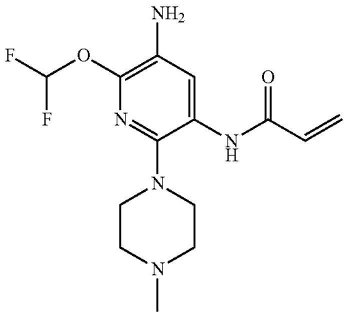 [SMILES: C=CC(=O)Nc1cc(N)c(OC(F)F)nc1N1CCN(C)CC1]

<Preparation Example 11> Preparation of N-(5-amino-6-methoxy-2-morpholinopyridin-3-yl)acrylamide

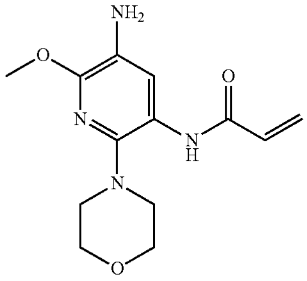 [SMILES: C=CC(=O)Nc1cc(N)c(OC)nc1N1CCOCC1]

<Preparation Example 12> Preparation of N-(5-amino-2-(4-(4-cyclopropylpiperazin-1-yl)piperidin-1-yl)-6-methoxypyridin-3-yl)acrylamide

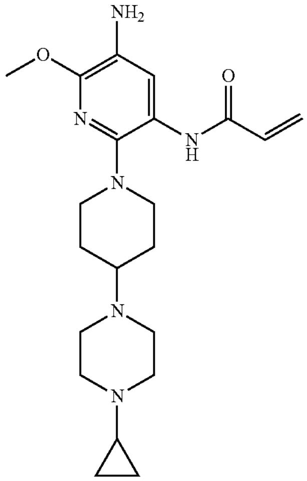 [SMILES: C=CC(=O)Nc1cc(N)c(OC)nc1N1CCC(N2CCN(C3CC3)CC2)CC1]

<Preparation Example 13> Preparation of (S)—N-(5-amino-2-(4-(4-cyclopropyl-3-methylpiperazin-1-yl)piperidin-1-yl)-6-methoxypyridin-3-yl)acrylamide

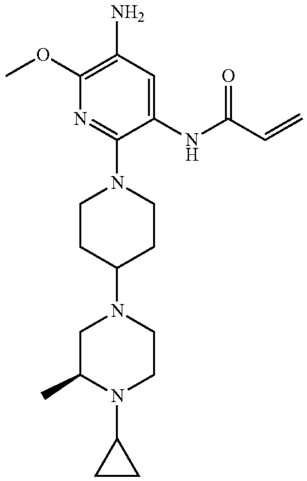 [SMILES: C=CC(=O)Nc1cc(N)c(OC)nc1N1CCC(N2CCN(C3CC3)[C@@H](C)C2)CC1]

<Preparation Example 14> Preparation of (R)—N-(5-amino-2-(4-(4-cyclopropyl-3-methylpiperazin-1-yl)piperidin-1-yl)-6-methoxypyridin-3-yl)acrylamide

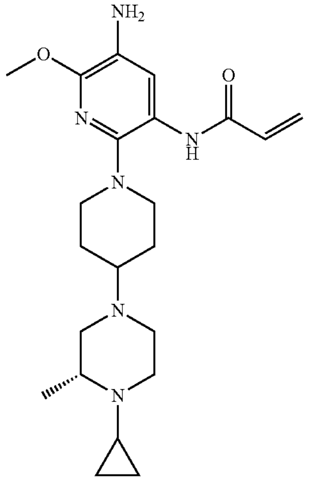 [SMILES: C=CC(=O)Nc1cc(N)c(OC)nc1N1CCC(N2CCN(C3CC3)[C@H](C)C2)CC1]

<Preparation Example 15> Preparation of N-(2-(4-((1R,4R)-2-oxa-5-azabecyclo[2.2.1]heptan-5-yl) pyperidin-1-yl)-5-amino-6-methoxypyridin-3-yl) acrylamide

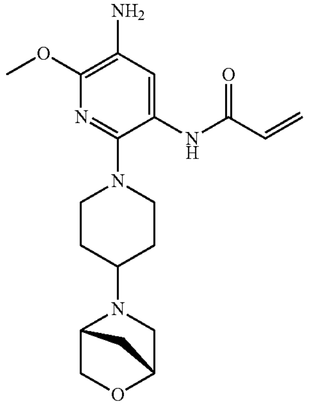 [SMILES: C=CC(=O)Nc1cc(N)c(OC)nc1N1CCC(N2C[C@H]3C[C@@H]2CO3)CC1]

<Preparation Example 16> Preparation of N-(2-(4-((1S,4S)-2-oxa-5-azabicyclo[2.2.1]heptan-5-yl)piperidin-1-yl)-5-amino-6-methoxypyridin-3-yl)acrylamide

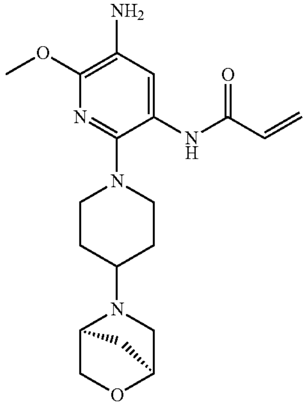 [SMILES: C=CC(=O)Nc1cc(N)c(OC)nc1N1CCC(N2C[C@@H]3C[C@H]2CO3)CC1]

<Preparation Example 17> Preparation of N-(5-amino-2-((2-(dimethylamino)ethyl)(methyl)amino)-6-(2,2,2-trifluoroethoxy)pyridin-3-yl) acrylamide

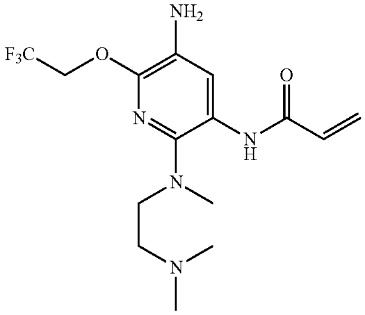 [SMILES: C=CC(=O)Nc1cc(N)c(OCC(F)(F)F)nc1N(C)CCN(C)C]

3. Preparation of the Example Compounds of the Present Invention

Embodiment 1

Preparation of (R)—N-(2-(4-(4-cyclopropyl-1-yl) pyperidin-1-yl)-5-((6-(3-(3-fluoro-5-(trifluoromethyl)phenyl)isoxazolidin-2-yl)pyrimidin-4-yl) amino)-4-methoxyphenyl)acrylamide

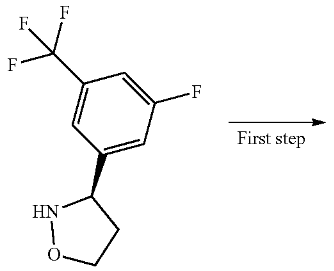

-continued

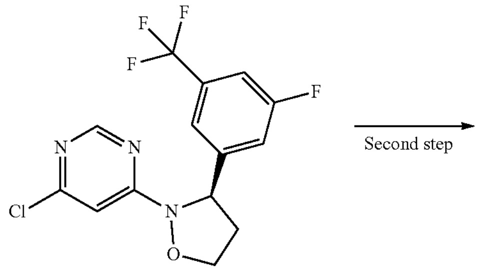

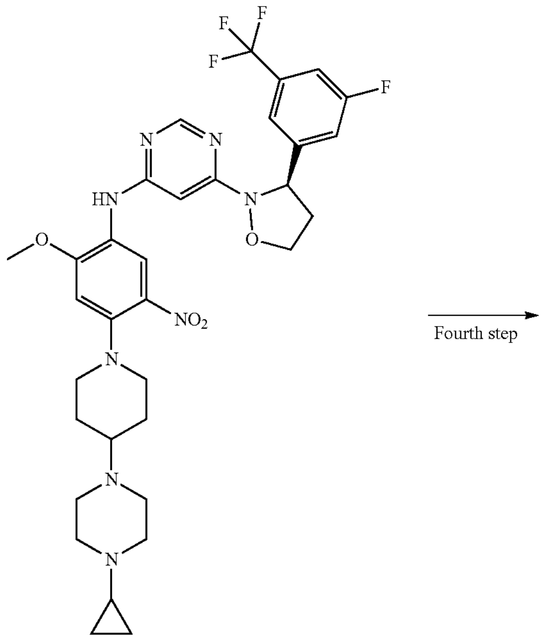

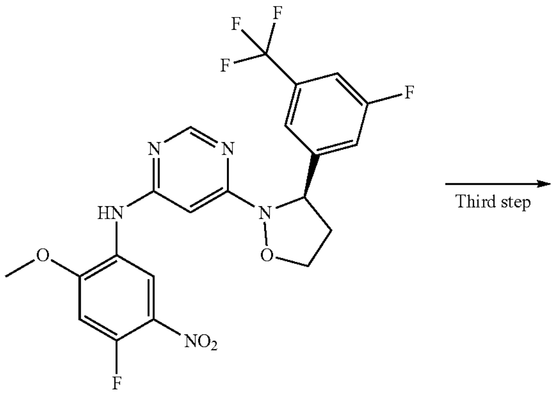

-continued

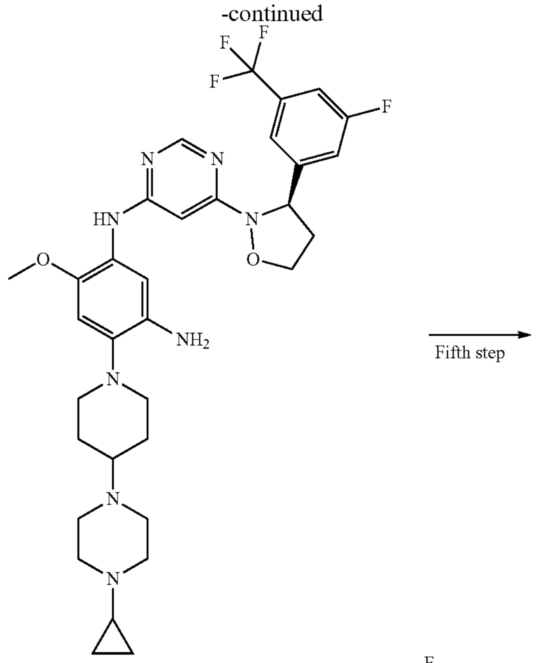

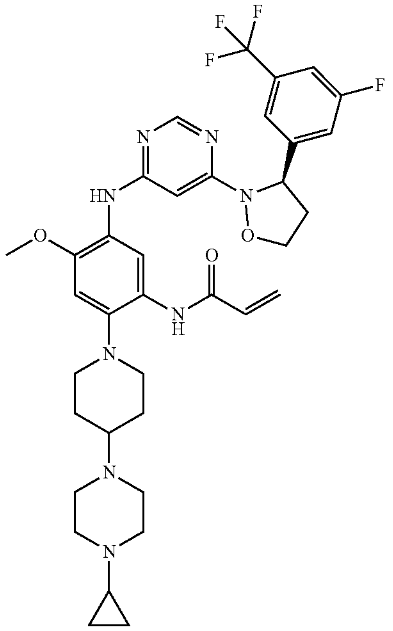

First Step: Preparation of (R)-2-(6-chloropyrimidin-4-yl)-3-(3-fluoro-5-(trifluoromethyl)phenyl) isoxazolidine After a 4,6-dichloropyrimidine (1.8 g, 1.1 eq), a (R)-3-3-(fluoro-5-trimethylfluoromethyl)phenyl)isoxazolidine (3 g, 1 eq) and a N—N-diisopropylethylamine (DIPEA; 5.8 ml, 3 eq) were dissolved in a dimethyl sulfoxide (DMSO; 37 ml) solvent, a resulting reaction solution was agitated for 60 minutes at 100° C. After the reaction was completed, extraction was performed using a dichloromethane and a water. A collected organic layer was washed with a salt water, dried with an anhydrous sodium sulfate, then concentrated under reduced pressure and purified using a medium pressure liquid chromatography (MPLC) (ethyl acetate/hexane), so that a target compound (3.95 g, 100% yield) in the form of a transparent liquid was obtained. Then, an obtained product was used in a subsequent reaction without any purification.

Second Step: Preparation of (R)—N-(4-fluoro-2-methoxy-5-nitropentyl)-6-)(3-(3-fluoro-5-(trifluoromethyl)phenyl) isoxazolidin-2-yl)pyrimidine-4-amine After the (R)-2-(6-chloropyrimidin-4-yl)-3-(3-fluoro-5-(trifluoromethyl)phenyl)isoxazolidine (3.95 g, 1 eq) obtained in the first step, a 4-fluoro-2-methoxy-5-nitroaniline (2.3 g, 1.1 eq) and a methane sulfonic acid (10 g, 5 eq) were added into a sec-butanol (114 ml) and dissolved therein, a resulting product was for 12 hours at 100° C. After the completed reaction, extraction was performed using a dichloromethane (DCM) and a water. A collected organic layer was washed with a salt water, dried with an anhydrous sodium sulfate, then concentrated under reduced pressure and purified using a medium pressure liquid chromatography (MPLC) (ethyl acetate/hexane), so that a target compound (2 g, 28% yield) was obtained.

Third Step: Preparation of (R)—N-(4-(4-(4-cyclopropylpiperazin-1-yl)piperidin-1-yl)-2-methoxy-5-nitrophenyl)-6-(3-(3-fluoro-5-(trifluoromethyl)phenyl)isoxazolidin-2-yl)pyrimidine-4-amine After the (R)—N-(4-fluoro-2-methoxy-5-nitropentyl)-6-(3-(3-fluoro-5-(trifluoromethyl)phenyl)isoxazolidin-2-yl) pyrimidine-4-amine (450 mg, 1 eq) obtained in the second step and a potassium carbonate (375 mg, 3 eq) were dissolved in a dimethyl sulfoxide (DMSO; 9 ml), a 1-cyclopropyl-4-(pyperidin-4-yl)piperazine) hydrochloride (245 mg, 1.1 eq) was added into a resulting product, and then this product was agitated for 2 hours at 70° C. After the completed reaction, extraction was performed using an ethyl acetate and a water. Then, a collected organic layer was washed with a salt water, dried with an anhydrous sodium sulfate, and then concentrated under reduced pressure, so that a desired target compound (621 mg, 100%) was obtained and then used in a subsequent reaction without any purification.

Fourth Step: Preparation of (R)-4-(4-(4-cyclopropylpiperazin-1-yl)piperidin-1-yl)-N1-(6-(3-(3-fluoro-5-(trifluoromethyl)phenyl)isoxazolidin-2-yl)pyrimidin-4-yl)-6-methoxybenzene-1,3-diamine After the (R)—N-(4-(4-(4-cyclopropylpiperazin-1-yl)piperidin-1-yl)-2-methoxy-5-nitrophenyl)-6-(3-(3-fluoro-5-(trifluoromethyl)phenyl)isoxazolidin-2-yl)pyrimidine-4-amine (621 mg, 1 eq) obtained in the third step and a $SnCl_2 2H_2O$ (1020 mg, 5 eq) were dissolved in an ethyl acetate (4.5 ml), a resulting product was agitated for 2 hours at 60° C. After the temperature of a resulting reaction solution was lowered to a room temperature, an aqueous ammonia solution was dropwise added until a pH value reached 5. Then, the pH value was adjusted to 7 by adding an anhydrous sodium carbonate into a resulting reaction mixture. Then the reaction mixture was filtered with a celite, and then washed several times with an ethyl acetate. A resulting filtrate was concentrated under reduced pressure, so that a target compound (491 mg, 83%) was obtained and then used in a subsequent reaction without any purification.

Fifth Step: Preparation of (R)—N-(2-(4-(4-cyclopropyl-1-yl)piperidin-1-yl)-5-((6-(3-(3-fluoro-5-(trifluoromethylphenyl)isoxazolidin-2-yl)pyrimidin-4-yl)amino)-4-methoxyphenyl)acrylamide After the (R)-4-(4-(4-cyclopropylpiperazin-1-yl)piperidin-1-yl)-N1-(6-(3-(3-fluoro-5-(trifluoromethyl)phenyl) isoxazolidin-2-yl)pyrimidin-4-yl)-6-methoxybenzene-1,3-diamine (491 mg, 1 eq) obtained in the fourth step was dissolved in a dichloromethane (DCM; 7.5 ml), an ethylene dichloride (EDC; 215 mg, 1.5 eq), an acrylic acid (77 ul, 1.5 eq) and a N—N-diisopropylethylamine (DIPEA; 261 ul, 2 eq) were added into a resulting product. And a resulting reaction solution was left reacted for 1 hour at room temperature, then the reaction was terminated using an aqueous sodium bicarbonate solution. A compound was extracted using an ethyl acetate solvent and a salt water. A resulting organic layer was dried under reduced pressure and concentrated also under reduced pressure, and then purified using a medium pressure liquid chromatography (MPLC) (dichloromethane/methanol), so that a target compound (488 mg, 87% yield) was obtained.

Embodiment 98

Preparation of (R)—N-(2-(4-(4-cyclopropylpiperazin-1-yl) piperidin-1-yl)-5-((4-(3-(3,5-difluorophenyl)isoxazolidin-2-yl)pyridin-2-yl)amino)-4-methoxyphenyl)acrylamide

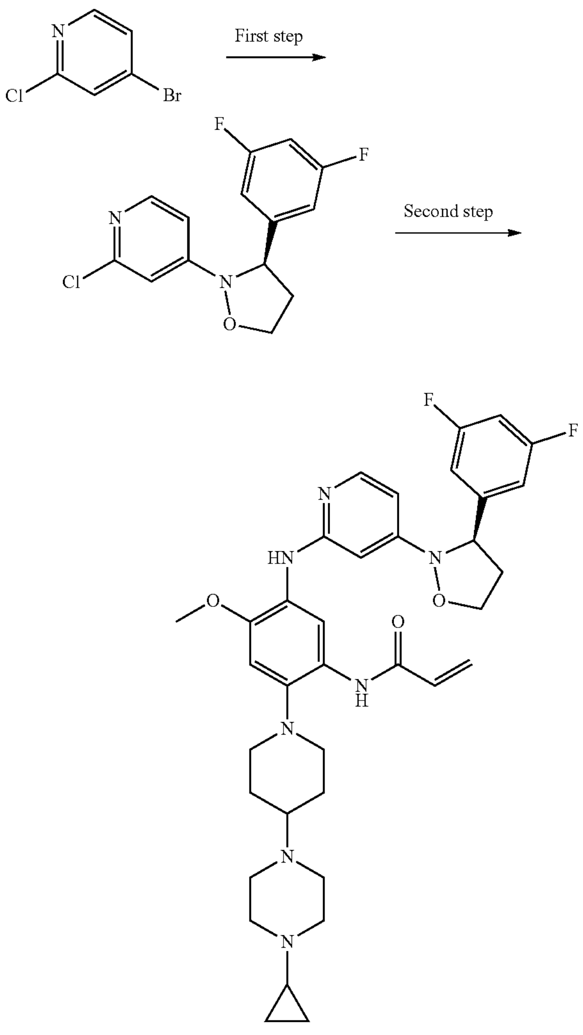

First Step: Preparation of (R)-2-(2-chloropyridin-4-yl)-3-(3,5-difluorophenyl)isoxazolidine A 4-bromo-2-chloropyridine (57.3 mg; 1.1 eq), the (R)-3-(3,5-difluorophenyl)isoxazolidine (50 m; 1 eq) obtained in the <preparation example 7> of 1. Preparation of isoxazolidine derivatives' above, and a cesium carbonate (176 mg; 2 eq) were inserted into a 1,4-dioxane (0.7 ml) solvent and dissolved therein. After the temperature of a resulting reaction solution was raised to 70° C., a xantphos (15 mg; 0.1 eq), and a tris(dibenzylideneacetone)dipalladium(0) ($Pd_2(dba)_3$; 15 mg; 0.1 eq) were inserted into a resulting reaction mixture. A resulting reaction solution was left reacted for 60 minutes at 100° C. After the reaction, a cataylst was removed from the reaction solution by using a celite filter, and then a resulting product was washed using an ethyl acetate. A resulting organic layer was concentrated under reduced pressure, and then purified using a medium pressure liquid chromatography (ethyl acetate/n-hexane), so that a target compound (30 mg; 37.4% yield) was obtained.

Second Step: Preparation of (R)—N-(2-(4-(4-cyclopropylpiperazin-1-yl)piperidin-1-yl)-5-((4-(3-(3,5-difluorophenyl)isoxazolidin-2-yl)pyridin-2-yl)amino)-4-methoxyphenyl)acrylamide The (R)-2-(2-chloropyridin-4-yl)-3-(3,5-difluorophenyl) isoxazolidine (30 mg, 1 eq) obtained in the first step directly above, the N-(5-amino-2-(4-(4-cyclopropylpiperazin-1-yl) piperidin-1-yl)-4-methoxyphenyl)acrylamide (36.4 mg, 0.9 eq) obtained in the <preparation example 5> of '2. Preparation of an aniline derivative' above, and a potassium carbonate (28 mg; 2 eq) were inserted into a sec-butanol (1 ml) solvent and dissolved therein. After the temperature of a resulting reaction solution was raised to 70° C., a xphos (10 mg; 0.2 eq), and a tris(dibenzylideneacetone)dipalladium(0) ($Pd_2(dba)_3$; 18 mg; 0.2 eq) were inserted into a resulting reaction mixture solution. Then, a resulting reaction solution was left reacted for 60 minutes at 100° C. After the reaction, a resulting organic layer was concentrated under reduced pressure, and then purified using a medium pressure liquid chromatography (dichloromethane/methanol), so that a target compound (45% yield) was obtained.

All of the example compounds of the present invention (i.e. the example compounds 1 through 129) were prepared by means of the method similar to that of the Embodiment 1 or 98. But a reaction intermediate needed to prepare the example compounds 108, 109 and 114 through 117 among those example compounds was prepared by means of the method similar to that of the first step of the Embodiment 98 above as follows:

<Preparation of a Reaction Intermediate for the Example Compounds 108 and 109> Preparation of (R)-2-(2-chloropyrimidin-4-yl)-3-pheynylisoxazolidine

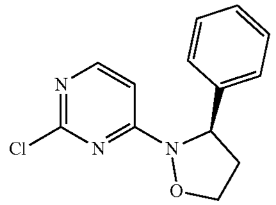 [SMILES: Clc1nccc(N2OCC[C@@H]2c2ccccc2)n1]

Preparation of a Reaction Intermediate for the Example Compounds 114, 115, 116 and 117

Preparation of (R)-2-(4-chloro-1,3,5-Triazin-2-yl)-3-(3,5-difluorophenyl)isoxazolidine

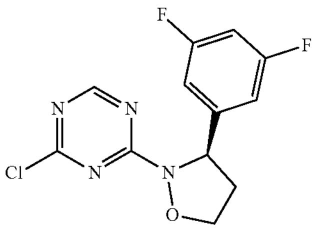 [SMILES: Fc1cc(F)cc([C@H]2CCON2c2ncnc(Cl)n2)c1]

The example compounds 108 and 109 were prepared by means of the method similar to that of the Embodiment 98 by using the compounds described in the <Preparation of a reaction intermediate for the example compounds 108 and 109>, whereas the example compounds 114 through 117 were prepared by means of the method similar to that of the Embodiment 98 by using the compounds described in the <Preparation of a reaction intermediate for the example compounds 114, 115, 116 and 117>.

The compound names, the chemical structural formulae, and the NMR and MS analysis results of the respective example compounds are described in a following Table 1:

TABLE 1

| Example Compound | Structure | Compound Name | $^1$H NMR; MS [M + H]$^+$ |
|---|---|---|---|
| 1 | 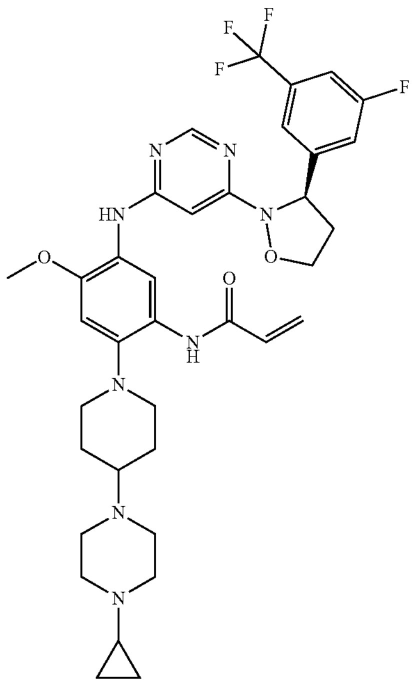 [SMILES: C=CC(=O)Nc1cc(Nc2cc(N3OCC[C@@H]3c3cc(F)cc(C(F)(F)F)c3)ncn2)c(OC)cc1N1CCC(N2CCN(C3CC3)CC2)CC1] | (R)-N-(2-(4-(4-cyclopropyl-1-yl)piperidin-1-yl)-5-((6-(3-(3-fluoro-5-(trifluoromethyl)phenyl)isoxazolidin-2-yl)pyrimidin-4-yl)amino)-4-methoxyphenyl)acrylamide | $^1$H NMR (400 MHz, $CDCl_3$) δ 8.85 (s, 1H), 8.36 (s, 1H), 7.52 (s, 1H), 7.41 (dt, J = 9.6, 2.0 Hz, 1H), 7.20 (dt, J = 8.4, 2.0 Hz, 1H), 7.02 (d, J = 4.0 Hz, 1H), 6.75 (d, J = 5.9 Hz, 2H), 6.35 (dd, J = 17.0, 1.6 Hz, 1H), 6.25 (dd, J = 16.9, 10.0 Hz, 1H), 5.78-5.71 (m, 2H), 4.17 (td, J = 8.1, 4.1 Hz, 1H), 3.84 (s, 4H), 3.10-3.01 (m, 3H), 2.87-2.79 (m, 2H), 2.78-2.67 (m, 7H), 2.62 (d, J = 8.9 Hz, 4H), 2.34 (dtt, J = 11.9, 8.2, 4.3 Hz, 3H), 2.08 (d, J = 12.5 Hz, 3H), 1.66 (ddp, J = 14.1, 6.7, 3.7 Hz, 4H), 0.50-0.44 (m, 3H), 0.43 (t, J = 3.7 Hz, 2H); 711.5 [M + H]$^+$ |
| 2 | 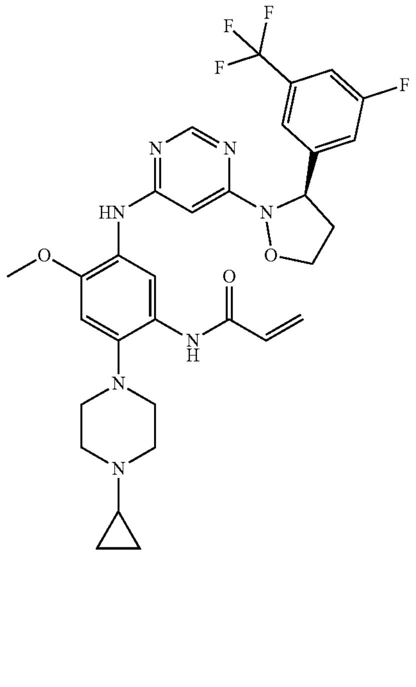 [SMILES: C=CC(=O)Nc1cc(Nc2cc(N3OCC[C@@H]3c3cc(F)cc(C(F)(F)F)c3)ncn2)c(OC)cc1N1CCN(C2CC2)CC1] | R)-N-(2-(4-cyclopropyl-1-yl)-5-((6-(3-(3-fluoro-5-(trifluoromethyl)phenyl)isoxazolidin-2-yl)pyrimidin-4-yl)amino)-4-methoxyphenyl)acrylamide | $^1$H NMR (400 MHz, CDCl3) δ 8.86 (s, 1H), 8.34 (s, 1H), 7.50 (s, 1H), 7.39 (d, J = 9.4 Hz, 1H), 7.18 (d, J = 8.3 Hz, 1H), 7.13 (s, 1H), 6.75 (d, J = 23.0 Hz, 3H), 6.38-6.22 (m, 3H), 5.73 (d, J = 9.3 Hz, 2H), 4.15 (td, J = 8.2, 3.9 Hz, 1H), 3.79 (s, 3H), 2.89-2.83 (m, 5H), 2.82-2.75 (m, 5H), 2.37-2.27 (m, 2H), 1.71 (h, J = 4.6, 4.1 Hz, 1H), 1.32-1.23 (m, 1H), 0.49 (t, J = 5.5 Hz, 2H), 0.47-0.41 (m, 3H); 628.4 [M + H]$^+$ |

TABLE 1-continued

| Example Compound | Structure | Compound Name | $^1H$ NMR; MS $[M + H]^+$ |
|---|---|---|---|
| 3 | 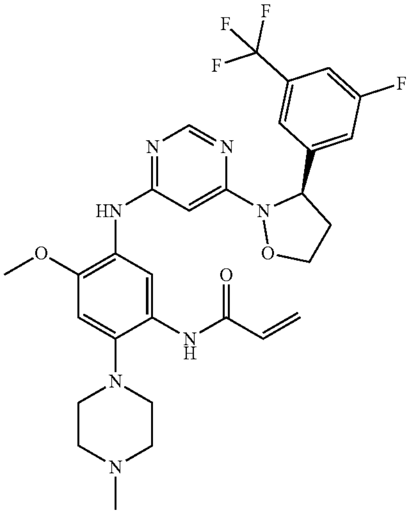 [SMILES: C=CC(=O)Nc1cc(Nc2cc(N3OCC[C@@H]3c3cc(F)cc(C(F)(F)F)c3)ncn2)c(OC)cc1N1CCN(C)CC1] | (R)-N-(5-((6-(3-(3-fluoro-5-(trifluoromethyl)phenyl)isoxazolidin-2-yl)pyrimidin-4-yl)amino)-4-methoxy-2-(4-methylpiperazin-1-yl)phenyl)acrylamide | $^1H$ NMR (400 MHz, $CDCl_3$) δ 8.86 (s, 1H), 8.33 (s, 1H), 7.49 (s, 1H), 7.41-7.36 (m, 1H), 7.18 (d, J = 8.4 Hz, 1H), 7.11 (s, 1H), 6.78 (s, 1H), 6.71 (s, 1H), 6.40-6.21 (m, 3H), 5.71 (s, 1H), 4.14 (td, J = 8.1, 4.0 Hz, 1H), 3.81 (s, 3H), 2.89 (d, J = 4.9 Hz, 4H), 2.78 (dddd, J = 19.7, 15.5, 9.9, 5.3 Hz, 3H), 2.67-2.56 (m, 4H), 2.37 (s, 4H), 2.31 (qd, J = 7.9, 3.9 Hz, 2H), 1.20-1.05 (m, 1H), 0.97-0.78 (m, 1H); 602.4 $[M + H]^+$ |
| 4 | 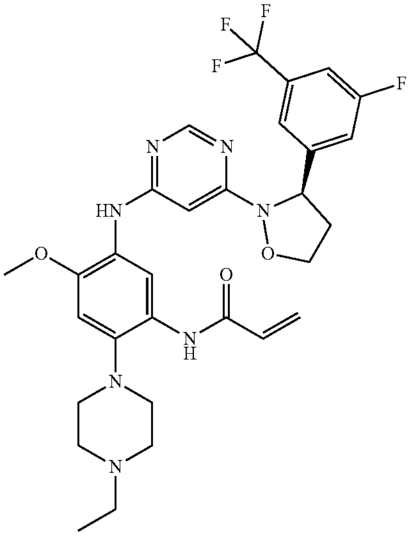 [SMILES: C=CC(=O)Nc1cc(Nc2cc(N3OCC[C@@H]3c3cc(F)cc(C(F)(F)F)c3)ncn2)c(OC)cc1N1CCN(CC)CC1] | (R)-N-(2-(4-ethylpiperazin-1-yl)-5-((6-(3-(3-fluoro-5-(trifluoromethyl)phenyl)isoxazolidin-2-yl)pyrimidin-4-yl)amino)-4-methoxyphenyl)acrylamide | $^1H$ NMR (400 MHz, $CDCl_3$) δ 8.87 (s, 1H), 8.34 (s, 1H), 7.50 (s, 1H), 7.42-7.36 (m, 1H), 7.18 (d, J = 8.3 Hz, 1H), 7.11 (s, 1H), 6.80 (s, 1H), 6.72 (s, 1H), 6.38-6.20 (m, 3H), 5.73 (dt, J = 9.7, 1.7 Hz, 2H), 4.15 (td, J = 8.1, 4.0 Hz, 1H), 3.81 (s, 3H), 2.91 (d, J = 5.0 Hz, 4H), 2.80 (dtd, J = 12.4, 8.2, 4.1 Hz, 2H), 2.61 (d, J = 17.3 Hz, 4H), 2.50 (q, J = 7.2 Hz, 3H), 2.33 (dtd, J = 12.5, 8.2, 4.6 Hz, 2H), 1.13 (t, J = 7.2 Hz, 4H); 616.4 $[M + H]^+$ |
| 5 | 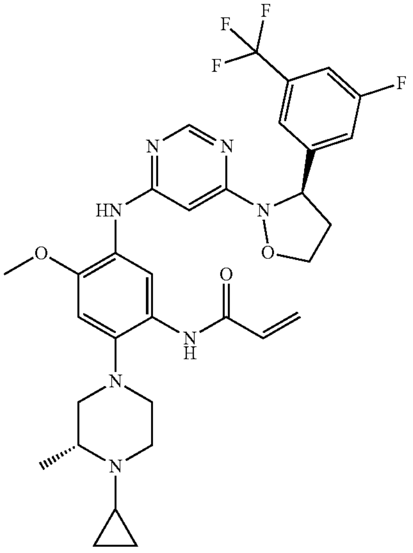 [SMILES: C=CC(=O)Nc1cc(Nc2cc(N3OCC[C@@H]3c3cc(F)cc(C(F)(F)F)c3)ncn2)c(OC)cc1N1CCN(C2CC2)[C@H](C)C1] | N-(2-((R)-4-cyclopropyl-3-methylpiperazin-1-yl)-5-((6-((R)-3-(3-fluoro-5-(trifluoromethyl)phenyl)isoxazolidin-2-yl)pyrimidin-4-yl)amino)-4-methoxyphenyl)acrylamide | $^1H$ NMR (400 MHz, $CDCl_3$) δ 8.86 (s, 1H), 8.34 (s, 1H), 7.50 (s, 1H), 7.39 (d, J = 9.5 Hz, 1H), 7.18 (d, J = 8.3 Hz, 1H), 7.14-7.09 (m, 1H), 6.77 (s, 1H), 6.72 (s, 1H), 6.39-6.20 (m, 3H), 5.73 (dd, J = 7.9, 3.4 Hz, 2H), 4.15 (td, J = 8.1, 4.0 Hz, 1H), 3.79 (s, 3H), 3.10 (dt, J = 11.7, 3.1 Hz, 1H), 2.90-2.84 (m, 2H), 2.81 (dt, J = 12.4, 3.8 Hz, 3H), 2.68 (t, J = 7.0 Hz, 2H), 2.58 (qd, J = 9.2, 8.8, 4.3 Hz, 3H), 2.33 (dtd, J = 12.5, 8.1, 4.6 Hz, 1H), 1.64 (dt, J = 7.0, 3.1 Hz, 1H), 1.24 (d, J = 6.0 Hz, 5H), 0.67 (dt, J = 9.7, 5.2 Hz, 1H), 0.60 (dq, J = 9.9, 5.3, 4.8 Hz, 1H), 0.47 (dq, J = 11.0, 5.9 Hz, 1H), 0.34 (h, J = 4.7 Hz, 1H); 642.4 $[M + H]^+$ |

TABLE 1-continued

| Example Compound | Structure | Compound Name | $^1$H NMR; MS [M + H]$^+$ |
|---|---|---|---|
| 6 | 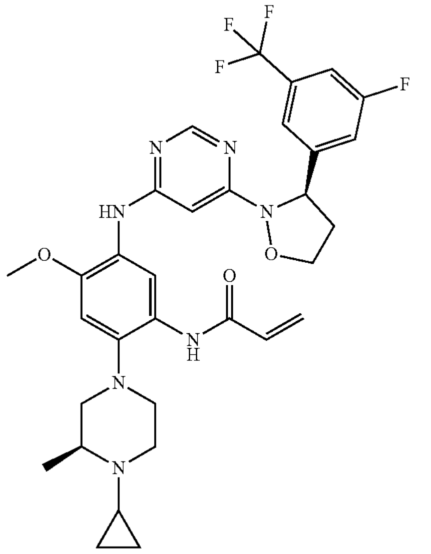 [SMILES: C=CC(=O)Nc1cc(Nc2cc(N3OCC[C@@H]3c3cc(F)cc(C(F)(F)F)c3)ncn2)c(OC)cc1N1CCN(C2CC2)[C@@H](C)C1] | N-(2-((S)-4-cyclopropyl-3-methylpiperazin-1-yl)-5-((6-((R)-3-(3-fluoro-5-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.87 (s, 1H), 8.35 (s, 1H), 7.51 (s, 1H), 7.40 (d, J = 9.4 Hz, 1H), 7.19 (d, J = 8.4 Hz, 1H), 7.06 (s, 1H), 6.78 (s, 1H), 6.73 (s, 1H), 6.36 (d, J = 16.6 Hz, 1H), 6.27 (dd, J = 16.9, 9.9 Hz, 1H), 5.74 (dd, J = 8.9, 4.0 Hz, 2H), 4.16 (td, J = 8.1, 4.0 Hz, 1H), 3.80 (s, 3H), 3.11 (dd, J = 11.7, 3.4 Hz, 1H), 2.87 (q, J = 3.2 Hz, 2H), 2.85-2.74 (m, 3H), 2.69 (t, J = 7.7 Hz, 1H), 2.59 (t, J = 9.7 Hz, 3H), 2.34 (dp, J = 12.1, 4.0, 3.6 Hz, 1H), 1.65 (dd, J = 7.4, 3.8 Hz, 1H), 1.25 (d, J = 6.2 Hz, 5H), 0.67 (dq, J = 11.7, 6.1 Hz, 1H), 0.60 (p, J = 4.9 Hz, 1H), 0.48 (dq, J = 11.2, 6.0 Hz, 2H), 0.35(h, J = 4.8 Hz, 1H); 642.4 [M + H]$^+$ |
| 7 | 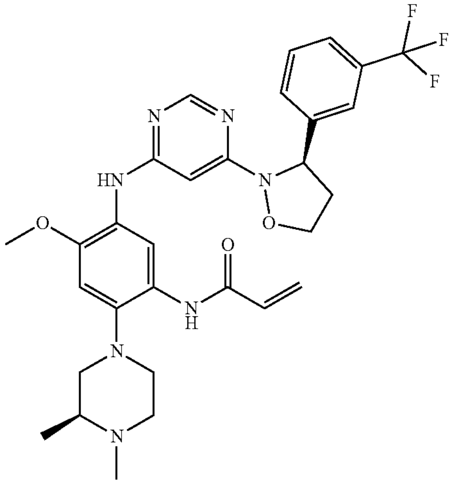 [SMILES: C=CC(=O)Nc1cc(Nc2cc(N3OCC[C@@H]3c3cccc(C(F)(F)F)c3)ncn2)c(OC)cc1N1CCN(C)[C@@H](C)C1] | N-(2-((S)-3,4-dimethylpiperazin-1-yl)-4-methoxy-5-((6-((R)-3-(3-(trifluoromethyl) phenyl) isoxazolidin-2-yl) pyrimidin-4-yl) amino)phenyl) acrylamide | $^1$H NMR (400 MHz, Chloroform-d) δ 8.90 (s, 1H), 8.55 (s, 1H), 8.37 (s, 1H), 7.73 (s, 1H), 7.66 (d, J = 7.5 Hz, 1H), 7.48 (dd, J = 16.9, 7.7 Hz, 2H), 7.05 (s, 1H), 6.79 (s, 1H), 6.73 (s, 1H), 6.41-6.33 (m, 1H), 6.26 (dd, J = 16.9, 9.9 Hz, 1H), 5.78-5.73 (m, 2H), 4.17 (td, J = 8.0, 4.2 Hz, 1H), 4.08 (q, J =8.0 Hz, 1H), 3.84 (s, 3H), 2.98-2.89 (m, 3H), 2.84-2.77 (m, 2H), 2.65-2.59 (m, 1H), 2.46 (td, J = 11.1, 10.7, 3.0 Hz, 1H), 2.38 (s, 3H), 2.35-2.25 (m, 2H), 1.13 (d, J = 6.2 Hz, 3H); 598.4 [M + H]$^+$ |
| 8 | 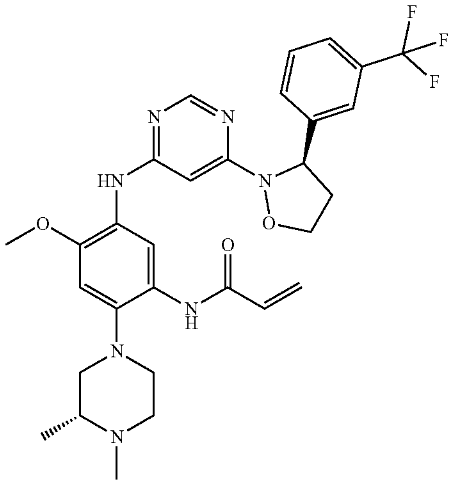 [SMILES: C=CC(=O)Nc1cc(Nc2cc(N3OCC[C@@H]3c3cccc(C(F)(F)F)c3)ncn2)c(OC)cc1N1CCN(C)[C@H](C)C1] | N-(2-((R)-3,4-dimethylpiperazin-1-yl)-4-methoxy-5-((6-((R)-3-(3-(trifluoromethyl) phenyl) isoxazolidin-2-yl) pyrimidin-4-yl) amino)phenyl) acrylamide | $^1$H NMR (400 MHz, Chloroform-d) δ 8.90 (s, 1H), 8.55 (s, 1H), 8.37 (s, 1H), 7.73 (s, 1H), 7.66 (d, J = 7.5 Hz, 1H), 7.54-7.41 (m, 2H), 6.99 (s, 1H), 6.79 (s, 1H), 6.74 (s, 1H), 6.37 (d, J = 16.4 Hz, 1H), 6.26 (dd, J = 16.9, 10.0 Hz, 1H), 5.81-5.71 (m, 2H), 4.17 (td, J = 8.0, 4.2 Hz, 1H), 4.09 (q, J = 8.0 Hz, 1H), 3.84 (s, 3H), 3.04-2.92 (m, 2H), 2.91-2.77 (m, 3H), 2.60 (t, J = 10.4 Hz, 1H), 2.46 (td, J = 11.3, 10.9, 3.0 Hz, 1H), 2.39 (s, 3H), 2.37-2.26 (m, 2H), 1.13 (d, J = 6.2 Hz, 3H); 598.4 [M + H]$^+$ |

TABLE 1-continued

| Example Compound | Structure | Compound Name | $^1$H NMR; MS $[M + H]^+$ |
|---|---|---|---|
| 9 | 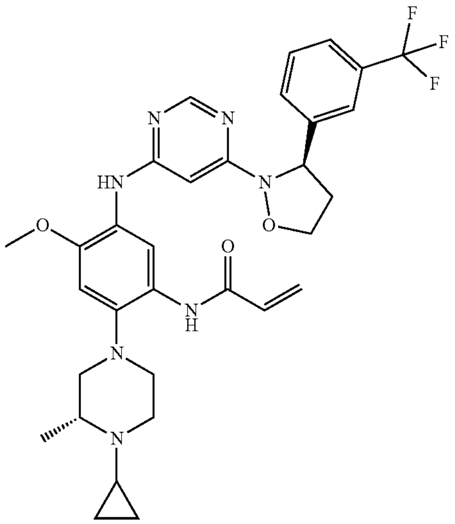 [SMILES: C=CC(=O)Nc1cc(Nc2cc(N3OCC[C@@H]3c3cccc(C(F)(F)F)c3)ncn2)c(OC)cc1N1CCN(C2CC2)[C@H](C)C1] | N-(2-((R)-4-cyclopropyl-3-methylpiperazin-1-yl)-4-methoxy-5-((6-((R)-3-(3-(trifluoromethyl)phenyl)isoxazolidin-2-yl)pyrimidin-4-yl)amino)phenyl)acrylamide | $^1$H NMR (400 MHz, Chloroform-d) δ 8.90 (s, 1H), 8.61 (s, 1H), 8.37 (d, J = 1.0 Hz, 1H), 7.73 (s, 1H), 7.66 (d, J = 7.6 Hz, 1H), 7.54-7.43 (m, 2H), 7.02 (s, 1H), 6.79 (s, 1H), 6.74 (s, 1H), 6.37 (dd, J = 17.0, 1.7 Hz, 1H), 6.28 (dd, J = 17.0, 9.9 Hz, 1H), 5.80-5.71 (m, 2H), 4.17 (td, J = 8.1, 4.3 Hz, 1H), 4.09 (q, J = 8.1 Hz, 1H), 3.81 (s, 3H), 3.12 (dt, J = 11.6, 3.1 Hz, 1H), 2.96-2.85 (m, 2H), 2.85-2.81 (m, 1H), 2.81-2.75 (m, 1H), 2.72-2.68 (m, 1H), 2.65-2.54 (m, 2H), 2.43-2.29 (m, 1H), 1.65 (tt, J = 7.1, 3.8 Hz, 1H), 1.25 (d, J = 2.5 Hz, 3H), 0.74-0.66 (m, 1H), 0.65-0.58 (m, 1H), 0.54-0.43 (m, 1H), 0.36 (tt, J = 10.3, 4.4 Hz, 1H); 624.4 $[M + H]^+$ |
| 10 | 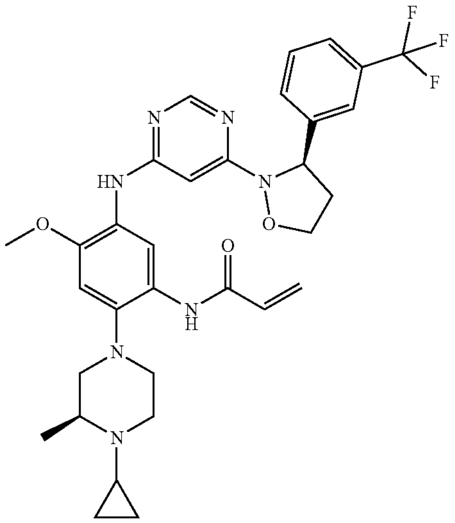 [SMILES: C=CC(=O)Nc1cc(Nc2cc(N3OCC[C@@H]3c3cccc(C(F)(F)F)c3)ncn2)c(OC)cc1N1CCN(C2CC2)[C@@H](C)C1] | N-(2-((S)-4-cyclopropyl-3-methylpiperazin-1-yl)-4-methoxy-5-((6-((R)-3-(3-(trifluoromethyl)phenyl)isoxazolidin-2-yl)pyrimidin-4-yl)amino)phenyl)acrylamide | $^1$H NMR (400 MHz, Chloroform-d) δ 8.89 (s, 1H), 8.61 (s, 1H), 8.37 (d, J = 1.0 Hz, 1H), 7.73 (s, 1H), 7.66 (d, J = 7.6 Hz, 1H), 7.54-7.43 (m, 2H), 7.05 (s, 1H), 6.79 (s, 1H), 6.74 (s, 1H), 6.37 (dd, J = 17.1, 1.7 Hz, 1H), 6.28 (dd, J = 17.0, 9.9 Hz, 1H), 5.80-5.71 (m, 2H), 4.17 (td, J = 8.1, 4.3 Hz, 1H), 4.09 (q, J = 8.1 Hz, 1H), 3.81 (s, 3H), 3.12 (dt, J = 11.5, 3.1 Hz, 1H), 2.93-2.85 (m, 2H), 2.85-2.74 (m, 2H), 2.72-2.68 (m, 1H), 2.65-2.55 (m, 2H), 2.42-2.30 (m, 1H), 1.69-1.62 (m, 1H), 1.26 (d, J = 6.1 Hz, 3H), 0.74-0.65 (m, 1H), 0.65-0.58 (m, 1H), 0.54-0.43 (m, 1H), 0.42-0.32 (m, 1H); 624.4 $[M + H]^+$ |
| 11 | 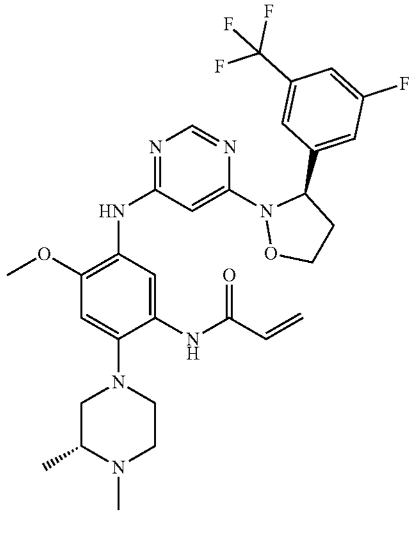 [SMILES: C=CC(=O)Nc1cc(Nc2cc(N3OCC[C@@H]3c3cc(F)cc(C(F)(F)F)c3)ncn2)c(OC)cc1N1CCN(C)[C@H](C)C1] | N-(2-((R)-3,4-dimethylpiperazin-1-yl)-5-((6-((R)-3-(3-fluoro-5-(trifluoromethyl)phenyl)isoxazolidin-2-yl)pyrimidin-4-yl)amino)-4-methoxyphenyl)acrylamide | $^1$H NMR (400 MHz, $CDCl_3$) δ 8.86 (s, 1H), 8.35 (s, 1H), 7.50 (s, 1H), 7.39 (dt, J = 9.5, 2.0 Hz, 1H), 7.19 (dt, J = 8.4, 2.0 Hz, 1H), 7.07 (s, 1H), 6.77 (s, 1H), 6.73 (s, 1H), 6.35 (dd, J = 16.9, 1.6 Hz, 1H), 6.25 (dd, J = 16.9, 9.9 Hz, 1H), 5.76-5.71 (m, 2H), 4.15 (td, J = 8.1, 4.1 Hz, 1H), 3.82 (s, 3H), 3.00-2.76 (m, 7H), 2.61-2.54 (m, 1H), 2.45 (dd, J = 11.4, 3.4 Hz, 1H), 2.36 (s, 4H), 2.30-2.25 (m, 1H), 2.22-2.19 (m, 1H), 1.11 (d, J = 6.2 Hz, 4H); 616.4 $[M + H]^+$ |

TABLE 1-continued

| Example Compound | Structure | Compound Name | $^1$H NMR; MS [M + H]$^+$ |
|---|---|---|---|
| 12 | 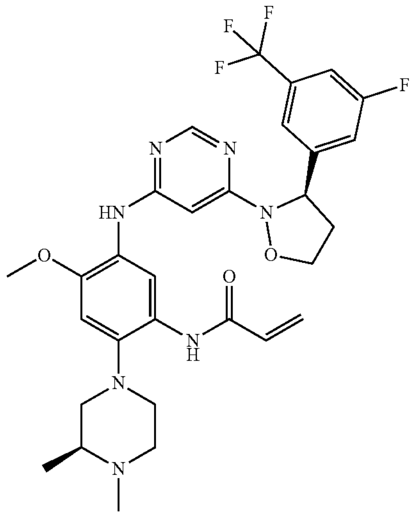 [SMILES: C=CC(=O)Nc1cc(Nc2cc(N3OCC[C@@H]3c3cc(F)cc(C(F)(F)F)c3)ncn2)c(OC)cc1N1CCN(C)[C@@H](C)C1] | N-(2-((S)-3,4-dimethylpiperazin-1-yl)-5-((6-((R)-3-(3-fluoro-5-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.88 (s, 1H), 8.36 (s, 1H), 7.51 (s, 1H), 7.40 (dt, J = 9.4, 2.0 Hz, 1H), 7.19 (dt, J = 8.4, 2.0 Hz, 1H), 7.02 (s, 1H), 6.78 (s, 1H), 6.73 (s, 1H), 6.36 (dd, J = 16.8, 1.6 Hz, 1H), 6.25 (dd, J = 16.9, 9.9 Hz, 1H), 5.77-5.71 (m, 2H), 4.16 (td, J = 8.1, 4.1 Hz, 1H), 3.83 (s, 3H), 3.01-2.76 (m, 7H), 2.65-2.61 (m, 1H), 2.45 (td, J = 11.1, 10.6, 3.0 Hz, 1H), 2.38 (s, 3H), 2.32 (ddt, J = 11.5, 7.5, 3.9 Hz, 3H), 1.13 (d, J = 6.3 Hz, 4H); 616.4 [M + H]$^+$ |
| 13 | 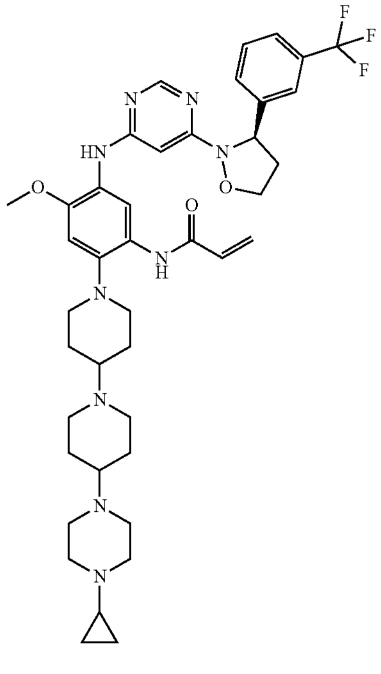 [SMILES: C=CC(=O)Nc1cc(Nc2cc(N3OCC[C@@H]3c3cccc(C(F)(F)F)c3)ncn2)c(OC)cc1N1CCC(N2CCC(N3CCN(C4CC4)CC3)CC2)CC1] | (R)-N-(2-(4-(4-cyclopropyl-1-yl)-[1,4'-bipiperidin]-1'-yl)-4-methoxy-5-((6-(3-(3-(trifluoromethyl) phenyl) isoxazolidin-2-yl) pyrimidin-4-yl) amino)phenyl) acrylamide | $^1$H NMR (400 MHz, $CDCl_3$) δ 8.84 (s, 1H), 8.34 (d, J = 1.0 Hz, 1H), 7.71 (d, J = 2.0 Hz, 1H), 7.66-7.62 (m, 1H), 7.51-7.41 (m, 3H), 7.02 (s, 1H), 6.71 (s, 2H), 6.35-6.23 (m, 3H), 5.76-5.71 (m, 2H), 4.16 (td, J = 8.0, 4.2 Hz, 1H), 3.83 (s, 3H), 3.64 (p, J = 6.7 Hz, 2H), 3.07 (q, J = 7.5 Hz, 5H), 2.40-2.30 (m, 2H), 2.18-2.07 (m, 5H), 2.06-1.92 (m, 4H), 1.87 (s, 2H), 1.53 (t, J = 7.4 Hz, 3H), 1.47 (d, J = 6.7 Hz, 10H), 1.27-1.21 (m, 1H), 1.18 (t, J = 7.3 Hz, 1H), 1.10 (t, J = 7.2 Hz, 1H), 0.50-0.40 (m, 5H); 776.6 [M + H]$^+$ |

TABLE 1-continued

| Example Compound | Structure | Compound Name | $^{1}H$ NMR; MS $[M + H]^{+}$ |
| --- | --- | --- | --- |
| 14 | 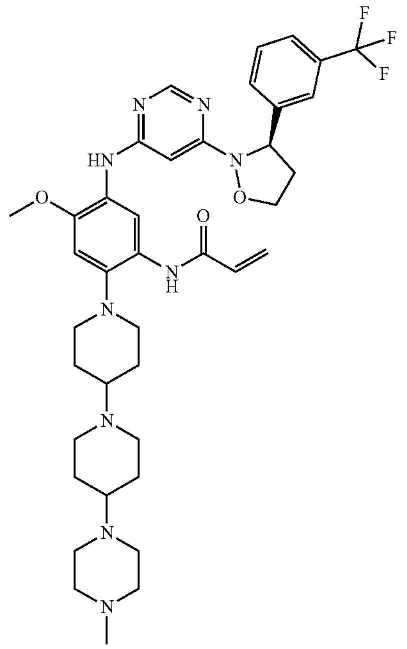 [SMILES: C=CC(=O)Nc1cc(Nc2cc(N3OCC[C@@H]3c3cccc(C(F)(F)F)c3)ncn2)c(OC)cc1N1CCC(N2CCC(N3CCN(C)CC3)CC2)CC1] | (R)-N-(4-methoxy-2-(4-(4-methylpiperazin-1-yl)-[1,4'-bipiperidin]-1'-yl)-5-((6-(3-(3-(trifluoromethyl) phenyl) isoxazolidin-2-yl) pyrimidin-4-yl) amino)phenyl) acrylamide | $^{1}H$ NMR (400 MHz, $CDCl_3$) δ 8.83 (s, 1H), 8.34 (d, J = 1.0 Hz, 1H), 7.70 (s, 1H), 7.64 (d, J = 7.5 Hz, 1H), 7.46 (dt, J = 15.3, 7.7 Hz, 3H), 6.97 (s, 1H), 6.71 (d, J = 11.0 Hz, 2H), 6.34 (dd, J = 17.0, 1.6 Hz, 1H), 6.24 (dd, J = 16.9, 10.0 Hz, 1H), 5.74-5.71 (m, 3H), 4.15 (td, J = 8.1, 4.2 Hz, 1H), 3.82 (s, 3H), 3.03 (d, J = 11.4Hz, 3H), 2.79 (dtt, J = 12.4, 8.6, 4.2 Hz, 2H), 2.72-2.68 (m, 2H), 2.64 (d, J = 14.6 Hz, 4H), 2.31-2.12 (m, 9H), 2.02 (d, J = 13.2 Hz, 3H), 1.86 (d, J = 12.3 Hz, 3H), 1.59 (td, J = 13.1, 12.4, 9.2 Hz, 4H), 0.88-0.79 (m, 8H); 750.6 $[M + H]^{+}$ |
| 15 | 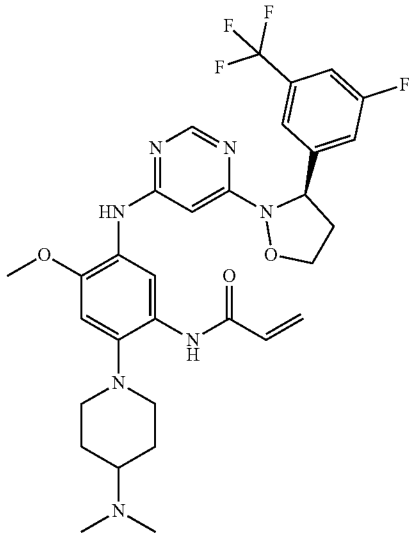 [SMILES: C=CC(=O)Nc1cc(Nc2cc(N3OCC[C@@H]3c3cc(F)cc(C(F)(F)F)c3)ncn2)c(OC)cc1N1CCC(N(C)C)CC1] | (R)-N-(2-(4-(dimethylamino) piperidin-1-yl)-5-((6-(3-(3-fluoro-5-(trifluoromethyl) phenyl) isoxazolidin-2-yl) pyrimidin-4-yl)amino)-4-methoxyphenyl) acrylamide | $^{1}H$ NMR (400 MHz, $CDCl_3$) δ 8.83 (s, 1H), 8.34 (d, J = 1.0 Hz, 2H), 7.50 (s, 1H), 7.39 (dt, J = 9.3, 2.0 Hz, 1H), 7.19 (dt, J = 8.4, 2.0 Hz, 1H), 7.05 (s, 1H), 6.71 (d, J = 3.9 Hz, 2H), 6.39-6.35 (m, 2H), 5.74 (ddd, J = 10.3, 7.5, 4.9 Hz, 3H), 4.17 (td, J = 8.1, 4.0 Hz, 1H), 3.83 (s, 3H), 3.63 (h, J = 6.7 Hz, 2H), 3.30 (qd, J = 7.3, 5.4 Hz, 1H), 3.19-3.12 (m, 3H), 3.07 (q, J = 7.4 Hz, 3H), 2.78 (s, 7H), 2.73 (s, 1H), 2.68 (s, 1H), 2.33 (ddt, J = 16.8, 8.3, 4.5 Hz, 2H), 2.14-2.06 (m, 3H); 630.5 $[M + H]^{+}$ |

TABLE 1-continued

| Example Compound | Structure | Compound Name | $^1H$ NMR; MS $[M + H]^+$ |
|---|---|---|---|
| 16 | 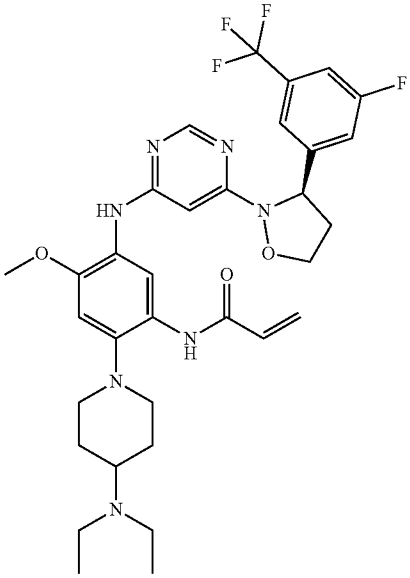 [SMILES: C=CC(=O)Nc1cc(Nc2cc(N3OCC[C@@H]3c3cc(F)cc(C(F)(F)F)c3)ncn2)c(OC)cc1N1CCC(N(CC)CC)CC1] | (R)-N-(2-(4-(diethylamino)piperidin-1-yl)-5-((6-(3-(3-fluoro-5-(trifluoromethyl)phenyl)isoxazolidin-2-yl)pyrimidin-4-yl)amino)-4-methoxyphenyl)acrylamide | $^1H$ NMR (400 MHz, $CDCl_3$) δ 8.83 (s, 1H), 8.34 (d, J = 1.1 Hz, 1H), 7.50 (s, 1H), 7.38 (dt, J = 9.4, 1.9 Hz, 1H), 7.18 (dt, J = 8.4, 2.0 Hz, 1H), 7.03 (d, J = 3.6 Hz, 1H), 6.80-6.70 (m, 2H), 6.38-6.33 (m, 2H), 5.73 (td, J = 8.5, 7.8, 4.4 Hz, 2H), 4.16 (td, J = 8.1, 4.0 Hz, 1H), 3.82 (s, 3H), 3.10 (d, J = 11.3 Hz, 3H), 2.98 (q, J = 7.2 Hz, 6H), 2.77 (dddd, J = 23.5, 13.8, 12.0, 8.8 Hz, 4H), 2.43-2.25 (m, 3H), 2.16 (d, J = 13.6 Hz, 2H), 2.03 (d, J = 12.1 Hz, 2H), 1.29 (t, J = 7.1 Hz, 6H); 658.5 $[M + H]^+$ |
| 17 | 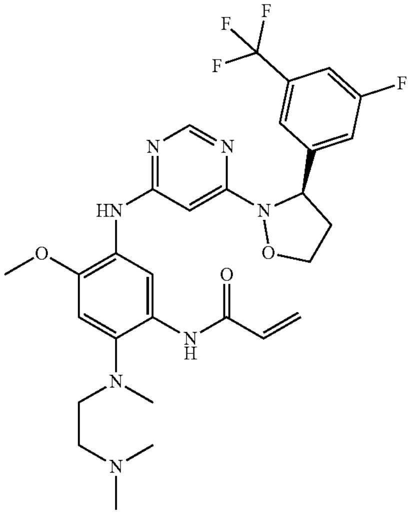 [SMILES: C=CC(=O)Nc1cc(Nc2cc(N3OCC[C@@H]3c3cc(F)cc(C(F)(F)F)c3)ncn2)c(OC)cc1N(C)CCN(C)C] | (R)-N-(2-((2-(dimethylamino)ethyl)(methyl)amino)-5-((6-(3-(3-fluoro-5-(trifluoromethyl)phenyl)isoxazolidin-2-yl)pyrimidin-4-yl)amino)-4-methoxyphenyl)acrylamide | $^1H$ NMR (400 MHz, $CDCl_3$) δ 9.91 (s, 1H), 8.35 (d, J = 1.0 Hz, 1H), 7.54-7.51 (m, 1H), 7.41 (d, J = 9.3 Hz, 1H), 7.20 (dd, J = 12.9, 4.8 Hz, 3H), 6.80-6.76 (m, 2H), 6.42-6.39 (m, 2H), 5.75 (dd, J = 8.8, 4.6 Hz, 1H), 5.69 (dd, J = 6.8, 5.0 Hz, 1H), 4.18 (td, J = 8.1, 4.1 Hz, 1H), 3.85 (s, 3H), 3.42 (s, 2H), 2.94 (dt, J = 6.9, 3.1 Hz, 2H), 2.69 (s, 3H), 2.45 (t, J = 5.7 Hz, 2H), 2.33 (s, 6H), 2.04 (s, 2H); 604.4 $[M + H]^+$ |

TABLE 1-continued

| Example Compound | Structure | Compound Name | $^1$H NMR; MS $[M + H]^+$ |
|---|---|---|---|
| 18 | 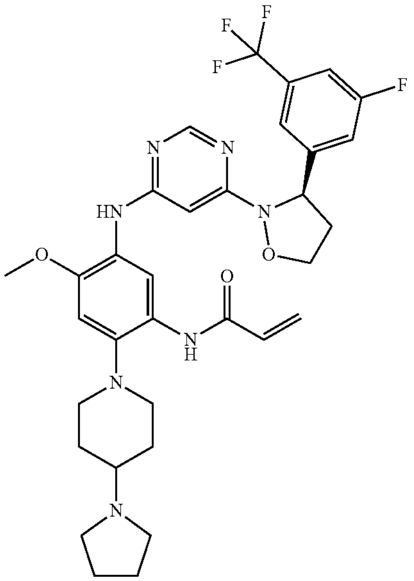 [SMILES: C=CC(=O)Nc1cc(Nc2cc(N3OCC[C@@H]3c3cc(F)cc(C(F)(F)F)c3)ncn2)c(OC)cc1N1CCC(N2CCCC2)CC1] | (R)-N-(5-((6-(3-(3-fluoro-5-(trifluoromethyl)phenyl)isoxazolidin-2-yl)pyrimidin-4-yl)amino)-4-methoxy-2-(4-(pyrrolidin-1-yl)piperidin-1-yl)phenyl)acrylamide | $^1$H NMR (400 MHz, $CDCl_3$) δ 8.83 (s, 1H), 8.35 (d, J = 1.0 Hz, 1H), 7.53-7.50 (m, 1H), 7.41 (dd, J = 9.7, 2.5 Hz, 1H), 7.20 (d, J = 8.2 Hz, 1H), 6.96 (s, 1H), 6.76-6.73 (m, 2H), 6.37-6.30 (m, 2H), 5.74 (dt, J = 8.7, 3.2 Hz, 3H), 4.17 (td, J = 8.1, 4.1 Hz, 1H), 3.84 (d, J = 1.6 Hz, 4H), 3.62 (p, J = 6.7 Hz, 1H), 3.35-3.24 (m, 2H), 3.08 (dd, J = 19.3, 9.7 Hz, 5H), 2.87-2.77 (m, 2H), 2.74 (d, J = 12.5 Hz, 2H), 2.41-2.30 (m, 3H), 2.14 (s, 4H), 2.02 (s, 4H); 656.5 $[M + H]^+$ |
| 19 | 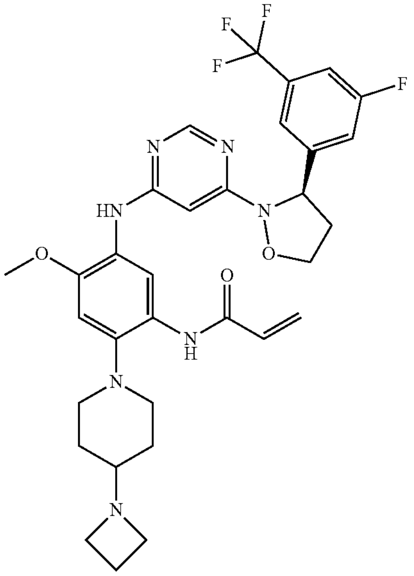 [SMILES: C=CC(=O)Nc1cc(Nc2cc(N3OCC[C@@H]3c3cc(F)cc(C(F)(F)F)c3)ncn2)c(OC)cc1N1CCC(N2CCC2)CC1] | (R)-N-(2-(4-(azetidin-1-yl)piperidin-1-yl)-5-((6-(3-(3-fluoro-5-(trifluoromethyl)phenyl)isoxazolidin-2-yl)pyrimidin-4-yl)amino)-4-methoxyphenyl)acrylamide | $^1$H NMR (400 MHz, $CDCl_3$) δ 8.82 (s, 1H), 8.34 (d, J = 1.0 Hz, 1H), 7.50 (s, 1H), 7.41-7.37 (m, 1H), 7.19 (dt, J = 8.3, 2.0 Hz, 1H), 7.00 (s, 1H), 6.78-6.70 (m, 2H), 6.36-6.18 (m, 2H), 5.71 (dd, J = 9.9, 1.7 Hz, 2H), 4.15 (td, J = 8.1, 4.0 Hz, 1H), 3.83 (s, 3H), 3.34 (t, J = 7.1 Hz, 4H), 3.26-3.18 (m, 2H), 3.08-2.96 (m, 4H), 2.81 (dtd, J = 12.3, 7.7, 4.1 Hz, 2H), 2.38-2.27 (m, 2H), 2.15 (p, J = 7.1 Hz, 2H), 1.91-1.86 (m, 2H), 1.55 (dd, J = 12.0, 8.5 Hz, 2H); 642.5 $[M + H]^+$ |

TABLE 1-continued

| Example Compound | Structure | Compound Name | $^1$H NMR; MS [M + H]$^+$ |
| --- | --- | --- | --- |
| 20 | 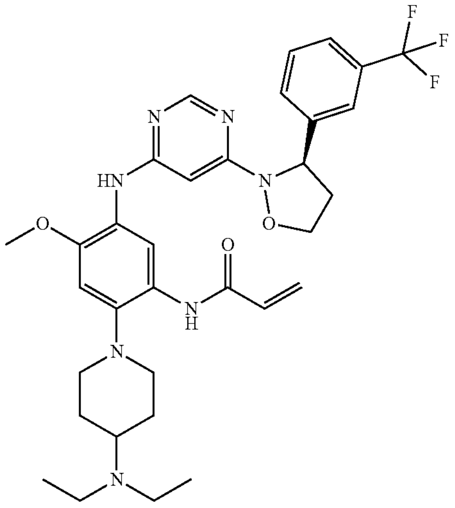 [SMILES: C=CC(=O)Nc1cc(Nc2cc(N3OCC[C@@H]3c3cccc(C(F)(F)F)c3)ncn2)c(OC)cc1N1CCC(N(CC)CC)CC1] | (R)-N-(2-(4-(diethylamino) piperidin-1-yl)-4-methoxy-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.87 (s, 1H), 8.50 (s, 1H), 8.36 (s, 1H), 7.73 (s, 1H), 7.66 (d, J = 7.6 Hz, 1H), 7.51 (d, J = 7.7 Hz, 1H), 7.45 (t, J = 7.7 Hz, 1H), 6.97 (s, 1H), 6.76 (s, 1H), 6.74 (s, 1H), 6.36 (d, J = 16.9 Hz, 1H), 6.26 (dd, J = 17.0, 9.9 Hz, 1H), 5.80-5.70 (m, 2H), 4.17 (td, J = 8.1, 4.1 Hz, 1H), 4.09 (q, J = 8.0 Hz, 1H), 3.84 (s, 3H), 3.05 (d, J = 11.6 Hz, 2H), 2.87-2.78 (m, 1H), 2.78-2.70 (m, 2H), 2.66 (q, J = 7.4 Hz, 4H), 2.63-2.55 (m, 1H), 2.43-2.30 (m, 1H), 1.98 (d, J = 12.5 Hz, 2H), 1.74-1.64 (m, 2H), 1.08 (t, 6H); 640.5 [M + H]$^+$ |
| 21 | 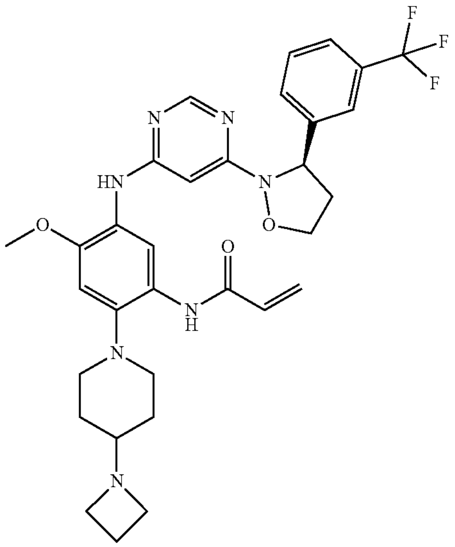 [SMILES: C=CC(=O)Nc1cc(Nc2cc(N3OCC[C@@H]3c3cccc(C(F)(F)F)c3)ncn2)c(OC)cc1N1CCC(N2CCC2)CC1] | (R)-N-(2-(4-(azetidin-1-yl) piperidin-1-yl)-4-methoxy-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.85 (s, 1H), 8.51 (s, 1H), 8.36 (s, 1H), 7.73 (s, 1H), 7.66 (d, J = 7.6 Hz, 1H), 7.51 (d, J = 7.8 Hz, 1H), 7.45 (t, J = 7.7 Hz, 1H), 6.92 (s, 1H), 6.76 (s, 1H), 6.74 (s, 1H), 6.32 (d, J = 16.9 Hz, 1H), 6.21 (dd, J = 17.0, 10.1 Hz, 1H), 5.80-5.68 (m, 2H), 4.16 (td, J = 8.0, 4.1 Hz, 1H), 4.09 (q, J = 7.9 Hz, 1H), 3.85 (s, 3H), 3.24 (t, J = 6.9 Hz, 4H), 3.05-2.96 (m, 2H), 2.87-2.75 (m, 1H), 2.75-2.64 (m, 2H), 2.42-2.30 (m, 1H), 2.21-2.14 (m, 1H), 2.10 (p, 2H), 1.92-1.84 (m, 2H), 1.52-1.40 (m, 2H); 624.5 [M + H]$^+$ |
| 22 | 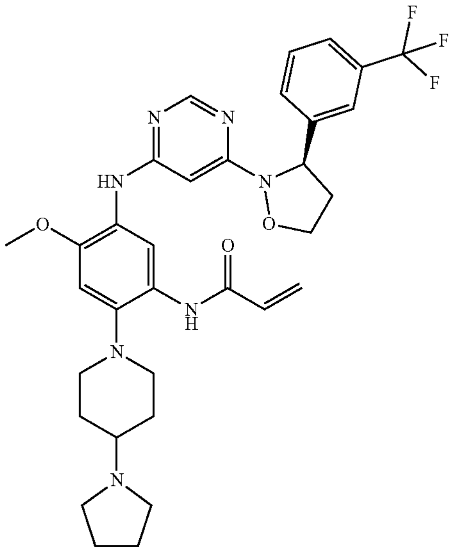 [SMILES: C=CC(=O)Nc1cc(Nc2cc(N3OCC[C@@H]3c3cccc(C(F)(F)F)c3)ncn2)c(OC)cc1N1CCC(N2CCCC2)CC1] | (R)-N-(4-methoxy-2-(4-(pyrrolidin-1-yl) piperidin-1-yl)-5-((6-(3-(3-(trifluoromethyl) phenyl) isoxazolidin-2-yl)-pyrimidin-4-yl) amino)phenyl) acrylamide | $^1$H NMR (400 MHz, Chloroform-d) δ 8.86 (s, 1H), 8.51 (s, 1H), 8.36 (s, 1H), 7.73 (s, 1H), 7.66 (d, J = 7.7 Hz, 1H), 7.51 (d, J = 7.8 Hz, 1H), 7.45 (t, J = 7.7 Hz, 1H), 6.93 (s, 1H), 6.78-6.72 (m, 2H), 6.34 (d, J = 16.9 Hz, 1H), 6.22 (dd, J = 16.9, 10.1 Hz, 1H), 5.80-5.69 (m, 2H), 4.16 (td, J = 12.3, 6.1 Hz, 1H), 4.09 (q, J = 8.0 Hz, 1H), 3.85 (s, 3H), 3.06-2.99 (m, 2H), 2.87-2.68 (m, 3H), 2.67-2.56 (m, 4H), 2.43-2.30 (m, 1H), 2.19-2.07 (m, 3H), 1.88-1.81 (m, 4H), 1.77-1.69 (m, 2H); 638.5 [M + H]$^+$ |

TABLE 1-continued

| Example Compound | Structure | Compound Name | $^1$H NMR; MS $[M + H]^+$ |
|---|---|---|---|
| 23 | 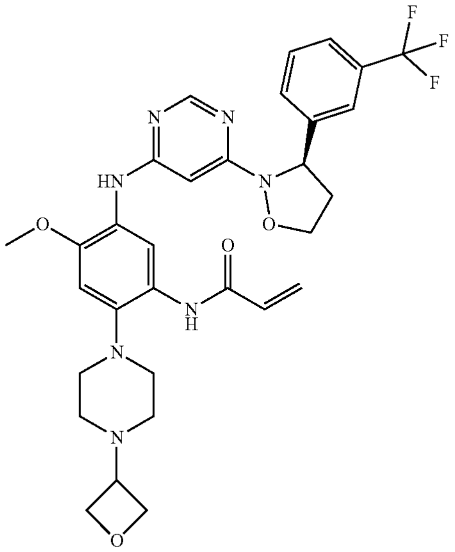 [SMILES: C=CC(=O)Nc1cc(Nc2cc(N3OCC[C@@H]3c3cccc(C(F)(F)F)c3)ncn2)c(OC)cc1N1CCN(C2COC2)CC1] | (R)-N-(4-methoxy-2-(4-(oxetan-3-yl)piperazin-1-yl)-5-((6-(3-(3-(trifluoromethyl) phenyl) isoxazolidin-2-yl)-pyrimidin-4-yl) amino)phenyl) acrylamide | $^1$H NMR (400 MHz, Chloroform-d) δ 8.92 (s, 1H), 8.50 (s, 1H), 8.38 (d, J = 1.0 Hz, 1H), 7.73 (d, J = 2.0 Hz, 1H), 7.70-7.63 (m, 1H), 7.54-7.44 (m, 2H), 7.01 (s, 1H), 6.82 (s, 1H), 6.77-6.72 (m, 1H), 6.37 (dd, J = 16.9, 1.5 Hz, 1H), 6.25 (dd, J = 16.9, 10.0 Hz, 1H), 5.80-5.71 (m, 2H), 4.72 (t, J = 6.6 Hz, 2H), 4.67 (t, J = 6.2 Hz, 2H), 4.18 (td, J = 8.1, 4.2 Hz, 1H), 4.08 (q, J = 8.0 Hz, 1H), 3.85 (s, 3H), 3.61 (p, J =6.4 Hz, 1H), 3.00-2.89 (m, 4H), 2.88-2.75 (m, 1H), 2.66-2.42 (m, 4H), 2.43-2.30 (m, 1H); 626.4 $[M + H]^+$ |
| 24 | 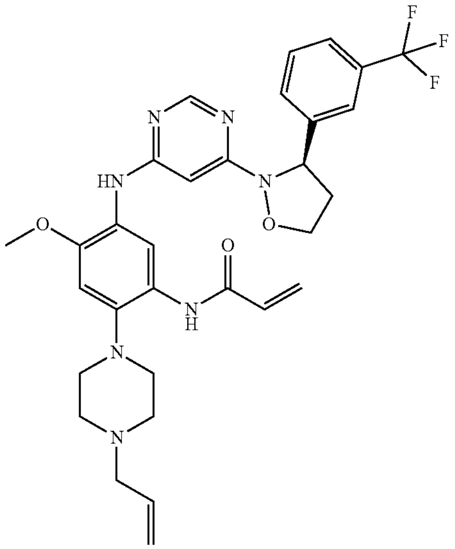 [SMILES: C=CCN1CCN(c2cc(OC)c(Nc3cc(N4OCC[C@@H]4c4cccc(C(F)(F)F)c4)ncn3)cc2NC(=O)C=C)CC1] | (R)-N-(2-(4-allylpiperazin-1-yl)-4-methoxy-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.91 (s, 1H), 8.56 (s, 1H), 8.37 (d, J = 1.0 Hz, 1H), 7.73 (dq, J = 1.9, 1.0 Hz, 1H), 7.67 (dd, J = 7.5, 1.6 Hz, 1H), 7.54-7.44 (m, 2H), 7.02 (s, 1H), 6.81 (s, 1H), 6.74 (d, J = 1.0 Hz, 1H), 6.37 (dd, J = 17.0, 1.6 Hz, 1H), 6.27 (dd, J = 16.9, 9.9 Hz, 1H), 5.91 (ddt, J = 16.8, 10.1, 6.6 Hz, 1H), 5.80-5.72 (m, 2H), 5.32-5.17 (m, 2H), 4.22-4.14 (m, 1H), 4.08 (q, J = 8.0 Hz, 1H), 3.83 (s, 3H), 3.11 (d, J = 6.6, 1.3 Hz, 2H), 2.98-2.88 (m, 4H), 2.86-2.77 (m, 1H), 2.77-2.48 (m, 4H), 2.43-2.30 (m, 1H); 610.4 $[M + H]^+$ |

TABLE 1-continued

| Example Compound | Structure | Compound Name | $^1$H NMR; MS $[M + H]^+$ |
|---|---|---|---|
| 25 | 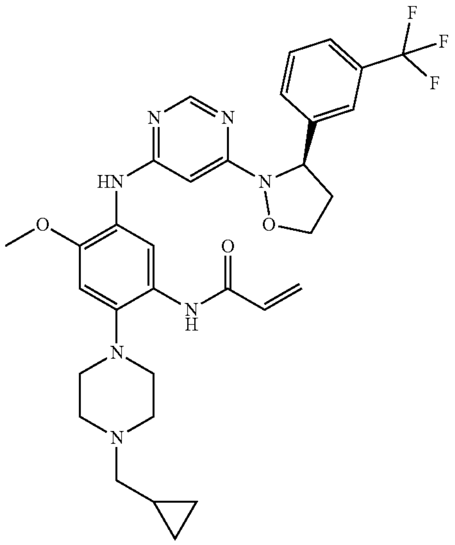 [SMILES: C=CC(=O)Nc1cc(Nc2cc(N3OCC[C@@H]3c3cccc(C(F)(F)F)c3)ncn2)c(OC)cc1N1CCN(CC2CC2)CC1] | (R)-N-(2-(4-(cyclopropyl methyl) piperazin-1-yl)-4-methoxy-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.92 (s, 1H), 8.59 (s, 1H), 8.38 (d, J = 1.0 Hz, 1H), 7.73 (d, J = 1.8, 0.9 Hz, 1H), 7.67 (dd, J = 7.6, 1.6 Hz, 1H), 7.54-7.42 (m, 2H), 7.00 (s, 1H), 6.83 (s, 1H), 6.77-6.72 (m, 1H), 6.37 (dd, J = 17.0, 1.6 Hz, 1H), 6.27 (dd, J = 16.9, 9.9 Hz, 1H), 5.81-5.71 (m, 2H), 4.22-4.14 (m, 1H), 4.09 (q, J = 8.1 Hz, 1H), 3.83 (s, 3H), 2.94 (d, J = 4.9 Hz, 4H), 2.88-2.80 (m, 1H), 2.85-2.58 (m, 4H), 2.41-2.37 (m, 1H), 2.36 (d, 2H), 0.98-0.86 (m, 1H), 0.63-0.49 (m, 2H), 0.21-0.09 (m, 2H); 624.4 $[M + H]^+$ |
| 26 | 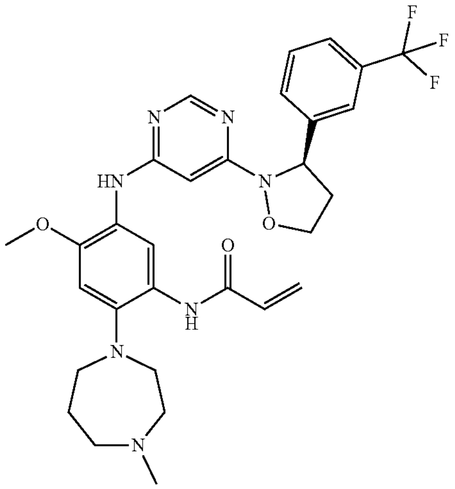 [SMILES: C=CC(=O)Nc1cc(Nc2cc(N3OCC[C@@H]3c3cccc(C(F)(F)F)c3)ncn2)c(OC)cc1N1CCCN(C)CC1] | (R)-N-(4-methoxy-2-(4-methyl-1,4-diazepan-1-yl)-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.93 (s, 1H), 8.77 (s, 1H), 8.36 (d, J = 1.0 Hz, 1H), 7.73 (dt, J = 2.2, 1.2 Hz, 1H), 7.66 (d, J = 7.6 Hz, 1H), 7.54-7.42 (m, 2H), 6.95 (s, 1H), 6.77-6.71 (m, 2H), 6.48-6.35 (m, 2H), 5.80-5.71 (m, 2H), 4.18 (td, J = 8.1, 4.3 Hz, 1H), 4.08 (q, J = 8.0 Hz, 1H), 3.83 (s, 3H), 3.24-3.17 (m, 2H), 3.14 (t, J = 6.0Hz, 2H), 2.94-2.81 (m, 4H), 2.81-2.75 (m, 1H), 2.57-2.53 (m, 2H), 2.43-2.30 (m, 1H), 1.25 (s, 3H); 598.4 $[M + H]^+$ |
| 27 | 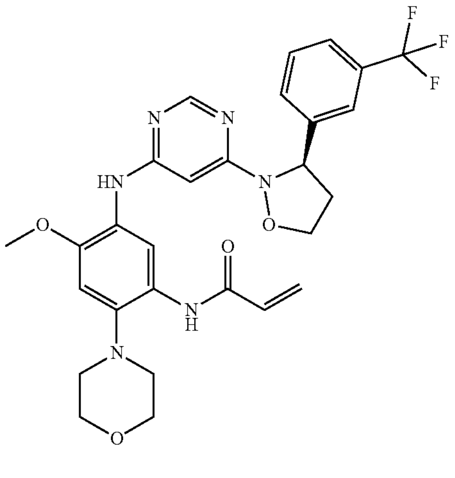 [SMILES: C=CC(=O)Nc1cc(Nc2cc(N3OCC[C@@H]3c3cccc(C(F)(F)F)c3)ncn2)c(OC)cc1N1CCOCC1] | (R)-N-(4-methoxy-2-morpholino-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 9.32 (s, 1H), 8.53 (s, 1H), 8.44 (s, 1H), 8.14-8.10 (m, 1H), 7.60 (d, J = 2.1 Hz, 1H), 7.58-7.55 (m, 1H), 7.54-7.47 (m, 2H), 6.79 (s, 1H), 6.43 (s, 1H), 6.39 (dd, J = 17.0, 2.0 Hz, 1H), 6.32 (dd, J = 16.9, 9.5 Hz, 1H), 5.80 (dd, J = 9.4, 2.0 Hz, 1H), 5.67 (dd, J = 8.7, 5.0 Hz, 1H), 4.30 (td, J = 7.8, 4.6 Hz, 1H), 4.16 (q, J = 7.9 Hz, 1H), 3.91 (t, J = 4.5 Hz, 4H), 3.87 (s, 3H), 3.00-2.95 (m, 1H), 2.95-2.90 (m, 4H), 2.50-2.37 (m, 1H); 571.3 $[M + H]^+$ |

TABLE 1-continued

| Example Compound | Structure | Compound Name | $^1$H NMR; MS [M + H]$^+$ |
|---|---|---|---|
| 28 | 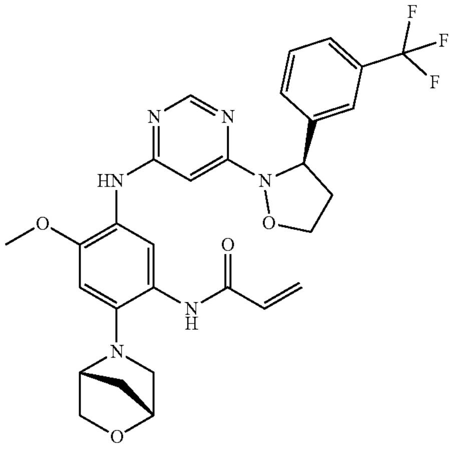 [SMILES: C=CC(=O)Nc1cc(Nc2cc(N3OCC[C@@H]3c3cccc(C(F)(F)F)c3)ncn2)c(OC)cc1N1C[C@H]2C[C@@H]1CO2] | N-(2-((1R,4R)-2-oxa-5-azabicyclo[2.2.1]heptan-5-yl)-4-methoxy-5-((6-((R)-3-(3-(trifluoromethyl)phenyl)isoxazolidin-2-yl)pyrimidin-4-yl)amino)phenyl)acrylamide | $^1$H NMR (400 MHz, Chloroform-d) δ 8.63 (s, 1H), 8.3811-8.33 (m, 1H), 7.97 (s, 1H), 7.73 (s, 1H), 7.66 (d, J = 7.5 Hz, 1H), 7.55-7.48 (m, 1H), 7.48-7.42 (m, 1H), 6.95 (s, 1H), 6.71 (d, J = 3.2 Hz, 2H), 6.39 (dd, J = 16.9, 1.6 Hz, 1H), 6.28 (dd, J = 16.9, 10.0 Hz, 1H), 5.81-5.72 (m, 2H), 4.65 (s, 1H), 4.18 (td, J = 8.0, 4.2 Hz, 1H), 4.09 (q, J = 8.0 Hz, 1H), 4.04 (d, J = 7.6 Hz, 1H), 3.88 (s, 1H), 3.86 (s, 3H), 3.79-3.71 (m, 1H), 3.47-3.41 (m, 1H), 3.24-3.16 (m, 1H), 2.87-2.74 (m, 1H), 2.43-2.30 (m, 1H), 2.09 (d, 1H), 2.00 (d, J = 9.0 Hz, 1H); 583.4 [M + H]$^+$ |
| 29 | 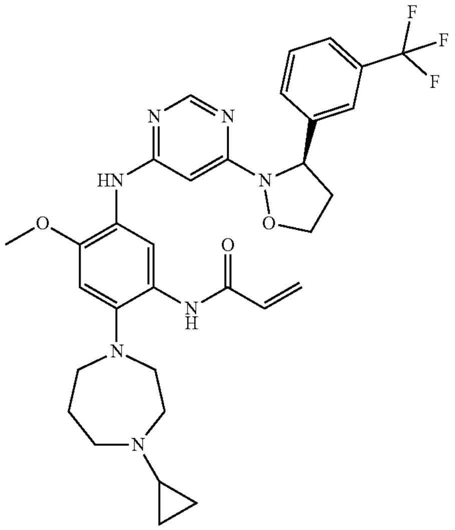 [SMILES: C=CC(=O)Nc1cc(Nc2cc(N3OCC[C@@H]3c3cccc(C(F)(F)F)c3)ncn2)c(OC)cc1N1CCCN(C2CC2)CC1] | (R)-N-(2-(4-cyclopropyl-1,4-diazepan-1-yl)-4-methoxy-5-((6-(3-(3-(trifluoromethyl)phenyl)isoxazolidin-2-yl)pyrimidin-4-yl)amino)phenyl)acrylamide | $^1$H NMR (400 MHz, Chloroform-d) δ 8.84 (s, 1H), 8.70 (s, 1H), 8.37 (d, J = 1.0 Hz, 1H), 7.73 (d, J = 2.2 Hz, 1H), 7.67 (d, J = 7.5 Hz, 1H), 7.54-7.42 (m, 2H), 6.93 (s, 1H), 6.80-6.72 (m, 2H), 6.38 (dd, J = 17.0, 1.5 Hz, 1H), 6.27 (dd, J = 16.9, 10.0 Hz, 1H), 5.80-5.71 (m, 2H), 4.17 (td, J = 8.1, 4.3 Hz, 1H), 4.09 (q, J = 8.0 Hz, 1H), 3.84 (s, 3H), 3.12-3.03 (m, 4H), 3.03-2.94 (m, 4H), 2.86-2.77 (m, 1H), 2.43-2.30 (m, 1H), 1.98 (td, J = 6.3, 3.1 Hz, 1H), 1.95-1.88 (m, 2H), 0.56-0.48 (m, 2H), 0.48-0.43 (m, 2H); 624.4 [M + H]$^+$ |
| 30 | 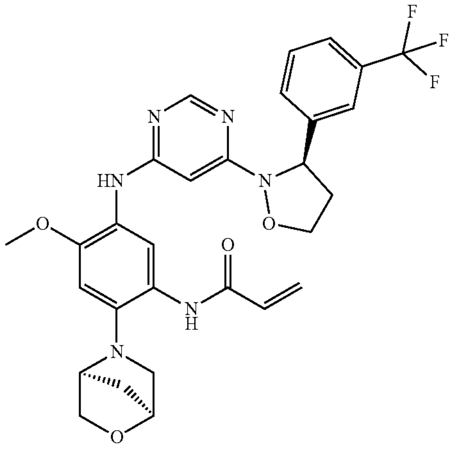 [SMILES: C=CC(=O)Nc1cc(Nc2cc(N3OCC[C@@H]3c3cccc(C(F)(F)F)c3)ncn2)c(OC)cc1N1C[C@@H]2C[C@H]1CO2] | N-(2-((1S,4S)-2-oxa-5-azabicyclo[2.2.1]heptan-5-yl)-4-methoxy-5-((6-((R)-3-(3-(trifluoromethyl)phenyl)isoxazolidin-2-yl)pyrimidin-4-yl)amino)phenyl)acrylamide | $^1$H NMR (400 MHz, Chloroform-d) δ 8.66 (s, 1H), 8.36 (s, 1H), 7.98 (s, 1H), 7.73 (s, 1H), 7.66 (d, J = 7.6 Hz, 1H), 7.53-7.42 (m, 2H), 6.97 (s, 1H), 6.70 (s, 1H), 6.65 (s, 1H), 6.39 (dd, J = 17.0, 1.6 Hz, 1H), 6.28 (dd, J = 16.9, 10.0 Hz, 1H), 5.80-5.72 (m, 2H), 4.65 (s, 1H), 4.16 (td, J = 8.0, 4.2 Hz, 1H), 4.04 (t, J = 7.9 Hz, 2H), 3.89-3.86 (m, 1H), 3.86 (s, 3H), 3.75 (dd, J = 7.8, 1.7 Hz, 1H), 3.42 (d, J = 10.1 Hz, 1H), 3.27-3.20 (m, 1H), 2.87-2.74 (m, 1H), 2.43-2.30 (m, 1H), 2.12-2.03 (m, 1H), 2.03-1.96 (m, 1H); 583.4 [M + H]$^+$ |

TABLE 1-continued

| Example Compound | Structure | Compound Name | $^1$H NMR; MS [M + H]$^+$ |
|---|---|---|---|
| 31 | 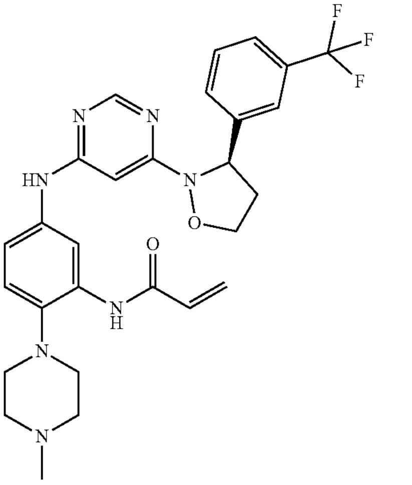 [SMILES: C=CC(=O)Nc1cc(Nc2cc(N3OCC[C@@H]3c3cccc(C(F)(F)F)c3)ncn2)ccc1N1CCN(C)CC1] | (R)-N-(2-(4-methylpiperazin-1-yl)-5-((6-(3-(3-(trifluoromethyl) phenyl) isoxazolidin-2-yl) pyrimidin-4-yl) amino)phenyl) acrylamide | $^1$H NMR (400 MHz, Chloroform-d) δ 8.79 (s, 1H), 8.45 (d, J = 2.4 Hz, 1H), 8.33 (d, J = 1.0 Hz, 1H), 7.72 (td, J = 1.9, 0.9 Hz, 1H), 7.68-7.61 (m, 1H), 7.54-7.42 (m, 2H), 7.21 (d, J = 8.5 Hz, 1H), 7.15 (dd, J = 8.5, 2.5 Hz, 1H), 6.96 (s, 1H), 6.62 (d, J = 1.1 Hz, 1H), 6.39 (dd, J = 16.9, 1.4 Hz, 1H), 6.28 (dd, J = 16.9, 10.0 Hz, 1H), 5.79 (dd, J = 10.0, 1.4 Hz, 1H), 5.75 (dd, J = 8.7, 4.7 Hz, 1H), 4.19-4.10 (m, 1H), 3.98 (q, J = 8.0 Hz, 1H), 2.96-2.89 (m, 4H), 2.86-2.74 (m, 1H), 2.73-2.48 (m, 4H), 2.39 (s, 3H), 2.38-2.32 (m, 1H); 554.4 [M + H]$^+$ |
| 32 | 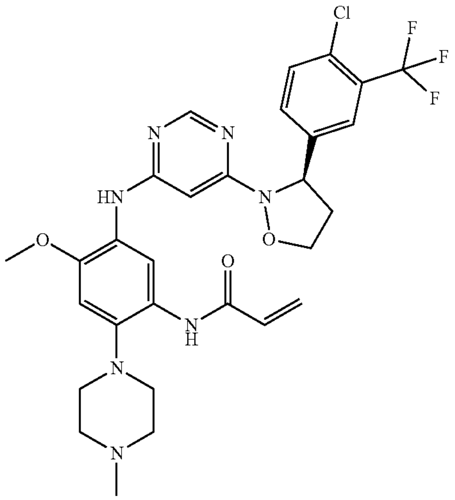 [SMILES: C=CC(=O)Nc1cc(Nc2cc(N3OCC[C@@H]3c3ccc(Cl)c(C(F)(F)F)c3)ncn2)c(OC)cc1N1CCN(C)CC1] | (R)-N-(5-((6-(3-(4-chloro-3-(trifluoromethyl) phenyl) isoxazolidin-2-yl) pyrimidin-4-yl)amino)-4-methoxy-2-(4-methylpiperazin-1-yl) phenyl) acrylamide | $^1$H NMR (400 MHz, Chloroform-d) δ 8.90 (s, 1H), 8.54 (s, 1H), 8.36 (d, J = 1.0 Hz, 1H), 7.79 (d, J = 2.2 Hz, 1H), 7.59 (dd, J = 8.3, 2.2 Hz, 1H), 7.47 (d, J = 8.3 Hz, 1H), 6.97 (s, 1H), 6.80 (s, 1H), 6.74 (d, J = 1.0 Hz, 1H), 6.37 (dd, J = 17.0, 1.6 Hz, 1H), 6.27 (dd, J = 16.9, 9.9 Hz, 1H), 5.75 (dd, J = 9.9, 1.7 Hz, 1H), 5.72 (dd, J = 8.6, 4.5 Hz, 1H), 4.22-4.13 (m, 1H), 4.08 (q, J = 8.1 Hz, 1H), 3.84 (s, 3H), 2.98-2.88 (m, 4H), 2.86-2.76 (m, 1H), 2.73-2.49 (m, 4H), 2.40 (s, 3H), 2.37-2.28 (m, 1H); 618.4 [M + H]$^+$ |
| 33 | 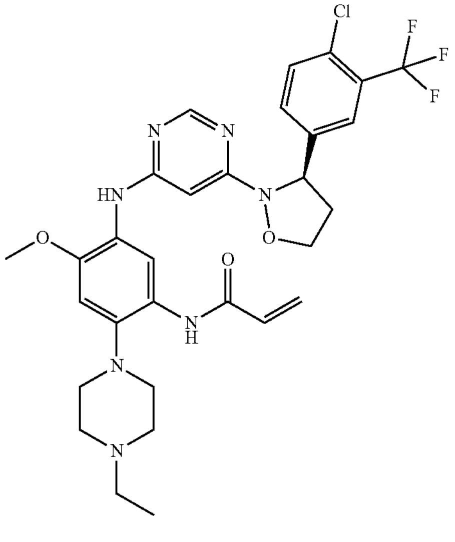 [SMILES: C=CC(=O)Nc1cc(Nc2cc(N3OCC[C@@H]3c3ccc(Cl)c(C(F)(F)F)c3)ncn2)c(OC)cc1N1CCN(CC)CC1] | (R)-N-(5-((6-(3-(4-chloro-3-(trifluoromethyl) phenyl) isoxazolidin-2-yl) pyrimidin-4-yl)amino)-2-(4-ethylpiperazin-1-yl)-4-methoxyphenyl) acrylamide | $^1$H NMR (400 MHz, Chloroform-d) δ 8.85 (s, 1H), 8.40 (s, 1H), 8.35 (d, J = 1.0 Hz, 1H), 7.77 (d, J = 2.2 Hz, 1H), 7.57 (dd, J = 8.3, 2.2 Hz, 1H), 7.46 (d, J = 8.3 Hz, 1H), 7.16 (s, 1H), 6.71-6.66 (m, 2H), 6.42-6.25 (m, 2H), 5.75-5.65 (m, 2H), 4.16 (td, J = 8.0, 4.1 Hz, 1H), 4.05 (q, J = 8.3 Hz, 1H), 3.79 (s, 3H), 3.35-2.97 (m, 8H), 2.94 (q, J = 7.3 Hz, 2H), 2.86-2.76 (m, 1H), 2.38-2.26 (m, 1H), 1.28 (t, J = 7.3 Hz, 3H); 632.4 [M + H]$^+$ |

TABLE 1-continued

| Example Compound | Structure | Compound Name | $^1H$ NMR; MS $[M + H]^+$ |
|---|---|---|---|
| 34 | 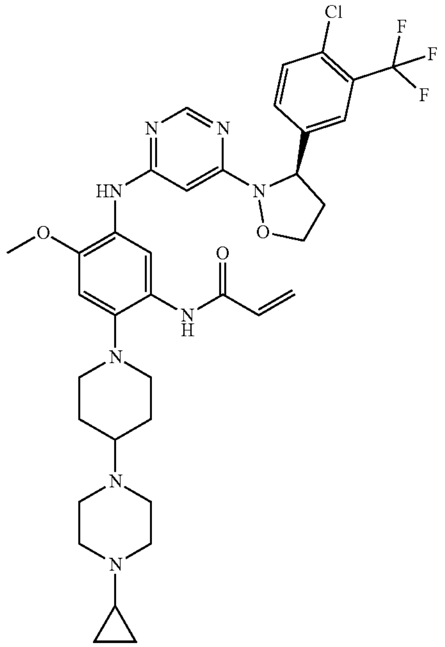 [SMILES: C=CC(=O)Nc1cc(Nc2cc(N3OCC[C@@H]3c3ccc(Cl)c(C(F)(F)F)c3)ncn2)c(OC)cc1N1CCC(N2CCN(C3CC3)CC2)CC1] | (R)-N-(5-((6-(3-(4-chloro-3-(trifluoromethyl)phenyl)isoxazolidin-2-yl)pyrimidin-4-yl)amino)-2-(4-(4-cyclopropyl-1-yl)piperidin-1-yl)-4-methoxyphenyl)acrylamide | $^1H$ NMR (400 MHz, Chloroform-d) δ 8.83 (s, 1H), 8.38 (s, 1H), 8.35 (d, J = 1.0Hz, 1H), 7.78 (d, J = 2.2 Hz, 1H), 7.59 (dd, J = 8.3, 2.2 Hz, 1H), 7.47 (d, J = 8.4 Hz, 1H), 7.02 (s, 1H), 6.75-6.68 (m, 2H), 6.41-6.23 (m, 2H), 5.76-5.67 (m, 2H), 4.16 (td, J = 8.1, 4.2 Hz, 1H), 4.07 (q, J = 8.1 Hz, 1H), 3.83 (s, 3H), 3.10-3.02 (m, 2H), 3.01-2.79 (m, 8H), 2.82-2.77 (m, 1H), 2.78-2.72 (m, 1H), 2.74-2.68 (m, 2H), 2.38-2.26 (m, 1H), 2.12 (d, J = 12.1 Hz, 2H), 1.91-1.79 (m, 2H), 1.74 (td, J = 6.0, 3.1 Hz, 1H), 0.57-0.47 (m, 4H); 727.5 $[M + H]^+$ |
| 35 | 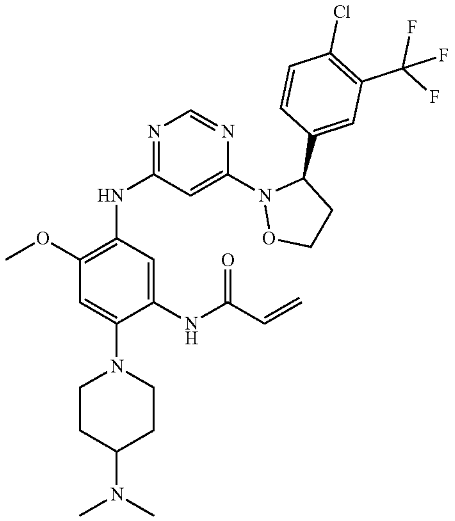 [SMILES: C=CC(=O)Nc1cc(Nc2cc(N3OCC[C@@H]3c3ccc(Cl)c(C(F)(F)F)c3)ncn2)c(OC)cc1N1CCC(N(C)C)CC1] | (R)-N-(5-((6-(3-(4-chloro-3-(trifluoromethyl)phenyl)isoxazolidin-2-yl)pyrimidin-4-yl)amino)-2-(4-(dimethylamino)piperidin-1-yl)-4-methoxyphenyl)acrylamide | $^1H$ NMR (400 MHz, Chloroform-d) δ 8.86 (s, 1H), 8.46 (s, 1H), 8.36 (d, J = 1.0 Hz, 1H), 7.79 (d, J = 2.2 Hz, 1H), 7.59 (dd, J = 8.3, 2.2 Hz, 1H), 7.47 (d, J = 8.3 Hz, 1H), 6.98 (s, 1H), 6.77-6.71 (m, 2H), 6.36 (dd, J = 16.9, 1.7 Hz, 1H), 6.27 (dd, J = 16.9, 9.8 Hz, 1H), 5.78-5.68 (m, 2H), 4.22-4.12 (m, 1H), 4.08 (q, J = 8.1 Hz, 1H), 3.85 (s, 3H), 3.08 (d, 2H), 2.86-2.77 (m, 1H), 2.77-2.69 (m, 2H), 2.44 (s, 6H), 2.41-2.36 (m, 1H), 2.35-2.26 (m, 1H), 2.10 (d, J = 12.5 Hz, 2H), 1.73 (q, J = 11.9 Hz, 2H); 646.4 $[M + H]^+$ |

TABLE 1-continued

| Example Compound | Structure | Compound Name | $^1H$ NMR; MS $[M + H]^+$ |
| --- | --- | --- | --- |
| 36 | 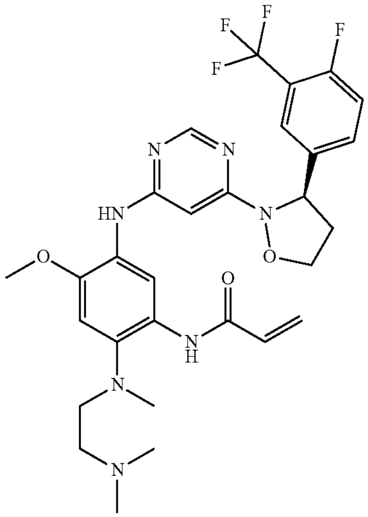 [SMILES: C=CC(=O)Nc1cc(Nc2cc(N3OCC[C@@H]3c3ccc(F)c(C(F)(F)F)c3)ncn2)c(OC)cc1N(C)CCN(C)C] | (R)-N-(2-((2-(dimethylamino)ethyl)(methyl)amino)-5-((6-(3-(4-fluoro-3-(trifluoromethyl)phenyl)isoxazolidin-2-yl)pyrimidin-4-yl)amino)-4-methoxyphenyl)acrylamide | $^1H$ NMR (400 MHz, DMSO-d6) δ 10.06 (s, 1H), 8.65 (s, 1H), 8.47 (s, 1H), 8.17 (d, J = 1.0 Hz, 1H), 7.78 (tt, J = 6.8, 3.5 Hz, 2H), 7.51 (dd, J = 10.7, 8.5 Hz, 1H), 6.99 (s, 1H), 6.44-6.31 (m, 2H), 6.21 (dd, J = 17.0, 2.2 Hz, 1H), 5.74 (dd, J = 10.0, 2.2 Hz, 1H), 5.63 (dd, J = 8.6, 5.0 Hz, 1H), 4.15 (td, J = 7.9, 3.8 Hz, 1H), 3.90-3.82 (m, 1H), 3.80 (s, 3H), 2.86 (t, J = 5.9 Hz, 2H), 2.79 (tt, J = 8.0, 4.4 Hz, 1H), 2.71 (s, 3H), 2.31 (t, J = 5.9 Hz, 2H), 2.25 (dt, J = 12.1, 4.1 Hz, 1H), 2.20 (s, 6H); 604.40 $[M + H]^+$ |
| 37 | 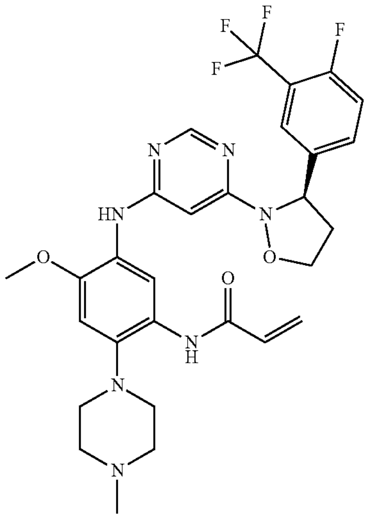 [SMILES: C=CC(=O)Nc1cc(Nc2cc(N3OCC[C@@H]3c3ccc(F)c(C(F)(F)F)c3)ncn2)c(OC)cc1N1CCN(C)CC1] | (R)-N-(5-((6-(3-(4-fluoro-3-(trifluoromethyl)phenyl)isoxazolidin-2-yl)pyrimidin-4-yl)amino)-4-methoxy-2-(4-methylpiperazin-1-yl)phenyl)acrylamide | $^1H$ NMR (400 MHz, DMSO-d6) δ 8.97 (s, 1H), 8.64 (s, 1H), 8.20-8.07 (m, 2H), 7.84-7.71 (m, 2H), 7.51 (dd, J = 10.8, 8.5 Hz, 1H), 6.84 (s, 1H), 6.59 (dd, J = 16.9, 10.2 Hz, 1H), 6.37 (s, 1H), 6.20 (dd, J = 17.1, 2.0 Hz, 1H), 5.75-5.66 (m, 1H), 5.62 (dd, J = 8.6, 5.1 Hz, 1H), 4.15 (td, J = 7.9, 3.8 Hz, 1H), 3.89-3.83 (m, 1H), 3.81 (s, 3H), 2.86 (t, J = 4.8 Hz, 4H), 2.79 (dq, J = 8.1, 4.1 Hz, 1H), 2.51 (s, 4H), 2.25 (s, 4H); 602.42 $[M + H]^+$ |
| 38 | 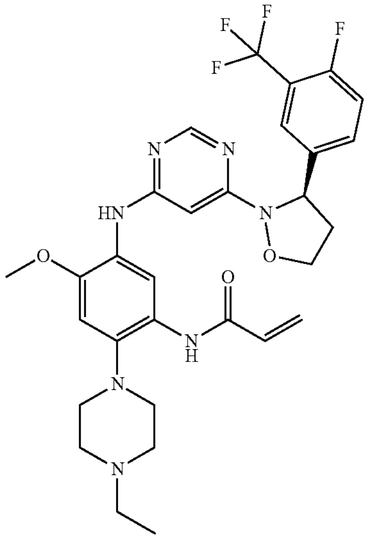 [SMILES: C=CC(=O)Nc1cc(Nc2cc(N3OCC[C@@H]3c3ccc(F)c(C(F)(F)F)c3)ncn2)c(OC)cc1N1CCN(CC)CC1] | (R)-N-(2-(4-ethylpiperazin-1-yl)-5-((6-(3-(4-fluoro-3-(trifluoromethyl)phenyl)isoxazolidin-2-yl)pyrimidin-4-yl)amino)-4-methoxyphenyl)acrylamide | $^1H$ NMR (400 MHz, DMSO-d6) δ 8.98 (s, 1H), 8.65 (s, 1H), 8.15 (d, J = 14.6 Hz, 2H), 7.78 (ddt, J = 9.3, 6.8, 2.6 Hz, 2H), 7.51 (dd, J = 10.8, 8.5 Hz, 1H), 6.86 (s, 1H), 6.59 (dd, J = 17.0, 10.2 Hz, 1H), 6.38 (s, 1H), 6.20 (dd, J = 17.0, 2.0 Hz, 1H), 5.72 (dd, J = 10.1, 2.0 Hz, 1H), 5.62 (dd, J = 8.6, 5.1 Hz, 1H), 4.15 (td, J = 7.9, 3.8 Hz, 1H), 3.89-3.82 (m, 1H), 3.81 (s, 3H), 2.88 (d, J = 6.3 Hz, 4H), 2.79 (dq, J = 8.4, 4.2 Hz, 1H), 2.57 (s, 3H), 2.41 (s, 2H), 2.30-2.20 (m, 1H), 1.04 (t, J = 7.2 Hz, 4H); 616.40 $[M + H]^+$ |

TABLE 1-continued

| Example Compound | Structure | Compound Name | $^1$H NMR; MS [M + H]$^+$ |
| --- | --- | --- | --- |
| 39 | 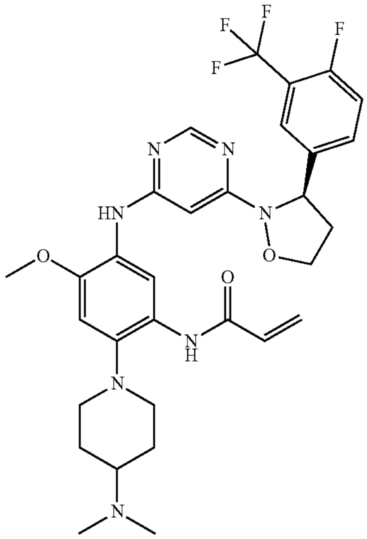 [SMILES: C=CC(=O)Nc1cc(Nc2cc(N3OCC[C@@H]3c3ccc(F)c(C(F)(F)F)c3)ncn2)c(OC)cc1N1CCC(N(C)C)CC1] | (R)-N-(2-(4-(dimethylamino) piperidin-1-yl)-5-((6-(3-(4-fluoro-3-(trifluoromethyl) phenyl) isoxazolidin-2-yl) pyrimidin-4-yl)amino)-4-methoxyphenyl) acrylamide | $^1$H NMR (400 MHz, DMSO-d6) δ 8.97 (s, 1H), 8.63 (s, 1H), 8.19-8.08 (m, 2H), 7.78 (dq, J = 6.7, 3.9, 2.3 Hz, 2H), 7.51 (dd, J = 10.7, 8.5 Hz, 1H), 6.83 (s, 1H), 6.65 (dd, J = 16.9, 10.1 Hz, 1H), 6.36 (s, 1H), 6.21 (dd, J = 17.0, 2.0 Hz, 1H), 5.72 (d, J = 10.3 Hz, 1H), 5.62 (dd, J = 8.7, 5.1 Hz, 1H), 4.15 (td, J = 7.9, 3.8 Hz, 1H), 3.86 (t, J = 8.1 Hz, 1H), 3.80 (s, 3H), 3.05 (d, J = 11.3 Hz, 2H), 2.80 (dtd, J = 11.9, 8.1, 3.7 Hz, 1H), 2.66 (t, J = 11.8 Hz, 2H), 2.30-2.23 (m, 1H), 2.22 (s, 6H), 2.16 (d, J = 11.3 Hz, 1H), 1.83 (d, J = 10.8 Hz, 2H), 1.73-1.63 (m, 2H); 630.43 [M + H]$^+$ |
| 40 | 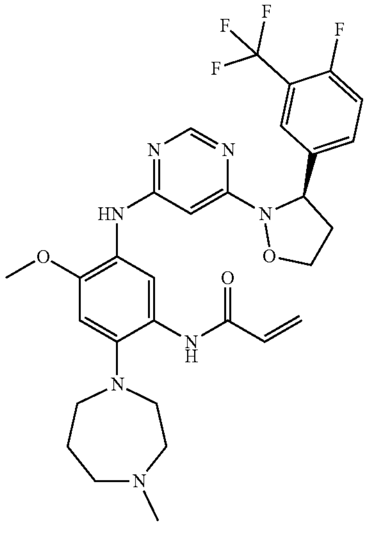 [SMILES: C=CC(=O)Nc1cc(Nc2cc(N3OCC[C@@H]3c3ccc(F)c(C(F)(F)F)c3)ncn2)c(OC)cc1N1CCCN(C)CC1] | (R)-N-(5-((6-(3-(4-fluoro-3-(trifluoromethyl) phenyl) isoxazolidin-2-yl) pyrimidin-4-yl)amino)-4-methoxy-2-(4-methyl-1,4-diazepan-1-yl) phenyl) acrylamide | $^1$H NMR (400 MHz, $CDCl_3$) δ 9.35 (s, 1H), 8.34 (s, 1H), 7.68 (d, J = 6.6 Hz, 1H), 7.63 (d, J = 8.2 Hz, 2H), 7.15 (t, J = 9.2 Hz, 3H), 6.64 (s, 1H), 6.42 (t, J = 14.9 Hz, 2H), 5.87 (dd, J = 10.4, 4.8 Hz, 1H), 5.67 (d, J = 12.9 Hz, 2H), 4.15 (d, J = 9.2 Hz, 1H), 3.87 (d, J = 11.2 Hz, 2H), 3.81 (s, 3H), 3.64 (p, J = 6.6 Hz, 5H), 3.08 (q, J = 7.4 Hz, 5H), 2.92 (s, 4H), 2.73 (d, J = 10.5 Hz, 4H); 616.4 [M + H]$^+$ |

TABLE 1-continued

| Example Compound | Structure | Compound Name | $^1$H NMR; MS $[M + H]^+$ |
|---|---|---|---|
| 41 | 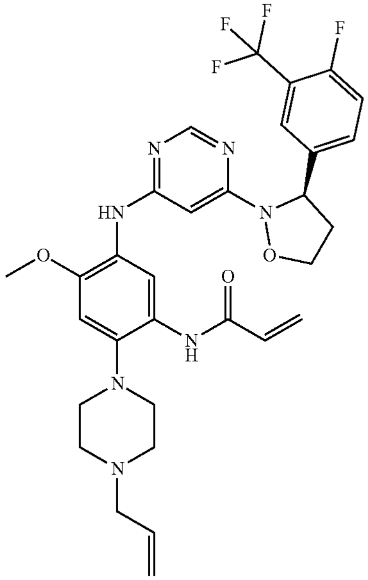 [SMILES: C=CCN1CCN(c2cc(OC)c(Nc3cc(N4OCC[C@@H]4c4ccc(F)c(C(F)(F)F)c4)ncn3)cc2NC(=O)C=C)CC1] | (R)-N-(2-(4-allylpiperazine-1-yl)-5-((6-(3-(4-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.88 (s, 1H), 8.36 (s, 1H), 7.69 (dd, J = 6.9, 2.3 Hz, 1H), 7.64 (ddd, J = 7.7, 4.6, 2.2 Hz, 1H), 7.15 (t, J = 9.3 Hz, 1H), 7.05 (s, 1H), 6.80 (s, 1H), 6.73 (s, 1H), 6.35 (dd, J = 17.0, 1.7 Hz, 1H), 6.26 (dd, J = 16.9, 9.9 Hz, 2H), 5.90 (ddt, J = 16.8, 10.1, 6.6 Hz, 2H), 5.77-5.73 (m, 1H), 5.73-5.67 (m, 2H), 5.24-5.17 (m, 2H), 4.16 (td, J = 8.1, 4.1 Hz, 1H), 3.82 (s, 3H), 3.10 (d, J = 6.6 Hz, 2H), 2.94-2.90 (m, 4H), 2.79 (dtd, J = 12.2, 8.1, 4.2 Hz, 2H), 2.71-2.58 (m, 4H), 2.32 (dtd, J = 12.5, 8.1, 4.6 Hz, 2H); 628.4 $[M + H]^+$ |
| 42 | 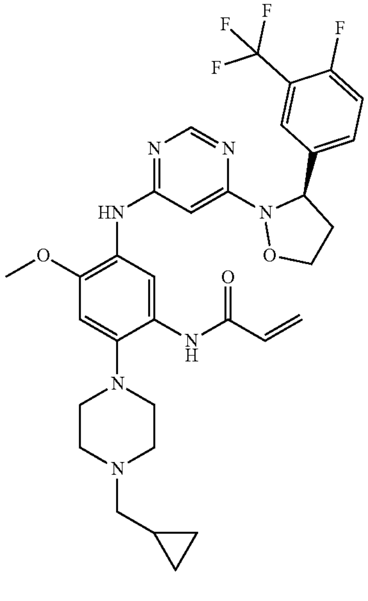 [SMILES: C=CC(=O)Nc1cc(Nc2cc(N3OCC[C@@H]3c3ccc(F)c(C(F)(F)F)c3)ncn2)c(OC)cc1N1CCN(CC2CC2)CC1] | (R)-N-(2-(4-(cyclopropyl methyl)piperazin-1-yl)-5-((6-(3-(4-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.89 (s, 1H), 8.36 (d, J = 1.0 Hz, 1H), 7.70 (dd, J = 6.8, 2.3 Hz, 1H), 7.65 (ddd, J = 7.5, 4.6, 2.3 Hz, 1H), 7.17 (t, J = 9.3 Hz, 1H), 7.05 (d, J = 3.2 Hz, 1H), 6.83 (s, 1H), 6.73 (s, 1H), 6.36 (dd, J = 17.0, 1.7 Hz, 1H), 6.31-6.22 (m, 2H), 5.75 (dd, J = 9.9, 1.7 Hz, 2H), 5.73-5.67 (m, 1H), 4.18 (dt, J = 8.1, 4.0 Hz, 1H), 3.83 (s, 3H), 2.95 (t, J = 5.0 Hz, 4H), 2.85-2.64 (m, 5H), 2.55-2.52 (m, 1H), 2.36 (d, J = 6.5 Hz, 3H), 2.28 (d, J = 6.7 Hz, 1H), 1.26 (d, J = 4.7 Hz, 1H), 0.97-0.82 (m, 2H), 0.60-0.55 (m, 2H), 0.16 (dt, J = 6.1, 4.5 Hz, 2H); 642.5 $[M + H]^+$ |

TABLE 1-continued

| Example Compound | Structure | Compound Name | $^1$H NMR; MS [M + H]$^+$ |
|---|---|---|---|
| 43 | 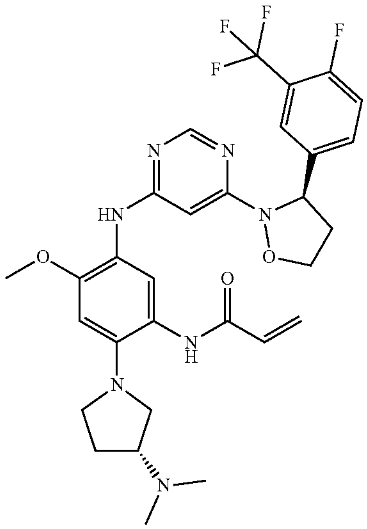 [SMILES: C=CC(=O)Nc1cc(Nc2cc(N3OCC[C@@H]3c3ccc(F)c(C(F)(F)F)c3)ncn2)c(OC)cc1N1CC[C@@H](N(C)C)C1] | N-(2-((R)-3-(dimethylamino) pyrrolidin-1-yl)-5-((6-((R)-3-(4-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.84 (s, 1H), 8.30 (d, J = 1.8 Hz, 1H), 7.68 (dd, J = 6.8, 2.3 Hz, 1H), 7.62 (ddd, J = 7.4, 4.7, 2.2 Hz, 1H), 7.14 (t, J = 9.3 Hz, 1H), 7.04 (d, J = 7.4 Hz, 1H), 6.90 (dd, J = 16.8, 10.2 Hz, 1H), 6.65 (d, J = 2.7 Hz, 1H), 6.60 (d, J = 2.2 Hz, 1H), 6.37 (dt, J = 16.9, 1.9 Hz, 1H), 5.68 (ddd, J = 9.2, 4.2, 2.4 Hz, 2H), 4.15 (td, J = 8.1, 4.0 Hz, 1H), 3.79 (d, J = 1.9 Hz, 3H), 3.50 (dd, J = 10.7, 3.3 Hz, 1H), 3.46-3.32 (m, 3H), 3.05-2.88 (m, 3H), 2.77 (dtd, J = 15.1, 7.9, 7.3, 3.8 Hz, 2H), 2.64 (s, 6H), 2.35-2.23 (m, 4H); 616.5 [M + H]$^+$ |
| 44 | 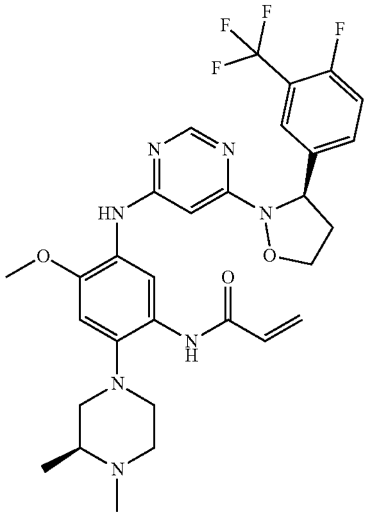 [SMILES: C=CC(=O)Nc1cc(Nc2cc(N3OCC[C@@H]3c3ccc(F)c(C(F)(F)F)c3)ncn2)c(OC)cc1N1CCN(C)[C@@H](C)C1] | N-(2-((S)-3,4-dimethylpiperazin-1-yl)-5-((6-((R)-3-(4-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.87 (s, 1H), 8.37-8.34 (m, 1H), 7.70 (dd, J = 6.9, 2.3 Hz, 1H), 7.65 (ddd, J = 7.6, 4.5, 2.2 Hz, 1H), 7.21-7.12 (m, 2H), 6.80 (s, 1H), 6.71 (s, 1H), 6.35 (d, J = 2.0 Hz, 1H), 6.34-6.30 (m, 1H), 5.75 (dd, J = 9.5, 2.0 Hz, 1H), 5.71 (dd, J = 8.7, 4.6 Hz, 1H), 4.17 (td, J = 8.0, 4.1 Hz, 1H), 3.85 (s, 3H), 3.65 (p, J = 6.7 Hz, 1H), 3.12 (d, J = 4.1 Hz, 2H), 2.97-2.87 (m, 2H), 2.80 (ddq, J = 12.3, 7.8, 4.4 Hz, 3H), 2.70-2.58 (m, 2H), 2.50 (s, 4H), 2.33 (dtd, J = 12.6, 8.1, 4.7 Hz, 1H), 1.54 (t, J = 7.4 Hz, 2H), 1.24 (d, J = 6.3 Hz, 3H); 616.4 [M + H]$^+$ |
| 45 | 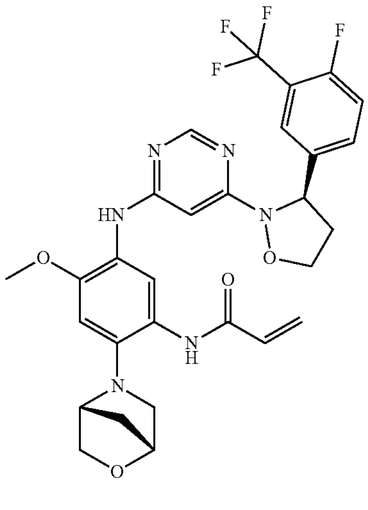 [SMILES: C=CC(=O)Nc1cc(Nc2cc(N3OCC[C@@H]3c3ccc(F)c(C(F)(F)F)c3)ncn2)c(OC)cc1N1C[C@H]2C[C@@H]1CO2] | N-(2-((1R,4R)-2-oxa-5-azabicyclo[2.2.1]heptan-5-yl)-5-((6-((R)-3-(4-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.60 (s, 1H), 7.97 (s, 1H), 7.69 (dd, J = 6.9, 2.3 Hz, 1H), 7.64 (ddd, J = 7.7, 4.5, 2.3 Hz, 1H), 7.20-7.12 (m, 1H), 6.95 (s, 1H), 6.70 (d, J = 5.6 Hz, 2H), 6.38 (dd, J = 16.9, 1.6 Hz, 1H), 6.28 (dd, J = 16.9, 9.9 Hz, 1H), 5.77-5.72 (m, 1H), 5.72-5.68 (m, 1H), 4.64 (s, 1H), 4.17 (td, J = 8.0, 4.1 Hz, 1H), 4.05 (dd, J = 12.8, 7.9 Hz, 2H), 3.87 (s, 1H), 3.85 (s, 3H), 3.77-3.72 (m, 1H), 3.44 (d, J = 10.1 Hz, 1H), 3.19 (d, J = 10.1 Hz, 1H), 2.78 (dtd, J = 12.2, 8.0, 4.1 Hz, 1H), 2.37-2.27 (m, 1H), 2.08 (d, J = 9.3 Hz, 1H), 1.99 (d, J = 10.8 Hz, 1H), 1.84 (d, J = 19.8 Hz, 2H), 1.38-1.20 (m, 2H); 601.4 [M + H]$^+$ |

TABLE 1-continued

| Example Compound | Structure | Compound Name | $^1H$ NMR; MS $[M + H]^+$ |
| --- | --- | --- | --- |
| 46 | 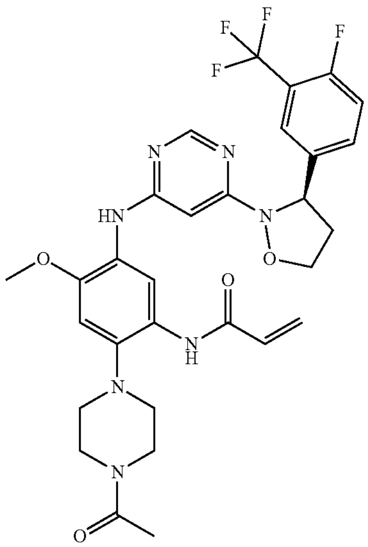 [SMILES: C=CC(=O)Nc1cc(Nc2cc(N3OCC[C@@H]3c3ccc(F)c(C(F)(F)F)c3)ncn2)c(OC)cc1N1CCN(C(C)=O)CC1] | (R)-N-(2-(4-acetylpiperazin-1-yl)-5-((6-(3-(4-fluoro-3-(trifluoromethyl)phenyl)isoxazolidin-2-yl)pyrimidin-4-yl)amino)-4-methoxyphenyl)acrylamide | $^1H$ NMR (400 MHz, $CDCl_3$) δ 8.93 (s, 1H), 8.38 (d, J = 1.0 Hz, 1H), 7.71 (dd, J = 6.8, 2.3 Hz, 1H), 7.65 (ddd, J = 7.4, 4.6, 2.3 Hz, 1H), 7.21-7.14 (m, 1H), 7.04 (s, 1H), 6.73 (d, J = 7.0 Hz, 3H), 6.38 (dd, J = 16.9, 1.5 Hz, 1H), 6.27 (dd, J = 16.9, 10.0 Hz, 1H), 5.77 (dd, J = 10.0, 1.5 Hz, 1H), 5.72 (dd, J = 8.7, 4.6 Hz, 1H), 4.21-4.15 (m, 1H), 3.85 (s, 3H), 3.80 (s, 2H), 3.65 (t, J = 5.0 Hz, 2H), 2.88 (p, J = 5.1, 4.6 Hz, 5H), 2.80 (ddd, J = 12.2, 8.2, 4.4 Hz, 1H), 2.38-2.29 (m, 1H), 2.17 (s, 4H), 1.78 (s, 1H), 1.28 (d, J = 19.9 Hz, 1H); 630.3 $[M + H]^+$ |
| 47 | 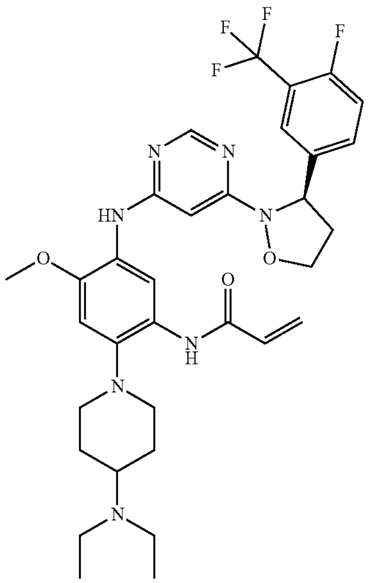 [SMILES: C=CC(=O)Nc1cc(Nc2cc(N3OCC[C@@H]3c3ccc(F)c(C(F)(F)F)c3)ncn2)c(OC)cc1N1CCC(N(CC)CC)CC1] | (R)-N-(2-(4-(diethylamino)piperidin-1-yl)-5-((6-(3-(4-fluoro-3-(trifluoromethyl)phenyl)isoxazolidin-2-yl)pyrimidin-4-yl)amino)-4-methoxyphenyl)acrylamide | $^1H$ NMR (400 MHz, DMSO-$d_6$) δ 8.96 (s, 1H), 8.63 (s, 1H), 8.16 (d, J = 3.0 Hz, 2H), 7.78 (dq, J = 6.9, 3.5, 2.3 Hz, 2H), 7.51 (dd, J = 10.8, 8.5 Hz, 1H), 6.83 (s, 1H), 6.66 (dd, J = 17.0, 10.2 Hz, 1H), 6.36 (s, 1H), 6.21 (dd, J = 16.9, 2.0 Hz, 1H), 5.72 (d, J = 10.3 Hz, 1H), 5.62 (dd, J = 8.7, 5.0 Hz, 1H), 4.15 (td, J = 7.8, 3.7 Hz, 1H), 3.85 (q, J = 8.0 Hz, 1H), 3.79 (s, 3H), 3.04 (d, J = 11.3 Hz, 2H), 2.81 (ddd, J = 12.0, 8.0, 3.9 Hz, 1H), 2.67 (s, 2H), 2.55 (q, J = 7.2 Hz, 5H), 2.29-2.20 (m, 1H), 1.78-1.67 (m, 4H), 0.99 (t, J = 7.1 Hz, 6H); 658.45 $[M + H]^+$ |

TABLE 1-continued

| Example Compound | Structure | Compound Name | $^1$H NMR; MS [M + H]$^+$ |
|---|---|---|---|
| 48 | 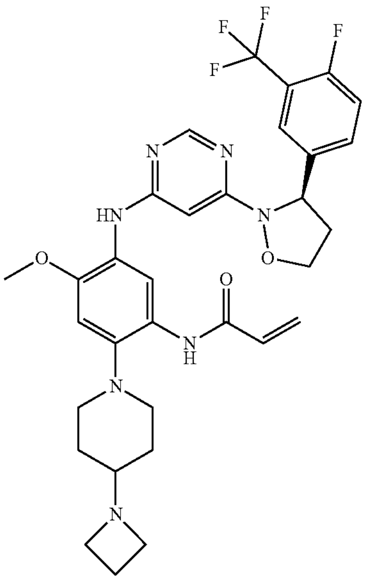 [SMILES: C=CC(=O)Nc1cc(Nc2cc(N3OCC[C@@H]3c3ccc(F)c(C(F)(F)F)c3)ncn2)c(OC)cc1N1CCC(N2CCC2)CC1] | (R)-N-(2-(4-(azetidin-1-yl)piperidin-1-yl)-5-((6-(3-(4-fluoro-3-(trifluoromethyl)phenyl)isoxazolidin-2-yl)pyrimidin-4-yl)amino)-4-methoxyphenyl)acrylamide | $^1$H NMR (400 MHz, DMSO-d6) δ 8.94 (s, 1H), 8.63 (s, 1H), 8.15 (d, J = 12.1 Hz, 2H), 7.78 (td, J = 8.6, 6.7, 3.8 Hz, 2H), 7.51 (dd, J = 10.7, 8.5 Hz, 1H), 6.82 (s, 1H), 6.62 (dd, J = 17.0, 10.2 Hz, 1H), 6.36 (s, 1H), 6.20 (dd, J = 17.0, 1.9 Hz, 1H), 5.74-5.66 (m, 1H), 5.62 (dd, J = 8.7, 5.1 Hz, 1H), 4.15 (td, J = 8.0, 3.8 Hz, 1H), 3.85 (q, J = 7.7 Hz, 1H), 3.80 (s, 3H), 3.08 (t, J = 6.8 Hz, 4H), 3.02-2.94 (m, 2H), 2.79 (dq, J = 8.4, 4.4 Hz, 1H), 2.63 (t, J = 10.7 Hz, 2H), 2.25 (dtd, J = 13.1, 8.2, 4.6 Hz, 1H), 2.10 (dt, J = 13.3, 5.1 Hz, 1H), 1.93 (p, J = 6.8 Hz, 2H), 1.73 (d, J = 12.4 Hz, 2H), 1.43 (d, J = 10.3 Hz, 2H); 642.43 [M + H]$^+$ |
| 49 | 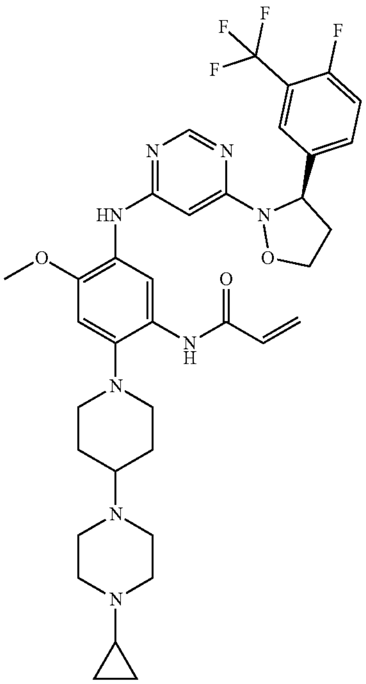 [SMILES: C=CC(=O)Nc1cc(Nc2cc(N3OCC[C@@H]3c3ccc(F)c(C(F)(F)F)c3)ncn2)c(OC)cc1N1CCC(N2CCN(C3CC3)CC2)CC1] | (R)-N-(2-(4-(4-cyclopropyl-1-yl)piperidin-1-yl)-5-((6-(3-(4-fluoro-3-(trifluoromethyl)phenyl)isoxazolidin-2-yl)pyrimidin-4-yl)amino)-4-methoxyphenyl)acrylamide | $^1$H NMR (400 MHz, DMSO-d6) δ 8.94 (s, 1H), 8.63 (s, 1H), 8.15 (d, J = 9.8 Hz, 2H), 7.76 (d, J = 7.3 Hz, 2H), 7.50 (t, J = 9.7 Hz, 1H), 6.82 (s, 1H), 6.65 (dd, J = 17.0, 10.2 Hz, 1H), 6.35 (s, 1H), 6.20 (d, J = 17.0 Hz, 1H), 5.71 (d, J = 10.3 Hz, 1H), 5.61 (d, J = 7.0 Hz, 1H), 4.14 (d, J = 8.5 Hz, 1H), 3.89-3.70 (m, 4H), 3.04 (d, J = 11.3 Hz, 2H), 2.86-2.74 (m, 1H), 2.70-2.61 (m, 2H), 2.59-2.50 (m, 7H), 2.32-2.18 (m, 3H), 1.83 (d, J = 12.1 Hz, 2H), 1.76-1.62 (m, 2H), 1.62-1.51 (m, 1H), 0.39 (d, J = 6.3 Hz, 2H), 0.27 (d, J = 3.7 Hz, 2H); 711.49 [M + H]$^+$ |

TABLE 1-continued

| Example Compound | Structure | Compound Name | $^1$H NMR; MS $[M + H]^+$ |
| --- | --- | --- | --- |
| 50 | 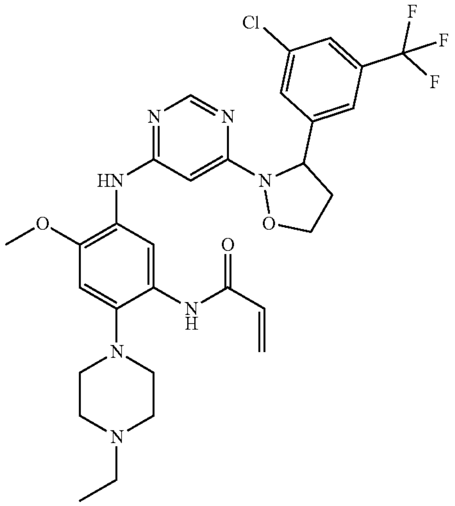 [SMILES: C=CC(=O)Nc1cc(Nc2cc(N3OCCC3c3cc(Cl)cc(C(F)(F)F)c3)ncn2)c(OC)cc1N1CCN(CC)CC1] | N-(5-((6-(3-(3-chloro-5-(trifluoromethyl)phenyl)isoxazolidin-2-yl)pyrimidin-4-yl)amino)-2-(4-ethylpiperazin-1-yl)-4-methoxyphenyl)acrylamide | $^1$H NMR (400 MHz, CDCl3) δ 11.05 (s, 1H), 8.19 (d, J = 6.4 Hz, 1H), 8.08 (s, 1H), 7.55 (s, 1H), 7.50 (s, 1H), 7.46 (s, 1H), 6.75 (s, 1H), 6.43 (dt, J = 33.6, 13.0 Hz, 2H), 6.00 (s, 1H), 5.75 (d, J = 10.9 Hz, 1H), 5.59 (dd, J = 8.7, 5.2 Hz, 1H), 4.30 (td, J = 7.6, 4.5 Hz, 1H), 4.09 (dd, J = 15.5, 8.0 Hz, 1H), 3.78 (s, 3H), 3.65 (s, 2H), 3.47-3.29 (m, 2H), 3.22-2.98 (m, 6H), 2.94 (dd, J = 11.9, 8.1 Hz, 1H), 2.38 (ddd, J = 17.5, 10.1, 4.1 Hz, 1H), 1.46-1.37 (m, 3H); 632.41 $[M + H]^+$ |
| 51 | 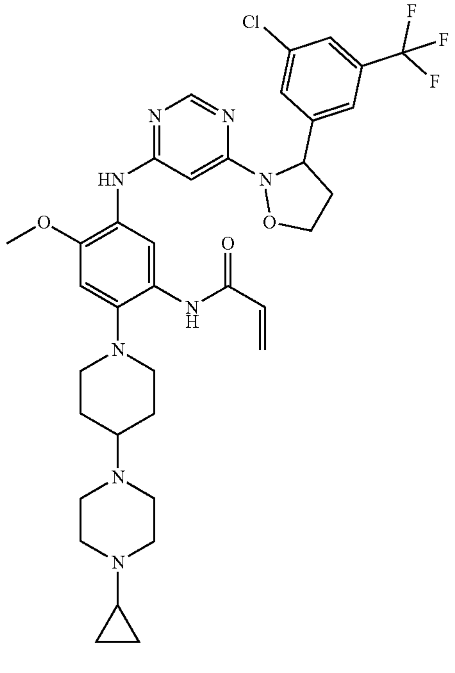 [SMILES: C=CC(=O)Nc1cc(Nc2cc(N3OCCC3c3cc(Cl)cc(C(F)(F)F)c3)ncn2)c(OC)cc1N1CCC(N2CCN(C3CC3)CC2)CC1] | N-(5-((6-(3-(3-chloro-5-(trifluoromethyl)phenyl)isoxazolidin-2-yl)pyrimidin-4-yl)amino)-2-(4-(4-cyclopropyl-1-yl)piperidin-1-yl)-4-methoxyphenyl)acrylamide | $^1$H NMR (400 MHz, CDCl3) δ 8.85 (s, 1H), 8.45 (s, 1H), 8.36 (d, J = 0.8 Hz, 1H), 7.67 (s, 1H), 7.61 (s, 1H), 7.49 (s, 1H), 6.97 (s, 1H), 6.77-6.71 (m, 2H), 6.31 (ddd, J = 26.9, 16.9, 5.7 Hz, 2H), 5.77-5.68 (m, 2H), 4.22-4.00 (m, 2H), 3.84 (s, 3H), 3.06 (d, J = 10.3 Hz, 2H), 2.87-2.55 (m, 10H), 2.40-2.28 (m, 2H), 2.08 (d, J = 11.8 Hz, 2H), 1.75-1.60 (m, 3H), 0.45 (dt, J = 21.6, 7.0 Hz, 4H); 727.50 $[M + H]^+$ |

TABLE 1-continued

| Example Compound | Structure | Compound Name | $^1$H NMR; MS $[M + H]^+$ |
|---|---|---|---|
| 52 | 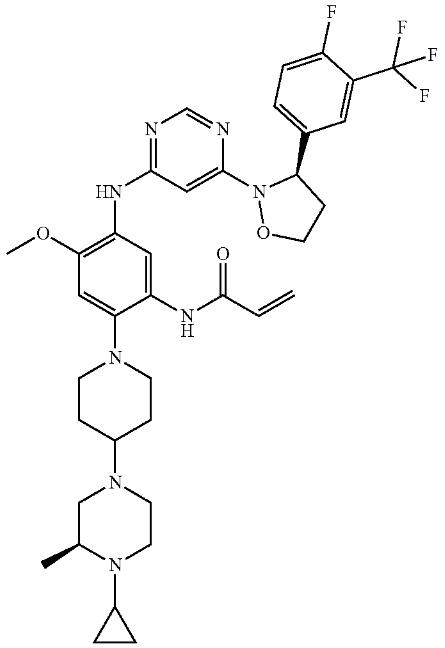 [SMILES: C=CC(=O)Nc1cc(Nc2cc(N3OCC[C@@H]3c3ccc(F)c(C(F)(F)F)c3)ncn2)c(OC)cc1N1CCC(N2CCN(C3CC3)[C@@H](C)C2)CC1] | N-(2-(4-((S)-4-cyclopropyl-3-methylpiperazin-1-yl)piperidin-1-yl)-5-((6-((R)-3-(4-fluoro-3-(trifluoromethyl) phenyl) isoxazolidin-2-yl) pyrimidin-4-yl)amino)-4-methoxyphenyl) acrylamide | $^1$H NMR (400 MHz, DMSO-d6) δ 8.94 (s, 1H), 8.63 (s, 1H), 8.15 (d, J = 11.1 Hz, 2H), 7.83-7.73 (m, 2H), 7.54-7.47 (m, 1H), 6.82 (s, 1H), 6.66 (dd, J = 17.0, 10.2 Hz, 1H), 6.35 (s, 1H), 6.20 (dd, J = 16.9, 2.0 Hz, 1H), 5.72 (d, J = 10.1 Hz, 1H), 5.62 (dd, J = 8.6, 5.0 Hz, 1H), 4.15 (td, J = 7.9, 3.8 Hz, 1H), 3.89-3.72 (m, 4H), 3.04 (d, J = 11.1 Hz, 2H), 2.86-2.62 (m, 6H), 2.41 (s, 1H), 2.27 (dt, J = 26.9, 10.8 Hz, 4H), 1.92 (t, J = 9.8 Hz, 1H), 1.83 (d, J = 12.0 Hz, 2H), 1.69 (d, J = 11.4 Hz, 2H), 1.49 (s, 1H), 1.10 (d, J = 6.3 Hz, 3H), 0.62-0.51 (m, 1H), 0.45-0.32 (m, 2H), 0.17 (dd, J = 9.8, 6.3 Hz, 1H); 725.56 $[M + H]^+$ |
| 53 | 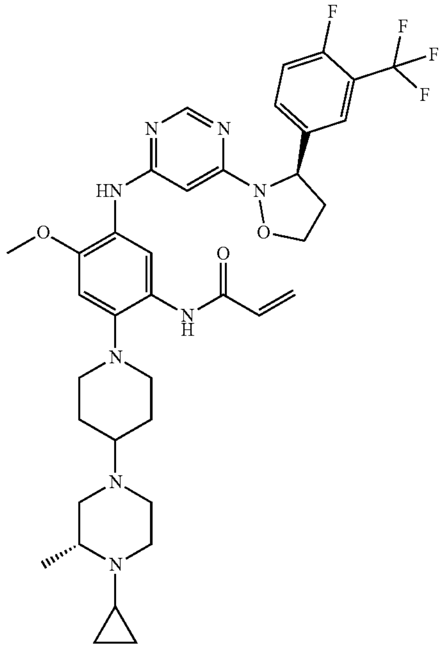 [SMILES: C=CC(=O)Nc1cc(Nc2cc(N3OCC[C@@H]3c3ccc(F)c(C(F)(F)F)c3)ncn2)c(OC)cc1N1CCC(N2CCN(C3CC3)[C@H](C)C2)CC1] | N-(2-(4-((R)-4-cyclopropyl-3-methylpiperazin-1-yl)piperidin-1-yl)-5-((6-((R)-3-(4-fluoro-3-(trifluoromethyl) phenyl) isoxazolidin-2-yl)pyrimidin-4-yl)amino)-4-methoxyphenyl) acrylamide | $^1$H NMR (400 MHz, DMSO-d6) δ 8.94 (s, 1H), 8.63 (s, 1H), 8.15 (d, J = 11.4 Hz, 2H), 7.76 (m, J = 7.4 Hz, 2H), 7.51 (t, J = 9.6 Hz, 1H), 6.82 (s, 1H), 6.66 (dd, J = 16.9, 10.1 Hz, 1H), 6.35 (s, 1H), 6.20 (d, J = 16.9 Hz, 1H), 5.72 (d, J = 10.3 Hz, 1H), 5.62 (dd, J = 8.7, 5.1 Hz, 1H), 4.18-4.11 (m, 1H), 3.89-3.72 (m, 4H), 3.04 (d, J = 11.3 Hz, 2H), 2.75 (m, J = 52.3, 24.2, 9.7 Hz, 6H), 2.41 (s, 1H), 2.27 (dt, J = 26.9, 10.7 Hz, 4H), 1.93 (t, J = 10.2 Hz, 1H), 1.83 (d, J = 12.4 Hz, 2H), 1.69 (t, J = 11.6 Hz, 2H), 1.49 (s, 1H), 1.10 (d, J = 6.3 Hz, 3H), 0.57 (m, 1H), 0.40 (m, J = 9.8 Hz, 2H), 0.17 (m, 1H); 725.56 $[M + H]^+$ |

TABLE 1-continued

| Example Compound | Structure | Compound Name | $^1H$ NMR; MS $[M + H]^+$ |
|---|---|---|---|
| 54 | 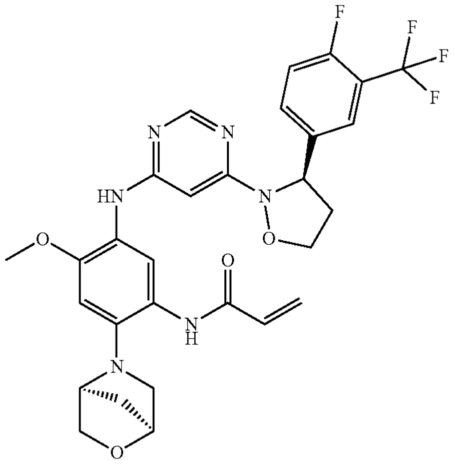 [SMILES: C=CC(=O)Nc1cc(Nc2cc(N3OCC[C@@H]3c3ccc(F)c(C(F)(F)F)c3)ncn2)c(OC)cc1N1C[C@@H]2C[C@H]1CO2] | N-(2-((1S,4S)-2-oxa-5-azabicyclo[2.2.1]heptan-5-yl)-5-((6-((R)-3-(4-fluoro-3-(trifluoromethyl)phenyl)isoxazolidin-2-yl)pyrimidin-4-yl)amino)-4-methoxyphenyl)acrylamide | $^1H$ NMR (400 MHz, DMSO-d6) δ 9.27 (s, 1H), 8.52 (s, 1H), 8.13 (d, J = 1.0 Hz, 1H), 7.82-7.73 (m, 2H), 7.56-7.45 (m, 1H), 7.37 (s, 1H), 6.51-6.40 (m, 2H), 6.25 (s, 1H), 6.18 (dd, J = 17.0, 2.1 Hz, 1H), 5.68 (dd, J = 10.1, 2.1 Hz, 1H), 5.61 (dd, J = 8.6, 5.0 Hz, 1H), 4.53 (s, 1H), 4.41 (s, 1H), 4.14 (td, J = 7.9, 3.9 Hz, 1H), 3.95 (d, J = 7.6 Hz, 1H), 3.87-3.72 (m, 5H), 3.49 (d, J = 9.4 Hz, 1H), 2.91 (d, J = 9.6 Hz, 1H), 2.84-2.73 (m, 1H), 2.29-2.20 (m, 1H), 1.88-1.77 (m, 2H); 601.35 $[M + H]^+$ |
| 55 | 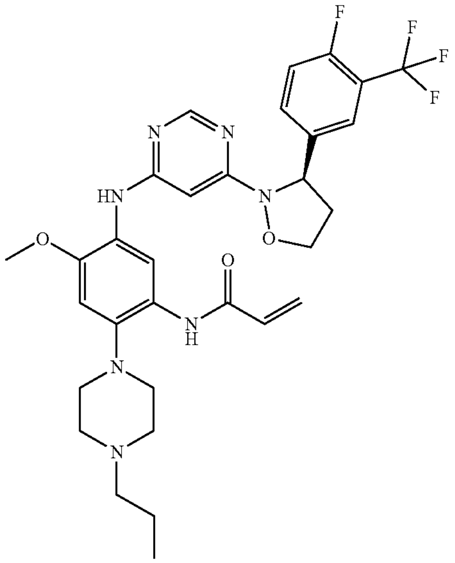 [SMILES: C=CC(=O)Nc1cc(Nc2cc(N3OCC[C@@H]3c3ccc(F)c(C(F)(F)F)c3)ncn2)c(OC)cc1N1CCN(CCC)CC1] | (R)-N-(5-((6-(3-(4-fluoro-3-(trifluoromethyl)phenyl)isoxazolidin-2-yl)pyrimidin-4-yl)amino)-4-methoxy-2-(4-propylpiperazin-1-yl)phenyl)acrylamide | $^1H$ NMR (400 MHz, DMSO-d6) δ 9.01 (s, 1H), 8.67 (s, 1H), 8.17 (d, J = 1.0 Hz, 2H), 7.78 (ddd, J = 11.8, 7.2, 2.4 Hz, 2H), 7.51 (dd, J = 10.8, 8.5 Hz, 1H), 6.85 (s, 1H), 6.71-6.53 (m, 1H), 6.40 (s, 1H), 6.21 (d, J = 16.9 Hz, 1H), 5.73 (d, J = 10.3 Hz, 1H), 5.62 (dd, J = 8.6, 5.0 Hz, 1H), 4.16 (td, J = 7.9, 3.8 Hz, 1H), 3.92-3.75 (m, 4H), 3.54 (m, 1H), 2.89 (s, 4H), 2.80 (qt, J = 7.9, 3.7 Hz, 2H), 2.54 (s, 1H), 2.35-2.19 (m, 2H), 1.51 (m, 3H), 0.92 (m, 4H); 630.43 $[M + H]^+$ |
| 56 | 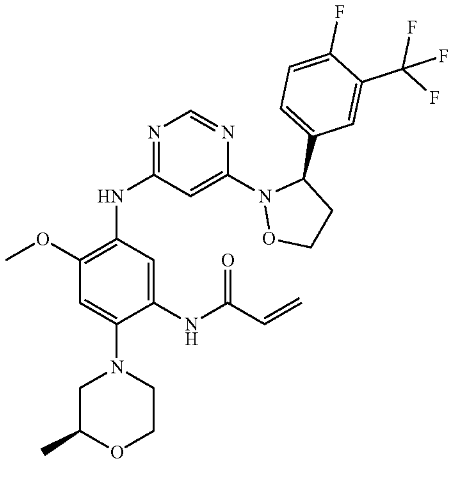 [SMILES: C=CC(=O)Nc1cc(Nc2cc(N3OCC[C@@H]3c3ccc(F)c(C(F)(F)F)c3)ncn2)c(OC)cc1N1CCO[C@@H](C)C1] | N-(5-((6-((R)-3-(4-fluoro-3-(trifluoromethyl)phenyl)isoxazolidin-2-yl)pyrimidin-4-yl)amino)-4-methoxy-2-((S)-2-methylmorpholino)phenyl)acrylamide | $^1H$ NMR (400 MHz, $CDCl_3$) δ 8.90 (s, 1H), 8.36 (d, J = 1.0 Hz, 1H), 7.70 (dd, J = 6.8, 2.3 Hz, 1H), 7.65 (ddd, J = 7.3, 4.6, 2.3 Hz, 1H), 7.16 (t, J = 9.3 Hz, 1H), 7.03 (s, 1H), 6.75 (d, J = 8.3 Hz, 2H), 6.36 (dd, J = 16.9, 1.5 Hz, 1H), 6.25 (dd, J = 16.9, 10.0 Hz, 1H), 5.75 (dd, J = 10.0, 1.6 Hz, 1H), 5.71 (dd, J = 8.7, 4.6 Hz, 1H), 4.17 (td, J = 8.1, 4.2 Hz, 1H), 3.86 (s, 3H), 3.85-3.74 (m, 3H), 2.93-2.74 (m, 5H), 2.59 (dd, J = 11.5, 9.7 Hz, 1H), 2.38-2.27 (m, 1H), 1.77 (s, 2H), 1.25 (s, 3H); 603.5 $[M + H]^+$ |

TABLE 1-continued

| Example Compound | Structure | Compound Name | $^1$H NMR; MS [M + H]$^+$ |
|---|---|---|---|
| 57 | 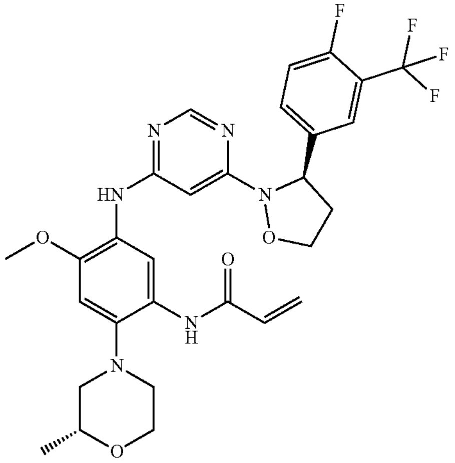 [SMILES: C=CC(=O)Nc1cc(Nc2cc(N3OCC[C@@H]3c3ccc(F)c(C(F)(F)F)c3)ncn2)c(OC)cc1N1CCO[C@H](C)C1] | N-(5-((6-((R)-3-(4-fluoro-3-(trifluoromethyl) phenyl) isoxazolidin-2-yl) pyrimidin-4-yl)amino)-4-methoxy-2-((R)-2-methylmorpholino) phenyl) acrylamide | 603.5 [M + H]$^+$ |
| 58 | 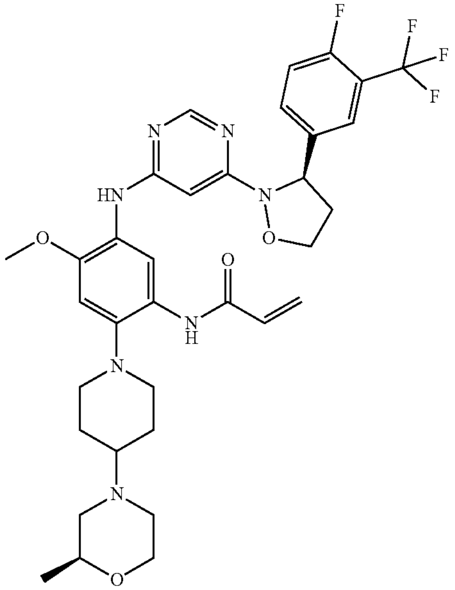 [SMILES: C=CC(=O)Nc1cc(Nc2cc(N3OCC[C@@H]3c3ccc(F)c(C(F)(F)F)c3)ncn2)c(OC)cc1N1CCC(N2CCO[C@@H](C)C2)CC1] | N-(5-((6-((R)-3-(4-fluoro-3-(trifluoromethyl) phenyl) isoxazolidin-2-yl) pyrimidin-4-yl)amino)-4-methoxy-2-(4-((S)-2-methylmorpholino) piperidin-1-yl) phenyl)acrylamide | $^1$H NMR (400 MHz, $CDCl_3$) δ 8.84 (s, 1H), 8.35 (d, J = 1.0 Hz, 1H), 7.69 (dd, J = 6.8, 2.3 Hz, 1H), 7.64 (ddd, J = 7.3, 4.6, 2.3 Hz, 1H), 7.15 (t, J = 9.3 Hz, 1H), 7.01 (s, 1H), 6.75-6.71 (m, 2H), 6.35 (dd, J = 16.9, 1.6 Hz, 1H), 6.24 (dd, J = 16.9, 10.0 Hz, 1H), 5.76-5.68 (m, 2H), 4.16 (td, J = 8.1, 4.1 Hz, 1H), 3.84 (s, 3H), 3.74-3.59 (m, 3H), 3.09-3.03 (m, 2H), 2.91-2.67 (m, 7H), 2.31 (dddd, J = 17.3, 14.5, 9.7, 3.9 Hz, 4H), 2.06 (t, J = 7.7 Hz, 2H), 1.96 (dd, J = 11.1, 10.0 Hz, 2H), 1.65 (qd, J = 12.2, 11.8, 3.8 Hz, 3H), 1.18 (d, J = 6.3 Hz, 3H); 686.4 [M + H]$^+$ |

TABLE 1-continued

| Example Compound | Structure | Compound Name | $^1$H NMR; MS $[M + H]^+$ |
|---|---|---|---|
| 59 | 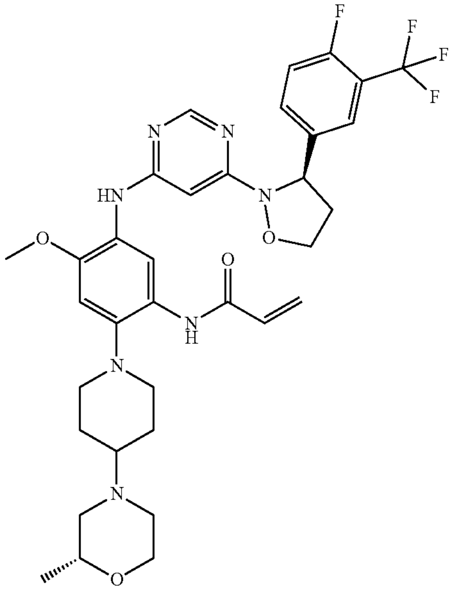 [SMILES: C=CC(=O)Nc1cc(Nc2cc(N3OCC[C@@H]3c3ccc(F)c(C(F)(F)F)c3)ncn2)c(OC)cc1N1CCC(N2CCO[C@H](C)C2)CC1] | N-(5-((6-((R)-3-(4-fluoro-3-(trifluoromethyl) phenyl) isoxazolidin-2-yl) pyrimidin-4-yl)amino)-4-methoxy-2-(4-((R)-2-methylmorpholino) piperidin-1-yl) phenyl) acrylamide | 686.4 $[M + H]^+$ |
| 60 | 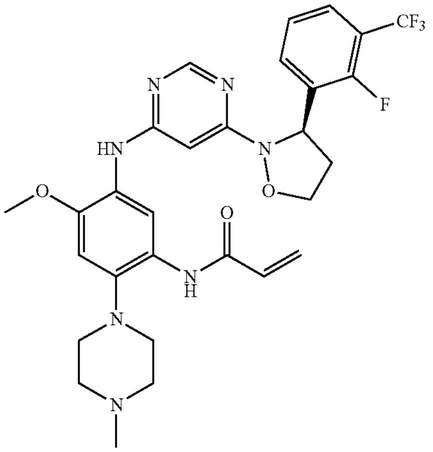 [SMILES: C=CC(=O)Nc1cc(Nc2cc(N3OCC[C@@H]3c3cccc(C(F)(F)F)c3F)ncn2)c(OC)cc1N1CCN(C)CC1] | (R)-N-(5-((6-(3-(2-fluoro-3-(trifluoromethyl) phenyl) isoxazolidin-2-yl) pyrimidin-4-yl)amino)-4-methoxy-2-(4-methylpiperazin-1-yl) phenyl) acrylamide | $^1$H NMR (400 MHz, $CDCl_3$) δ 8.89 (s, 1H), 8.52 (s, 1H), 8.36 (s, 1H), 7.83 (t, J = 7.4 Hz, 1H), 7.50 (t, J = 7.2 Hz, 1H), 7.21 (t, J = 7.8 Hz, 1H), 7.12 (s, 1H), 6.81 (s, 1H), 6.76 (s, 1H), 6.37 (d, J = 16.7 Hz, 1H), 6.27 (dd, J = 17.0, 9.8 Hz, 1H), 5.96 (dd, J = 9.1, 4.5 Hz, 1H), 5.75 (d, J = 10.0 Hz, 1H), 4.19-4.02 (m, 2H), 3.85 (s, 3H), 2.97-2.90 (m, 4H), 2.90-2.86 (m, 1H), 2.75-2.52 (m, 4H), 2.41 (s, 3H), 2.30 (dtd, J = 12.6, 8.2, 4.5 Hz, 1H); 602.4 $[M + H]^+$ |
| 61 | 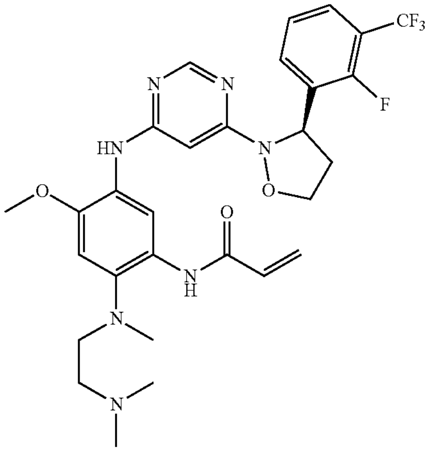 | (R)-N-(2-((2-(dimethylamino) ethyl)(methyl) amino)-5-((6-(3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 10.08 (s, 1H), 8.94 (s, 1H), 8.36 (s, 1H), 7.84 (t, J = 7.4 Hz, 1H), 7.50 (t, J = 7.1 Hz, 1H), 7.21 (t, J = 7.8 Hz, 1H), 6.85-6.78 (m, 2H), 6.44-6.35 (m, 2H), 5.97 (dd, J = 9.1, 4.5 Hz, 1H), 5.72-5.64 (m, 1H), 5.30 (s, 1H), 4.18-4.07 (m, 2H), 3.85 (s, 3H), 2.97-2.82 (m, 4H), 2.72 (s, 3H), 2.41-2.36 (m, 2H), 2.31 (s, 6H); 604.5 $[M + H]^+$ |

TABLE 1-continued

| Example Compound | Structure | Compound Name | $^1$H NMR; MS [M + H]$^+$ |
|---|---|---|---|
| 62 | 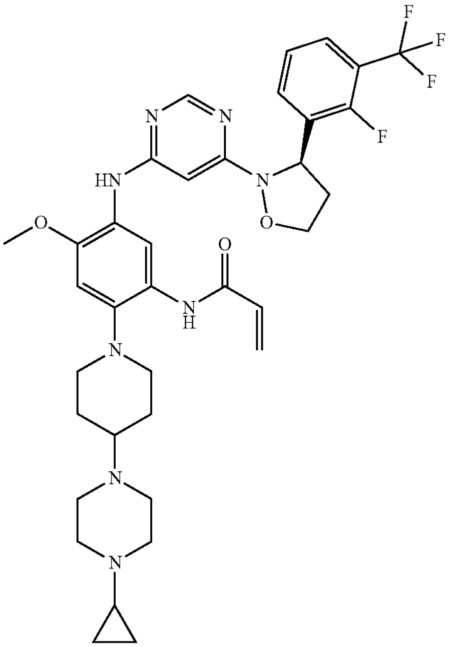 [SMILES: C=CC(=O)Nc1cc(Nc2cc(N3OCC[C@@H]3c3cccc(C(F)(F)F)c3F)ncn2)c(OC)cc1N1CCC(N2CCN(C3CC3)CC2)CC1] | (R)-N-(2-(4-(4-cyclopropyl piperazin-1-yl) piperidin-1-yl)-5-((6-(3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.84 (s, 1H), 8.45 (s, 1H), 8.35 (s, 1H), 7.82 (t, J = 7.3 Hz, 1H), 7.50 (t, J = 7.2 Hz, 1H), 7.21 (t, J = 7.8 Hz, 1H), 7.11 (s, 1H), 6.78-6.70 (m, 2H), 6.36 (d, J = 16.6 Hz, 1H), 6.26 (dd, J = 16.9, 9.9 Hz, 1H), 5.95 (dd, J = 8.9, 4.5 Hz, 1H), 5.74 (d, J = 9.9 Hz, 1H), 4.18-4.02 (m, 2H), 3.84 (s, 3H), 3.06 (d, J = 11.4 Hz, 2H), 2.94-2.82 (m, 2H), 2.80-2.68 (m, 7H), 2.68-2.64 (m, 2H), 2.42-2.25 (m, 2H), 2.09 (d, J = 12.4 Hz, 2H), 1.77-1.62 (m, 3H), 0.45 (dt, J = 14.0, 3.6 Hz, 4H); 711.5 [M + H]$^+$ |
| 63 | 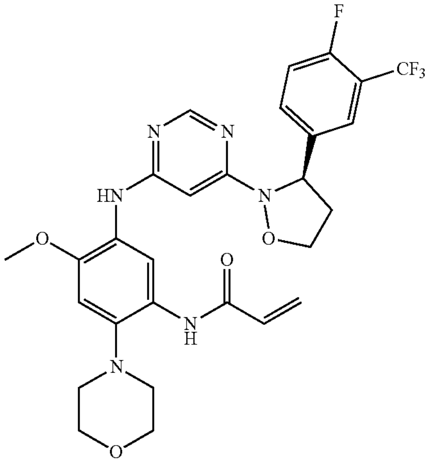 [SMILES: C=CC(=O)Nc1cc(Nc2cc(N3OCC[C@@H]3c3ccc(F)c(C(F)(F)F)c3)ncn2)c(OC)cc1N1CCOCC1] | (R)-N-(5-((6-(3-(4-fluoro-3-(trifluoromethyl) phenyl) isoxazolidin-2-yl) pyrimidin-4-yl)amino)-4-methoxy-2-morpholinophenyl) acrylamide | $^1$H NMR (400 MHz, Chloroform-d) δ 8.92 (s, 1H), 8.52 (s, 1H), 8.38 (d, J = 2.1 Hz, 1H), 7.71 (d, J = 6.4 Hz, 1H), 7.65 (s, 1H), 7.17 (t, J = 9.3 Hz, 1H), 6.99 (s, 1H), 6.80-6.73 (m, 2H), 6.38 (d, J = 16.9 Hz, 1H), 6.31-6.23 (m, 1H), 5.77 (dt, J = 9.8, 2.0 Hz, 1H), 5.72 (s, 1H), 4.18 (s, 1H), 4.13-4.05 (m, 1H), 3.90-3.85 (m, 7H), 2.89 (dd, J = 5.1, 2.5 Hz, 4H), 2.81 (s, 1H), 2.39-2.30 (m, 1H); 589.38 [M + H]$^+$ |

TABLE 1-continued

| Example Compound | Structure | Compound Name | $^1$H NMR; MS [M + H]$^+$ |
|---|---|---|---|
| 64 | 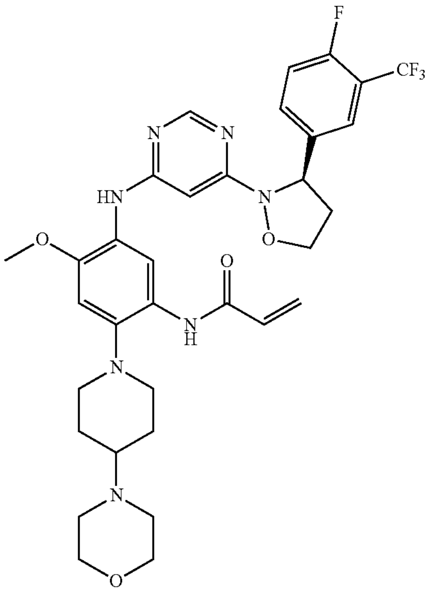 [SMILES: C=CC(=O)Nc1cc(Nc2cc(N3OCC[C@@H]3c3ccc(F)c(C(F)(F)F)c3)ncn2)c(OC)cc1N1CCC(N2CCOCC2)CC1] | (R)-N-(5-((6-(3-(4-fluoro-3-(trifluoromethyl) phenyl) isoxazolidin-2-yl) pyrimidin-4-yl)amino)-4-methoxy-2-(4-morpholino piperidin-1-yl) phenyl) acrylamide | $^1$H NMR (400 MHz, Chloroform-d) δ 8.86 (s, 1H), 8.44 (s, 1H), 8.36 (d, J = 1.0 Hz, 1H), 7.73-7.68 (m, 1H), 7.65 (ddd, J = 7.5, 4.7, 2.4 Hz, 1H), 7.20-7.13 (m, 1H), 6.94 (s, 1H), 6.78-6.71 (m, 2H), 6.36 (dd, J = 17.0, 1.5 Hz, 1H), 6.25 (dd, J = 16.9, 10.0 Hz, 1H), 5.74 (dd, J = 10.0, 1.5 Hz, 1H), 5.73-5.69 (m, 1H), 4.21-4.14 (m, 1H), 4.08 (q, J = 8.0 Hz, 1H), 3.85 (s, 3H), 3.78 (t, J = 4.7 Hz, 4H), 3.07 (d, J = 11.3 Hz, 2H), 2.85-2.68 (m, 3H), 2.66-2.57 (m, 4H), 2.38-2.26 (m, 2H), 2.13-2.00 (m, 2H), 1.65 (d, J = 12.1 Hz, 2H); 672.38 [M + H]$^+$ |
| 65 | 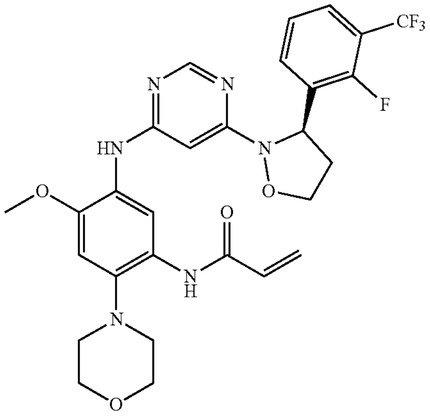 [SMILES: C=CC(=O)Nc1cc(Nc2cc(N3OCC[C@@H]3c3cccc(C(F)(F)F)c3F)ncn2)c(OC)cc1N1CCOCC1] | (R)-N-(5-((6-(3-(2-fluoro-3-(trifluoromethyl) phenyl) isoxazolidin-2-yl) pyrimidin-4-yl)amino)-4-methoxy-2-morpholinophenyl) acrylamide | $^1$H NMR (400 MHz, Chloroform-d) δ 8.91 (s, 1H), 8.51 (s, 1H), 8.37 (d, J = 1.0 Hz, 1H), 7.82 (td, J = 7.5, 1.8 Hz, 1H), 7.55-7.46 (m, 1H), 7.21 (t, J = 7.8 Hz, 1H), 7.10 (s, 1H), 6.81-6.73 (m, 2H), 6.37 (dd, J = 16.9, 1.6 Hz, 1H), 6.27 (dd, J = 16.9, 9.9 Hz, 1H), 5.96 (dd, J = 8.8, 4.5 Hz, 1H), 5.76 (dd, J = 9.9, 1.6 Hz, 1H), 4.19-4.03 (m, 2H), 3.92-3.84 (m, 7H), 2.96-2.82 (m, 5H), 2.37-2.24 (m, 1H); 589.4 [M + H]$^+$ |
| 66 | 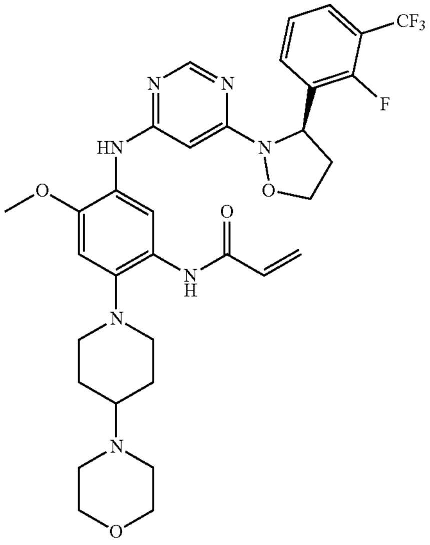 [SMILES: C=CC(=O)Nc1cc(Nc2cc(N3OCC[C@@H]3c3cccc(C(F)(F)F)c3F)ncn2)c(OC)cc1N1CCC(N2CCOCC2)CC1] | (R)-N-(5-((6-(3-(2-fluoro-3-(trifluoromethyl) phenyl) isoxazolidin-2-yl) pyrimidin-4-yl)amino)-4-methoxy-2-(4-morpholino piperidin-1-yl) phenyl) acrylamide | $^1$H NMR (400 MHz, Chloroform-d) δ 8.86 (s, 1H), 8.44 (s, 1H), 8.36 (d, J = 1.0 Hz, 1H), 7.82 (td, J = 7.5, 1.8 Hz, 1H), 7.55-7.46 (m, 1H), 7.21 (t, J = 7.8 Hz, 1H), 7.06 (s, 1H), 6.79-6.73 (m, 2H), 6.36 (dd, J = 17.0, 1.6 Hz, 1H), 6.25 (dd, J = 16.9, 10.0 Hz, 1H), 5.96 (dd, J = 8.8, 4.5 Hz, 1H), 5.74 (dd, J = 10.0, 1.6 Hz, 1H), 4.19-4.10 (m, 1H), 4.10-4.02 (m, 1H), 3.85 (s, 3H), 3.77 (t, J = 4.6 Hz, 4H), 3.12-3.03 (m, 2H), 2.95-2.82 (m, 1H), 2.77 (dd, J = 12.2, 2.2 Hz, 1H), 2.71 (dd, J = 12.1, 2.2 Hz, 1H), 2.65-2.58 (m, 4H), 2.37-2.24 (m, 2H), 2.08 (d, J = 12.2 Hz, 2H), 1.73-1.58 (m, 2H); 672.5 [M + H]$^+$ |

TABLE 1-continued

| Example Compound | Structure | Compound Name | $^1$H NMR; MS [M + H]$^+$ |
|---|---|---|---|
| 67 | 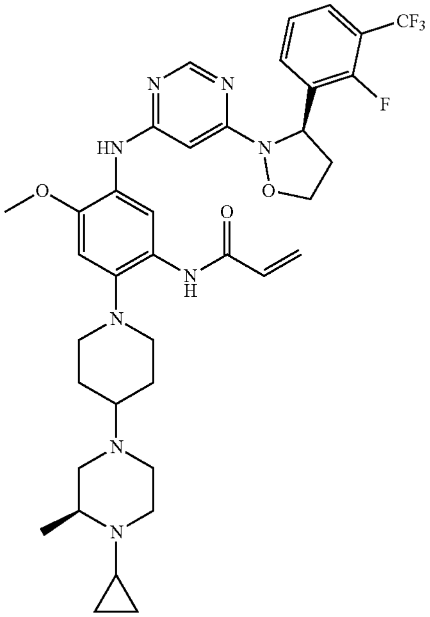 [SMILES: C=CC(=O)Nc1cc(Nc2cc(N3OCC[C@@H]3c3cccc(C(F)(F)F)c3F)ncn2)c(OC)cc1N1CCC(N2CCN(C3CC3)[C@@H](C)C2)CC1] | N-(2-(4-((S)-4-cyclopropyl-3-methylpiperazin-1-yl)piperidin-1-yl)-5-((6-(R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Chloroform-d) δ 8.85 (s, 1H), 8.45 (s, 1H), 8.35 (d, J = 1.0 Hz, 1H), 7.82 (td, J = 7.5, 1.8 Hz, 1H), 7.54-7.46 (m, 1H), 7.21 (t, J = 7.8 Hz, 1H), 7.07 (d, J = 2.2 Hz, 1H), 6.79-6.73 (m, 2H), 6.36 (dd, J = 17.0, 1.6 Hz, 1H), 6.25 (dd, J = 16.9, 10.0 Hz, 1H), 5.95 (dd, J = 8.9, 4.5 Hz, 1H), 5.74 (dd, J = 10.0, 1.6 Hz, 1H), 4.18-4.02 (m, 2H), 3.84 (s, 3H), 3.10-2.99 (m, 3H), 2.99-2.94 (m, 1H), 2.94-2.82 (m, 2H), 2.73 (qd, J = 12.0, 2.2 Hz, 2H), 2.60-2.43 (m, 2H), 2.35-2.26 (m, 3H), 2.12-1.96 (m, 3H), 1.75-1.59 (m, 2H), 1.54 (tt, J = 7.0, 3.9 Hz, 1H), 1.21 (d, J = 6.3 Hz, 3H), 0.71-0.55 (m, 2H), 0.50-0.38 (m, 1H), 0.37-0.27 (m, 1H); 725.6 [M + H]$^+$ |
| 68 | 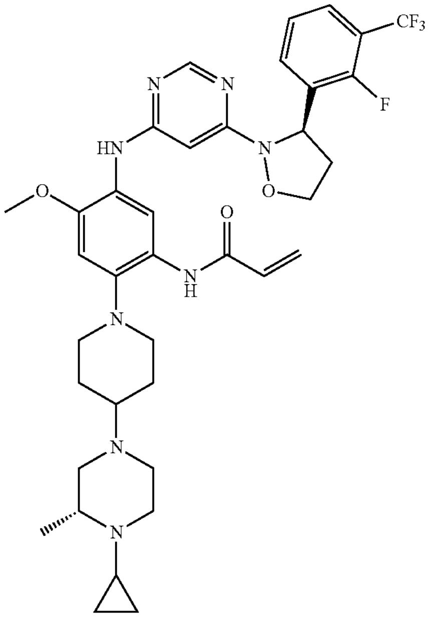 [SMILES: C=CC(=O)Nc1cc(Nc2cc(N3OCC[C@@H]3c3cccc(C(F)(F)F)c3F)ncn2)c(OC)cc1N1CCC(N2CCN(C3CC3)[C@H](C)C2)CC1] | N-(2-(4-((R)-4-cyclopropyl-3-methylpiperazin-1-yl)piperidin-1-yl)-5-((6-(R)-3-(2-fluoro-3-(trifluoromethyl)phenyl)isoxazolidin-2-yl)pyrimidin-4-yl)amino)-4-methoxyphenyl)acrylamide | $^1$HNMR (400 MHz, Chloroform-d) δ 8.84 (s, 1H), 8.45 (s, 1H), 8.35 (s, 1H), 7.87-7.78 (m, 1H), 7.54-7.46 (m, 1H), 7.21 (t, J = 7.8 Hz, 1H), 7.10 (s, 1H), 6.79-6.73 (m, 2H), 6.36 (dd, J = 16.9, 1.6 Hz, 1H), 6.25 (dd, J = 16.9, 9.9 Hz, 1H), 5.95 (dd, J = 8.9, 4.5 Hz, 1H), 5.74 (dd, J = 9.9, 1.6 Hz, 1H), 4.18-4.02 (m, 2H), 3.84 (s, 3H), 3.10-3.06 (m, 1H), 3.06-2.98 (m, 2H), 2.98-2.93 (m, 1H), 2.93-2.82 (m, 2H), 2.78-2.67 (m, 2H), 2.58-2.43 (m, 2H), 2.37-2.23 (m, 3H), 2.12-1.97 (m, 3H), 1.75-1.60 (m, 2H), 1.54 (tt, J = 6.9, 3.8 Hz, 1H), 1.21 (d, J = 6.4 Hz, 3H), 0.71-0.55 (m, 2H), 0.44 (dtd, J = 9.4, 6.6, 4.8 Hz, 1H), 0.32 (tt, J = 10.3, 4.4 Hz, 1H); 725.6 [M + H]$^+$ |

TABLE 1-continued

| Example Compound | Structure | Compound Name | $^1H$ NMR; MS $[M + H]^+$ |
|---|---|---|---|
| 69 | 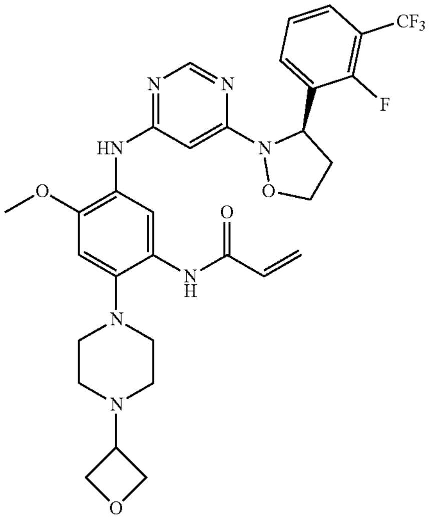 [SMILES: C=CC(=O)Nc1cc(Nc2cc(N3OCC[C@@H]3c3cccc(C(F)(F)F)c3F)ncn2)c(OC)cc1N1CCN(C2COC2)CC1] | (R)-N-(5-((6-(3-(2-fluoro-3-(trifluoromethyl) phenyl) isoxazolidin-2-yl) pyrimidin-4-yl)amino)-4-methoxy-2-(4-(oxetan-3-yl) piperazin-1-yl) phenyl) acrylamide | $^1H$ NMR (400 MHz, Chloroform-d) δ 8.86 (s, 1H), 8.34 (d, J = 1.1 Hz, 1H), 7.84-7.77 (m, 1H), 7.53-7.47 (m, 1H), 7.27 (s, 1H), 7.21 (t, J = 7.8 Hz, 1H), 6.82 (s, 1H), 6.75 (s, 1H), 6.35 (dd, J = 16.9, 1.5 Hz, 1H), 6.25 (dd, J = 16.9, 10.0 Hz, 1H), 5.95 (dd, J = 8.9, 4.5 Hz, 1H), 5.74 (dd, J = 10.0, 1.5 Hz, 1H), 4.69 (dt, J = 19.9, 6.4 Hz, 5H), 4.13 (tt, J = 8.7, 4.4 Hz, 2H), 3.85 (s, 3H), 3.61 (p, J = 6.4 Hz, 1H), 2.96 (td, J = 4.7, 2.3 Hz, 4H), 2.87 (ddd, J = 12.4, 8.3, 4.3 Hz, 2H), 2.54 (s, 4H), 2.37-2.18 (m, 2H); 644.4 $[M + H]^+$ |
| 70 | 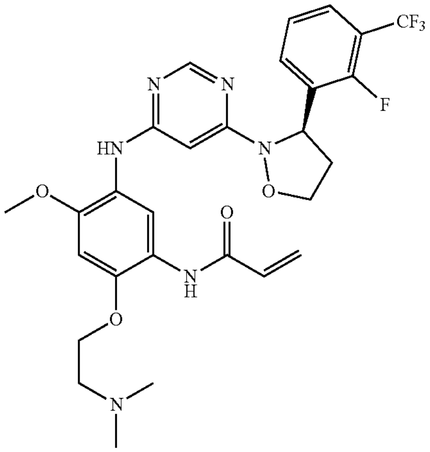 [SMILES: C=CC(=O)Nc1cc(Nc2cc(N3OCC[C@@H]3c3cccc(C(F)(F)F)c3F)ncn2)c(OC)cc1OCCN(C)C] | (R)-N-(2-(2-(dimethylamino) ethoxy)-5-((6-(3-(2-fluoro-3-(trifluoromethyl) phenyl) isoxazolidin-2-yl) pyrimidin-4-yl)amino)-4-methoxyphenyl) acrylamide | $^1H$ NMR (400 MHz, Chloroform-d) δ 8.80 (s, 1H), 8.34 (d, J = 1.0 Hz, 1H), 7.86-7.79 (m, 1H), 7.53-7.46 (m, 1H), 7.21 (t, J = 7.8 Hz, 1H), 6.90 (s, 1H), 6.69 (d, J = 1.1 Hz, 1H), 6.64 (s, 1H), 6.40 (dd, J = 16.9, 1.8 Hz, 1H), 6.27 (dd, J = 17.0, 10.0 Hz, 1H), 5.95 (dd, J = 8.9, 4.5 Hz, 1H), 5.69 (dd, J = 10.0, 1.8 Hz, 1H), 4.15-4.11 (m, 3H), 4.05 (q, J = 8.1 Hz, 1H), 3.83 (s, 3H), 2.61 (dd, J = 6.5, 4.0 Hz, 2H), 2.36 (s, 6H), 2.28 (dddd, J = 14.5, 12.0, 6.1, 4.8 Hz, 2H), 2.08 (s, 2H); 591.4 $[M + H]^+$ |
| 71 | 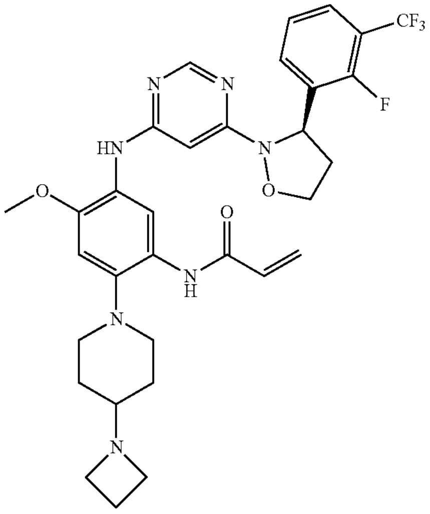 [SMILES: C=CC(=O)Nc1cc(Nc2cc(N3OCC[C@@H]3c3cccc(C(F)(F)F)c3F)ncn2)c(OC)cc1N1CCC(N2CCC2)CC1] | (R)-N-(2-(4-(azetidin-1-yl) piperidin-1-yl)-5-((6-(3-(2-fluoro-3-(trifluoromethyl) phenyl) isoxazolidin-2-yl) pyrimidin-4-yl)amino)-4-methoxyphenyl) acrylamide | $^1H$ NMR (400 MHz, Chloroform-d) δ 8.73 (s, 1H), 8.30 (s, 1H), 7.78 (t, J = 7.2 Hz, 1H), 7.48 (t, J = 6.9 Hz, 1H), 7.32 (t, J = 7.6 Hz, 1H), 7.19 (t, J = 7.8 Hz, 2H), 6.79 (s, 1H), 6.71 (s, 1H), 6.39-6.32 (m, 2H), 5.92 (dd, J = 8.8, 4.6 Hz, 1H), 5.73 (dd, J = 9.5, 2.1 Hz, 1H), 4.15 (d, J = 4.2 Hz, 2H), 3.83 (s, 3H), 3.64 (p, J = 6.7 Hz, 7H), 3.22-3.12 (m, 5H), 2.73-2.65 (m, 3H), 2.29 (ddd, J = 12.3, 8.3, 4.7 Hz, 2H), 2.16-2.10 (m, 2H), 2.03 (d, J = 4.3 Hz, 2H); 642.4 $[M + H]^+$ |

TABLE 1-continued

| Example Compound | Structure | Compound Name | $^1$H NMR; MS [M + H]$^+$ |
|---|---|---|---|
| 72 | 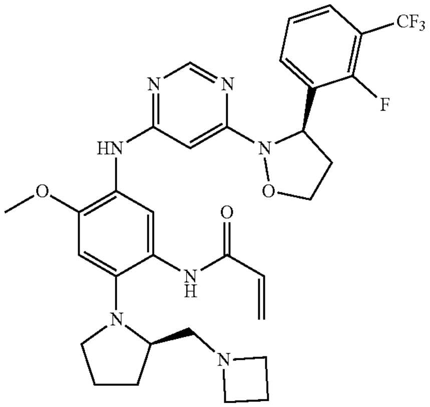 [SMILES: C=CC(=O)Nc1cc(Nc2cc(N3OCC[C@@H]3c3cccc(C(F)(F)F)c3F)ncn2)c(OC)cc1N1CCC[C@@H]1CN1CCC1] | N-(2-((R)-2-(azetidin-1-ylmethyl) pyrrolidin-1-yl)-5-((6-((R)-3-(2-fluoro-3-(trifluoromethyl) phenyl) isoxazolidin-2-yl) pyrimidin-4-yl)amino)-4-methoxyphenyl) acrylamide | $^1$H NMR (400 MHz, Chloroform-d) δ 8.71 (s, 1H), 8.35 (d, J = 1.0 Hz, 1H), 7.81 (d, J = 7.3 Hz, 1H), 7.49 (d, J = 7.1 Hz, 1H), 7.31 (d, J = 6.0 Hz, 1H), 6.97 (s, 1H), 6.79 (s, 1H), 6.73 (s, 1H), 6.41 (d, J = 7.4 Hz, 1H), 6.37 (d, J = 8.6 Hz, 1H), 5.95 (dd, J = 8.8, 4.5 Hz, 1H), 5.73 (d, J = 10.4 Hz, 1H), 4.24-4.20 (m, 1H), 3.84 (s, 3H), 3.58 (d, J = 6.2 Hz, 2H), 3.52-3.40 (m, 4H), 3.29 (dd, J = 13.9, 6.7 Hz, 3H), 2.96 (s, 2H), 2.88 (dt, J = 9.2, 4.2 Hz, 4H), 2.35-2.26 (m, 4H); 642.5 [M + H]$^+$ |
| 73 | 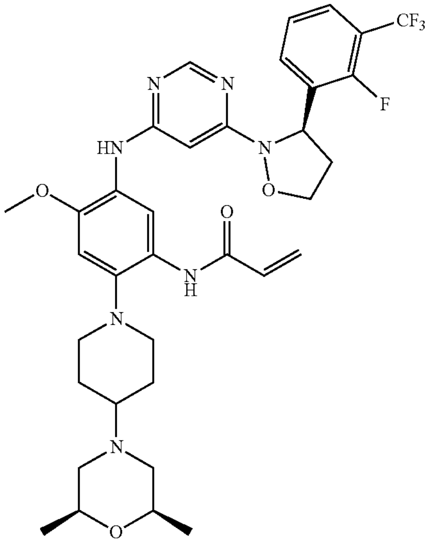 [SMILES: C=CC(=O)Nc1cc(Nc2cc(N3OCC[C@@H]3c3cccc(C(F)(F)F)c3F)ncn2)c(OC)cc1N1CCC(N2C[C@@H](C)O[C@@H](C)C2)CC1] | N-(2-(4-((2S,6R)-2,6-dimethyl morpholino) piperidin-1-yl)-5-((6-((R)-3-(2-fluoro-3-(trifluoromethyl) phenyl) isoxazolidin-2-yl) pyrimidin-4-yl)amino)-4-methoxyphenyl) acrylamide | $^1$H NMR (400 MHz, Chloroform-d) δ 8.85 (s, 1H), 8.35 (d, J = 1.0 Hz, 1H), 7.82 (t, J = 7.2 Hz, 1H), 7.52-7.48 (m, 1H), 7.21 (t, J = 7.8 Hz, 1H), 7.00 (s, 1H), 6.76 (d, J = 6.0 Hz, 2H), 6.37 (dd, J = 16.9, 1.5 Hz, 1H), 6.25 (dd, J = 16.9, 10.0 Hz, 1H), 5.95 (dd, J = 8.9, 4.5 Hz, 1H), 5.74 (dd, J = 10.0, 1.6 Hz, 1H), 4.14 (td, J = 8.2, 4.3 Hz, 1H), 3.85 (s, 3H), 3.70 (dtd, J = 12.4, 6.1, 2.0 Hz, 2H), 3.07 (d, J = 11.4 Hz, 2H), 2.89 (t, J = 1.9 Hz, 1H), 2.87 (s, 1H), 2.78-2.67 (m, 3H), 2.30 (ddt, J = 11.6, 7.8, 3.1 Hz, 3H), 2.07 (d, J = 12.5 Hz, 2H), 1.90 (t, J = 10.7 Hz, 3H), 1.72-1.61 (m, 3H), 1.27-1.23 (m, 3H), 1.20 (d, J = 6.3 Hz, 6H); 700.6 [M + H]$^+$ |
| 74 | 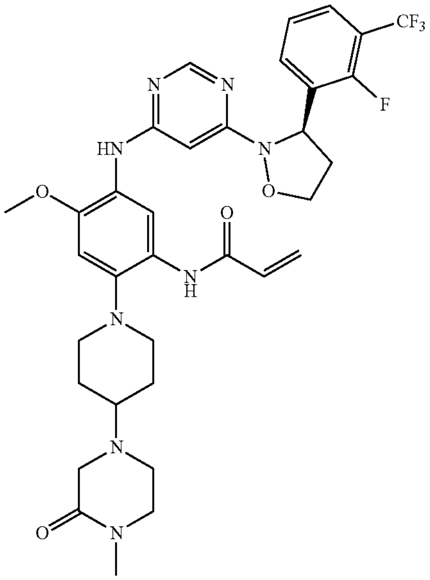 [SMILES: C=CC(=O)Nc1cc(Nc2cc(N3OCC[C@@H]3c3cccc(C(F)(F)F)c3F)ncn2)c(OC)cc1N1CCC(N2CCN(C)C(=O)C2)CC1] | (R)-N-(5-((6-(3-(2-fluoro-3-(trifluoromethyl) phenyl) isoxazolidin-2-yl) pyrimidin-4-yl)amino)-4-methoxy-2-(4-(4-methyl-3-oxopiperazin-1-yl)piperidin-1-yl) phenyl) acrylamide | $^1$H NMR (400 MHz, Chloroform-d) δ 8.84 (s, 1H), 8.35 (d, J = 1.0 Hz, 1H), 7.81 (t, J = 7.1 Hz, 1H), 7.52-7.48 (m, 1H), 7.21 (t, J = 7.8 Hz, 1H), 7.11 (s, 1H), 6.75 (d, J = 3.1 Hz, 2H), 6.36 (dd, J = 16.9, 1.6 Hz, 1H), 6.25 (dd, J = 16.9, 10.0 Hz, 1H), 5.95 (dd, J = 8.9, 4.6 Hz, 1H), 5.75 (dd, J = 10.0, 1.5 Hz, 1H), 4.13 (tt, J = 7.5, 3.8 Hz, 1H), 3.85 (s, 3H), 3.36 (dd, J = 6.3, 4.5 Hz, 2H), 3.33 (s, 2H), 3.07 (d, J = 11.6 Hz, 2H), 2.98 (s, 3H), 2.86-2.82 (m, 3H), 2.74 (td, J = 12.7, 10.3 Hz, 3H), 2.43 (ddt, J = 10.7, 7.4, 3.7 Hz, 2H), 2.30 (h, J = 7.9 Hz, 4H), 2.04 (d, J = 12.4 Hz, 3H), 1.74-1.62 (m, 3H); 699.5 [M + H]$^+$ |

TABLE 1-continued

| Example Compound | Structure | Compound Name | $^1$H NMR; MS [M + H]$^+$ |
|---|---|---|---|
| 75 | 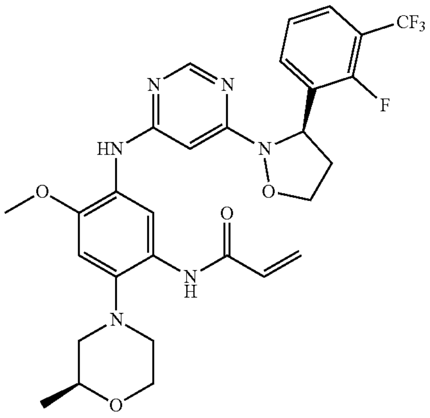 [SMILES: C=CC(=O)Nc1cc(Nc2cc(N3OCC[C@@H]3c3cccc(C(F)(F)F)c3F)ncn2)c(OC)cc1N1CCO[C@@H](C)C1] | N-(5-((6-((R)-3-(2-fluoro-3-(trifluoromethyl)phenyl)isoxazolidin-2-yl)pyrimidin-4-yl)amino)-4-methoxy-2-((S)-2-methylmorpholino)phenyl)acrylamide | 603.23 [M + H] $^1$H NMR (400 MHz, Chloroform-d) δ 8.91 (s, 1H), 8.51 (s, 1H), 8.37 (d, J = 1.0 Hz, 1H), 7.82 (t, J = 7.3 Hz, 1H), 7.51 (t, J = 7.2 Hz, 1H), 7.21 (d, J = 7.8 Hz, 1H), 7.06 (s, 1H), 6.77 (d, J = 5.2 Hz, 2H), 6.41-6.34 (m, 1H), 6.26 (dd, J = 16.9, 10.0 Hz, 1H), 5.96 (dd, J = 8.8, 4.6 Hz, 1H), 5.76 (dd, J = 10.0, 1.5 Hz, 1H), 4.15-4.01 (m, 3H), 3.87 (s, 3H), 3.84-3.77 (m, 2H), 2.93-2.77 (m, 4H), 2.60 (dd, J = 11.5, 9.8 Hz, 1H), 2.36-2.26 (m, 1H), 1.25 (d, J = 6.3 Hz, 3H); 603.38 [M + H]$^+$ |
| 76 | 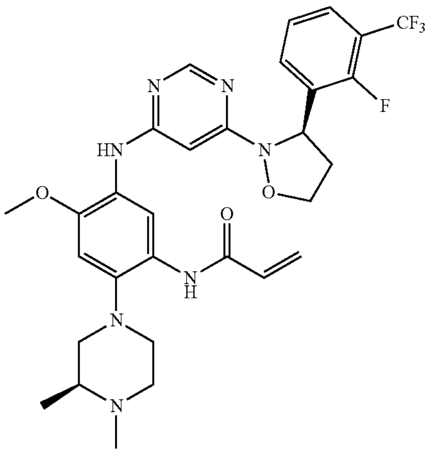 [SMILES: C=CC(=O)Nc1cc(Nc2cc(N3OCC[C@@H]3c3cccc(C(F)(F)F)c3F)ncn2)c(OC)cc1N1CCN(C)[C@@H](C)C1] | N-(2-((S)-3,4-dimethylpiperazin-1-yl)-5-((6-((R)-3-(2-fluoro-3-(trifluoromethyl)phenyl)isoxazolidin-2-yl)pyrimidin-4-yl)amino)-4-methoxyphenyl)acrylamide | 616.26 [M + H] $^1$H NMR (400 MHz, Chloroform-d) δ 8.88 (s, 1H), 8.52 (s, 1H), 8.36 (d, J = 1.0 Hz, 1H), 7.82 (t, J = 7.3 Hz, 1H), 7.51 (t, J = 6.9 Hz, 1H), 7.21 (t, J = 7.8 Hz, 1H), 7.13 (s, 1H), 6.78 (d, J = 16.2 Hz, 2H), 6.40-6.33 (m, 1H), 6.26 (dd, J = 16.9, 10.1 Hz, 1H), 5.96 (dd, J = 8.8, 4.6 Hz, 1H), 5.75 (dd, J = 9.9, 1.6 Hz, 1H), 4.19-4.03 (m, 2H), 3.85 (s, 3H), 3.05-2.97 (m, 2H), 2.93-2.81 (m, 3H), 2.72-2.65 (m, 1H), 2.55-2.46 (m, 1H), 2.42 (s, 4H), 2.33-2.27 (m, 1H), 1.17 (d, J = 6.2 Hz, 3H); 616.45 [M + H]$^+$ |
| 77 | 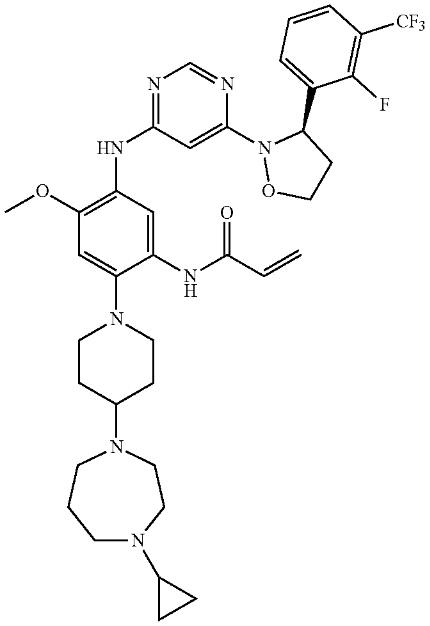 [SMILES: C=CC(=O)Nc1cc(Nc2cc(N3OCC[C@@H]3c3cccc(C(F)(F)F)c3F)ncn2)c(OC)cc1N1CCC(N2CCCN(C3CC3)CC2)CC1] | (R)-N-(2-(4-(4-cyclopropyl-1,4-diazepan-1-yl)piperidin-1-yl)-5-((6-(3-(2-fluoro-3-(trifluoromethyl)phenyl)isoxazolidin-2-yl)pyrimidin-4-yl)amino)-4-methoxyphenyl)acrylamide | 725.35 [M + H]$^+$ |

TABLE 1-continued

| Example Compound | Structure | Compound Name | $^1$H NMR; MS $[M + H]^+$ |
|---|---|---|---|
| 78 | 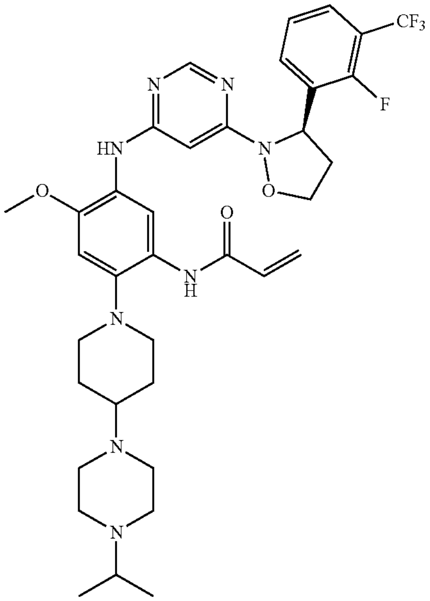 [SMILES: C=CC(=O)Nc1cc(Nc2cc(N3OCC[C@@H]3c3cccc(C(F)(F)F)c3F)ncn2)c(OC)cc1N1CCC(N2CCN(C(C)C)CC2)CC1] | (R)-N-(5-((6-(3-(2-fluoro-3-(trifluoromethyl) phenyl) isoxazolidin-2-yl) pyrimidin-4-yl)amino)-2-(4-(4-isopropyl piperazin-1-yl) piperidin-1-yl)-4-methoxyphenyl) acrylamide | 713.35 [M + H] $^1$H NMR (400 MHz, Chloroform-d) δ 8.85 (s, 1H), 8.37 (d, J = 8.6 Hz, 2H), 7.82 (t, J = 7.3 Hz, 1H), 7.51 (t, J = 7.0 Hz, 1H), 7.21 (t, J = 8.0 Hz, 1H), 7.08 (s, 1H), 6.75 (d, J = 8.5 Hz, 2H), 6.31-6.22 (m, 1H), 5.95 (dd, J = 8.6, 4.5 Hz, 1H), 5.90-5.85 (m, 1H), 5.75 (d, J = 10.1 Hz, 1H), 4.17-4.05 (m, 2H), 3.86 (s, 3H), 3.66 (p, J = 6.7 Hz, 3H), 3.32 (s, 1H), 3.16 (s, 4H), 3.11-3.06 (m, 4H), 2.91-2.86 (m, 1H), 2.78-2.68 (m, 3H), 2.59 (s, 1H), 2.31 (dt, J = 8.3, 4.2 Hz, 1H), 2.07 (s, 2H), 1.42 (s, 6H); 713.56 $[M + H]^+$ |
| 79 | 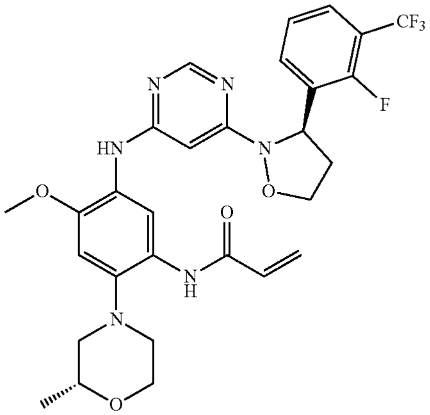 [SMILES: C=CC(=O)Nc1cc(Nc2cc(N3OCC[C@@H]3c3cccc(C(F)(F)F)c3F)ncn2)c(OC)cc1N1CCO[C@H](C)C1] | N-(5-((6-((R)-3-(2-fluoro-3-(trifluoromethyl) phenyl) isoxazolidin-2-yl) pyrimidin-4-yl)amino)-4-methoxy-2-((R)-2-methylmorpholino) phenyl) acrylamide | $^1$H NMR (400 MHz, $CDCl_3$) δ 8.89 (s, 1H), 8.52 (s, 1H), 8.37 (d, J = 1.0 Hz, 1H), 7.86-7.78 (m, 1H), 7.55-7.46 (m, 1H), 7.24-7.15 (m, 2H), 6.79-6.75 (m, 2H), 6.37 (dd, J = 17.0, 1.6 Hz, 1H), 6.26 (dd, J = 16.9, 9.9 Hz, 1H), 5.95 (dd, J = 8.9, 4.5 Hz, 1H), 5.76 (dd, J = 9.9, 1.6 Hz, 1H), 4.16-4.02 (m, 3H), 3.87 (s, 3H), 3.85-3.74 (m, 2H), 2.98-2.74 (m, 4H), 2.65-2.52 (m, 1H), 2.37-2.24 (m, 1H), 1.24 (d, J = 6.2 Hz, 3H); 603.4 $[M + H]^+$ |
| 80 | 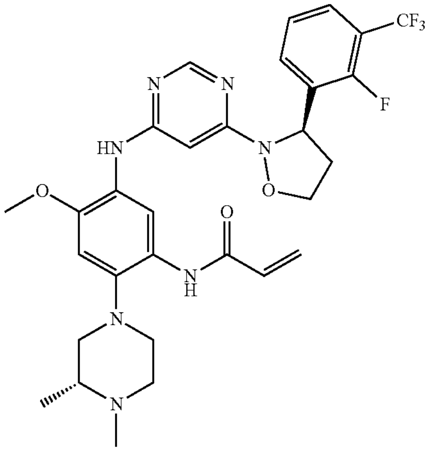 [SMILES: C=CC(=O)Nc1cc(Nc2cc(N3OCC[C@@H]3c3cccc(C(F)(F)F)c3F)ncn2)c(OC)cc1N1CCN(C)[C@H](C)C1] | N-(2-((R)-3,4-dimethylpiperazin-1-yl)-5-((6-((R)-3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.88 (s, 1H), 8.54 (s, 1H), 8.36 (d, J = 1.1 Hz, 1H), 7.87-7.78 (m, 1H), 7.55-7.46 (m, 1H), 7.21 (t, J = 7.8 Hz, 1H), 7.08 (s, 1H), 6.79 (s, 1H), 6.77 (s, 1H), 6.37 (dd, J = 16.9, 1.6 Hz, 1H), 6.26 (dd, J = 16.9, 10.0 Hz, 1H), 5.96 (dd, J = 8.9, 4.5 Hz, 1H), 5.75 (dd, J = 9.9, 1.6 Hz, 1H), 4.16-4.06 (m, 2H), 3.85 (s, 3H), 3.04-2.94 (m, 2H), 2.92-2.85 (m, 2H), 2.85-2.79 (m, 1H), 2.61 (dd, J = 11.4, 9.6 Hz, 1H), 2.50-2.43 (m, 1H), 2.39 (s, 3H), 2.35-2.28 (m, 2H), 1.14 (d, J = 6.2 Hz, 3H); 616.5 $[M + H]^+$ |

TABLE 1-continued

| Example Compound | Structure | Compound Name | $^1$H NMR; MS [M + H]$^+$ |
| --- | --- | --- | --- |
| 81 | 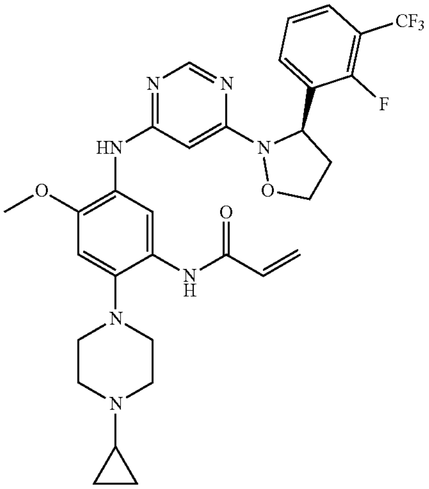 [SMILES: C=CC(=O)Nc1cc(Nc2cc(N3OCC[C@@H]3c3cccc(C(F)(F)F)c3F)ncn2)c(OC)cc1N1CCN(C2CC2)CC1] | (R)-N-(2-(4-cyclopropyl piperazin-1-yl)-5-((6-(3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.88 (s, 1H), 8.60 (s, 1H), 8.36 (d, J = 1.0 Hz, 1H), 7.87-7.78 (m, 1H), 7.54-7.46 (m, 1H), 7.21 (t, J = 7.8 Hz, 1H), 7.12 (s, 1H), 6.80 (s, 1H), 6.77 (s, 1H), 6.37 (dd, J = 16.9, 1.8 Hz, 1H), 6.29 (dd, J = 16.9, 9.8 Hz, 1H), 5.96 (dd, J = 8.9, 4.5 Hz, 1H), 5.76 (dd, J = 9.8, 1.8 Hz, 1H), 4.19-4.02 (m, 2H), 3.82 (s, 3H), 2.95-2.73 (m, 9H), 2.36-2.24 (m, 1H), 1.73 (ddd, J = 8.8, 6.6, 3.7 Hz, 1H), 0.57-0.44 (m, 4H); 628.5 [M + H]$^+$ |
| 82 | 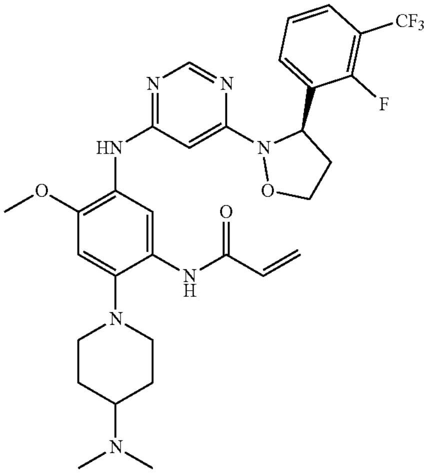 [SMILES: C=CC(=O)Nc1cc(Nc2cc(N3OCC[C@@H]3c3cccc(C(F)(F)F)c3F)ncn2)c(OC)cc1N1CCC(N(C)C)CC1] | (R)-N-(2-(4-(dimethylamino) piperidin-1-yl)-5-((6-(3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.86 (s, 1H), 8.49 (s, 1H), 8.36 (d, J = 1.0 Hz, 1H), 7.83 (td, J = 7.5, 1.8 Hz, 1H), 7.55-7.46 (m, 1H), 7.21 (t, J = 7.8 Hz, 1H), 7.06 (s, 1H), 6.79-6.73 (m, 2H), 6.35 (dd, J = 17.0, 1.6 Hz, 1H), 6.26 (dd, J = 17.0, 10.0 Hz, 1H), 5.96 (dd, J = 8.9, 4.5 Hz, 1H), 5.74 (dd, J = 9.9, 1.6 Hz, 1H), 4.19-4.02 (m, 2H), 3.85 (s, 3H), 3.05 (dd, J = 9.0, 5.8 Hz, 2H), 2.88 (dtd, J = 12.3, 8.0, 4.2 Hz, 1H), 2.73 (qd, J = 12.0, 2.2 Hz, 2H), 2.36 (s, 6H), 2.32-2.22 (m, 2H), 2.09-2.01 (m, 2H), 1.71-1.61 (m, 2H); 630.5 [M + H]$^+$ |
| 83 | 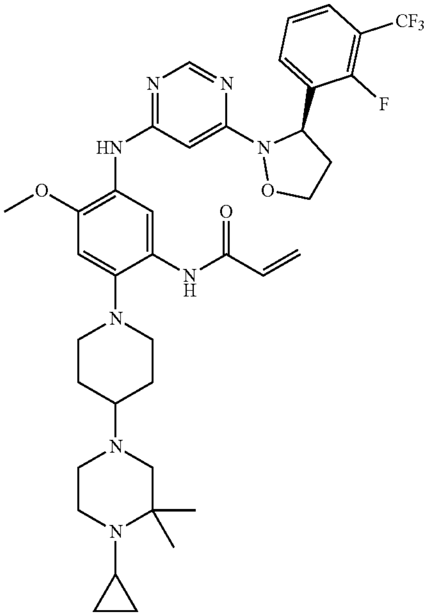 [SMILES: C=CC(=O)Nc1cc(Nc2cc(N3OCC[C@@H]3c3cccc(C(F)(F)F)c3F)ncn2)c(OC)cc1N1CCC(N2CCN(C3CC3)C(C)(C)C2)CC1] | (R)-N-(2-(4-(4-cyclopropyl-3,3-dimethylpiperazin-1-yl) piperidin-1-yl)-5-((6-(3-(2-fluoro-3-(trifluoromethyl) phenyl) isoxazolidin-2-yl) pyrimidin-4-yl)amino)-4-methoxyphenyl) acrylamide | $^1$H NMR (400 MHz, $CDCl_3$) δ 8.84 (s, 1H), 8.45 (s, 1H), 8.35 (d, J = 1.0 Hz, 1H), 7.82 (td, J = 7.5, 1.8 Hz, 1H), 7.54-7.46 (m, 1H), 7.21 (t, J = 7.8 Hz, 1H), 7.07 (s, 1H), 6.79-6.74 (m, 2H), 6.37 (dd, J = 16.9, 1.7 Hz, 1H), 6.28 (dd, J = 16.9, 9.9 Hz, 1H), 5.96 (dd, J = 8.9, 4.5 Hz, 1H), 5.75 (dd, J = 9.8, 1.7 Hz, 1H), 4.18-4.02 (m, 2H), 3.85 (s, 3H), 3.04 (dd, J = 10.0, 6.5 Hz, 2H), 2.88 (dtd, J = 12.3, 8.0, 4.2 Hz, 1H), 2.75 (t, J = 5.1 Hz, 2H), 2.73-2.65 (m, 2H), 2.63-2.54 (m, 2H), 2.33-2.25 (m, 4H), 1.98 (d, J = 12.5 Hz, 2H), 1.76-1.70 (m, 1H), 1.70-1.59 (m, 2H), 1.19 (s, 6H), 0.54-0.48 (m, 2H), 0.45-0.39 (m, 2H); 739.6 [M + H]$^+$ |

TABLE 1-continued

| Example Compound | Structure | Compound Name | $^1$H NMR; MS [M + H]$^+$ |
|---|---|---|---|
| 84 | 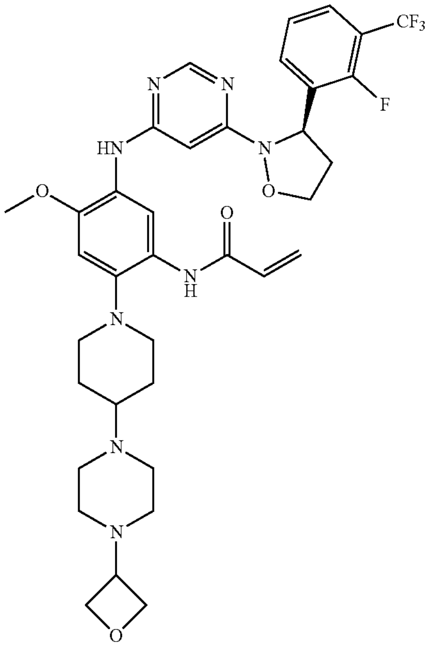 [SMILES: C=CC(=O)Nc1cc(Nc2cc(N3OCC[C@@H]3c3cccc(C(F)(F)F)c3F)ncn2)c(OC)cc1N1CCC(N2CCN(C3COC3)CC2)CC1] | (R)-N-(5-((6-(3-(2-fluoro-3-(trifluoromethyl)phenyl)isoxazolidin-2-yl)pyrimidin-4-yl)amino)-4-methoxy-2-(4-(4-(oxetan-3-yl)piperazin-1-yl)piperidin-1-yl)phenyl)acrylamide | $^1$H NMR (400 MHz, $CDCl_3$) δ 8.85 (s, 1H), 8.44 (s, 1H), 8.35 (s, 1H), 7.82 (t, J = 6.9 Hz, 1H), 7.55-7.46 (m, 1H), 7.21 (t, J = 7.8 Hz, 1H), 7.09 (s, 1H), 6.78-6.73 (m, 2H), 6.36 (dd, J = 16.9, 1.6 Hz, 1H), 6.25 (dd, J = 16.9, 10.0 Hz, 1H), 5.95 (dd, J = 8.9, 4.5 Hz, 1H), 5.74 (dd, J = 9.9, 1.6 Hz, 1H), 4.66 (dt, J = 21.4, 6.4 Hz, 4H), 4.19-4.02 (m, 2H), 3.85 (s, 3H), 3.53 (p, J = 6.4 Hz, 1H), 3.07 (d, J = 11.4 Hz, 2H), 2.93-2.84 (m, 1H), 2.82-2.66 (m, 6H), 2.51-2.36 (m, 5H), 2.33-2.26 (m, 1H), 2.13-2.02 (m, 2H), 1.70 (qd, J = 12.2, 3.9 Hz, 2H); 727.6 [M + H]$^+$ |
| 85 | 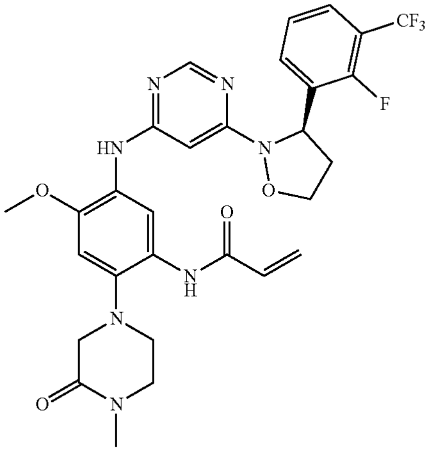 | (R)-N-(5-((6-(3-(2-fluoro-3-(trifluoromethyl)phenyl)isoxazolidin-2-yl)pyrimidin-4-yl)amino)-4-methoxy-2-(4-methyl-3-oxopiperazin-1-yl)phenyl)acrylamide | $^1$H NMR (400 MHz, $CDCl_3$) δ 8.93 (s, 1H), 8.38 (d, J = 1.0 Hz, 1H), 8.19 (s, 1H), 7.82 (t, J = 7.3 Hz, 1H), 7.56-7.47 (m, 1H), 7.22 (t, J = 7.8 Hz, 1H), 7.06 (s, 1H), 6.78 (s, 1H), 6.70 (s, 1H), 6.40 (dd, J = 16.9, 1.5 Hz, 1H), 6.28 (dd, J = 16.9, 10.0 Hz, 1H), 5.96 (dd, J = 8.9, 4.6 Hz, 1H), 5.76 (dd, J = 10.0, 1.5 Hz, 1H), 4.19-4.12 (m, 1H), 4.12-4.04 (m, 1H), 3.86 (s, 3H), 3.63 (s, 2H), 3.48-3.42 (m, 2H), 3.17 (td, J = 5.1, 2.0 Hz, 2H), 3.07 (s, 3H), 2.96-2.83 (m, 1H), 2.38-2.25 (m, 1H); 616.5 [M + H]$^+$ |
| 86 | 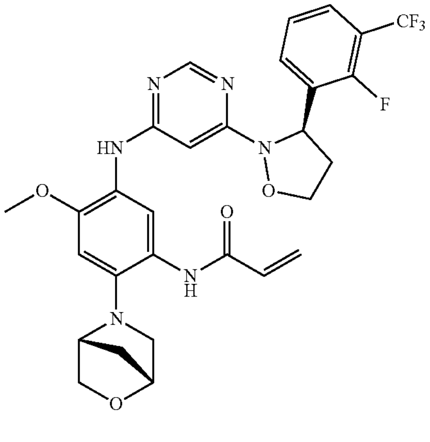 [SMILES: C=CC(=O)Nc1cc(Nc2cc(N3OCC[C@@H]3c3cccc(C(F)(F)F)c3F)ncn2)c(OC)cc1N1C[C@H]2C[C@@H]1CO2] | N-(2-((1R,4R)-2-oxa-5-azabicyclo[2.2.1]heptan-5-yl)-5-((6-((R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Chloroform-d) δ 8.49 (s, 1H), 8.29 (s, 1H), 7.95 (s, 1H), 7.80 (t, J = 7.3 Hz, 1H), 7.56 (s, 1H), 7.53-7.48 (m, 1H), 7.21 (t, J = 7.8 Hz, 1H), 6.70 (d, J = 16.2 Hz, 2H), 6.38 (dd, J = 17.1, 1.7 Hz, 1H), 6.29 (dd, J = 16.9, 9.9 Hz, 1H), 5.94 (dd, J = 8.9, 4.6 Hz, 1H), 5.76 (dd, J = 9.8, 1.7 Hz, 1H), 4.18-4.11 (m, 1H), 4.07-4.03 (m, 2H), 3.86 (s, 3H), 3.76 (d, J = 7.7 Hz, 1H), 3.46 (d, J = 10.2 Hz, 1H), 3.20 (d, J = 10.1 Hz, 1H), 2.92-2.83 (m, 1H), 2.63 (s, 1H), 2.34-2.24 (m, 1H), 2.07 (s, 3H); 601.5 [M + H]$^+$ |

TABLE 1-continued

| Example Compound | Structure | Compound Name | $^1$H NMR; MS [M + H]$^+$ |
|---|---|---|---|
| 87 | 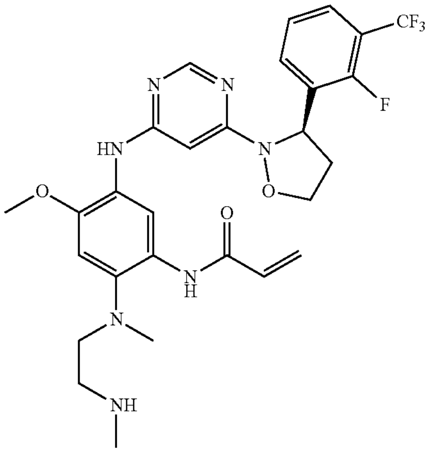 [SMILES: C=CC(=O)Nc1cc(Nc2cc(N3OCC[C@@H]3c3cccc(C(F)(F)F)c3F)ncn2)c(OC)cc1N(C)CCNC] | (R)-N-(5-((6-(3-(2-fluoro-3-(trifluoromethyl)phenyl)isoxazolidin-2-yl)pyrimidin-4-yl)amino)-4-methoxy-2-(methyl(2-(methylamino ethyl)amino)phenyl)acrylamide | $^1$H NMR (400 MHz, Chloroform-d) δ 9.33-9.21 (m, 2H), 8.04 (s, 1H), 7.88 (s, 1H), 7.57 (t, J = 7.3 Hz, 1H), 7.50 (t, J = 7.4 Hz, 1H), 7.26-7.21 (m, 1H), 6.80 (s, 1H), 6.73-6.61 (m, 1H), 6.34-6.27 (m, 1H), 5.95 (s, 1H), 5.84 (dd, J = 8.8, 5.0 Hz, 1H), 5.72 (d, J = 10.1 Hz, 1H), 4.31-4.23 (m, 1H), 4.10 (q, J = 7.7 Hz, 1H), 3.80 (s, 3H), 3.18 (s, 2H), 3.10 (s, 2H), 3.02-2.93 (m, 2H), 2.70 (s, 3H), 2.62 (s, 3H), 2.44-2.37 (m, 1H); 590.4 [M + H]$^+$ |
| 88 | 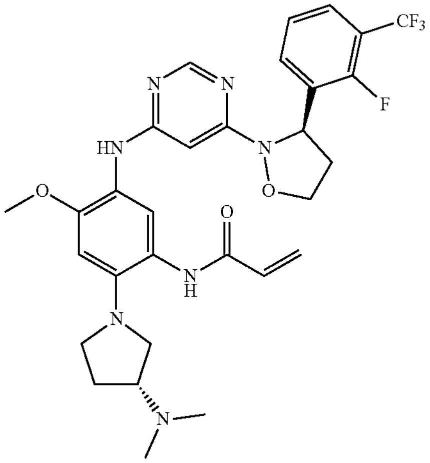 [SMILES: C=CC(=O)Nc1cc(Nc2cc(N3OCC[C@@H]3c3cccc(C(F)(F)F)c3F)ncn2)c(OC)cc1N1CC[C@@H](N(C)C)C1] | N-(2-((R)-3-(dimethylamino)pyrrolidin-1-yl)-5-((6-((R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Chloroform-d) δ 8.95 (s, 1H), 8.50 (d, J = 6.4 Hz, 2H), 8.30 (d, J = 1.1 Hz, 1H), 7.81 (t, J = 7.3 Hz, 1H), 7.53-7.48 (m, 1H), 7.38 (s, 1H), 7.21 (t, J = 7.8 Hz, 1H), 6.70 (d, J = 3.8 Hz, 2H), 6.47-6.41 (m, 1H), 5.95 (dd, J = 8.8, 4.6 Hz, 1H), 5.72 (dd, J = 9.7, 2.1 Hz, 1H), 4.14 (td, J = 8.0, 4.2 Hz, 1H), 4.10-4.02 (m, 1H), 3.85 (s, 3H), 3.68-3.62 (m, 2H), 3.48-3.42 (m, 1H), 3.36-3.26 (m, 2H), 3.15-3.09 (m, 2H), 3.08-3.05 (m, 1H), 2.90-2.83 (m, 1H), 2.46 (s, 6H); 616.5 [M + H]$^+$ |
| 89 | 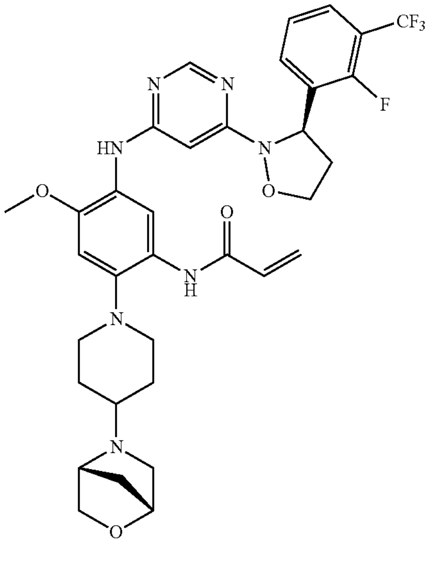 [SMILES: C=CC(=O)Nc1cc(Nc2cc(N3OCC[C@@H]3c3cccc(C(F)(F)F)c3F)ncn2)c(OC)cc1N1CCC(N2C[C@H]3C[C@@H]2CO3)CC1] | N-(2-(4-((1R,4R)-2-oxa-5-azabicyclo[2.2.1]heptan-5-yl)piperidin-1-yl)-5-((6-((R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Chloroform-d) δ 8.76 (s, 1H), 8.48 (s, 1H), 8.32 (s, 1H), 7.80 (t, J = 7.3 Hz, 1H), 7.56-7.48 (m, 2H), 7.22 (t, J = 7.8 Hz, 1H), 6.73 (s, 2H), 6.41-6.40 (m, 1H), 6.18-6.10 (m, 1H), 5.97-5.91 (m, 1H), 5.78 (dd, J = 9.4, 2.1 Hz, 1H), 4.67-4.63 (m, 1H), 4.48 (s, 1H), 4.18-4.12 (m, 1H), 4.10-4.04 (m, 1H), 3.85 (s, 3H), 3.28-3.14 (m, 4H), 2.94-2.84 (m, 2H), 2.83-2.71 (m, 2H), 2.67-2.59 (m, 2H), 2.54-2.44 (m, 1H), 2.36-2.26 (m, 1H), 2.20-2.13 (m, 2H), 2.12-2.04 (m, 2H), 2.04-2.01 (m, 1H); 684.5 [M + H]$^+$ |

TABLE 1-continued

| Example Compound | Structure | Compound Name | $^1$H NMR; MS [M + H]$^+$ |
| --- | --- | --- | --- |
| 90 | 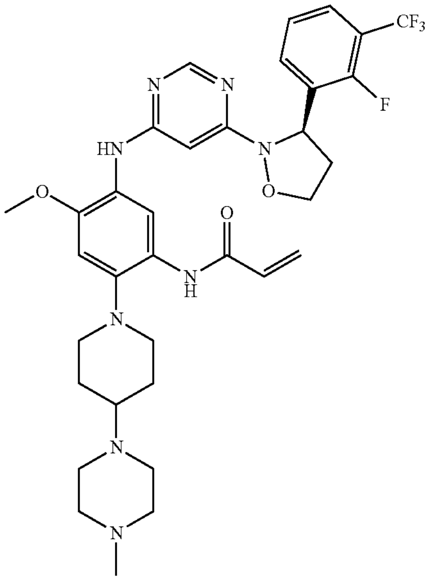 [SMILES: C=CC(=O)Nc1cc(Nc2cc(N3OCC[C@@H]3c3cccc(C(F)(F)F)c3F)ncn2)c(OC)cc1N1CCC(N2CCN(C)CC2)CC1] | (R)-N-(5-((6-(3-(2-fluoro-3-(trifluoromethyl)phenyl)isoxazolidin-2-yl)pyrimidin-4-yl)amino)-4-methoxy-2-(4-(4-methylpiperazin-1-yl)piperidin-1-yl)phenyl)acrylamide | 685.5 [M + H]$^+$ |
| 91 | 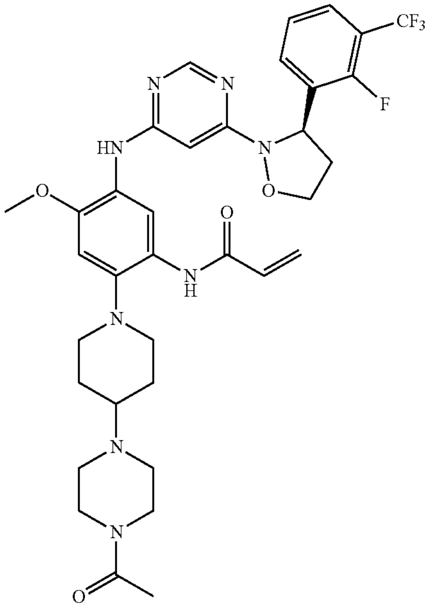 [SMILES: C=CC(=O)Nc1cc(Nc2cc(N3OCC[C@@H]3c3cccc(C(F)(F)F)c3F)ncn2)c(OC)cc1N1CCC(N2CCN(C(C)=O)CC2)CC1] | (R)-N-(2-(4-(4-acetylpiperazin-1-yl)piperidin-1-yl)-5-((6-(3-(2-fluoro-3-(trifluoromethyl)phenyl)isoxazolidin-2-yl)pyrimidin-4-yl)amino)-4-methoxyphenyl)acrylamide | 713.31 [M + H] |
| 92 | 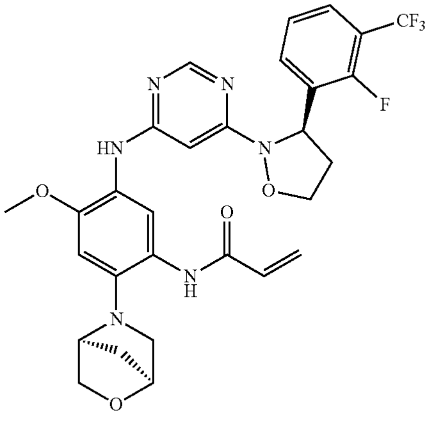 [SMILES: C=CC(=O)Nc1cc(Nc2cc(N3OCC[C@@H]3c3cccc(C(F)(F)F)c3F)ncn2)c(OC)cc1N1C[C@@H]2C[C@H]1CO2] | N-(2-((1S,4S)-2-oxa-5-azabicyclo[2.2.1]heptan-5-yl)-5-((6-((R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Methanol-$d_4$) δ 8.13 (s, 1H), 7.83 (t, J = 7.4 Hz, 1H), 7.62 (t, J = 7.2 Hz, 1H), 7.47 (s, 1H), 7.35 (t, J = 7.8 Hz, 1H), 6.56 (s, 1H), 6.51-6.42 (m, 1H), 6.42-6.32 (m, 2H), 5.87-5.75 (m, 2H), 4.39 (s, 1H), 4.19-4.14 (m, 1H), 4.14-4.10 (m, 1H), 4.00-3.94 (m, 1H), 3.89-3.85 (m, 4H), 3.54 (d, J = 9.6 Hz, 1H), 3.12 (d, J = 9.7 Hz, 1H), 2.91 (dt, J = 4.1, 8.3 Hz, 1H), 2.27 (dtd, J = 4.8, 8.1, 12.7 Hz, 2H), 2.06 (d, J = 9.3 Hz, 1H), 1.94 (d, J = 10.2 Hz, 1H); 601.2 [M + H]$^+$ |

TABLE 1-continued

| Example Compound | Structure | Compound Name | $^1H$ NMR; MS $[M + H]^+$ |
|---|---|---|---|
| 93 | 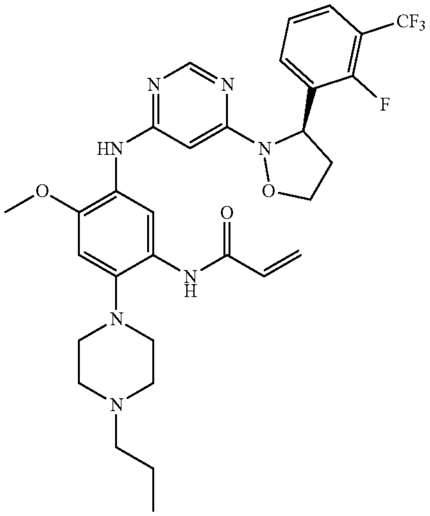 | (R)-N-(5-((6-(3-(2-fluoro-3-(trifluoromethyl)phenyl)isoxazolidin-2-yl)pyrimidin-4-yl)amino)-4-methoxy-2-(4-propylpiperazin-1-yl)phenyl)acrylamide | $^1H$ NMR (400 MHz, Methanol-$d_4$) δ 8.33 (s, 1H), 8.19 (s, 1H), 7.84 (t, J = 7.4 Hz, 1H), 7.63 (t, J = 7.2 Hz, 1H), 7.36 (t, J = 7.8 Hz, 1H), 6.95 (s, 1H), 6.63-6.49 (m, 2H), 6.38 (d, J = 16.9 Hz, 1H), 5.89-5.76 (m, 2H), 4.19-4.12 (m, 1H), 4.04-3.98 (m, 1H), 3.91 (s, 3H), 3.17-3.10 (m, 8H), 2.97-2.89 (m, 1H), 2.88-2.82 (m, 2H), 2.33-2.24 (m, 1H), 1.79-1.70 (m, 2H), 1.04 (t, J = 7.4 Hz, 3H); 630.3 $[M + H]^+$ |
| 94 | 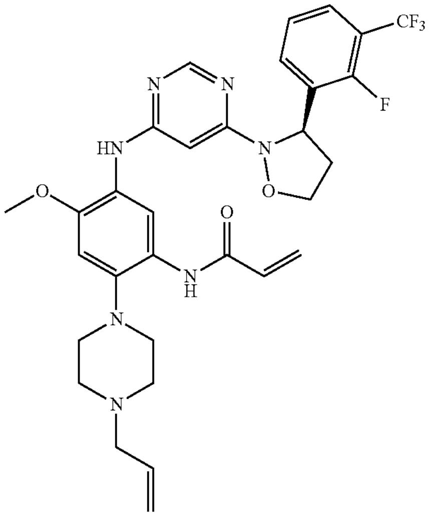 [SMILES: C=CCN1CCN(c2cc(OC)c(Nc3cc(N4OCC[C@@H]4c4cccc(C(F)(F)F)c4F)ncn3)cc2NC(=O)C=C)CC1] | (R)-N-(2-(4-allylpiperazine-1-yl)-5-((6-(3-(2-fluoro-3-(trifluoromethyl)phenyl)isoxazolidin-2-yl)pyrimidin-4-yl)amino)-4-methoxyphenyl)acrylamide | $^1H$ NMR (400 MHz, Methanol-$d_4$) δ 8.31 (s, 1H), 8.18 (s, 1H), 7.84 (t, J = 7.2 Hz, 1H), 7.63 (t, J = 7.0 Hz, 1H), 7.35 (t, J = 7.8 Hz, 1H), 6.96 (s, 1H), 6.60-6.49 (m, 2H), 6.37 (dd, J = 1.7, 17.0 Hz, 1H), 6.04-5.90 (m, 1H), 5.88-5.77 (m, 2H), 5.43-5.35 (m, 2H), 4.20-4.14 (m, 1H), 4.02-3.97 (m, 1H), 3.91 (s, 3H), 3.11-3.02 (m, 5H), 2.99-2.85 (m, 6H), 2.32-2.23 (m, 1H); 628.3 $[M + H]^+$ |
| 95 | 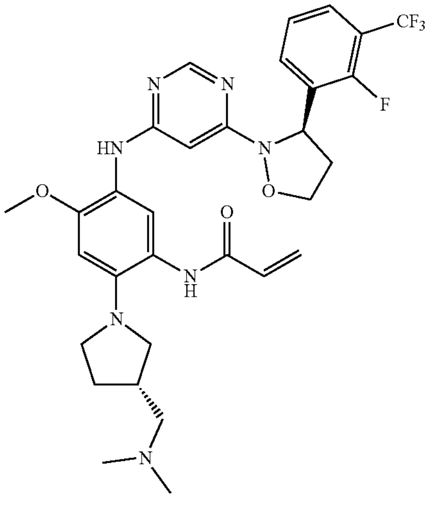 [SMILES: C=CC(=O)Nc1cc(Nc2cc(N3OCC[C@@H]3c3cccc(C(F)(F)F)c3F)ncn2)c(OC)cc1N1CC[C@@H](CN(C)C)C1] | N-(2-((S)-3-((dimethylamino)methyl)pyrrolidin-1-yl)-5-((6-((R)-3-(2-fluoro-3-(trifluoromethyl)phenyl)isoxazolidin-2-yl)pyrimidin-4-yl)amino)-4-methoxyphenyl)acrylamide | 630.3 [M + H] |

TABLE 1-continued

| Example Compound | Structure | Compound Name | $^1$H NMR; MS $[M + H]^+$ |
| --- | --- | --- | --- |
| 96 | 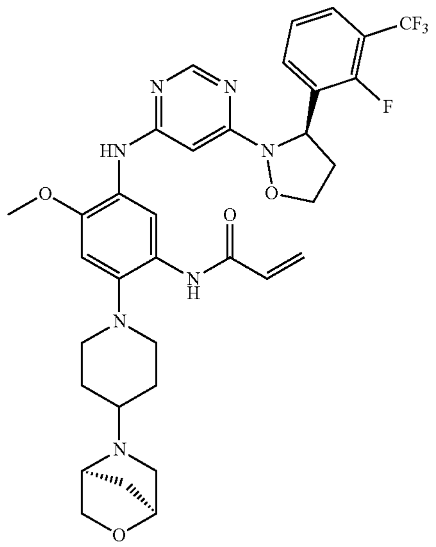 [SMILES: C=CC(=O)Nc1cc(Nc2cc(N3OCC[C@@H]3c3cccc(C(F)(F)F)c3F)ncn2)c(OC)cc1N1CCC(N2C[C@@H]3C[C@H]2CO3)CC1] | N-(2-(4-((1S,4S)-2-oxa-5-azabicyclo[2.2.1]heptan-5-yl)piperidin-1-yl)-5-((6-((R)-3-(2-fluoro-3-(trifluoromethyl)phenyl)isoxazolidin-2-yl)pyrimidin-4-yl)amino)-4-methoxyphenyl)acrylamide | $^1$H NMR (400 MHz, Methanol-$d_4$) δ 8.27 (s, 1H), 8.18 (s, 1H), 7.84 (t, J = 7.3 Hz, 1H), 7.63 (t, J = 7.3 Hz, 1H), 7.35 (t, J = 7.8 Hz, 1H), 6.94 (s, 1H), 6.62-6.47 (m, 2H), 6.37 (d, J = 17.0 Hz, 1H), 5.88-5.76 (m, 2H), 4.31 (s, 1H), 4.22-4.14 (m, 3H), 4.03-3.97 (m, 1H), 3.90 (s, 3H), 3.80 (d, J = 8.1 Hz, 1H), 3.21-3.14 (m, 2H), 3.09-3.01 (m, 2H), 2.98-2.90 (m, 1H), 2.89-2.82 (m, 2H), 2.32-2.25 (m, 1H), 2.24-2.18 (m, 1H), 2.15-2.08 (m, 2H), 2.09-2.05 (m, 2H), 1.87-1.79 (m, 2H); 684.3 $[M + H]^+$ |
| 97 | 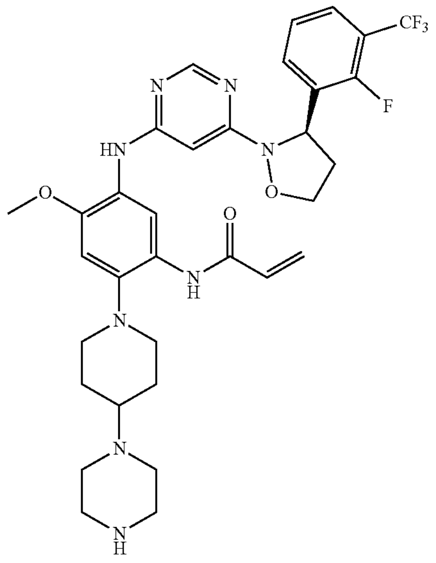 [SMILES: C=CC(=O)Nc1cc(Nc2cc(N3OCC[C@@H]3c3cccc(C(F)(F)F)c3F)ncn2)c(OC)cc1N1CCC(N2CCNCC2)CC1] | (R)-N-(5-((6-(3-(2-fluoro-3-(trifluoromethyl)phenyl)isoxazolidin-2-yl)pyrimidin-4-yl)amino)-4-methoxy-2-(4-(piperazin-1-yl)piperidin-1-yl)phenyl)acrylamide | 671.30 [M + H] |

TABLE 1-continued

| Example Compound | Structure | Compound Name | $^1$H NMR; MS $[M+H]^+$ |
|---|---|---|---|
| 98 | 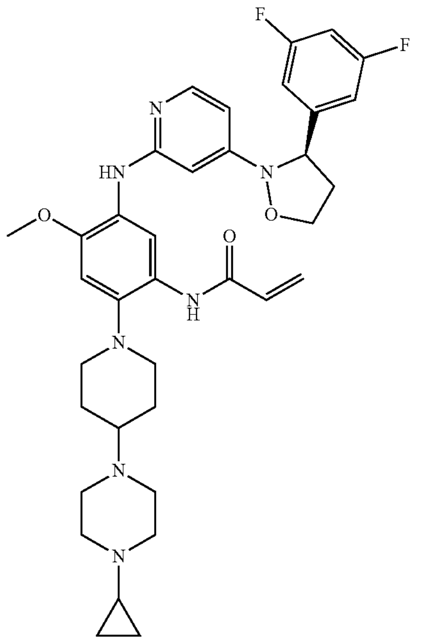 [SMILES: C=CC(=O)Nc1cc(Nc2cc(N3OCC[C@@H]3c3cc(F)cc(F)c3)ccn2)c(OC)cc1N1CCC(N2CCN(C3CC3)CC2)CC1] | (R)-N-(2-(4-(4-cyclopropyl piperazin-1-yl) piperidin-1-yl)-5-((4-(3-(3,5-difluorophenyl) isoxazolidin-2-yl)pyridin-2-yl)amino)-4-methoxyphenyl) acrylamide | $^1$H NMR (400 MHz, Methanol-d4) δ 8.00 (s, 1H), 7.61 (d, J = 6.5 Hz, 1H), 6.96-6.89 (m, 2H), 6.83-6.70 (m, 2H), 6.52-6.39 (m, 1H), 6.38-6.32 (m, 1H), 6.32-6.22 (m, 1H), 6.22-6.13 (m, 1H), 5.71 (d, J = 10.3 Hz, 1H), 5.02-4.99 (m, 1H), 4.16-4.12 (m, 1H), 3.97-3.90 (m, 1H), 3.73 (s, 3H), 3.08-3.02 (m, 2H), 2.92-2.81 (m, 4H), 2.76-2.61 (m, 7H), 2.28-2.20 (m, 1H), 2.05-1.98 (m, 2H), 1.77-1.65 (m, 3H), 0.82-0.77 (m, 1H), 0.49-0.40 (m, 2H), 0.40-0.33 (m, 2H); 660.3 $[M+H]^+$ |
| 99 | 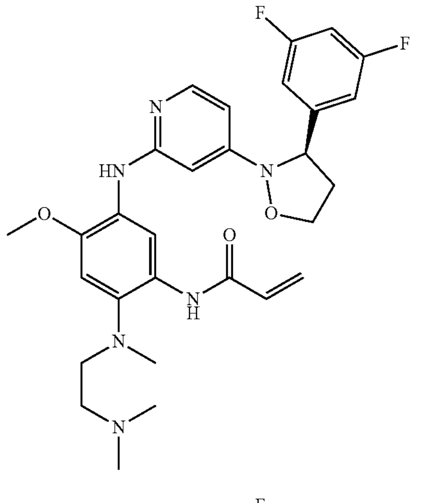 | (R)-N-(5-((4-(3-(3,5-difluorophenyl) isoxazolidin-2-yl)pyridin-2-yl)amino)-2-((2-(dimethylamino) ethyl)(methyl) amino)-4-methoxyphenyl) acrylamide | $^1$H NMR (400 MHz, Chloroform-d) δ 9.86 (s, 1H), 8.78 (s, 1H), 7.90 (d, J = 6.1 Hz, 1H0, 7.05-6.89 (m, 2H), 6.73 (s, 1H), 6.66 = 6.60 (m, 1H), 6.57-6.56 (m, 1H), 6.52-6.50 (m, 1H), 6.48-6.44 (m, 1H), 6.43 (d, J = 2.4 Hz, 1H), 5.71 (dd, J = 9.5, 2.4 Hz, 1H), 5.35 (t, J = 4.7 Hz, 1H), 5.21 (dd, J = 8.6, 3.4 Hz, 1H), 4.19-4.13 (m, 1H), 4.05-3.99 (m, 1H), 3.81 (s, 3H), 3.42 (s, 1H), 2.98-2.90 (m, 3H), 2.49-2.43 (m, 2H), 2.17 (s, 3H), 2.06 (s, 6H); 553.5 $[M+H]^+$ |
| 100 | 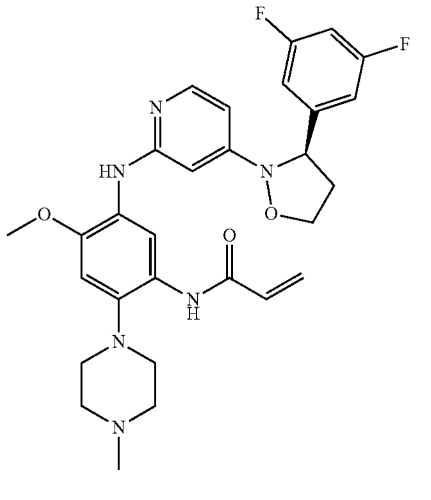 [SMILES: C=CC(=O)Nc1cc(Nc2cc(N3OCC[C@@H]3c3cc(F)cc(F)c3)ccn2)c(OC)cc1N1CCN(C)CC1] | (R)-N-(5-((4-(3-(3,5-difluorophenyl) isoxazolidin-2-yl)pyridin-2-yl)amino) 4-methoxy-2-(4-methylpiperazin-1-yl)phenyl) acrylamide | $^1$H NMR (400 MHz, Chloroform-d) δ 8.80 (s, 1H), 8.59 (s, 1H), 7.98 (d, J = 5.38 Hz, 1H), 7.06-7.02 (m, 2H), 6.76 (s, 1H), 6.69-6.62 (m, 1H), 6.59 (s, 1H), 6.49 (d, J = 6.0 Hz, 1H), 6.41-6.35 (m, 1H), 6.32-6.23 (m, 1H), 5.77 (dd, J = 9.9, 1.6 Hz, 1H), 5.36-5.34 (m, 1H), 5.14-5.10 (m, 1H), 4.17-4.13 (m, 1H), 4.05-4.02 (m, 1H), 3.81 (s, 3H), 2.92-2.88 (m, 4H), 2.86 (dd, J = 5.0, 0.8 Hz, 1H), 2.40 (s, 3H), 2.34-2.32 (m, 1H), 2.24-2.20 (m, 4H); 551.5 $[M+H]^+$ |

TABLE 1-continued

| Example Compound | Structure | Compound Name | $^1$H NMR; MS $[M + H]^+$ |
|---|---|---|---|
| 101 | 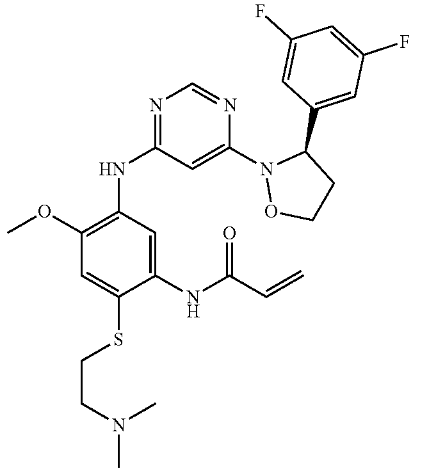 [SMILES: C=CC(=O)Nc1cc(Nc2cc(N3OCC[C@@H]3c3cc(F)cc(F)c3)ncn2)c(OC)cc1SCCN(C)C] | (R)-N-(5-((6-(3-(3,5-difluorophenyl) isoxazolidin-2-yl) pyrimidin-4-yl)amino)-2-((2-(dimethylamino) ethyl)thio)-4-methoxyphenyl) acrylamide | $^1$H NMR (400 MHz, Chloroform-d) δ 9.95 (s, 1H), 8.92 (s, 1H), 8.39 (s, 1H), 7.46 (s, 1H), 7.11 (s, 1H), 7.06-6.95 (m, 2H), 6.81 (s, 1H), 6.74-6.64 (m, 1H), 6.43 (dt, J = 16.9, 1.3 Hz, 1H), 6.31 (dd, J = 17.0, 10.0 Hz, 1H), 5.75 (dt, J = 10.0, 1.3 Hz, 1H), 5.67 (dd, J = 8.8, 4.6 Hz, 1H), 4.19 (td, J = 8.0, 4.1 Hz, 1H), 4.06 (q, J = 8.1 Hz, 1H), 3.91-3.86 (m, 3H), 2.87 (t, J = 6.3 Hz, 2H), 2.85-2.72 (m, 1H), 2.43-2.30 (m, 3H), 2.27 (s, 6H); 557.4 $[M + H]^+$ |
| 102 | 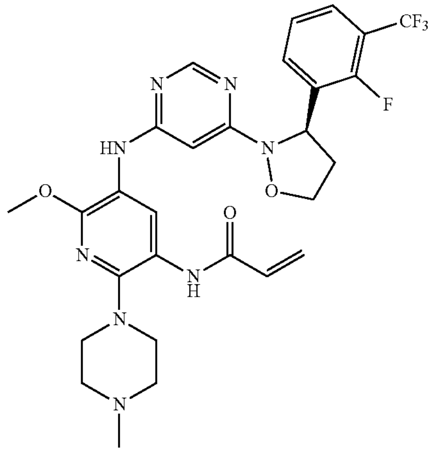 | (R)-N-(5-((6-(3-(2-fluoro-3-(trifluoromethyl) phenyl) isoxazolidin-2-yl) pyrimidin-4-yl)amino)-6-methoxy-2-(4-methylpiperazin-1-yl)pyridin-3-yl)acrylamide | $^1$H NMR (400 MHz, Chloroform-d) δ 9.21 (s, 1H), 8.40 (s, 1H), 7.95 (s, 1H), 7.82 (t, J = 7.2 Hz, 1H), 7.51 (t, J = 7.2 Hz, 1H), 7.21 (d, J = 7.7 Hz, 1H), 6.83 (s, 1H), 6.63 (s, 1H), 6.40 (d, J = 16.8 Hz, 1H), 6.27 (dd, J = 16.9, 10.1 Hz, 1H), 5.95 (dd, J = 8.7, 4.6 Hz, 1H), 5.78 (dd, J = 10.1, 1.4 Hz, 1H), 4.14 (dd, J = 8.0, 4.2 Hz, 1H), 4.03 (t, J = 8.0 Hz, 1H), 3.96 (s, 3H), 3.07 (s, 4H), 2.88 (d, J = 8.0 Hz, 1H), 2.60 (s, 4H), 2.38 (s, 3H), 2.32 (dt, J = 8.3, 4.3 Hz, 1H); 603.38 $[M + H]^+$ |
| 103 | 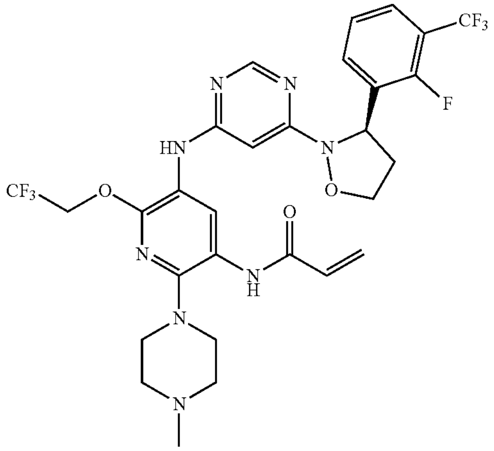 [SMILES: C=CC(=O)Nc1cc(Nc2cc(N3OCC[C@@H]3c3cccc(C(F)(F)F)c3F)ncn2)c(OCC(F)(F)F)nc1N1CCN(C)CC1] | (R)-N-(5-((6-(3-(2-fluoro-3-(trifluoromethyl) phenyl) isoxazolidin-2-yl) pyrimidin-4-yl)amino)-2-(4-methylpiperazin-1-yl)-6-(2,2,2-trifluoroethoxy) pyridine-3-yl)acrylamide | $^1$H NMR (400 MHz, Chloroform-d) δ 9.32 (s, 1H), 8.41 (s, 1H), 7.94 (s, 1H), 7.81 (t, J = 7.4 Hz, 1H), 7.52 (t, J = 7.3 Hz, 1H), 7.25-7.20 (m, 1H), 6.75 (s, 1H), 6.64 (s, 1H), 6.41 (d, J = 17.0 Hz, 1H), 6.27 (dd, J = 16.9, 10.1 Hz, 1H), 5.96 (dd, J = 8.8, 4.6 Hz, 1H), 5.80 (d, J = 10.2 Hz, 1H), 4.80 (q, J = 8.4 Hz, 2H), 4.17 (td, J = 8.0, 4.0 Hz, 1H), 4.03 (q, J = 8.1 Hz, 1H), 3.04 (d, J = 6.2 Hz, 4H), 2.93-2.85 (m, 1H), 2.60 (s, 4H), 2.39 (s, 3H), 2.35-2.30 (m, 1H); 671. 2 $[M + H]^+$ |

TABLE 1-continued

| Example Compound | Structure | Compound Name | $^1$H NMR; MS [M + H]$^+$ |
|---|---|---|---|
| 104 | 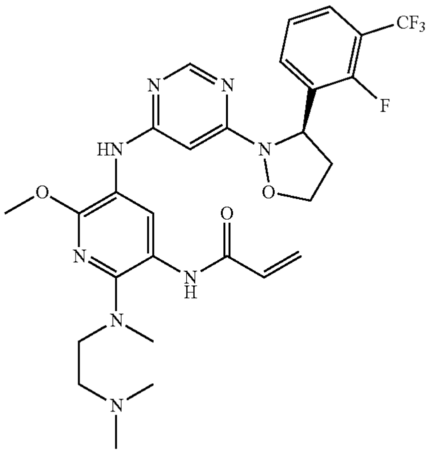 [SMILES: C=CC(=O)Nc1cc(Nc2cc(N3OCC[C@@H]3c3cccc(C(F)(F)F)c3F)ncn2)c(OC)nc1N(C)CCN(C)C] | (R)-N-(2-((2-(dimethylamino) ethyl)(methyl) amino)-5-((6-(3-(2-fluoro-3-(trifluoromethyl) phenyl) isoxazolidin-2-yl) pyrimidin-4-yl)amino)-6-methoxypyridin-3-yl)acrylamide | 605.2 [M + H] |
| 105 | 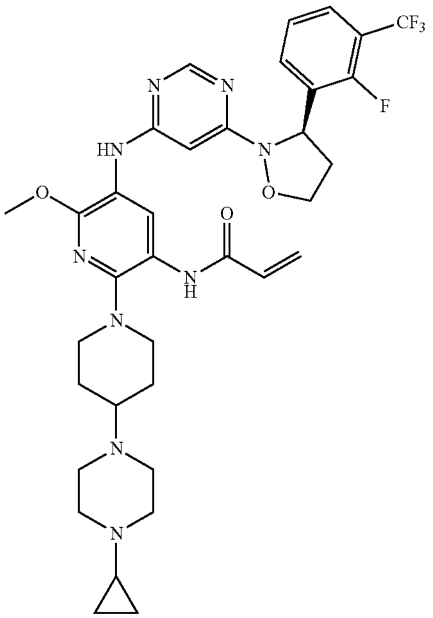 [SMILES: C=CC(=O)Nc1cc(Nc2cc(N3OCC[C@@H]3c3cccc(C(F)(F)F)c3F)ncn2)c(OC)nc1N1CCC(N2CCN(C3CC3)CC2)CC1] | (R)-N-(2-(4-(4-cyclopropyl piperazin-1-yl) piperidin-1-yl)-5-((6-(3-(2-fluoro-3-(trifluoromethyl) phenyl) isoxazolidin-2-yl) pyrimidin-4-yl)amino)-6-methoxypyridine-3-yl)acrylamide | 712.3 [M + H] |
| 106 | 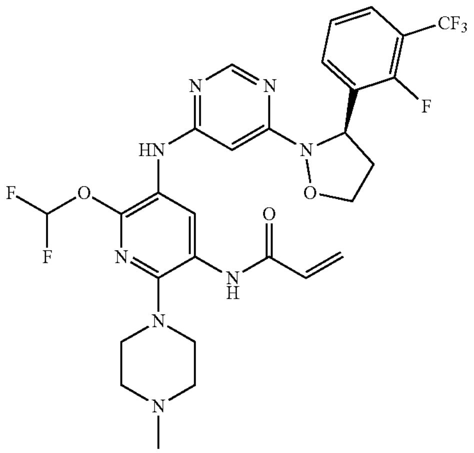 [SMILES: C=CC(=O)Nc1cc(Nc2cc(N3OCC[C@@H]3c3cccc(C(F)(F)F)c3F)ncn2)c(OC(F)F)nc1N1CCN(C)CC1] | (R)-N-(6-(difluoromethoxy)-5-((6-(3-(2-fluoro-3-(trifluoromethyl) phenyl) isoxazolidin-2-yl) pyrimidin-4-yl)amino)-2-(4-methylpiperazin-1-yl)pyridin-3-yl)acrylamide | 639.2 [M + H] |

TABLE 1-continued

| Example Compound | Structure | Compound Name | $^1$H NMR; MS [M + H]$^+$ |
| --- | --- | --- | --- |
| 107 | 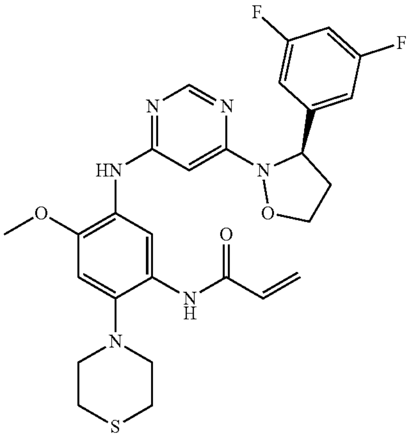 [SMILES: C=CC(=O)Nc1cc(Nc2cc(N3OCC[C@@H]3c3cc(F)cc(F)c3)ncn2)c(OC)cc1N1CCSCC1] | (R)-N-(5-((6-(3-(3,5-difluorophenyl) isoxazolidin-2-yl) pyrimidin-4-yl)amino)-4-methoxy-2-thiomorpholino phenyl)acrylamide | $^1$H NMR (400 MHz, Chloroform-d) δ 8.87 (s, 1H), 8.44 (s, 1H), 8.35 (s, 1H), 7.20 (s, 1H), 7.04-6.97 (m, 2H), 6.76 (s, 1H), 6.73-6.64 (m, 2H), 6.37 (d, J = 17.0 Hz, 1H), 6.31-6.21 (m, 1H), 5.79-5.74 (m, 1H), 5.66 (dd, J = 8.7, 4.6 Hz, 1H), 4.15 (td, J = 8.1, 4.2 Hz, 1H), 4.05 (q, J = 8.0 Hz, 1H), 3.86 (s, 3H), 3.49 (s, 1H), 3.15-3.09 (m, 3H), 2.84 (t, J = 4.9 Hz, 3H), 2.82-2.73 (m, 1H), 2.41-2.29 (m, 2H); 555.4 [M + H]$^+$ |
| 108 | 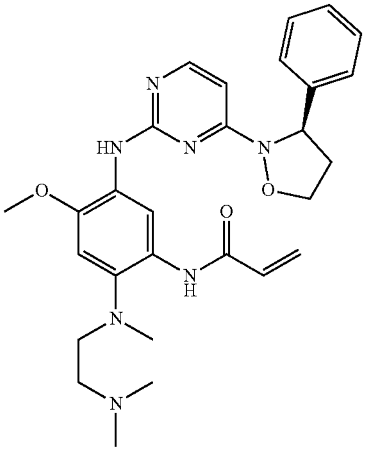 [SMILES: C=CC(=O)Nc1cc(Nc2nccc(N3OCC[C@@H]3c3ccccc3)n2)c(OC)cc1N(C)CCN(C)C] | (R)-N-(2-((2-(dimethylamino) ethyl)(methyl) amino)-4-methoxy-5-((4-(3-phenylisoxazolidin-2-yl)pyrimidin-2-yl)amino) phenyl)acrylamide | $^1$H NMR (400 MHz, Chloroform-d) δ 9.90 (s, 1H), 9.43 (s, 1H), 8.16 (d, J = 5.7 Hz, 1H), 7.53-7.40 (m, 3H), 7.26-7.22 (m, 2H), 7.20-7.13 (m, 1H), 6.71 (s, 1H), 6.60 (d, J = 5.6 Hz, 1H), 6.40-6.35 (m, 2H), 6.21-6.14 (m, 1H), 5.68 (dd, J = 8.1, 3.7 Hz, 1H), 4.20-4.08 (m, 1H), 3.94 (q, J = 7.9 Hz, 1H), 3.82 (s, 3H), 3.71-3.70 (m, 1H), 2.96-2.82 (m, 3H), 2.66 (s, 3H), 2.46-2.37 (m, 2H), 2.27 (s, 6H); 518.4 [M + H]$^+$ |
| 109 | 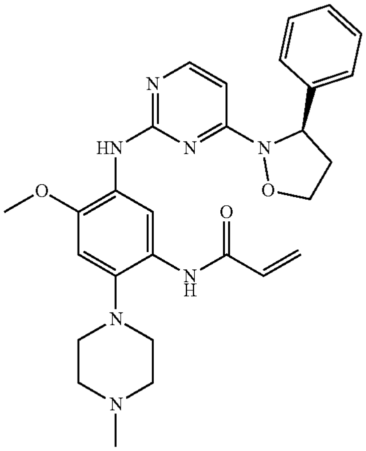 [SMILES: C=CC(=O)Nc1cc(Nc2nccc(N3OCC[C@@H]3c3ccccc3)n2)c(OC)cc1N1CCN(C)CC1] | (R)-N-(4-methoxy-2-(4-methylpiperazin-1-yl)-5-((4-(3-phenylisoxazolidin-2-yl)pyrimidin-2-yl)amino) phenyl) acrylamide | $^1$H NMR (400 MHz, Methanol-d4) δ 8.81 (s, 1H), 8.09-8.01 (m, 1H), 7.40-7.31 (m, 2H), 7.29-7.14 (m, 3H), 6.85 (s, 1H), 6.65-6.49 (m, 2H), 6.35 (d, J = 16.7 Hz, 1H), 5.92-5.77 (m, 2H), 4.25-4.16 (m, 1H), 4.01-3.92 (m, 1H), 3.89 (s, 3H), 3.59 (s, 3H), 3.05-2.94 (m, 8H), 2.64-2.59 (m, 3H), 2.42-2.31 (m, 1H); 516.4 [M + H]$^+$ |

TABLE 1-continued

| Example Compound | Structure | Compound Name | $^1H$ NMR; MS $[M + H]^+$ |
|---|---|---|---|
| 110 | 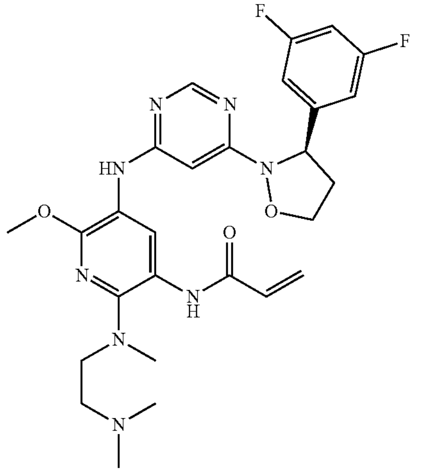 [SMILES: C=CC(=O)Nc1cc(Nc2cc(N3OCC[C@@H]3c3cc(F)cc(F)c3)ncn2)c(OC)nc1N(C)CCN(C)C] | (R)-N-(5-((6-(3-(3,5-difluorophenyl)isoxazolidin-2-yl)pyrimidin-4-yl)amino)-2-((2-(dimethylamino)ethyl)(methyl)amino)-6-methoxypyridin-3-yl)acrylamide | $^1H$ NMR (400 MHz, Chloroform-d) δ 10.10 (s, 1H), 9.24 (s, 1H), 8.38 (s, 1H), 7.04-6.98 (m, 2H), 6.77 (s, 1H), 6.72-6.65 (m, 1H), 6.59 (s, 1H), 6.47-6.40 (m, 1H), 6.33 (d, J = 11.8 Hz, 1H), 5.73-5.63 (m, 2H), 4.16 (td, J = 8.0, 4.2 Hz, 1H), 4.02 (q, J = 8.0 Hz, 1H), 3.95 (s, 3H), 2.99 (s, 2H), 2.82-2.71 (m, 4H), 2.43 (s, 2H), 2.39-2.28 (m, 7H); 555.38 $[M + H]^+$ |
| 111 | 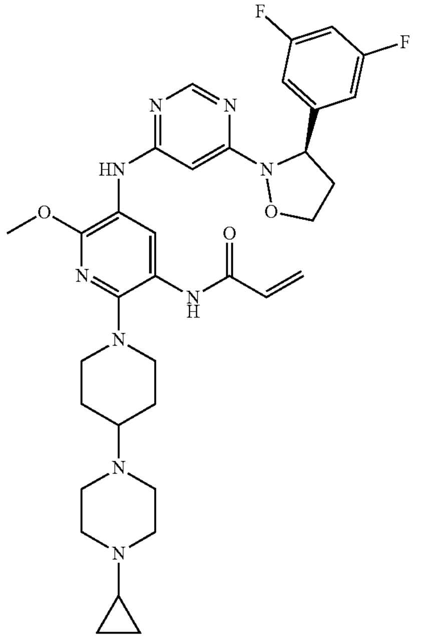 [SMILES: C=CC(=O)Nc1cc(Nc2cc(N3OCC[C@@H]3c3cc(F)cc(F)c3)ncn2)c(OC)nc1N1CCC(N2CCN(C3CC3)CC2)CC1] | (R)-N-(2-(4-(4-cyclopropyl piperazin-1-yl)piperidin-1-yl)-5-((6-(3-(3,5-difluorophenyl)isoxazolidin-2-yl)pyrimidin-4-yl)amino)-6-methoxypyridin-3-yl)acrylamide | 662.3 [M + H] |
| 112 | 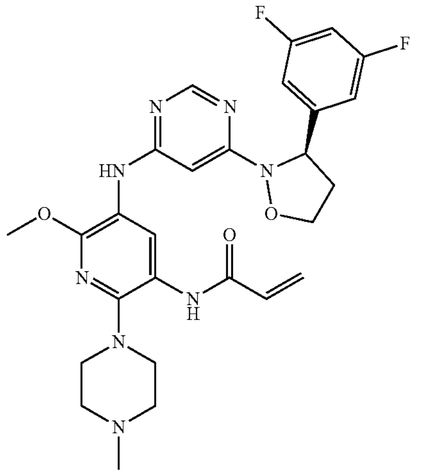 [SMILES: C=CC(=O)Nc1cc(Nc2cc(N3OCC[C@@H]3c3cc(F)cc(F)c3)ncn2)c(OC)nc1N1CCN(C)CC1] | (R)-N-(5-((6-(3-(3,5-difluorophenyl)isoxazolidin-2-yl)pyrimidin-4-yl)amino)-6-methoxy-2-(4-methylpiperazin-1-yl)pyridin-3-yl)acrylamide | $^1H$ NMR (400 MHz, Chloroform-d) δ 9.21 (s, 1H), 8.40 (s, 1H), 7.95 (s, 1H), 7.04-6.97 (m, 2H), 6.82 (s, 1H), 6.74-6.65 (m, 1H), 6.58 (s, 1H), 6.40 (d, J = 17.0 Hz, 1H), 6.27 (dd, J = 16.9, 10.1 Hz, 1H), 5.78 (d, J = 10.2 Hz, 1H), 5.67 (dd, J = 8.8, 4.6 Hz, 1H), 4.16 (td, J = 8.0, 4.2 Hz, 1H), 4.01 (t, J = 8.0 Hz, 1H), 3.96 (s, 3H), 3.07 (s, 4H), 2.77 (dtd, J = 12.3, 8.1, 4.2 Hz, 1H), 2.60 (s, 4H), 2.38 (s, 3H), 2.36-2.31 (m, 1H); 553.39 $[M + H]^+$ |

TABLE 1-continued

| Example Compound | Structure | Compound Name | $^1$H NMR; MS [M + H]$^+$ |
| --- | --- | --- | --- |
| 113 | 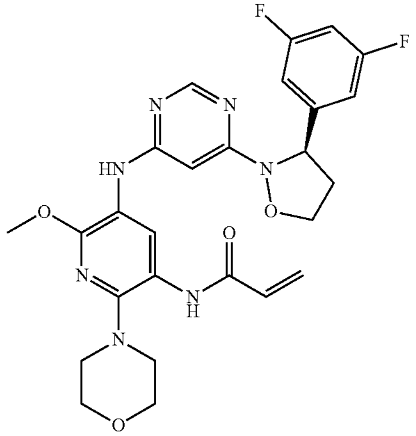 [SMILES: C=CC(=O)Nc1cc(Nc2cc(N3OCC[C@@H]3c3cc(F)cc(F)c3)ncn2)c(OC)nc1N1CCOCC1] | (R)-N-(5-((6-(3-(3,5-difluorophenyl) isoxazolidin-2-yl) pyrimidin-4-yl)amino)-6-methoxy-2-morpholinopyridin-3-yl) acrylamide | 540.2 [M + H] |
| 114 | 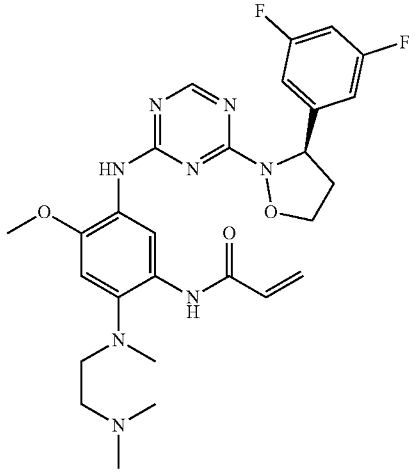 [SMILES: C=CC(=O)Nc1cc(Nc2ncnc(N3OCC[C@@H]3c3cc(F)cc(F)c3)n2)c(OC)cc1N(C)CCN(C)C] | (R)-N-(5-((4-(3-(3,5-difluorophenyl) isoxazolidin-2-yl)-1,3,5-triazin-2-yl)amino)-2-((2-(dimethylamino) ethyl)(methyl) amino)-4-methoxyphenyl) acrylamide | $^1$H NMR (400 MHz, Methanol-d4) δ 8.33 (s, 1H), 7.04-6.89 (m, 3H), 6.83 (t, J = 9.1 Hz, 1H), 6.55 (dd, J = 9.9, 16.9 Hz, 1H), 6.44 (dd, J = 1.9, 16.9 Hz, 1H), 5.88 (dd, J = 1.9, 9.9 Hz, 1H), 5.78-5.68 (m, 1H), 4.32-4.29 (m, 1H), 4.01 (q, J = 8.0 Hz, 1H), 3.94 (s, 3H), 3.44-3.36 (m, 2H), 3.18-3.11 (m, 2H), 2.99 (dt, J = 4.7, 8.5 Hz, 1H), 2.78 (s, 6H), 2.71 (s, 3H), 2.43-2.34 (m, 1H); 555.3 [M + H]$^+$ |
| 115 | 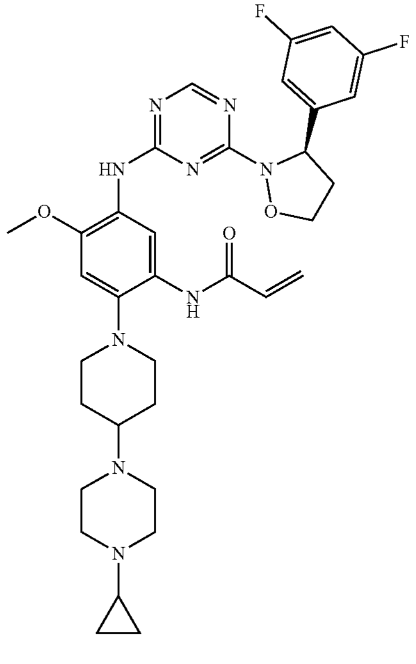 [SMILES: C=CC(=O)Nc1cc(Nc2ncnc(N3OCC[C@@H]3c3cc(F)cc(F)c3)n2)c(OC)cc1N1CCC(N2CCN(C3CC3)CC2)CC1] | (R)-N-(2-(4-(4-cyclopropyl piperazin-1-yl) piperidin-1-yl)-5-((4-(3-(3,5-difluorophenyl) isoxazolidin-2-yl)-1,3,5-triazin-2-yl)amino)-4-methoxyphenyl) acrylamide | $^1$H NMR (400 MHz, Methanol-d4) δ 8.73 (s, 1H), 8.32 (s, 1H), 6.98-6.85 (m, 3H), 6.80-6.71 (m, 1H), 6.57 (dd, J = 10.1, 17.0 Hz, 1H), 6.39 (d, J = 17.0 Hz, 1H), 5.84 (d, J = 10.3 Hz, 1H), 4.32-4.29 (m, 1H), 4.01 (t, J = 8.0 Hz, 1H), 3.88 (s, 3H), 3.19-3.10 (m, 3H), 3.10-2.95 (m, 5H), 2.95-2.86 (m, 4H), 2.84-2.75 (m, 2H), 2.43-2.34 (m, 1H), 2.18-2.11 (m, 2H), 1.94-1.79 (m, 3H), 0.58 (d, J = 6.6 Hz, 2H), 0.53-0.45 (m, 2H); 662.3 [M + H]$^+$ |

TABLE 1-continued

| Example Compound | Structure | Compound Name | ¹H NMR; MS [M + H]⁺ |
|---|---|---|---|
| 116 | 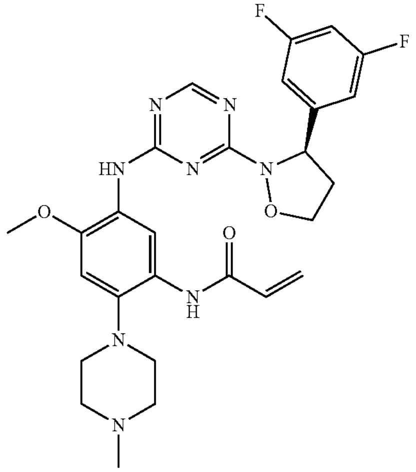 [SMILES: C=CC(=O)Nc1cc(Nc2ncnc(N3OCC[C@@H]3c3cc(F)cc(F)c3)n2)c(OC)cc1N1CCN(C)CC1] | (R)-N-(5-((4-(3-(3,5-difluorophenyl) isoxazolidin-2-yl)-1,3,5-triazin-2-yl)amino)-4-methoxy-2-(4-methylpiperazin-1-yl)phenyl) acrylamide | $^1$H NMR (400 MHz, Methanol-d4) δ 8.76 (s, 1H), 8.33 (s, 1H), 7.02-6.85 (m, 3H), 6.78 (t, J = 9.6 Hz, 1H), 6.58 (dd, J = 10.2, 16.9 Hz, 1H), 6.40 (d, J = 16.9 Hz, 1H), 5.85 (d, J = 10.2 Hz, 2H), 4.31 (q, J = 4.1 Hz, 1H), 4.02 (q, J = 7.9 Hz, 1H), 3.90 (s, 3H), 3.11-3.04 (m, 8H), 3.01-2.95 (m, 1H), 2.69 (s, 3H), 2.39 (ddt, J = 4.1, 8.1, 12.8 Hz, 1H); 553.2 [M + H]$^+$ |
| 117 | 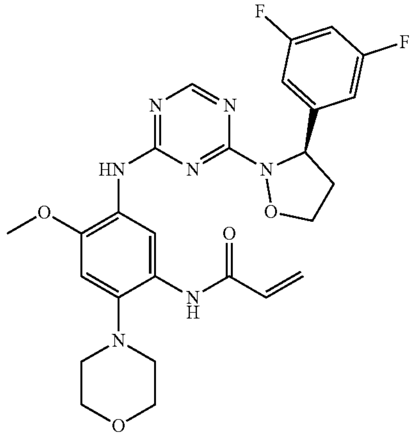 [SMILES: C=CC(=O)Nc1cc(Nc2ncnc(N3OCC[C@@H]3c3cc(F)cc(F)c3)n2)c(OC)cc1N1CCOCC1] | (R)-N-(5-((4-(3-(3,5-difluorophenyl) isoxazolidin-2-yl)-1,3,5-triazin-2-yl)amino)-4-methoxy-2-morpholinophenyl) acrylamide | 540.2 [M + H] |
| 118 | 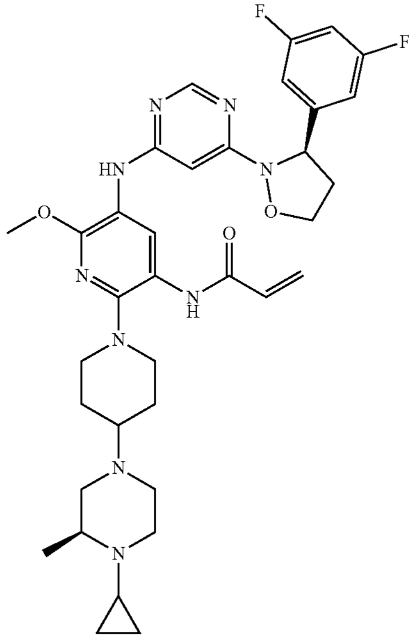 [SMILES: C=CC(=O)Nc1cc(Nc2cc(N3OCC[C@@H]3c3cc(F)cc(F)c3)ncn2)c(OC)nc1N1CCC(N2CCN(C3CC3)[C@@H](C)C2)CC1] | N-(2-(4-((S)-4-cyclopropyl-3-methylpiperazin-1-yl)piperidin-1-yl)-5-((6-((R)-3-(3,5-difluorophenyl) isoxazolidin-2-yl) pyrimidin-4-yl)amino)-6-methoxypyridin-3-yl)acrylamide | 676.3 [M + H] |

TABLE 1-continued

| Example Compound | Structure | Compound Name | $^1$H NMR; MS [M + H]$^+$ |
| --- | --- | --- | --- |
| 119 | 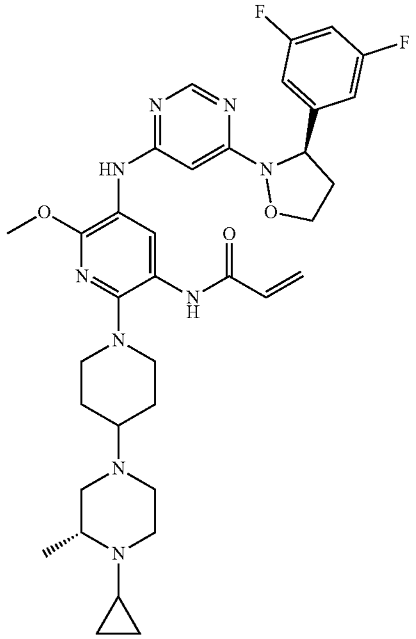 [SMILES: C=CC(=O)Nc1cc(Nc2cc(N3OCC[C@@H]3c3cc(F)cc(F)c3)ncn2)c(OC)nc1N1CCC(N2CCN(C3CC3)[C@H](C)C2)CC1] | N-(2-(4-((R)-4-cyclopropyl-3-methylpiperazin-1-yl)piperidin-1-yl)-5-((6-((R)-3-(3,5-difluorophenyl)isoxazolidin-2-yl)pyrimidin-4-yl)amino)-6-methoxypyridin-3-yl)acrylamide | 676.3 [M + H] |
| 120 | 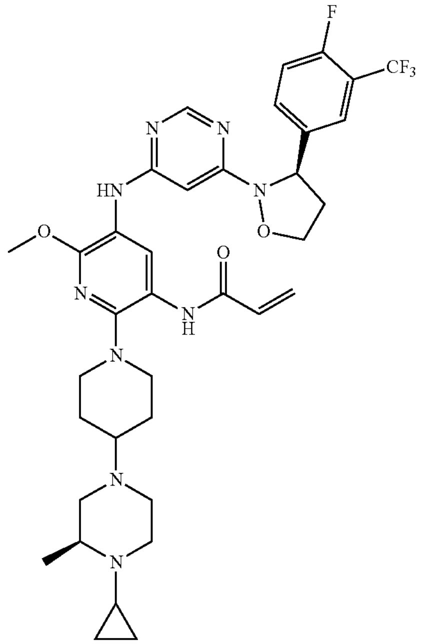 [SMILES: C=CC(=O)Nc1cc(Nc2cc(N3OCC[C@@H]3c3ccc(F)c(C(F)(F)F)c3)ncn2)c(OC)nc1N1CCC(N2CCN(C3CC3)[C@@H](C)C2)CC1] | N-(2-(4-((S)-4-cyclopropyl-3-methylpiperazin-1-yl)piperidin-1-yl)-5-((6-((R)-3-(4-fluoro-3-(trifluoromethyl)phenyl)isoxazolidin-2-yl)pyrimidin-4-yl)amino)-6-methoxypyridin-3-yl)acrylamide | 726.3 [M + H] |

TABLE 1-continued
| Example Compound | Structure | Compound Name | $^1$H NMR; MS [M + H]$^+$ |
|---|---|---|---|
| 121 | 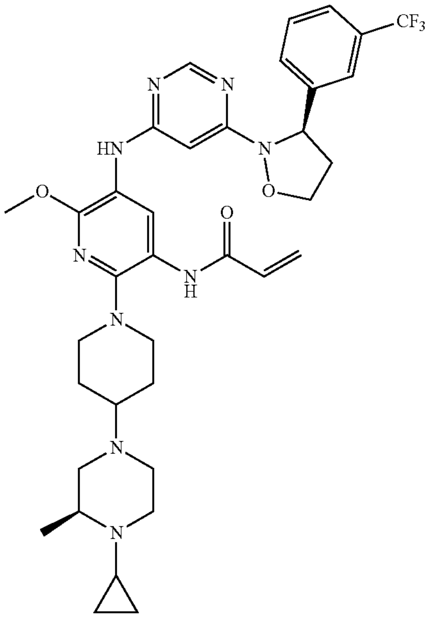 | N-(2-(4-((S)-4-cyclopropyl-3-methylpiperazin-1-yl)piperidin-1-yl)-6-methoxy-5-((6-((R)-3-(3-(trifluoromethyl) phenyl) isoxazolidin-2-yl) pyrimidin-4-yl) amino)pyridin-3-yl)acrylamide | 726.3 [M + H] |
| 122 | 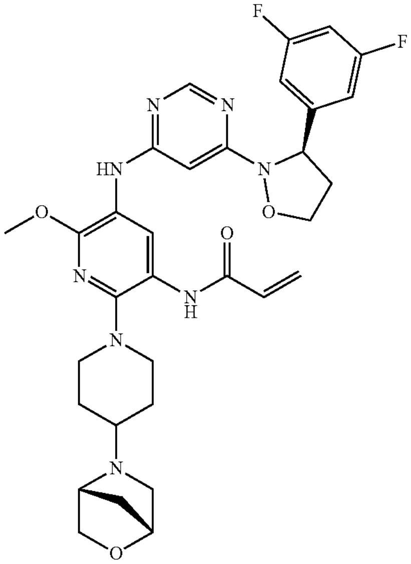 [SMILES: C=CC(=O)Nc1cc(Nc2cc(N3OCC[C@@H]3c3cc(F)cc(F)c3)ncn2)c(OC)nc1N1CCC(N2C[C@H]3C[C@@H]2CO3)CC1] | N-(2-(4-((1R,4R)-2-oxa-5-azabicyclo [2.2.1]heptan-5-yl)piperidin-1-yl)-5-((6-((R)-3-(3,5-difluorophenyl) isoxazolidin-2-yl) pyrimidin-4-yl)amino)-6-methoxypyridin-3-yl)acrylamide | 635.2 [M + H] |

TABLE 1-continued

| Example Compound | Structure | Compound Name | $^{1}$H NMR; MS [M + H]$^{+}$ |
|---|---|---|---|
| 123 | 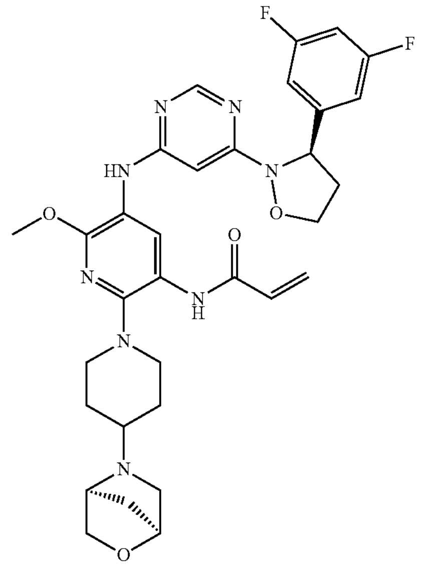 [SMILES: C=CC(=O)Nc1cc(Nc2cc(N3OCC[C@@H]3c3cc(F)cc(F)c3)ncn2)c(OC)nc1N1CCC(N2C[C@@H]3C[C@H]2CO3)CC1] | N-(2-(4-((1S,4S)-2-oxa-5-azabicyclo[2.2.1]heptan-5-yl)piperidin-1-yl)-5-((6-((R)-3-(3,5-difluorophenyl)isoxazolidin-2-yl)pyrimidin-4-yl)amino)-6-methoxypyridin-3-yl)acrylamide | 635.2 [M + H] |
| 124 | 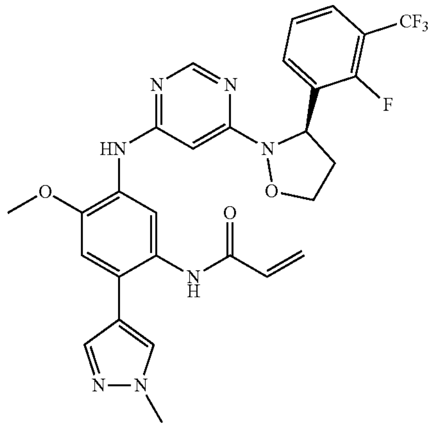 [SMILES: C=CC(=O)Nc1cc(Nc2cc(N3OCC[C@@H]3c3cccc(C(F)(F)F)c3F)ncn2)c(OC)cc1-c1cnn(C)c1] | (R)-N-(5-((6-(3-(2-fluoro-3-(trifluoromethyl)phenyl)isoxazolidin-2-yl)pyrimidin-4-yl)amino)-4-methoxy-2-(1-methyl-1H-pyrazol-4-yl)phenyl)acrylamide | $^{1}$H NMR (400 MHz, Chloroform-d) δ 8.65 (s, 1H), 8.35 (s, 1H), 7.81 (t, J = 7.4 Hz, 1H), 7.62 (s, 1H), 7.55-7.48 (m, 2H), 7.30-7.19 (m, 4H), 6.81 (s, 1H), 6.35 (d, J = 16.8 Hz, 1H), 6.16 (dd, J = 16.9, 10.2 Hz, 1H), 5.95 (dd, J = 9.0, 4.7 Hz, 1H), 5.73 (d, J = 10.2 Hz, 1H), 4.16 (dd, J = 8.1, 4.0 Hz, 1H), 3.99 (s, 3H), 3.88 (s, 3H), 2.94-2.85 (m, 1H), 2.37-2.28 (m, 2H), 2.09 (s, 1H), 1.25 (s, 1H); 584.4 [M + H]$^{+}$ |
| 125 | 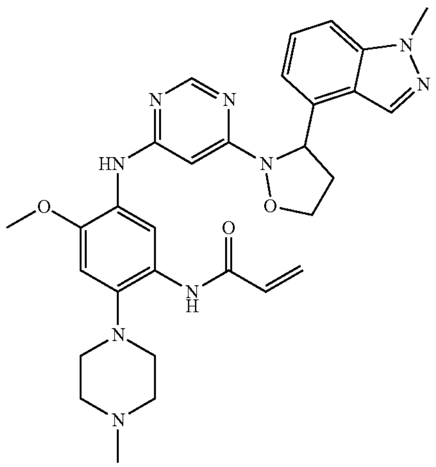 | N-(4-methoxy-5-((6-(3-(1-methyl-1H-indazol-4-yl)isoxazolidin-2-yl)pyrimidin-4-yl)amino)-2-(4-methylpiperazin-1-yl)phenyl)acrylamide | $^{1}$H NMR (400 MHz, Chloroform-d) δ 8.92 (s, 1H), 8.44 (s, 1H), 8.37 (d, J = 1.0 Hz, 1H), 8.19 (d, J = 0.9 Hz, 1H), 7.38-7.28 (m, 3H), 7.04 (s, 1H), 6.81 (s, 1H), 6.42-6.35 (m, 1H), 6.31-6.23 (m, 1H), 6.03 (dd, J = 8.8, 4.9 Hz, 1H), 5.76 (dd, J = 9.9, 1.6 Hz, 1H), 4.23 (td, J = 7.9, 3.8 Hz, 2H), 4.08 (s, 4H), 3.85 (s, 3H), 3.66 (p, J = 6.7 Hz, 2H), 3.47 (t, J = 7.0 Hz, 1H), 3.07 (dd, J = 17.9, 10.5 Hz, 5H), 2.88 (dd, J = 8.2, 4.0 Hz, 1H), 2.53 (d, J = 13.4 Hz, 4H); 570.47 [M + H]$^{+}$ |

TABLE 1-continued

| Example Compound | Structure | Compound Name | $^1$H NMR; MS [M + H]$^+$ |
|---|---|---|---|
| 126 | 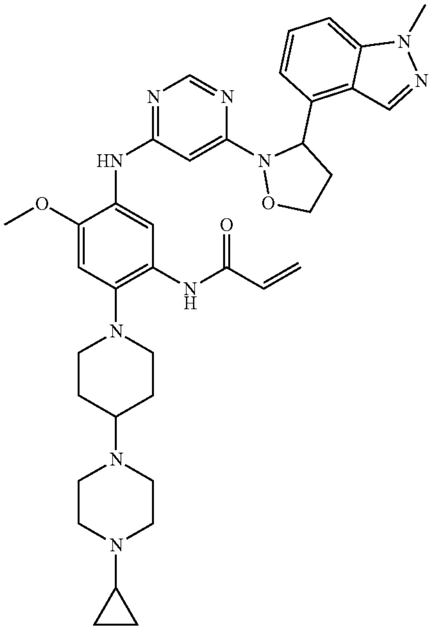 | N-(2-(4-(4-cyclopropyl piperazin-1-yl) piperidin-1-yl)-4-methoxy-5-((6-(3-(1-methyl-1H-indazol-4-yl) isoxazolidin-2-yl)pyrimidin-4-yl) amino)phenyl) acrylamide | $^1$H NMR (400 MHz, Chloroform-d) δ 8.88 (s, 1H), 8.45 (s, 1H), 8.36 (s, 1H), 8.19 (s, 1H), 7.38-7.28 (m, 3H), 6.90 (s, 1H), 6.75 (s, 2H), 6.36 (d, J = 16.9 Hz, 1H), 6.25 (dd, J = 17.0, 10.1 Hz, 1H), 6.03 (dd, J = 8.9, 4.9 Hz, 1H), 5.79-5.69 (m, 1H), 4.23 (td, J = 7.9, 3.8 Hz, 1H), 4.12 (t, J = 8.1 Hz, 1H), 4.08 (s, 3H), 3.84 (s, 3H), 3.06 (d, J = 11.2 Hz, 2H), 2.87 (ddd, J = 12.1, 8.2, 4.1 Hz, 2H), 2.70 (dd, J = 26.0, 15.0 Hz, 9H), 2.57-2.47 (m, 2H), 2.33 (s, 1H), 2.08 (d, J = 12.5 Hz, 2H), 1.69 (s, 2H), 0.50-0.39 (m, 4H); 679.59 [M + H]$^+$ |
| 127 | 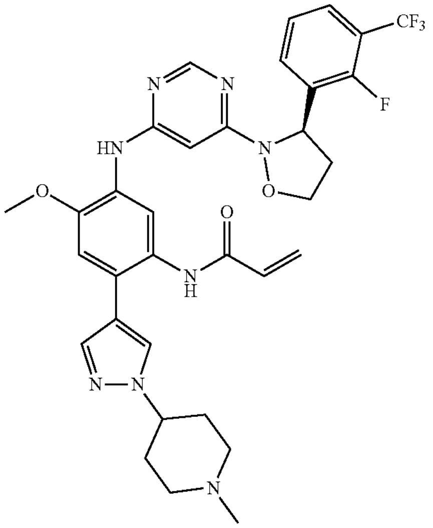 [SMILES: C=CC(=O)Nc1cc(Nc2cc(N3OCC[C@@H]3c3cccc(C(F)(F)F)c3F)ncn2)c(OC)cc1-c1cnn(C2CCN(C)CC2)c1] | (R)-N-(5-((6-(3-(2-fluoro-3-(trifluoromethyl) phenyl) isooxazolidin-2-yl) pyrimidin-4-yl)amino)-4-methoxy-2-(1-(1-methylpiperidin-4-yl)-1H-pyrazol-4-yl) phenyl)acrylamide | $^1$H NMR (400 MHz, Chloroform-d) δ 8.72 (s, 1H), 8.39 (s, 1H), 7.83 (t, J = 7.5 Hz, 2H), 7.63 (s, 1H), 7.56 (s, 1H), 7.51 (t, J = 7.2 Hz, 2H), 7.11 (s, 2H), 6.83 (d, J = 10.5 Hz, 2H), 6.35 (d, J = 16.9 Hz, 1H), 6.14 (dd, J = 16.7, 10.1 Hz, 1H), 5.96 (dd, J = 8.9, 4.7 Hz, 2H), 5.73 (d, J = 10.2 Hz, 1H), 4.08 (t, J = 8.4 Hz, 1H), 3.89 (s, 4H), 3.03 (s, 2H), 3.00 (s, 2H), 2.95-2.83 (m, 2H), 2.35 (d, J = 1.7 Hz, 4H), 2.33-2.26 (m, 2H), 2.14 (d, J = 5.8 Hz, 2H), 2.10 (s, 2H), 2.07 (s, 1H); 667. 3 [M + H]$^+$ |

TABLE 1-continued

| Example Compound | Structure | Compound Name | $^1H$ NMR; MS $[M + H]^+$ |
|---|---|---|---|
| 128 | 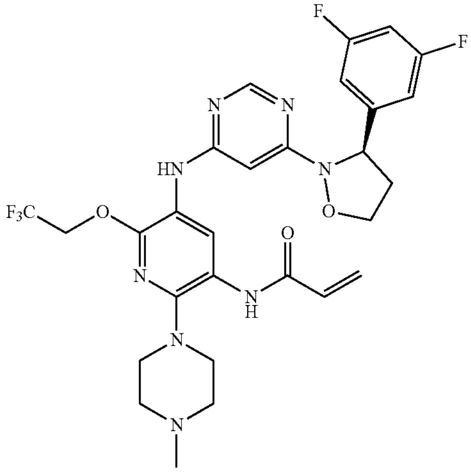 [SMILES: C=CC(=O)Nc1cc(Nc2cc(N3OCC[C@@H]3c3cc(F)cc(F)c3)ncn2)c(OCC(F)(F)F)nc1N1CCN(C)CC1] | (R)-N-(5-((6-(3-(3,5-difluorophenyl) isoxazolidin-2yl)pyrimidin-4-yl)amino)-2-(4-methylpiperazin-1-yl)-6-(2,2,2-trifluoroethoxy) pyridin-3-yl)acrylamide | $^1H$ NMR (400 MHz, Chloroform-d) δ 9.32 (s, 1H), 8.41 (s, 1H), 7.94 (s, 1H), 7.04-6.97 (m, 2H), 6.73 (s, 1H), 6.69 (tt, J = 9.0, 2.4 Hz, 1H), 6.60 (s, 1H), 6.41 (d, J = 16.8 Hz, 1H), 6.27 (dd, J = 16.9, 10.1 Hz, 1H), 5.80 (dd, J = 10.1, 1.3 Hz, 1H), 5.67 (dd, J = 8.8, 4.7 Hz, 1H), 4.79 (q, J = 8.5 Hz, 2H), 4.18 (td, J = 8.0, 4.2 Hz, 1H), 4.01 (q, J = 8.0 Hz, 1H), 3.05 (q, J = 4.2 Hz, 4H), 2.78 (dtd, J = 12.3, 8.1, 4.2 Hz, 1H), 2.60 (s, 4H), 2.38 (s, 3H), 2.35 (td, J = 8.0, 4.3 Hz, 1H); 621.3 $[M + H]^+$ |
| 129 | 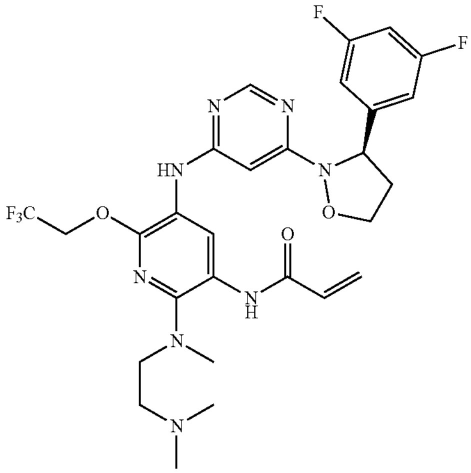 [SMILES: C=CC(=O)Nc1cc(Nc2cc(N3OCC[C@@H]3c3cc(F)cc(F)c3)ncn2)c(OCC(F)(F)F)nc1N(C)CCN(C)C] | (R)-N-(5-((6-3-(3,5-difluorophenyl) isoxazolidin-2yl)pyrimidin-4-yl)amino)-2-((2-(dimehtylamino) ethyl) (methyl)amino)-6-(2,2,2-trifluoroethoxy) pyridin-3-yl)acrylamide | $^1H$ NMR (400 MHz, Chloroform-d) δ 10.21 (s, 1H), 9.34 (s, 1H), 8.39 (s, 1H), 7.04-6.97 (m, 2H), 6.73-6.65 (m, 2H), 6.57 (d, J = 22.1 Hz, 1H), 6.44 (dd, J = 17.0, 1.5 Hz, 1H), 6.31 (dd, J = 17.0, 9.9 Hz, 1H), 5.70 (ddd, J = 18.2, 9.4, 3.3 Hz, 2H), 4.78 (qq, J = 8.9, 4.0 Hz, 2H), 4.17 (td, J = 8.0, 4.1 Hz, 1H), 4.03 (q, J = 8.1 Hz, 1H), 3.02-2.95 (m, 2H), 2.82-2.78 (m, 1H), 2.76 (s, 3H), 2.67 (ddd, J = 11.8, 8.8, 4.9 Hz, 1H), 2.49-2.44 (m, 2H), 2.38-2.32 (m, 6H); 623.37 $[M + H]^+$ |

<Experiment Example 1> Evaluation of Ba/F3 Proliferation Suppression Activity A following experiment was carried out to evaluate the suppression activity of the compounds according to the present invention against the proliferation of Ba/F3 which expresses EGFR mutations.

For the Ba/F3 cells, a RPMI-1640 medium containing 10% FBS and 5 ng/ml IL-3 (R&D Systems) was used. The transduced Ba/F3 cells were cultured in a medium, which is same as the above medium, but 1 µg/ml puromycin (Invitrogen) was additionally added to.

24 hours before the treatment of the cells with the compounds, 3000 to 5000 cells were distributed into each well of a white clear bottom 96 well plate (Corning). The compounds were diluted in a dimethyl sulfoxide (e.g. dilution ratio of 3:1 and total 12 concentrations) and then injected by 0.5 ul respectively, such that a final concentration amounted to 0.3 nM to 50 uM. 72 hours after the treatment with the compounds, the measurement of live cells was made in such way that these cells were stored for 10 minutes at a room temperature using a CellTiter-Glo luminescent cell-viability reagent (Promega) and then their luminescence intensities were measured using a reader (i.e. Synergy Neo, Biotek). Each test was repeated three times.

Resulting values were calculated as a cell growth ratio (%) compared to a control. Then, the graphs were drawn and the $GI_{50}$ values were calculated by using a program, GraphPad Prism version 5.0.

A following table 2 shows the evaluation results of the suppression activity against the proliferation of Ba/F3 cells expressing EGFR mutations:

TABLE 2

| Example Compound | EGFR Exon20ins NPH |
|---|---|
| 1 | A |
| 2 | B |
| 3 | B |
| 4 | A |
| 5 | B |
| 6 | B |
| 7 | A |
| 8 | A |
| 9 | B |
| 10 | B |
| 11 | B |
| 12 | B |
| 13 | B |

TABLE 2-continued

| Example Compound | EGFR Exon20ins NPH |
|---|---|
| 14 | B |
| 15 | B |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | B |
| 29 | B |
| 30 | B |
| 31 | B |
| 32 | B |
| 33 | B |
| 34 | B |
| 35 | B |
| 36 | A |
| 37 | A |
| 38 | A |
| 39 | A |
| 40 | A |
| 41 | A |
| 42 | A |
| 43 | A |
| 44 | A |
| 45 | B |
| 46 | A |
| 47 | A |
| 48 | A |
| 49 | A |
| 50 | B |
| 51 | B |
| 52 | A |
| 53 | A |
| 54 | B |
| 55 | A |
| 56 | B |
| 57 | B |
| 58 | A |
| 59 | A |
| 60 | A |
| 61 | A |
| 62 | A |
| 63 | B |
| 64 | A |
| 65 | B |
| 66 | A |
| 67 | B |
| 68 | B |
| 69 | A |
| 70 | A |
| 71 | A |
| 72 | B |
| 73 | A |
| 74 | B |
| 75 | B |
| 76 | A |
| 77 | B |
| 78 | A |
| 79 | B |
| 80 | A |
| 81 | B |
| 82 | A |
| 83 | B |
| 84 | A |
| 85 | B |
| 86 | B |
| 87 | A |
| 88 | B |
| 89 | A |

TABLE 2-continued

| Example Compound | EGFR Exon20ins NPH |
|---|---|
| 90 | A |
| 91 | B |
| 92 | B |
| 93 | A |
| 94 | A |
| 95 | A |
| 96 | A |
| 97 | A |
| 98 | B |
| 99 | B |
| 100 | C |
| 101 | A |
| 102 | — |
| 103 | — |
| 104 | — |
| 105 | — |
| 106 | — |
| 107 | B |
| 108 | B |
| 109 | — |
| 110 | — |
| 111 | — |
| 112 | — |
| 113 | — |
| 114 | — |
| 115 | — |
| 116 | — |
| 117 | — |
| 118 | — |
| 119 | — |
| 120 | — |
| 121 | — |
| 122 | — |
| 123 | — |
| 124 | — |
| 125 | B |
| 126 | A |
| 128 | B |
| TAK788 | A |

A: $GI_{50}$ < 50 nM;
B: 50 nM ≤ $GI_{50}$ < 500 nM;
C: 500 nM ≤ $GI_{50}$ < 5000 nM;
D: 5000 nM ≤ $GI_{50}$;

A following table 3 shows the evaluation results of the suppression activity against the proliferation of the Ba/F3 cells expressing ErbB2 (HER2) wild types or mutations:

TABLE 3

| Example Compound | HER2 WT | HER2 YVMA Exon20ins |
|---|---|---|
| 1 | — | B |
| 37 | — | A |
| 41 | A | A |
| 52 | A | A |
| 53 | — | A |
| 55 | A | A |
| 58 | — | A |
| 60 | — | A |
| 61 | — | A |
| 62 | — | A |

A: $GI_{50}$ < 50 nM;
B: 50 nM ≤ $GI_{50}$ < 500 nM;
C: 500 nM ≤ $GI_{50}$ < 5000 nM;
D: 5000 nM ≤ $GI_{50}$;

As shown in the Table 2 and the Table 3, it may be identified that the example compounds according to the present invention exhibit a high suppression ability against the EGFR mutations as well as against the ErbB2 wild types or the mutations thereof in the Ba/F3 cell strains.

Although the present invention has been explained in detail in the above through preferred preparation examples and example compounds and also the experiment example, the scope of the present invention is not limited to such specific example compounds and shall be defined by appended claims. Further, it shall be understood that a person who is skilled in the art may make various modifications and changes without departing from the scope of the present invention.

The invention claimed is:

1. A compound of Formula 1, or a pharmaceutically acceptable salt thereof:

Formula 1

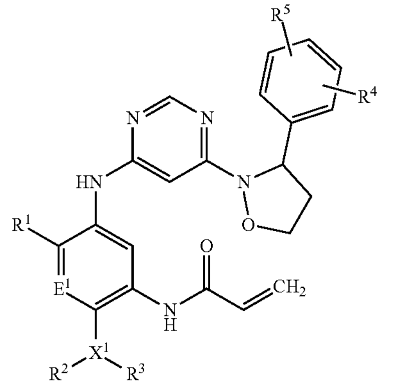

wherein:

$E^1$ is N;

$R^1$ is hydrogen, $C_{1-5}$ alkoxy, or alkoxy substituted by halogen;

$X^1$ is CH, N, O or S;

wherein when $X^1$ is CH, $R^2$ and $R^3$ form, together with a bonded C, a 3 to 12 atom heteroaryl comprising at least one N, and the 3 to 12 atom heteroaryl is substituted or unsubstituted by a $C_{1-5}$ straight chain or branched chain alkyl or a 3 to 12 atom heterocycloalkyl, wherein when $X^1$ is N, $R^2$ and $R^3$ are each independently selected from the group consisting of: hydrogen and $C_{1-5}$ straight chain or branched chain alkyl, or $R^2$ and $R^3$ form, together with a bonded N, a 3 to 12 atom heterocycloalkyl, wherein the 3 to 12 atom heterocycloalkyl comprises one or more heteroatoms, and wherein each heteroatom of the one or more heteroatoms is selected from the group consisting of: N, O and S, wherein the $C_{1-5}$ straight chain or branched chain alkyl is substituted or unsubstituted by a $C_{1-5}$ alkylamino, wherein the 3 to 12 atom heterocycloalkyl comprises one or more heteroatoms, each heteroatom of the one or more heteroatoms being selected from the group consisting of: N, O and S, is substituted or unsubstituted by one or more substituents A, wherein each substituent A of the one or more substituents A is selected from the group consisting of: $C_{1-5}$ straight chain or branched chain alkyl, $C_{3-6}$ cycloalkyl, $C_{1-5}$ alkylamino, allyl, oxo, $C_{1-3}$ alkylcarbonyl, and 3 to 12 atom heterocycloalkyl, wherein the 3 to 12 atom heterocycloalkyl comprises one or more heteroatoms, wherein each heteroatom of the one or more heteroatoms is selected from the group consisting of: N and O, wherein the $C_{1-5}$ straight chain or branched chain alkyl is additionally substituted or unsubstituted by a $C_{3-6}$ cycloalkyl, a $C_{1-5}$ alkylamino, or a 3 to 12 atom heterocycloalkyl that comprises at least one N, wherein the 3 to 12 atom heterocycloalkyl is substituted or unsubstituted by a substituent B, wherein the substituent B is selected from the group consisting of: $C_{1-5}$ straight chain or branched chain alkyl, $C_{3-6}$ cycloalkyl, $C_{1-5}$ alkylcarbonyl, a 3 to 12 atom heterocycloalkyl that includes one or more heteroatoms, and oxo, and wherein each heteroatom of the one or more heteroatoms is selected from the group consisting of: N and O, wherein the 3 to 12 atom heterocycloalkyl is additionally substituted or unsubstituted by a $C_{1-5}$ straight chain or branched chain alkyl or a $C_{3-6}$ cycloalkyl;

wherein when $X^1$ is S or O, $R^2$ does not exist and $R^3$ is $C_{1-5}$ alkyl substituted by $C_{1-5}$ alkylamino; and $R^4$ and $R^5$ are each independently selected from the group consisting of: hydrogen, halogen, and haloalkyl, or $R^4$ and $R^5$ form, together with a benzene, a 7 to 12 atom heteroaryl that includes one or more heteroatoms, wherein each heteroatom of the one or more heteroatoms is selected from the group consisting of: N, O and S, and wherein the 7 to 12 atom heteroaryl is substituted or unsubstituted by a $C_{1-5}$ straight chain or branched chain alkyl.

2. The compound of claim 1, or a pharmaceutically acceptable salt thereof, wherein:

$R^1$ is hydrogen, methoxy, difluoromethoxy, or trifluoroethoxy;

$X^1$ is N;

$R^2$ is methyl, and $R^3$ is dimethylaminoethyl or methylaminoethyl; or $R^2$ and $R^3$ form, together with a N bonded thereto, a morpholino, a piperazine, or a piperidine, wherein the morpholino, the piperazine, or the piperidine is substituted or unsubstituted by one or more substituents E, wherein each substituent E of the one or more substituents E is selected from the group consisting of: methyl, piperazinyl, morpholino, and oxazabicycloheptane, and wherein when E is piperazinyl, the piperazinyl is additionally substituted or unsubstituted by a methyl or a cyclopropyl; and $R^4$ and $R^5$ are each independently hydrogen, fluoro, or trifluoromethyl.

3. A compound, or a pharmaceutically acceptable salt thereof, selected from the group consisting of:

(R)—N-(5-((6-(3-(2-fluoro-3-(trifluoromethyl)phenyl) isoxazolidine-2-yl)pyrimidine-4-yl)amino)-6-methoxy-2-(4-methylpiperazine-1-yl)pyridine-3-yl) acrylamide;

(R)—N-(5-((6-(3-(2-fluoro-3-(trifluoromethyl)phenyl) isoxazolidine-2-yl)pyrimidine-4-yl)amino)-2-(4-methylpiperazine-1-yl)-6-(2,2,2-trifluoroethoxy)pyridine-3-yl)acrylamide;

(R)—N-(2-((2-(dimethylamino)ethyl)(methyl)amino)-5-((6-(3-(2-fluoro-3-(trifluoromethyl)phenyl)isoxazolidine-2-yl)pyrimidine-4-yl)amino)-6-methoxypyridine-3-yl)acrylamide;

(R)—N-(2-(4-(4-cyclopropylpiperazin-1-yl)piperidine-1-yl)-5-((6-(3-(2-fluoro-3-(trifluoromethyl)phenyl)isoxazolidine-2-yl)pyrimidine-4-yl)amino)-6-methoxypyridine-3-yl)acrylamide;

(R)—N-(6-(difluoromethoxy)-5-((6-(3-(2-fluoro-3-(trifluoromethyl)phenyl)isoxazolidine-2-yl)pyrimidine-4-yl)amino)-2-(4-methylpiperazine-1-yl)pyridine-3-yl) acrylamide;

(R)—N-(5-((6-(3-(3,5-difluorophenyl)isoxazolidine-2-yl)pyrimidine-4-yl)amino)-2-((2-(dimethylamino) ethyl)(methyl)amino)-6-methoxypyridine-3-yl)acrylamide;

(R)—N-(2-(4-(4-cyclopropylpiperazin-1-yl)piperidine-1-yl)-5-((6-(3-(3,5-difluorophenyl)isoxazolidine-2-yl) pyrimidine-4-yl)amino)-6-methoxypyridine-3-yl)acrylamide;

(R)—N-(5-((6-(3-(3,5-difluorophenyl)isoxazolidine-2-yl)pyrimidine-4-yl)amino)-6-methoxy-2-(4-methylpiperazine-1-yl)pyridine-3-yl)acrylamide;

(R)—N-(5-((6-(3-(3,5-difluorophenyl)isoxazolidine-2-yl)pyrimidine-4-yl)amino)-6-methoxy-2-morpholinopyridine-3-yl)acrylamide;

N-(2-(4-((S)-4-cyclopropyl-3-methylpiperazine-1-yl)piperidine-1-yl)-5-((6-((R)-3-(3,5-difluorophenyl)isoxazolidine-2-yl)pyrimidine-4-yl)amino)-6-methoxypyridine-3-yl)acrylamide;

N-(2-(4-((R)-4-cyclopropyl-3-methylpiperazine-1-yl)piperidine-1-yl)-5-((6-((R)-3-(3,5-difluorophenyl)isoxazolidine-2-yl)pyrimidine-4-yl)amino)-6-methoxypyridine-3-yl)acrylamide;

N-(2-(4-((S)-4-cyclopropyl-3-methylpiperazine-1-yl)piperidine-1-yl)-5-((6-((R)-3-(4-fluoro-3-(trifluoromethyl)phenyl)isoxazolidine-2-yl)pyrimidine-4-yl) amino)-6-methoxypyridine-3-yl)acrylamide;

N-(2-(4-((S)-4-cyclopropyl-3-methylpiperazine-1-yl)piperidine-1-yl)-6-methoxy-5-((6-((R)-3-(3-(trifluoromethyl)phenyl)isoxazolidine-2-yl)pyrimidine-4-yl) amino)pyridine-3-yl)acrylamide;

N-(2-(4-((1R,4R)-2-oxa-5-azabicyclo[2.2.1]heptane-5-yl)piperidine-1-yl)-5-((6-((R)-3-(3,5-difluorophenyl) isoxazolidine-2-yl)pyrimidine-4-yl)amino)-6-methoxypyridine-3-yl)acrylamide; and N-(2-(4-((1S,4S)-2-oxa-5-azabicyclo[2.2.1]heptane-5-yl) piperidine-1-yl)-5-((6-((R)-3-(3,5-difluorophenyl) isoxazolidine-2-yl)pyrimidine-4-yl)amino)-6-methoxypyridine-3-yl)acrylamide.

4. A compound, or a pharmaceutically acceptable salt thereof, selected from the group consisting of:

(R)—N-(5-((6-(3-(3,5-difluorophenyl)isoxazolidin-2-yl) pyrimidin-4-yl)amino)-2-(4-methylpiperazin-1-yl)-6-(2,2,2-trifluoroethoxy)pyridin-3-yl)acrylamide; and (R)—N-(5-((6-(3-(3,5-difluorophenyl)isoxazolidin-2-yl) pyrimidin-4-yl)amino)-2-((2-(dimethylamino)ethyl) (methyl)amino)-6-(2,2,2-trifluoroethoxy)pyridin-3-yl) acrylamide.

5. A pharmaceutical composition comprising a compound of claim 1, or a pharmaceutically acceptable salt thereof, and at least one pharmaceutically acceptable carrier.

6. A method of treating cancer in a subject, the method comprising administering to the subject a compound of claim 1, or a pharmaceutically acceptable salt thereof.

7. The method of claim 6, wherein the cancer comprises one or more EGFR mutations, wherein each EGFR mutation of the one or more EGFR mutations is selected from the group consisting of EGFR (E746-A750del), EGFR (G719C), EGFR (G719S), EGFR (L747-E749del, A750P), EGFR (L747-S752del, P753S), EGFR (L747-T751del, Sins), EGFR (L858R), EGFR (L858R, T790M), EGFR (L861Q), EGFR (S752-I759del), EGFR (T790M), EGFR Del19, EGFR Del19/T790M, EGFR L858RMT790M/C797S, EGFR Del19/T790M/C797S, EGFR Exon20 ins NPH, and EGFR Exon20 ins SVD.

8. The method of claim 6, wherein the cancer is selected from the group consisting of: pseudomyxoma, intrahepatic cholangiocarcinoma, hepatoblastoma, liver cancer, thyroid cancer, colon cancer, testis cancer, myelodysplastic syndrome, glioblastoma, oral cancer, lip cancer, mycosis fungoides, acute myeloid leukemia, acute lymphocytic leukemia, basal cell carcinoma, epithelial ovarian cancer, ovarian seminoma, male breast cancer, brain cancer, pituitary adenoma, multiple myeloma, gallbladder cancer, cholangiocarcinoma, colorectal cancer, chronic myeloid leukemia, chronic lymphocytic leukemia, retinoblastoma, choroidal melanoma, ampullar of Vater cancer, bladder cancer, peritoneal cancer, parathyroid cancer, adrenal cancer, nasal and paranasal cavity cancer, non-small cell lung cancer, tongue cancer, astrocytoma, small cell lung cancer, pediatric brain cancer, pediatric lymphoma, pediatric leukemia, small intestine cancer, meningioma, esophageal cancer, glioma, renal pelvis cancer, renal cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal tumor, Wilms' tumor, breast cancer, sarcoma, penile cancer, pharyngeal cancer, gestational choriocarcinoma, cervical cancer, endometrial cancer, uterine sarcoma, prostate cancer, metastatic bone cancer, metastatic brain cancer, mediastinal cancer, rectal cancer, rectal carcinoid, vaginal cancer, spinal cancer, vestibular schwannoma, pancreatic cancer, salivary gland cancer, Kaposi's sarcoma, Paget's disease, tonsillar cancer, squamous cell cancer, adenocarcinoma of lung, lung cancer, squamous cell lung cancer, skin cancer, anal cancer, rhabdomyosarcoma, laryngeal cancer, pleura cancer, hematologic malignancy, thymic cancer, and non-small cell lung cancer.

9. The method of claim 8, wherein the cancer is non-small cell lung cancer.

* * * * *